US008642603B2

(12) United States Patent  
Cao et al.

(10) Patent No.: US 8,642,603 B2  
(45) Date of Patent: Feb. 4, 2014

(54) SUBSTITUTED DIHYDRO AND TETRAHYDRO OXAZOLOPYRIMIDINONES, PREPARATION AND USE THEREOF

(75) Inventors: Bin Cao, Bedminster, NJ (US); Vieroslava Gurunian, Allamuchy, NJ (US); Sathapana Kongsamut, Madison, NJ (US); Raymond W. Kosley, Jr., Bridgewater, NJ (US); Rosy Sher, Bridgewater, NJ (US); Ryan E. Hartung, Bridgewater, NJ (US)

(73) Assignee: Sanofi, Paris (FR)

( * ) Notice: Subject to any disclaimer, the term of this patent is extended or adjusted under 35 U.S.C. 154(b) by 3504 days.

(21) Appl. No.: 12/554,129

(22) Filed: Sep. 4, 2009

(65) Prior Publication Data

US 2010/0075994 A1 Mar. 25, 2010

Related U.S. Application Data

(63) Continuation of application No. PCT/US2008/056002, filed on Mar. 6, 2008.

(60) Provisional application No. 60/893,991, filed on Mar. 9, 2007.

(51) Int. Cl.
| C07D 491/04 | (2006.01) |
| A61K 31/519 | (2006.01) |
| A61P 25/28 | (2006.01) |
| A61P 25/22 | (2006.01) |
| A61P 25/18 | (2006.01) |
| A61P 25/06 | (2006.01) |
| A61P 25/02 | (2006.01) |

(52) U.S. Cl.
USPC .................................. 514/259.2; 544/278

(58) Field of Classification Search
USPC ........................ 544/278; 514/259.2
See application file for complete search history.

(56) References Cited

U.S. PATENT DOCUMENTS

| 3,743,663 | A | 7/1973 | Baschang et al. |
| 5,641,785 | A | 6/1997 | Jegham et al. |
| 2005/0148590 | A1 | 7/2005 | Tsang et al. |
| 2006/0100460 | A1 | 5/2006 | Inoue et al. |
| 2010/0075994 | A1 | 3/2010 | Cao et al. |

FOREIGN PATENT DOCUMENTS

| EA | 6747 B1 | 4/2006 |
| RU | 95114741 A | 8/1997 |
| WO | 02/066484 A1 | 8/2002 |
| WO | 2008/112483 | 9/2008 |
| WO | 2008/112483 A1 | 9/2008 |
| WO | 2011/034830 A1 | 3/2011 |

OTHER PUBLICATIONS

Adetchessi, O-S., et. al., Synthesis and Rearrangement of Cycloalkyl[1,2-e]Oxazolo[3,2-a]Pyrlmidin-8/9-Ones: An Access to Cycloalkyl[l,2-d]Oxazolo[3,2-a]Pyrimidin-5-Ones, Tetrahedron, vol. 61, (2005), pp. 4453-4460.

Alexander, G. M., et. al., Metabotropic Glutamate Receptors as a Strategic Target for the Treatment of Epilepsy, Epilepsy Research, vol. 71, pp. 1-22, (2006).

Baltzly, R., et al., The Addition of Secondary Amines to Some A-Benzal Ketones, Journal of the American Chemical Society, (1995), vol. 77, pp. 624-628.

Borsini, F., et. al., A Model to Measure Anticipatory Anxiety in Mice?, Psychopharmacology, (1989), vol. 98, pp. 207-211.

Cai, G., et. al., A Sequential Reactio Process to Assemble Polysubstituted Indolizidines, Quinolizidines and Quinolizidine Analogues, Tetrahedron, vol. 62, (2006), pp. 5697-5708.

Camps, F., et. al., Improved Synthesis of Methyl Alkoxyacetylenecarboxylates, Synthesis, (1989), pp. 123-124.

Carmen Carreno, M., et. al., Ring Selectivity in the Na/EtOH Reduction of 1-Aryl-7-Methoxynaphthalenes, Synlett, (2005), vol. 10, pp. 1601-1605.

Chavez-Noriega, L. E., et. al., Metabotropic Glutamate Receptors: Potential Drug Targets for the Treatment of Schizophrenia, Current Drug Targets,—CNS & Neurological Disorders, (2002), vol. 1, pp. 261-281.

Feinberg, I., et. al., The Selective Group Mglu2/3 Receptor Agonist Ly379268 Supresses Rem Sleep and Fast Eeg in the Rat, Pharmacology, Biochemistry and Behavior, vol. 73, (2002), pp. 467-474.

Forfar, I., et. al., An easy Route to 2-Substituted-2, 3-Dihydro-5(7)H-Oxazolo[3,2-a]Pyrimidin-5-ones and 7-ones Starting from the Corresponding 2-Amino-2-Oxazolines, Journal of Heterocyclic Chemistry, (2001), vol. 38, No. 4, pp. 823-827.

(Continued)

*Primary Examiner* — Susanna Moore

(74) *Attorney, Agent, or Firm* — Scully, Scott, Murphy & Presser, P.C.

(57) ABSTRACT

The present invention relates to a series of substituted dihydro and tetrahydro oxazolopyrimidinones, specifically, to a series of 2-substituted-2,3-dihydro-oxazolo[3,2-a]pyrimidin-7-ones and 2-substituted-2,3,5,6-tetra-hydro-oxazolo[3,2-a]pyrimidin-7-ones of formula (I):

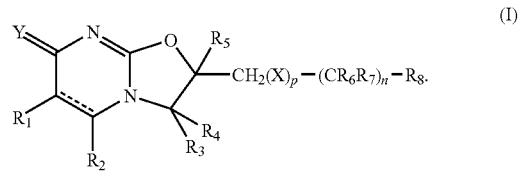

Wherein p, n, X, Y, $R_1$, $R_2$, $R_3$, $R_4$, $R_5$, $R_6$, $R_7$ and $R_8$ are as defined herein. This invention also relates to methods of making these compounds including novel intermediates. The compounds of this invention are modulators of metabotropic glutamate receptors (mGluR), particularly, mGluR2 receptor. Therefore, the compounds of this invention are useful as pharmaceutical agents, especially in the treatment and/or prevention of a variety of central nervous system disorders (CNS), including but not limited to acute and chronic neurodegenerative conditions, psychoses, convulsions, anxiety, depression, migraine, pain, sleep disorders and emesis.

42 Claims, No Drawings

(56) References Cited

OTHER PUBLICATIONS

Forfar, I., et. al., Synthesis: Structure, and Preliminary Pharmacological Evaluation of Cycloaddition Compounds with Unsaturated Carboxylic Esters, Archiv der Pharmazie, (1990), vol. 323, No. 11, pp. 905-909.

Galici, R, et, al., Biphenyl-Indanone A, A Positive Allosteric Modulator of the Metabotropic Glutamate Receptor Subtype 2, Has Antipsychotic- and Anxiolytic-Like Effects in Mice, The Journal of Pharmacology and Experimental Therapeutics, (2006), vol. 318, No. 1, pp. 173-185.

Gewirtz. J. C., et. al., Modulation of DOI-Induced increases in Cortical Bdnf Expression by Group II Mglu Receptors, Pharmacology, Biochemistry and Behaviour, vol. 73, (2002), pp. 317-326.

Helton, D. R., et. al., Anxiolytic and Side-Effect Profile of Ly354740: A Potent, Highly Selective, Orally Active Agonist for Group II Metabotropic Glutamate Receptors, The Journal of Pharmacology and Experimental Therapeutics, vol. 284, No. 2, pp. 651-660, (1998).

Jirgensons, A., et. al., Synthesis and Structure-Affinity Relationships of 1,3,5-Alkylsubstituted Cyclohexylamines Binding at NMDA Receptor PCP Site, Eur. J. Med. Chem., vol. 35, (2000), pp. 555-565.

Jones, C. K., et. al., Analgesic Effects of the Selective Group II (mGlu2/3) Metabotropic Glutamate Receptor Agonists Ly379268 and Ly389795 in Persistent and Inflammatory Pain Models after Acute and Repeated Dosing, Neuropharmacology, vol. 49, (2005), pp. 206-218.

Kawashima, N., et. al., Neuropharmacological Profiles of Antagonists of Group II Metabotropic Glutamate Receptors, Neuroscience Letters, vol. 378, (2005), pp. 131-134.

Konishi, H., et. al., A Mild Selective Monobromination Reagent System for Alkoxybenzenes; N-Bromosuccinimide-Silica Gel, The Chemical Society of Japan, vol. 62, pp. 591-593, (1989).

Lissavetzky, J., et al., Synthesis of 4-Substituted Methyl 3-(2,3-Epoxy)Propoxythiophene-2-Carboxylates, Heterocycles, vol. 43, No. 4, (1996), pp. 775-780.

Martinez, A. .G, et. al., A New and Convenient Synthesis of Alkyl and Aryl Pyrimidines, J. Heterocyclic Chem. vol. 25, pp. 1237-1241, (1988).

Monaghan, D. T., et. al., The Excitatory Amino Acid Receptors: Their Classes, Pharmacology, and Distinct Properties in the Function of the Central Nervous System, Annu. Rev, Pharmacol. Toxiol., (1989), vol. 29, pp. 365-402.

Olivier, B., et. al., Stress-Induced Hyperthermia and Anxiety: Pharmacological Validation , European Journal of Pharmacology, vol. 463, (2003), pp. 117-132.

Patil, S. T, et. al., Activation of MGlu2/3 Receptors as a New Approach to Treat Schizophrenia: A Randonmized Phase 2 Clinical Trial, Nature Medicine, vol. 13, No. 9, (2007), pp. 1102-1107.

Poulter, C. D., , Synthesis of Fluorinated Analogues of Geraniol, J. Org. Chem., (1981), vol. 46, pp. 1532-1538.

Rorick-Kehn, L., et. al., Improved Bioavailability of the MGlu2/3 Receptor Agonist Ly354740 Using a Prodrug Strategy: In Vivo Pharmacology of Ly54434, The Journal of Pharmacology and Experimental Therapeutics, (2006), vol. 316, No. 2, pp. 905-913.

Sabbatni, F. M., et. al., Metabotropic Glutamate Receptors: Potential Therapeutic Applications of Recently Disclosed New Chemical Entities, Expert Opin. Ther. Patents, (2004), vol. 14, No. 11, pp. 1593-1604.

Schechter, L. E., et. al., Innovative Approaches for the Development of Antidepressant Drugs: Current and Future Strategies, NeuroRx: The Journal of the American Society for Experimental NeuroTherapeutics, vol. 2, pp. 590-611, (2005).

Thomsen, C., et. al., (S)-4-Carboxy-3-Hydroxyphenylglycine, An Antagonist of Metabotropic Glutamate Receptor (MGlur)la and an Agonist of Mglur2, Protects Against Audiogenic Seizures in DBA/2 Mice, Journal of Neurochemistry, vol. 62, No. 6, pp. 2492-2495, (1994).

Thomsen, C., et. al., Roles of Metabotropic Glutamate Receptor Subtypes in Modulation of Pentylenetetrazole-Induced Seizure Activity in Mice, Neuropharmacology, vol. 37, (1998), pp. 1465-1473.

Urgaonkar, S., et. al. Palladium/Proazaphosphatrane-Catalyzed Amination of Aryl Halides Possessing a Phenol, Alcohol, Acetanilide, Amide or an Enolizable Ketone Functional Group; Efficacy of Lithium Bis(Trimethylsilyl)Amide as the Base, Adv. Synth. Catal., (2004), vol. 346, pp. 611-616.

Watkins, J. C., et al., Excitatory Amine Acid Transmitters, Ann. Rev. Pharmacol. Toxicol., (1981), vol. 21, pp. 165-204.

Yang, C-G., et. al., Gold(I)-Catalyzed Intermolecular Additions of Phenols and Carboxylic Acids to Olefins. J. Am. Chem Soc., (2005), vol. 127, pp. 6966-6967.

Yeager, G. W., et. al., A Convenient Method for the Preparation of 4-Aryloxyphenols, Synthesis, (1991), pp. 63-68.

Zhang, H., et. al., Synthesis of B- and Y-Carbolines by the Palladium-Catalyzed Iminoannulation of Alkynes, J. Org. Chem., (2002), vol. 67, pp. 9318-9330.

Kimaru, M,, et. al., Silver(I)-Catalyzed Aminocyclization of 2,3-Butadienyl and 3,4-Pentadienyl Carbamates: Ar Efficient and Stereoselective Synthesis of 4-Vinyl-2-Oxazolidines and 4-Vinyltetrahydro-2H-1,3-Oxazine-2-Ones, Bull. Chem. Soc. Jpn., vol. 68, pp. 1689-1705, (1995).

U.S. Appl. No. 13/410,723, filed Mar. 2, 2012.

Russian Patent Office Decision for Application No. 2009137369/04(052839) together with English language translation, 2009.

Andrews, I. P., et al., "Use of Methyllithium in Metal/Halogen Exchange; A Mild and Efficient Method for the Synthesis of Ortho Substituted Toluenes", Synthetic Communications, 31 (15):2323-2327 (2001).

Bradley, S. R., et al., "Activation of Group II Metabotropic Glutamate Receptors Inhibits Synaptic Excitation of the Substantia Nigra Pars Reticulata", The Journal of Neuroscience, 20(9):3085-3094, May 1, 2000.

Conn, P. J., et al., "Activation of metabotropic glutamate receptors as a novel approach for the treatmetn of schizophrenia", Trends in Pharmacological Sciences, 30(1):25-31 (2008).

Johnson, M. P., et al., "Metabotropic glutamate 2 receptor potentiators: receptor modulation, frequency-dependent synaptic activity, and efficacy in preclinical anxiety and psychosis model(s)", Pshchopharmacology, 179:271-283 (2005).

Kellner, M., et al., "Effects of a metabotripic glutamate2/3 receptor agonist (LY544344/LY354740) on panic anxiety induced by cholecystokinin tetrapeptide in healthy humans: preliminary results" Psychopharmacology, 179:310-315 (2005).

Klodzinska, A., et al., "Selective Group II Glutamate Metabotropic Receptor Agonist LY354740 Attenuates Pentetrazole- and Picrotoxin-Induced Seizures", Polish Journal of Pharmacology, 51:543-545 (1999).

Krystal, J. H., et al., "NMDA receptor antagonist effects, cortical glutamatergic function, and schizophrenia: toward a paradigm shift in medication development", Psychopharmacology, 169:215-233 (2003).

Krystal, J. H., et al., "Preliminary evidence of attenuation of the disruptive effects of the NMDA glutamate receptor antagonist, ketamine, on working memory by pretreatment with the group II metabotropic glutamate receptor agonist, LY354740, in healthy human subjects", Psychopharmacology 179:303-309 (2005).

Lee, H., et al., "The effect of mGluR2 activation on signal transduction pathways and neuronal cell survival", Brain Research, 1249:244-250 (2009).

Lorrain, D. S., et al., Effects of Ketamine and N-Methyl-D-Asparate on Glutamate and Dopamine Release in the Rat Prefrontal Cortex: Modulation by a Group II Selective Metabotropic Glutamate Receptor Agonist LY379268, Neuroscience, 117:697-706 (2003).

Moghaddam, B., "Targeting metabotropic glutamate receptors for treatment of the cognitive symptoms of schizophrenia", Psychopharmacology, 174:39-44 (2004).

Rouse, S. T., et al., "Distribution and roles of metabotropic glutamate receptors in the basal ganglia motor circuit: implications for treatment of Parkinson's Disease and related disorders", Pharmacology & Therapeutics, 88:427-435 (2000).

(56) References Cited

OTHER PUBLICATIONS

Samadi, P., et al., "Basal ganglia group II metabotropic glutamate receptors specific binding in non-human primate model of L-Dopa-induced dyskinesias", Neuropharmacology, 54:258-268 (2008).

Tatarczynska, E., et al., "The antianxiety-like effects of antagonists of group I and agonists of group II and III metabotropic glutamate receptors after intrahippocampal administration", Psychopharmacology, 158:94-99 (2001).

Watkins, J. C., et al., "Structure-activity relationships in the development of excitatory amino acid receptor agonists and competitive antagonists", TiPS, 11:25-33, Jan. 1990.

United States Office Action dated Sep. 19, 2012 issued in U.S. Appl. No. 13/410,723.

SUBSTITUTED DIHYDRO AND TETRAHYDRO OXAZOLOPYRIMIDINONES, PREPARATION AND USE THEREOF

CROSS REFERENCE TO RELATED APPLICATIONS

This application is a continuation of International application No. PCT/US2008/056,002, filed Mar. 6, 2008, which claims the benefit of U.S. Provisional Application No. 60/893,991, filed Mar. 9, 2007, both of which are incorporated herein by reference in their entirety.

BACKGROUND OF THE INVENTION

1. Field of the Invention

The present invention relates to a series of substituted dihydro and tetrahydro oxazolopyrimidinones. More specifically, the present invention relates to a series of 2-substituted-2,3-dihydro-oxazolo[3,2-a]pyrimidin-7-ones and 2-substituted-2,3,5,6-tetra-hydro-oxazolo[3,2-a]pyrimidin-7-ones. This invention also relates to methods of making these compounds. The compounds of this invention are allosteric modulators of metabotropic glutamate receptors (mGluR), particularly, mGluR2. Therefore, the compounds of this invention are useful as pharmaceutical agents, especially in the treatment and/or prevention of a variety of diseases including diseases associated with the central nervous system.

2. Description of the Art

Recently, there has been a considerable amount of research involving L-glutamate, which is the most abundant neurotransmitter in the central nervous system (CNS). More specifically, L-glutamate mediates the major excitatory pathways in mammals, and is therefore referred to as an excitatory amino acid (EAA). Thus the receptors that respond to glutamate are known as excitatory amino acid receptors (EAA receptors). Based on the extensive research performed lately it can be readily discerned that EAAs are of great physiological importance. Particularly, EAAs are known to play a role in several physiological processes including long-term potentiation (learning and memory), the development of synaptic plasticity, motor control, respiration, cardiovascular regulation and sensory perception, just to name a few. See, e.g., Watkins & Evans, Annual Reviews in Pharmacology and Toxicology, 21:165 (1981); Monaghan, Bridges, and Coltman, Annual Reviews in Pharmacology and Toxicology, 29:365 (1989); Watkins, Krogsgaard-Larsen and Honore, Transactions in Pharmaceutical Science, 11:25 (1990).

Broadly, the EAA receptors are classified into two types: 1) "ionotropic"—which are directly coupled to the opening of cation channels in the cell membrane of the neurons; and 2) "metabotropic"—which are G-protein coupled receptors (GPCR). The excessive or inappropriate stimulation of EAA receptors leads to neuronal cell damage or loss by way of a mechanism known as excitotoxicity. This process has been suggested to mediate neuronal degeneration in a variety of conditions. Thus there is a renewed interest in developing small molecule new drugs to alleviate these conditions.

The metabotropic glutamate receptors (mGluR) are a highly heterogeneous family of glutamate receptors that are linked to multiple second-messenger pathways. One function of these receptors is to modulate the presynaptic release of glutamate and the postsynaptic sensitivity of the neuronal cell to glutamate excitation. Thus it has been reported widely in the literature that agonists and antagonists of these receptors are useful in the treatment of a variety of disease conditions including acute and chronic neurodegenerative conditions, psychoses, convulsions, anxiety, depression, migraine, pain, sleep disorders and emesis.

The metabotropic glutamate receptors (mGluR) are again classified into three groups based on receptor homology and signaling mechanisms. Among them, recent pharmacological and histochemical studies have suggested that the group II mGluR (mGluR2 and mGluR3) plays crucial roles in the control of emotional states. For example, MGS0039, a selective group II mGluR antagonist, has been shown to exhibit dose-dependent antidepressant-like effects in some animal models. See, e.g., Kawashima, et al., Neurosci. Lett., 2005, 378(3):131-4.

Recently, it has also been reported that glutamate/N-methyl-D-aspartate glutamate receptors (NMDAR) are implicated in schizophrenia. This was indeed supported by the observation that administration of NMDAR blockers to human volunteers is psychotomimetic and administration to schizophrenia patients exacerbates pre-existing symptoms. For example, systemic administration of group II mGluR agonists suppress phencyclidine (PCP) induced behavioral effects and the increase in glutamate efflux. It has also been observed that activation of group II mGluRs (mGluR2 and mGluR3) decreases glutamate release from presynaptic nerve terminals, suggesting that group II mGluR agonists may be beneficial in the treatment of schizophrenia. See, e.g., Chavez-Noriega et al., Current Drug Targets—CNS & Neurological Disorders, 2002, 1, 261-281.

Although there is a great deal of interest in developing small molecule drugs that are active at the mGluR sites, the researchers are faced with a lack of potent and selective molecules. In spite of this, there are innumerable reports highlighting the great interest around these potential therapeutic targets. See, e.g., Sabbatini and Micheli, Expert Opin. Ther. Patents (2004) 14(11):1593-1604.

However, there is still a need to develop selective compounds for one subtype over another metabotropic glutamate receptor site. One strategy that has recently emerged involves the discovery of allosteric modulators that do not bind at the glutamate binding site. An allosteric modulator only works if the agonist (glutamate) is present at the orthosteric binding site; thus, an allosteric modulator will only potentiate or block effects produced by the presence of an agonist, but have no activity on its own. Such a strategy is believed to confer greater specificity to desired pharmacological effects because they affect the normal physiological activity of the agonist.

In addition, there is still a considerable interest in developing small molecule "drug like" compounds that exhibit improved potency and modulation of mGluR2 as well as improved brain penetration. There is also an interest in developing modulators of mGluR2 that are devoid of typical side effects exhibited by typical and atypical antipsychotic compounds, such as for example extrapyramidal symptoms including tardive dyskinesia, weight gain, etc. It is also expected that allosteric modulators that exhibit improved subtype selectivity will feature an improved pharmacological safety profile. It is further believed that a selective modulator of mGluR2 will also exhibit efficacy on cognitive dysfunction in schizophrenia patients thereby improving working memory and positive symptoms.

All of the references described herein are incorporated herein by reference in their entirety.

Accordingly, it is an object of this invention to provide a series of substituted dihydro and tetrahydro oxazolopyrimidinones which are potent modulators of mGluR2.

It is also an object of this invention to provide processes for the preparation of the substituted dihydro and tetrahydro oxazolopyrimidinones as disclosed herein.

Other objects and further scope of the applicability of the present invention will become apparent from the detailed description that follows.

SUMMARY OF THE INVENTION

Thus in accordance of this invention there are provided compounds of the formula I:

$$\text{(I)}$$

wherein:
----- is a single or a double bond;
p is 0 or 1;
n is an integer from 0 to 3;
X is oxygen, sulfur or $NR_{21}$, wherein $R_{21}$ is hydrogen or $(C_1-C_4)$alkyl;
Y is oxygen or sulfur;
$R_1$ and $R_2$ are the same or different and independently of each other selected from the group consisting of hydrogen, $CF_3$, straight or branched chain $(C_1-C_{10})$alkyl, mono- or di-fluoro$(C_1-C_4)$alkyl, mono- or di-fluoro$(C_1-C_4)$alkoxy$(C_0-C_4)$alkyl, mono- or di-fluoro$(C_1-C_4)$alkylsulfanyl$(C_0-C_4)$alkyl, mono- or di-fluoro$(C_1-C_4)$alkylsulfinyl$(C_0-C_4)$alkyl, mono- or di-fluoro$(C_1-C_4)$alkylsulfonyl$(C_0-C_4)$alkyl, $(C_1-C_{10})$alkoxy$(C_0-C_4)$alkyl, $(C_1-C_{10})$alkylsulfanyl$(C_0-C_4)$alkyl, $(C_1-C_{10})$alkylsulfinyl$(C_0-C_4)$alkyl, $(C_1-C_{10})$alkylsulfonyl$(C_0-C_4)$alkyl, $(C_1-C_{10})$alkoxy mono- or di-fluoro$(C_1-C_4)$alkyl, $(C_1-C_{10})$alkylsulfanyl mono- or di-fluoro$(C_1-C_4)$alkyl, $(C_1-C_{10})$alkylsulfinyl mono- or di-fluoro$(C_1-C_4)$alkyl, $(C_1-C_{10})$alkylsulfonyl mono- or di-fluoro$(C_1-C_4)$alkyl, $(C_6,C_{10})$aryl$(C_0-C_4)$alkyl, $(C_6,C_{10})$aryl mono- or difluoro$(C_1-C_4)$alkyl, $(C_6,C_{10})$aryl mono- or difluoro$(C_2-C_4)$alkyloxy, $(C_6,C_{10})$aryloxy$(C_0-C_4)$alkyl, $(C_6,C_{10})$arylsulfanyl$(C_0-C_4)$alkyl, $(C_6,C_{10})$arylsulfinyl$(C_0-C_4)$alkyl, $(C_6,C_{10})$arylsulfonyl$(C_0-C_4)$alkyl, $(C_3-C_8)$cycloalkyl$(C_0-C_4)$alkyl, mono- or difluoro$(C_3-C_8)$cycloalkyl$(C_0-C_4)$alkyl, $(C_3-C_8)$cycloalkoxy$(C_0-C_4)$alkyl, mono- or difluoro$(C_3-C_8)$cycloalkyloxy$(C_0-C_4)$alkyl, $(C_3-C_8)$cycloalkyl mono- or difluoro$(C_1-C_4)$alkyl, $(C_3-C_8)$cycloalkyl mono- or difluoro$(C_2-C_4)$alkyloxy, $(C_3-C_8)$cycloalkylsulfanyl$(C_0-C_4)$alkyl, $(C_3-C_8)$cycloalkylsulfinyl$(C_0-C_4)$alkyl, $(C_3-C_8)$cycloalkylsulfonyl$(C_0-C_4)$alkyl, hydroxy$(C_1-C_4)$alkyl, heteroaryl$(C_0-C_4)$alkyl, heteroaryl mono- or difluoro$(C_1-C_4)$alkyl, heteroaryloxy$(C_0-C_4)$alkyl, heteroaryloxy mono- or difluoro$(C_2-C_4)$alkyl, heteroarylsulfanyl$(C_0-C_4)$alkyl, heteroarylsulfinyl$(C_0-C_4)$alkyl, heteroarylsulfonyl$(C_0-C_4)$alkyl, saturated heterocyclic$(C_0-C_4)$alkyl, saturated heterocyclic mono- or di-fluoro$(C_1-C_4)$alkyl, saturated heterocyclyloxy$(C_0-C_4)$alkyl, saturated heterocyclyloxy mono- or di-fluoro$(C_2-C_4)$alkyl, saturated heterocyclylsulfanyl$(C_0-C_4)$alkyl, heterocyclylsulfinyl$(C_0-C_4)$alkyl, heterocyclylsulfonyl$(C_0-C_4)$alkyl, —$CO_2R_{22}$ or —$CONR_{23}R_{24}$ wherein $R_{22}$, $R_{23}$ and $R_{24}$ are the same or different and independently of each other selected from hydrogen or $(C_1-C_4)$alkyl; and
wherein $R_1$ and $R_2$ are optionally further substituted;
$R_3$ and $R_4$ are the same or different and independently of each other selected from the group consisting of hydrogen, $(C_1-C_4)$alkyl, $(C_3-C_8)$cycloalkyl, and $(C_6,C_{10})$aryl$(C_1-C_4)$alkyl; or
$R_3$ and $R_4$ taken together with the carbon atom to which they are attached form a substituted or unsubstituted $C_5-C_7$ carbocyclic ring;
$R_5$, $R_6$ and $R_7$ are the same or different and independently of each other selected from the group consisting of hydrogen, $(C_1-C_4)$alkyl and $(C_3-C_8)$cycloalkyl;
$R_8$ is selected from the group consisting of substituted or unsubstituted phenyl, substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted $(C_3-C_8)$cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, substituted or unsubstituted tetrahydrodibenzofuranyl and substituted or unsubstituted hexahydrodibenzofuranyl;
wherein said substituents are selected from the group consisting of $CF_3$, $OCF_3$, halogen, CN, $SF_5$, straight or branched chain $(C_1-C_{20})$alkyl, $(C_1-C_4)$alkylsulfonyl, substituted or unsubstituted $(C_3-C_{10})$cycloalkyl $(CR_9R_{10})_m$, substituted or unsubstituted $(C_6-C_{16})$spirocycloalkyl, substituted or unsubstituted $(C_6,C_{10})$aryl$(CR_9R_{10})_m$, substituted or unsubstituted heteroaryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3-C_{10})$cycloalkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$, substituted or unsubstituted $(C_4-C_7)$ lactam, substituted or unsubstituted tetrahydropyranyl$(CR_9R_{10})_m$, substituted or unsubstituted tetrahydrofuranyl$(CR_9R_{10})_m$, substituted or unsubstituted 1,3-dioxanyl, substituted or unsubstituted 1,3-dioxolanyl, $(C_1-C_4)$alkoxyethoxy, substituted or unsubstituted $(C_3-C_8)$cycloalkyloxyethoxy, substituted or unsubstituted $(C_6,C_{10})$aryloxyethoxy and substituted or unsubstituted heteroaryloxyethoxy;
wherein
m is an integer from 0 to 10;
$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3$-$C_8$ carbocyclic ring;

and wherein said substituents are selected from the aforementioned substituents.

The compound of formula I can be present as a salt. It can also present as an enantiomer, a stereoisomer or a tautomer or a racemic mixture thereof. All of these forms are part of this invention.

However, with the proviso that:
when ----- is a double bond, X and Y are oxygen, p is 1, n is 0, $R_1$, $R_3$, $R_4$, $R_5$, $R_6$, $R_7$ are hydrogen and $R_2$ is either hydrogen or methyl, then $R_8$ is not 2-methylphenyl; and
when ----- is a double bond, X and Y are oxygen, p is 1, n is 0 and $R_1$, $R_2$, $R_3$, $R_4$, $R_5$, $R_6$, $R_7$ are hydrogen, then $R_8$ is not phenyl.

More specifically, the following compounds are excluded from this invention:
2-(2-methyl-phenoxymethyl)-2,3-dihydro-oxazolo[3,2-a]pyrimidin-7-one;
5-methyl-2-(2-methyl-phenoxymethyl)-2,3-dihydro-oxazolo[3,2-a]pyrimidin-7-one;
2-(phenoxymethyl)-2,3-dihydro-oxazolo[3,2-a]pyrimidin-7-one;
5-methyl-2-phenoxymethyl-2,3,5,6-tetrahydro-oxazolo[3,2-a]pyrimidin-7-one; and
2-phenoxymethyl-2,3,5,6-tetrahydro-oxazolo[3,2-a]pyrimidin-7-one.

In addition, various embodiments of this invention including pharmaceutical compositions comprising various compounds of this invention as well as their use in the treatment of a variety of disorders and/or disease conditions as disclosed herein are also part of this invention all of which are described in detail below.

DETAILED DESCRIPTION OF THE INVENTION

The terms as used herein have the following meanings:

As used herein, the expression "$(C_1$-$C_4)$alkyl" includes methyl and ethyl groups, and straight-chained or branched propyl and butyl groups. Particular alkyl groups are methyl, ethyl, n-propyl, isopropyl and tert-butyl. Similarly, the expression "$(C_1$-$C_{10})$alkyl" includes all of the $(C_1$-$C_4)$alkyl as described above and further includes straight chained or branched pentyl, hexyl, heptyl, octyl, nonyl and decyl groups. Further, the expression "$(C_1$-$C_{20})$alkyl" includes all of the possible straight chained or branched alkyl groups containing from 1 to 20 carbon atoms. It should particularly be noted that any of the feasible branched $(C_1$-$C_4)$alkyl group, $(C_1$-$C_{10})$alkyl group or $(C_1$-$C_{20})$alkyl group known in the art is encompassed by this expression. Derived expressions such as "$(C_1$-$C_4)$alkoxy" or "$(C_1$-$C_{10})$alkoxy", "$(C_1$-$C_4)$thioalkyl" or "$(C_1$-$C_{10})$thioalkyl", "$(C_1$-$C_4)$alkoxy$(C_1$-$C_4)$alkyl" or "$(C_1$-$C_{10})$alkoxy$(C_1$-$C_{10})$alkyl", "hydroxy$(C_1$-$C_4)$alkyl" or "hydroxy$(C_1$-$C_{10})$alkyl", "$(C_1$-$C_4)$alkylcarbonyl" or "$(C_1$-$C_{10})$alkylcarbonyl", "$(C_1$-$C_4)$alkoxycarbonyl$(C_1$-$C_4)$alkyl", "$(C_1$-$C_4)$alkoxycarbonyl", "amino$(C_1$-$C_4)$alkyl", "$(C_1$-$C_4)$alkylamino", "$(C_1$-$C_4)$alkylcarbamoyl$(C_1$-$C_6)$alkyl", "$(C_1$-$C_4)$dialkylcarbamoyl$(C_1$-$C_4)$alkyl" "mono- or di-$(C_1$-$C_4)$alkylamino$(C_1$-$C_4)$alkyl", "amino$(C_1$-$C_4)$alkylcarbonyl" "diphenyl$(C_1$-$C_4)$alkyl", "phenyl$(C_1$-$C_4)$alkyl", "phenylcarboyl$(C_1$-$C_4)$alkyl", "phenoxy$(C_1$-$C_4)$alkyl" and "$(C_1$-$C_4)$alkylsulfonyl," are to be construed accordingly. Similarly other derived expressions, such as $(C_1$-$C_4)$alkoxyethoxy shall be construed accordingly. Another derived expression mono- or di-fluoro$(C_1$-$C_4)$alkyl shall mean that one or two of the hydrogens are replaced with fluorine. Representative examples of monofluoro$(C_1$-$C_4)$alkyl include fluoromethyl, 2-fluoro-eth-1-yl or 1-fluoro-eth-1-yl, 1-fluoro-1-methyl-eth-1-yl, 2-fluoro-1-methyl-eth-1-yl, 3-fluoro-prop-1-yl, and the like. Representative examples of difluoro$(C_1$-$C_4)$alkyl include difluoromethyl, 2,2-difluoro-eth-1-yl, 1,2-difluoro-eth-1-yl or 1,1-difluoro-eth-1-yl, 1,2-difluoro-1-methyl-eth-1-yl, 2,2-difluoro-1-methyl-eth-1-yl, 1,3-difluoro-prop-1-yl, and the like.

As used herein, the expression "$(C_3$-$C_8)$cycloalkyl" includes all of the known cyclic radicals. Representative examples of "cycloalkyl" includes without any limitation cyclopropyl, cyclobutyl, cyclopentyl, cyclohexyl, cycloheptyl, cyclooctyl, and the like. Derived expressions such as "cycloalkoxy" or "cycloalkyloxy", "cycloalkyloxyethoxy", "cycloalkylalkyl", "cycloalkylaryl", "cycloalkylcarbonyl" are to be construed accordingly. It should further be noted that the expression "$(C_5$-$C_8)$carbocyclic" shall have the same meaning as "$(C_5$-$C_8)$cycloalkyl".

As used herein the expression "$(C_1$-$C_6)$acyl" shall have the same meaning as "$(C_1$-$C_6)$alkanoyl", which can also be represented structurally as "R—CO—," where R is a $(C_1$-$C_5)$ alkyl as defined herein. Additionally, "$(C_1$-$C_5)$alkylcarbonyl" shall mean same as $(C_1$-$C_6)$acyl. Specifically, "$(C_1$-$C_6)$acyl" shall mean formyl, acetyl or ethanoyl, propanoyl, n-butanoyl, etc. Derived expressions such as "$(C_1$-$C_6)$acyloxy" and "$(C_1$-$C_6)$acyloxyalkyl" are to be construed accordingly.

As used herein, the expression "$(C_4$-$C_7)$lactam" represents all of the known $(C_4$-$C_7)$cyclic amide. Representative examples of "$(C_4$-$C_7)$lactam" includes azetidin-2-one, pyrrolidin-2-one, piperidin-2-one and azepan-2-one.

As used herein, the expression "$(C_1$-$C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1$-$C_6)$perfluoroalkoxy", is to be construed accordingly.

As used herein, the expression "mono- or difluoro$(C_1$-$C_4)$alkyl" means that any of the alkyl groups are substituted with one or two fluorine atoms. Such examples include, without any limitation, fluoromethyl, 1-fluoroethyl, 1-fluoropropyl, 1,1- or 1,2-difluoroethyl, 1,1-, 1,2- or 1,3-difluoropropyl, 1,1-, 1,2-, 1,3- or 1,4-difluorobutyl and so on. The derived expressions, "mono- or di-fluoro$(C_1$-$C_4)$alkoxy$(C_0$-$C_4)$alkyl, mono- or di-fluoro$(C_1$-$C_4)$alkylsulfanyl$(C_0$-$C_4)$alkyl, mono- or di-fluoro$(C_1$-$C_4)$alkylsulfinyl$(C_0$-$C_4)$-alkyl, mono- or di-fluoro$(C_1$-$C_4)$alkylsulfonyl$(C_0$-$C_4)$alkyl" shall be construed accordingly. However, in these situations, the placement of fluorine atom does become important. It is generally preferred that there is no fluorine atom on the carbon next to the oxygen, sulfur, sulfinyl or sulfonyl group. Thus, for instance, when the generic group is mono- or difluoroethoxymethyl, the preferred examples include only 2-fluoroethoxymethyl or 2,2-difluoroethoxymethyl, and the like.

As used herein mono- or difluoro$(C_3$-$C_8)$cycloalkyl shall mean one or two of the hydrogen atoms are replaced with fluorine atoms. Representative examples include fluorocyclohexyl, 1,2-, 2,2- or 1,3-difluorocyclohexyl, fluorocyclopentyl, 1,2-, 2,2- or 1,3-difluorocyclopentyl, and the like.

As used herein, the expression "$(C_6,C_{10})$aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expressions "$(C_6,C_{10})$aryloxy" and "$(C_6,C_{10})$aryloxyethoxy" shall be construed accordingly.

As used herein, the expression "$(C_6,C_{10})$aryl$(C_1$-$C_4)$alkyl" means that the $(C_6,C_{10})$aryl as defined herein is further attached to $(C_1$-$C_4)$alkyl as defined herein. Representative examples include benzyl, phenylethyl, 2-phenylpropyl, 1-naphthylmethyl, 2-naphthylmethyl and the like. Similarly, another derived expression "$(C_6,C_{10})$aryl$(C_3$-$C_8)$cycloalkyl" shall be construed accordingly. Representative examples of said expression include without any limitation, phenylcyclopropyl, 1-naphthylcyclopropyl, phenylcyclohexyl, 2-naphthylcyclopentyl, and the like.

As used herein, the expression "heteroaryl" includes all of the known heteroatom containing aromatic radicals. Representative 5-membered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, furopyridyl, thienopyridyl, and the like radicals. Derived expressions "heteroaryloxy" and "heteroaryloxyethoxy" shall be construed accordingly.

As used herein, the expression "heterocycle" or "saturated heterocyclic" includes all of the known reduced heteroatom containing cyclic radicals. Representative 5-membered heterocycle radicals include tetrahydrofuranyl, 1,3-dioxolanyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, pyranyl, 1,3-dioxanyl, thiomorpholinyl, and the like. Various other heterocycle radicals include, without limitation, aziridinyl, azepanyl, diazepanyl, diazabicyclo[2.2.1]hept-2-yl, and triazocanyl, and the like.

As used herein, the expression "$(C_6$-$C_{13})$bicyclic" includes all of the known bicyclic radicals. Representative examples of "bicyclic" includes without any limitation bicyclo[2.1.1]hexane, bicyclo[2.2.1]heptane, bicyclo[[3.2.1]octane, bicyclo[2.2.2]octane, bicyclo[3.2.2]nonane, bicyclo[3.3.1]nonane, bicyclo[3.3.2]decane, bicyclo[4.3.1]decane, bicyclo[4.4.1]undecane, bicyclo[5.4.1]dodecane, and the like. Derived expressions such as "bicycloalkoxy", "bicycloalkylalkyl", "bicycloalkylaryl", "bicycloalkylcarbonyl" are to be construed accordingly.

"Halogen" (or "halo") means chlorine (chloro), fluorine (fluoro), bromine (bromo), and iodine (iodo).

As used herein, "patient" means a warm blooded animal, such as for example rats, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

As used herein, the term "prodrug" shall have the generally accepted meaning in the art. One such definition includes a pharmacologically inactive chemical entity that when metabolized or chemically transformed by a biological system such as a mammalian system is converted into a pharmacologically active substance.

The expression "stereoisomers" is a general term used for all isomers of the individual molecules that differ only in the orientation of their atoms in space. Typically it includes mirror image isomers that are usually formed due to at least one asymmetric center (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

The term "solvate" as used herein means that an aggregate that consists of a solute ion or molecule with one or more solvent molecules. Similarly, a "hydrate" means that a solute ion or molecule with one or more water molecules.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1$-$C_{20})$alkyl, $(C_2$-$C_6)$alkenyl, $(C_1$-$C_6)$perfluoroalkyl, phenyl, hydroxy, —$CO_2H$, an ester, an amide, $(C_1$-$C_6)$alkoxy, $(C_1$-$C_6)$thioalkyl, $(C_1$-$C_6)$perfluoroalkoxy, —$NH_2$, Cl, Br, I, F, CN, $SF_5$, —NH-lower alkyl, and —N(lower alkyl)$_2$, unless otherwise noted. However, any of the other suitable substituents known to one skilled in the art can also be used in these embodiments.

"Therapeutically effective amount" means an amount of the compound which is effective in treating the named disease, disorder or condition.

The term "treating" refers to:

(i) preventing a disease, disorder or condition from occurring in a patient that may be predisposed to the disease, disorder and/or condition, but has not yet been diagnosed as having it;

(ii) inhibiting the disease, disorder or condition, i.e., arresting its development; and (iii) relieving the disease, disorder or condition, i.e., causing regression of the disease, disorder and/or condition.

Thus, in accordance with the practice of this invention there is provided a compound of the formula I:

$$\text{(I)}$$

wherein:
----- is a single or a double bond;
p is 0 or 1;
n is an integer from 0 to 3;
X is oxygen, sulfur or $NR_{21}$, wherein $R_{21}$ is hydrogen or $(C_1\text{-}C_4)$alkyl;
Y is oxygen or sulfur;
$R_1$ and $R_2$ are the same or different and independently of each other selected from the group consisting of hydrogen, $CF_3$, straight or branched chain $(C_1\text{-}C_{10})$alkyl, mono- or di-fluoro$(C_1\text{-}C_4)$alkyl, mono- or di-fluoro$(C_1\text{-}C_4)$alkoxy$(C_0\text{-}C_4)$alkyl, mono- or di-fluoro$(C_1\text{-}C_4)$alkylsulfanyl$(C_0\text{-}C_4)$alkyl, mono- or di-fluoro$(C_1\text{-}C_4)$alkylsulfinyl$(C_0\text{-}C_4)$alkyl, mono- or di-fluoro$(C_1\text{-}C_4)$alkylsulfonyl$(C_0\text{-}C_4)$alkyl, $(C_1\text{-}C_{10})$alkoxy$(C_0\text{-}C_4)$alkyl, $(C_1\text{-}C_{10})$alkylsulfanyl$(C_0\text{-}C_4)$alkyl, $(C_1\text{-}C_{10})$alkylsulfinyl$(C_0\text{-}C_4)$alkyl, $(C_1\text{-}C_{10})$alkylsulfonyl$(C_0\text{-}C_4)$alkyl, $(C_1\text{-}C_{10})$alkoxy mono- or di-fluoro$(C_1\text{-}C_4)$alkyl, $(C_1\text{-}C_{10})$alkylsulfanyl mono- or di-fluoro$(C_1\text{-}C_4)$alkyl, $(C_1\text{-}C_{10})$alkylsulfinyl mono- or di-fluoro$(C_1\text{-}C_4)$alkyl, $(C_1\text{-}C_{10})$alkylsulfonyl mono- or di-fluoro$(C_1\text{-}C_4)$alkyl, $(C_6,C_{10})$aryl$(C_0\text{-}C_4)$alkyl, $(C_6,C_{10})$aryl mono- or difluoro$(C_1\text{-}C_4)$alkyl, $(C_6,C_{10})$aryl mono- or difluoro$(C_2\text{-}C_4)$alkyloxy, $(C_6,C_{10})$aryloxy$(C_0\text{-}C_4)$alkyl, $(C_6,C_{10})$arylsulfanyl$(C_0\text{-}C_4)$alkyl, $(C_6,C_{10})$arylsulfinyl$(C_0\text{-}C_4)$alkyl, $(C_6,C_{10})$arylsulfonyl$(C_0\text{-}C_4)$alkyl, $(C_3\text{-}C_8)$cycloalkyl$(C_0\text{-}C_4)$alkyl, mono- or difluoro$(C_3\text{-}C_8)$cycloalkyl$(C_0\text{-}C_4)$alkyl, $(C_3\text{-}C_8)$cycloalkoxy$(C_0\text{-}C_4)$alkyl, mono- or difluoro$(C_3\text{-}C_8)$cycloalkyloxy$(C_0\text{-}C_4)$alkyl, $(C_3\text{-}C_8)$cycloalkyl mono- or difluoro$(C_1\text{-}C_4)$alkyl, $(C_3\text{-}C_8)$cycloalkyl mono- or difluoro$(C_2\text{-}C_4)$alkyloxy, $(C_3\text{-}C_8)$cycloalkylsulfanyl$(C_0\text{-}C_4)$alkyl, $(C_3\text{-}C_8)$cycloalkylsulfinyl$(C_0\text{-}C_4)$alkyl, $(C_3\text{-}C_8)$cycloalkylsulfonyl$(C_0\text{-}C_4)$alkyl, hydroxy$(C_1\text{-}C_4)$alkyl, heteroaryl$(C_0\text{-}C_4)$alkyl, heteroaryl mono- or difluoro$(C_1\text{-}C_4)$alkyl, heteroaryloxy$(C_0\text{-}C_4)$alkyl, heteroaryloxy mono- or difluoro$(C_2\text{-}C_4)$alkyl, heteroarylsulfanyl$(C_0\text{-}C_4)$alkyl, heteroarylsulfinyl$(C_0\text{-}C_4)$alkyl, heteroarylsulfonyl$(C_0\text{-}C_4)$alkyl, saturated heterocyclic$(C_0\text{-}C_4)$alkyl, saturated heterocyclic mono- or di-fluoro$(C_1\text{-}C_4)$alkyl, saturated heterocyclyloxy$(C_0\text{-}C_4)$alkyl, saturated heterocyclyloxy mono- or di-fluoro$(C_2\text{-}C_4)$alkyl, saturated heterocyclylsulfanyl$(C_0\text{-}C_4)$alkyl, heterocyclylsulfinyl$(C_0\text{-}C_4)$alkyl, heterocyclylsulfonyl$(C_0\text{-}C_4)$alkyl, $-CO_2R_{22}$ or $-CONR_{23}R_{24}$ wherein $R_{22}$, $R_{23}$ and $R_{24}$ are the same or different and independently of each other selected from hydrogen or $(C_1\text{-}C_4)$alkyl; and wherein $R_1$ and $R_2$ are optionally further substituted;

$R_3$ and $R_4$ are the same or different and independently of each other selected from the group consisting of hydrogen, $(C_1\text{-}C_4)$alkyl, $(C_3\text{-}C_8)$cycloalkyl and $(C_6,C_{10})$aryl $(C_1\text{-}C_4)$alkyl; or $R_3$ and $R_4$ taken together with the carbon atom to which they are attached form a substituted or unsubstituted $C_5\text{-}C_7$ carbocyclic ring;

$R_5$, $R_6$ and $R_7$ are the same or different and independently of each other selected from the group consisting of hydrogen, $(C_1\text{-}C_4)$alkyl and $(C_3\text{-}C_8)$cycloalkyl;

$R_8$ is selected from the group consisting of substituted or unsubstituted phenyl, substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted $(C_3\text{-}C_8)$cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, substituted or unsubstituted tetrahydrodibenzofuranyl and substituted or unsubstituted hexahydrodibenzofuranyl;

wherein said substituents are selected from the group consisting of $CF_3$, $OCF_3$, halogen, CN, $SF_5$, straight or branched chain $(C_1\text{-}C_{20})$alkyl, $(C_1\text{-}C_4)$alkylsulfonyl, substituted or unsubstituted $(C_3\text{-}C_{10})$cycloalkyl $(CR_9R_{10})_m$, substituted or unsubstituted $(C_6\text{-}C_{16})$spirocycloalkyl, substituted or unsubstituted $(C_6,C_{10})$aryl$(CR_9R_{10})_m$, substituted or unsubstituted heteroaryl$(CR_9R_{10})_m$, substituted or unsubstituted $(C_6,C_{10})$aryl$(C_3\text{-}C_8)$cycloalkyl, substituted or unsubstituted $(C_8\text{-}C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1\text{-}C_{20})$alkoxy, substituted or unsubstituted $(C_3\text{-}C_{10})$cycloalkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$, substituted or unsubstituted $(C_4\text{-}C_7)$ lactam, substituted or unsubstituted tetrahydropyranyl$(CR_9R_{10})_m$, substituted or unsubstituted tetrahydrofuranyl$(CR_9R_{10})_m$, substituted or unsubstituted 1,3-dioxanyl, substituted or unsubstituted 1,3-dioxolanyl, $(C_1\text{-}C_4)$alkoxyethoxy, substituted or unsubstituted $(C_3\text{-}C_8)$cycloalkyloxyethoxy, substituted or unsubstituted $(C_6,C_{10})$aryloxyethoxy and substituted or unsubstituted heteroaryloxyethoxy;

wherein
m is an integer from 0 to 10;
$R_9$ and $R_{10}$ are the same or different and independently of each other chosen from hydrogen or $(C_1\text{-}C_4)$alkyl; or $R_9$ and $R_{10}$ taken together with the carbon atom to which they are attached form a substituted or unsubstituted $C_3$-$C_8$ carbocyclic ring;

and wherein said substituents are selected from the aforementioned substituents.

The compound of formula I can be present as a salt. It can also present as an enantiomer, a stereoisomer or a tautomer or a racemic mixture thereof. All of these forms are part of this invention.

However, with the proviso that:

when ----- is a double bond, X and Y are oxygen, p is 1, n is 0, $R_1$, $R_3$, $R_4$, $R_5$, $R_6$, $R_7$ are hydrogen and $R_2$ is either hydrogen or methyl, then $R_8$ is not 2-methylphenyl;

when ----- is a double bond, X and Y are oxygen, p is 1, n is 0 and $R_1$, $R_2$, $R_3$, $R_4$, $R_5$, $R_6$, $R_7$ are hydrogen, then $R_8$ is not phenyl; and when ----- is a single bond, X and Y are oxygen, p is 1, n is 0, $R_1$, $R_3$, $R_4$, $R_5$, $R_6$, $R_7$ are hydrogen and $R_2$ is either hydrogen or methyl, then $R_8$ is not phenyl.

More specifically, the following compounds are excluded from this invention:

2-(2-methyl-phenoxymethyl)-2,3-dihydro-oxazolo[3,2-a]pyrimidin-7-one;

5-methyl-2-(2-methyl-phenoxymethyl)-2,3-dihydro-oxazolo[3,2-a]pyrimidin-7-one;

2-(phenoxymethyl)-2,3-dihydro-oxazolo[3,2-a]pyrimidin-7-one;

5-methyl-2-phenoxymethyl-2,3,5,6-tetrahydro-oxazolo[3,2-a]pyrimidin-7-one; and 2-phenoxymethyl-2,3,5,6-tetrahydro-oxazolo[3,2-a]pyrimidin-7-one.

The compounds that are excluded from this invention are known in the prior art. For instance, Forfar et. al., J. Heterocyclic Chem., 38, 823-827 (2001), discloses two of the above excluded compounds. The other three excluded compounds are disclosed by Forfar et. al., Arch. Pharm. (Weinheim), 323, 905-909 (1990). Both of these references are incorporated herein by reference in their entirety.

As also noted above, various substituents as defined for formula (I) can further be optionally substituted by any of the art recognized substituents some of which are generically described herein and a few of the specific substituents are enumerated by way of specific examples. More particularly, various $R_1$ and $R_2$ as described herein can further be optionally substituted with one or more substituents as described herein.

In an embodiment of this invention the compound of formula (I) of this invention has the following substituents:

----- is a double bond;

p is 1;

n is 0;

X and Y are oxygen;

$R_1$ and $R_2$ are the same or different and independently of each other selected from hydrogen, $CF_3$, straight or branched ($C_1$-$C_{10}$)alkyl, mono- or di-fluoro($C_1$-$C_4$)alkyl, mono- or di-fluoro($C_1$-$C_4$)alkoxy($C_0$-$C_4$)alkyl, ($C_1$-$C_{10}$)alkoxy($C_0$-$C_4$)alkyl, ($C_6$,$C_{10}$)aryl, ($C_6$,$C_{10}$)aryl($C_1$-$C_4$)alkyl ($C_3$-$C_8$)cycloalkyl($C_0$-$C_4$)alkyl, ($C_3$-$C_8$)cycloalkoxy($C_0$-$C_4$)alkyl, hydroxy($C_1$-$C_4$)alkyl or —$CO_2C_2H_5$;

$R_3$, $R_4$ and $R_5$ are hydrogen;

$R_8$ is selected from the group consisting of substituted or unsubstituted phenyl, substituted or unsubstituted indanyl, substituted or unsubstituted tetralinyl, substituted or unsubstituted benzocycloheptanyl, substituted or unsubstituted hexahydrofluorenyl and substituted or unsubstituted cyclohexyl; wherein said substituents are selected from the group consisting of $CF_3$, $OCF_3$, $SF_5$, fluorine, chlorine, bromine, CN, straight or branched chain ($C_1$-$C_{20}$)alkyl, substituted or unsubstituted ($C_3$-$C_{10}$)cycloalkyl($CR_9R_{10}$)$_m$, substituted or unsubstituted ($C_6$,$C_{10}$)aryl($CR_9R_{10}$)$_m$, substituted or unsubstituted ($C_6$,$C_{10}$)aryl($C_3$-$C_8$)cycloalkyl, substituted or unsubstituted ($C_8$-$C_{13}$)bicyclic, substituted or unsubstituted adamantyl, substituted or unsubstituted indanyl, substituted or unsubstituted tetralinyl, substituted or unsubstituted benzocycloheptyl, straight or branched chain ($C_1$-$C_{20}$) alkoxy, substituted or unsubstituted ($C_3$-$C_{10}$)cycloalkoxy, substituted or unsubstituted ($C_6$,$C_{10}$)aryloxy, substituted or unsubstituted heteroaryloxy, and substituted or unsubstituted tetrahydropyranyl($CR_9R_{10}$)$_m$;

wherein m is an integer from 0 to 2;

$R_9$ and $R_{10}$ are the same or different and independently of each other chosen from hydrogen or ($C_1$-$C_4$)alkyl; or $R_9$ and $R_{10}$ taken together with the carbon atom to which they are attached form a substituted or unsubstituted $C_3$-$C_8$ ring.

As noted above, the substituents of $R_8$ moiety can be any of the suitable art recognized substituents including the specific moieties enumerated for $R_8$ above. Further, this embodiment of the invention includes compound of formula (I) in the salt form as well as it can also present in any of the stereoisomeric form including an enantiomer, stereoisomer or a tautomer thereof or a racemic mixture thereof.

In another embodiment, the compound of this invention can be represented by formula II:

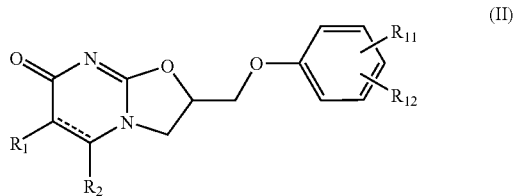

wherein:

----- is a single or a double bond;

$R_1$ and $R_2$ are the same or different and independently of each other selected from hydrogen, $CF_3$, straight or branched ($C_1$-$C_{10}$)alkyl, mono- or di-fluoro($C_1$-$C_4$)alkyl, mono- or di-fluoro($C_1$-$C_4$)alkoxy($C_0$-$C_4$)alkyl, ($C_1$-$C_{10}$)alkoxy($C_0$-$C_4$)alkyl, ($C_6$,$C_{10}$)aryl, ($C_6$,$C_{10}$)aryl($C_1$-$C_4$)alkyl, phenylsulfanyl($C_0$-$C_4$)alkyl, phenylsulfinyl($C_0$-$C_4$)alkyl, phenylsulfonyl($C_0$-$C_4$)alkyl, ($C_3$-$C_8$)cycloalkyl($C_0$-$C_4$)alkyl, ($C_3$-$C_8$)cycloalkoxy($C_0$-$C_4$)alkyl, hydroxy($C_1$-$C_4$)alkyl or —$CO_2C_2H_5$;

$R_{11}$ and $R_{12}$ are the same or different and independently of each other selected from the group consisting of hydrogen, $CF_3$, $OCF_3$, $SF_5$, fluorine, chlorine, bromine, CN, straight or branched chain ($C_1$-$C_{20}$)alkyl, substituted or unsubstituted ($C_3$-$C_{10}$)cycloalkyl($CR_9R_{10}$)$_m$, substituted or unsubstituted ($C_6$,$C_{10}$)aryl($CR_9R_{10}$)$_m$, substituted or unsubstituted ($C_6$,$C_{10}$)aryl($C_3$-$C_8$)cycloalkyl, substituted or unsubstituted ($C_8$-$C_{13}$)bicyclic, substituted or unsubstituted adamantyl, substituted or unsubstituted indanyl, substituted or unsubstituted tetralinyl, substituted or unsubstituted benzocycloheptyl, straight or branched chain ($C_1$-$C_{20}$)alkoxy, substituted or unsubstituted ($C_3$-$C_{10}$)cycloalkoxy, substituted or unsubstituted tetrahydropyranyl($CR_9R_{10}$)$_m$, substituted or unsubstituted ($C_6$,$C_{10}$)aryloxy and substituted or unsubstituted heteroaryloxy; and wherein m is 0 or 1;

$R_9$ and $R_{10}$ are the same or different and independently of each other chosen from hydrogen or ($C_1$-$C_4$)alkyl;

Again, the substituents on some of the groups listed for $R_{11}$ and $R_{12}$ can be same as the ones listed for $R_{11}$ and $R_{12}$ or any of the suitable art recognized substituents can be used as described herein. For instance, said substituents are selected from the group consisting of halogen, straight or branched chain ($C_1$-$C_{10}$)alkyl, phenyl, indanyl and imidazolyl. The compound of formula (II) can be present in the form of a salt. Also, this invention encompasses an enantiomer, stereoisomer or a tautomer or a racemic mixture of compound of formula (II).

As specific examples of compound of formula (II), the following compounds may be enumerated without any limitations.

2-(4-isopropyl-phenoxymethyl)-2,3-dihydro-oxazolo[3,2-a]pyrimidin-7-one;

2-[4-(1,1,3,3-tetramethyl-butyl)-phenoxymethyl]-2,3-dihydro-oxazolo[3,2-a]-pyrimidin-7-one;

2-(3-tert-butyl-phenoxymethyl)-2,3-dihydro-oxazolo[3,2-a]pyrimidin-7-one;

2-(4-tert-butyl-phenoxymethyl)-2,3-dihydro-oxazolo[3,2-a]pyrimidin-7-one;

2-[4-(1,1-dimethyl-propyl)-phenoxymethyl]-2,3-dihydro-oxazolo[3,2-a]pyrimidin-7-one;

2-(3,4-dimethyl-phenoxymethyl)-2,3-dihydro-oxazolo[3,2-a]pyrimidin-7-one;

2-(4-isopropyl-3-methyl-phenoxymethyl)-2,3-dihydro-oxazolo[3,2-a]pyrimidin-7-one;

2-(4-tert-butyl-2-methyl-phenoxymethyl)-2,3-dihydro-oxazolo[3,2-a]pyrimidin-7-one;

2-(2,4-di-tert-butyl-phenoxymethyl)-2,3-dihydro-oxazolo[3,2-a]pyrimidin-7-one;

2-[4-(1-methyl-1-phenyl-ethyl)-phenoxymethyl]-2,3-dihydro-oxazolo[3,2-a]-pyrimidin-7-one;

2-[4-(1-phenyl-ethyl)-phenoxymethyl]-2,3-dihydro-oxazolo[3,2-a]pyrimidin-7-one;

2-[2-chloro-4-(1,1-dimethyl-propyl)-phenoxymethyl]-2,3-dihydro-oxazolo[3,2-a]pyrimidin-7-one;

2-(4-bromo-phenoxymethyl)-2,3-dihydro-oxazolo[3,2-a]pyrimidin-7-one;

2-(4-chloro-phenoxymethyl)-2,3-dihydro-oxazolo[3,2-a]pyrimidin-7-one;

2-(4-fluoro-phenoxymethyl)-2,3-dihydro-oxazolo[3,2-a]pyrimidin-7-one;

2-(3,4-dichloro-phenoxymethyl)-2,3-dihydro-oxazolo[3,2-a]pyrimidin-7-one;

2-(3,4-difluoro-phenoxymethyl)-2,3-dihydro-oxazolo[3,2-a]pyrimidin-7-one;

2-chloro-4-(7-oxo-2,3-dihydro-7H-oxazolo[3,2-a]pyrimidin-2-ylmethoxy)-benzonitrile;

2-(4-trifluoromethyl-phenoxymethyl)-2,3-dihydro-oxazolo[3,2-a]pyrimidin-7-one;

2-(3-trifluoromethoxy-phenoxymethyl)-2,3-dihydro-oxazolo[3,2-a]pyrimidin-7-one;

2-(4-trifluoromethoxy-phenoxymethyl)-2,3-dihydro-oxazolo[3,2-a]pyrimidin-7-one;

2-(3,4-dimethoxy-phenoxymethyl)-2,3-dihydro-oxazolo[3,2-a]pyrimidin-7-one;

2-(4-cyclopentyl-phenoxymethyl)-2,3-dihydro-oxazolo[3,2-a]pyrimidin-7-one;

2-(4-cyclohexyl-phenoxymethyl)-2,3-dihydro-oxazolo[3,2-a]pyrimidin-7-one;

2-(4-cyclohexyl-phenoxymethyl)-5-methyl-2,3-dihydro-oxazolo[3,2-a]pyrimidin-7-one;

2-(4-cyclohexyl-phenoxymethyl)-5-ethyl-2,3-dihydro-oxazolo[3,2-a]pyrimidin-7-one;

2-(4-cyclohexyl-phenoxymethyl)-5-trifluoromethyl-2,3-dihydro-oxazolo[3,2-a]pyrimidin-7-one;

2-[4-(4,4-dimethyl-cyclohexyl)-phenoxymethyl]-2,3-dihydro-oxazolo[3,2-a]pyrimidin-7-one;

2-[4-(3,3-dimethyl-cyclohexyl)-phenoxymethyl]-2,3-dihydro-oxazolo[3,2-a]pyrimidin-7-one;

2-[4-(4-tert-butyl-cyclohexyl)-phenoxymethyl]-2,3-dihydro-oxazolo[3,2-a]-pyrimidin-7-one;

2-(biphenyl-4-yloxymethyl)-2,3-dihydro-oxazolo[3,2-a]pyrimidin-7-one;

2-[4-(tetrahydro-pyran-4-yl)-phenoxymethyl]-2,3-dihydro-oxazolo[3,2-a]-pyrimidin-7-one;

2-(4-indan-1-yl-phenoxymethyl)-2,3-dihydro-oxazolo[3,2-a]pyrimidin-7-one;

2-(4-tricyclo[3.3.1.13,7]decan-2-yl-phenoxymethyl)-2,3-dihydro-oxazolo[3,2-a]-pyrimidin-7-one;

2-(4-imidazol-1-yl-phenoxymethyl)-2,3-dihydro-oxazolo[3,2-a]pyrimidin-7-one;

2-(4-(1-phenyl)-cyclohexyl)-phenoxymethyl)-2,3-dihydro-oxazolo[3,2-a]pyrimidin-7-one;

2-(4-cyclohexyl-phenoxymethyl)-2,3,5,6-tetrahydro-oxazolo[3,2-a]pyrimidin-7-one;

2-(4-tert-butyl-phenoxymethyl)-2,3,5,6-tetrahydro-oxazolo[3,2-a]pyrimidin-7-one;

(S)-2-(4-cyclohexyl-phenoxymethyl)-6-methylsulfanyl-2,3-dihydro-oxazolo[3,2-a]pyrimidin-7-one;

(S)-6-benzenesulfonyl-2-(4-cyclohexyl-phenoxymethyl)-2,3-dihydro-oxazolo[3,2-a]pyrimidin-7-one;

6-benzenesulfinyl-2-(4-cyclohexyl-phenoxymethyl)-2,3-dihydro-oxazolo[32-a]pyrimidin-7-one;

(S)-2-(4-cyclohexyl-phenoxymethyl)-6-methanesulfonyl-2,3-dihydro-oxazolo[3,2a]pyrimidin-7-one;

(S)-2-(4-cyclohexyl-phenoxymethyl)-6-methanesulfinyl-2,3-dihydro-oxazolo[3,2-a]pyrimidin-7-one;

(S)-2-(4-cyclohexyl-phenoxymethyl)-5-phenylsulfanylmethyl-2,3-dihydro-oxazolo[3,2-a]pyrimidin-7-one;

(S)-5-benzenesulfonylmethyl-2-(4-cyclohexyl-phenoxymethyl)-2,3-dihydro-oxazolo[3,2-a]pyrimidin-7-one; and 2-(4-cyclohexyl-phenoxymethyl)-5-ethanesulfonylmethyl-2,3-dihydro-oxazolo[3,2-a]pyrimidin-7-one;

All of the above enumerated compounds can also present in the form of a salt as well as an enantiomer, stereoisomer or a tautomer thereof or a racemic mixture thereof; all of which are part of this invention.

More specifically, the following compounds are enumerated as compounds of formula (II):

2-[4-(1,1-dimethyl-propyl)-phenoxymethyl]-2,3-dihydro-oxazolo[3,2-a]pyrimidin-7-one;

2-(4-isopropyl-3-methyl-phenoxymethyl)-2,3-dihydro-oxazolo[3,2-a]pyrimidin-7-one;

2-[4-(1-methyl-1-phenyl-ethyl)-phenoxymethyl]-2,3-dihydro-oxazolo[3,2-a]-pyrimidin-7-one;

2-[4-(1-phenyl-ethyl)-phenoxymethyl]-2,3-dihydro-oxazolo[3,2-a]pyrimidin-7-one;

2-(4-cyclopentyl-phenoxymethyl)-2,3-dihydro-oxazolo[3,2-a]pyrimidin-7-one;

2-(4-cyclohexyl-phenoxymethyl)-5-methyl-2,3-dihydro-oxazolo[3,2-a]pyrimidin-7-one;

2-(4-cyclohexyl-phenoxymethyl)-5-ethyl-2,3-dihydro-oxazolo[3,2-a]pyrimidin-7-one;

2-(4-cyclohexyl-phenoxymethyl)-5-trifluoromethyl-2,3-dihydro-oxazolo[3,2-a]pyrimidin-7-one;

2-[4-(4,4-dimethyl-cyclohexyl)-phenoxymethyl]-2,3-dihydro-oxazolo[3,2-a]pyrimidin-7-one;
2-[4-(4-tert-butyl-cyclohexyl)-phenoxymethyl]-2,3-dihydro-oxazolo[3,2-a]-pyrimidin-7-one;
2-(4-indan-1-yl-phenoxymethyl)-2,3-dihydro-oxazolo[3,2-a]pyrimidin-7-one;
(S)-2-(4-cyclohexyl-3,5-dimethyl-phenoxymethyl)-2,3-dihydro-oxazolo[3,2-a]pyrimidin-7-one;
2-[3-methyl-4-(3,3,5,5-tetramethyl-cyclohexyl)-phenoxymethyl]-2,3-dihydro-oxazolo[3,2-a]pyrimidin-7-one;
(S)-2-(4-cyclohexyl-phenoxymethyl)-6-isopropyl-2,3-dihydro-oxazolo[3,2-a]pyrimidin-7-one;
2-(4-cyclohexyl-phenoxymethyl)-6-(2-methoxy-ethyl)-2,3-dihydro-oxazolo[3,2-a]pyrimidin-7-one;
2-(4-cyclohexyl-phenoxymethyl)-5,6-diethyl-2,3-dihydro-oxazolo[3,2-a]pyrimidin-7-one;
2-(4-cyclohexyl-phenoxymethyl)-6-phenylsulfanyl-2,3-dihydro-oxazolo[3,2-a]pyrimidin-7-one;
(S)-2-(4-cyclohexyl-phenoxymethyl)-5-hydroxymethyl-2,3-dihydro-oxazolo[3,2-a]pyrimidin-7-one;
(S)-5-cyclohexyl-2-(4-cyclohexyl-phenoxymethyl)-2,3-dihydro-oxazolo[3,2-a]pyrimidin-7-one;
(S)-2-(4-cyclohexyl-phenoxymethyl)-5-(1-hydroxy-1-methyl-ethyl)-2,3-dihydro-oxazolo[3,2-a]pyrimidin-7-one;
(S)-2-(4-cyclohexyl-phenoxymethyl)-5-(2-hydroxy-ethyl)-2,3-dihydro-oxazolo[3,2-a]pyrimidin-7-one;
(S)-2-(4'-propyl-biphenyl-4-yloxymethyl)-2,3-dihydro-oxazolo[3,2-a]pyrimidin-7-one;
(S)-2-(2',3'-dimethyl-biphenyl-4-yloxymethyl)-2,3-dihydro-oxazolo[3,2-a]pyrimidin-7-one;
(S)-2-(4'-tert-butyl-biphenyl-4-yloxymethyl)-2,3-dihydro-oxazolo[3,2-a]pyrimidin-7-one;
(S)-2-(4'-ethoxy-biphenyl-4-yloxymethyl)-2,3-dihydro-oxazolo[3,2-a]pyrimidin-7-one;
(S)-2-(2'-chloro-biphenyl-4-yloxymethyl)-2,3-dihydro-oxazolo[3,2-a]pyrimidin-7-one;
2-(4-cyclohexyl-phenoxymethyl)-5-ethylsulfanylmethyl-2,3-dihydro-oxazolo[3,2-a]pyrimidin-7-one;
2-(4-tert-butyl-phenoxymethyl)-6-ethyl-2,3-dihydro-oxazolo[3,2-a]pyrimidin-7-one;
(S)-2-(4-bicyclo[3.3.1]non-9-yl-phenoxymethyl)-5-fluoromethyl-2,3-dihydro-oxazolo[3,2-a]pyrimidin-7-one;
(S)-2-(4-tert-butyl-phenoxymethyl)-5-methoxymethyl-2,3-dihydro-oxazolo[3,2-a]pyrimidin-7-one;
(S)-2-(4-tert-butyl-phenoxymethyl)-5-fluoromethyl-2,3-dihydro-oxazolo[3,2-a]pyrimidin-7-one;
(S)-2-(4-tert-butyl-phenoxymethyl)-5-ethyl-2,3-dihydro-oxazolo[3,2-a]pyrimidin-7-one; and
2-(4-cyclohexyl-phenoxymethyl)-2-methyl-2,3-dihydro-oxazolo[3,2-a]pyrimidin-7-one.

As noted above, any of the above enumerated compounds can exist in the form of a salt or as an enantiomer, stereoisomer or a tautomer or a racemic mixture; all of which are part of this invention.

In another embodiment, as examples of stereospecific isomers, the following compounds encompassed by the compound of form
2(S)-(4-bromo-phenoxymethyl)-2,3(S)-dihydro-oxazolo[3,2-a]pyrimidin-7-one;
2(S)-[4-(1,1,3,3-tetramethyl-butyl)-phenoxymethyl]-2,3-dihydro-oxazolo[3,2-a]-pyrimidin-7-one;
2(S)-(4-tert-butyl-phenoxymethyl)-2,3-dihydro-oxazolo[3,2-a]pyrimidin-7-one;
(S)-2-[4-(4-trifluoromethyl-phenoxy)-benzyloxy]-2,3-dihydro-oxazolo[3,2a]pyrimidin-7-one;
2(S)-(4-cyclohexyl-phenoxymethyl)-2,3-dihydro-oxazolo[3,2-a]pyrimidin-7-one;
(S)-2-(4-cyclohexyl-phenoxymethyl)-5-ethyl-2,3-dihydro-oxazolo[3,2-a]pyrimidin-7-one;
(S)-2-(4-cyclohexyl-3-methyl-phenoxymethyl)-2,3-dihydro-oxazolo[3,2-a]pyrimidin-7-one;
(S)-2-[4-(3,3-dimethyl-cyclohexyl)-phenoxymethyl]-2,3-dihydro-oxazolo[3,2-a]pyrimidin-7-one;
(S)-2-[4-(4,4-difluoro-cyclohexyl)-phenoxymethyl]-2,3-dihydro-oxazolo[3,2-a]pyrimidin-7-one;
(S)-2-(4-cyclohexyloxy-phenoxymethyl)-2,3-dihydro-oxazolo[3,2-a]pyrimidin-7-one;
(S)-2-(4-phenoxy-phenoxymethyl)-2,3-dihydro-oxazolo[3,2-a]pyrimidin-7-one;
(S)-2-(4-bicyclo[3.3.1]non-9-yl-phenoxymethyl)-2,3-dihydro-oxazolo[3,2-a]pyrimidin-7-one;
(S)-2-(4-tert-butyloxy-phenoxymethyl)-2,3-dihydro-oxazolo[3,2-a]pyrimidin-7-one;
(S)-2-(4-bicyclo[3.3.1]non-9-yl-phenoxymethyl)-5-ethyl-2,3-dihydro-oxazolo[3,2-a]pyrimidin-7-one;
(2S,6R)-2-(4-cyclohexyl-phenoxymethyl)-6-methyl-2,3,5,6-tetrahydro-oxazolo[3,2-a]pyrimidin-7-one;
(2S,6S)-2-(4-cyclohexyl-phenoxymethyl)-6-methyl-2,3,5,6-tetrahydro-oxazolo[3,2-a]pyrimidin-7-one;
(S)-2-(4-cyclohexyl-phenoxymethyl)-6-methyl-2,3-dihydro-oxazolo[3,2-a]pyrimidin-7-one;
(2S,6R)-2-(4-cyclohexyl-phenoxymethyl)-6-ethyl-2,3,5,6-tetrahydro-oxazolo[3,2-a]pyrimidin-7-one;
(2S,6S)-2-(4-cyclohexyl-phenoxymethyl)-6-ethyl-2,3,5,6-tetrahydro-oxazolo[3,2-a]pyrimidin-7-one;
(S)-2-[4-(3,3,5,5-tetramethyl-cyclohexyl)-phenoxymethyl]-2,3-dihydro-oxazolo[3,2-a]pyrimidin-7-one;
(S)-2-(4-cyclohexyl-phenoxymethyl)-5-propyl-2,3-dihydro-oxazolo[3,2-a]pyrimidin-7-one;
(S)-2-(4-cyclohexyl-phenoxymethyl)-5-phenyl-2,3-dihydro-oxazolo[3,2-a]pyrimidin-7-one;
(S)-2-[4-(4-tert-butyl-phenoxy)-phenoxymethyl]-2,3-dihydro-oxazolo[3,2-a]pyrimidin-7-one;
(S)-2-(4-cyclohexyl-phenoxymethyl)-7-oxo-2,3-dihydro-7H-oxazolo[3,2-a]pyrimidine-5-carboxylic acid ethyl ester;
(S)-2-[4-(4-cyclohexyl-phenoxy)-phenoxymethyl]-2,3-dihydro-oxazolo[3,2-a]pyrimidin-7-one;
(S)-2-(4-cyclohexyl-phenoxymethyl)-6-ethyl-2,3-dihydro-oxazolo[3,2-a]pyrimidin-7-one;
(S)-5-ethyl-2-[4-(3,3,5,5-tetramethyl-cyclohexyl)-phenoxymethyl]-2,3-dihydro-oxazolo[3,2-a]pyrimidin-7-one;
(S)-2-(4-pentafluorosulfur-benzyloxymethyl)-2,3-dihydro-oxazolo[3,2a]pyrimidin-7-one;
(S)-5-ethyl-2-[4-(3,3,5,5-tetramethyl-cyclohexyl)-phenoxymethyl]-2,3-dihydro-oxazolo[3,2-a]pyrimidin-7-one;
(S)-2-(4-cyclohexyl-3-isopropyl-phenoxymethyl)-2,3-dihydro-oxazolo[3,2-a]pyrimidin-7-one;
(S)-2-(4-cyclohexyl-3-ethyl-phenoxymethyl)-2,3-dihydro-oxazolo[3,2-a]pyrimidin-7-one;
(S)-2-(4-cyclohexyl-phenoxymethyl)-5-cyclopropyl-2,3-dihydro-oxazolo[3,2-a]pyrimidin-7-one;
(S)-5-n-butyl-2-(4-cyclohexyl-phenoxymethyl)-2,3-dihydro-oxazolo[3,2-a]pyrimidin-7-one;
(S)-2-(4-cyclohexyl-phenoxymethyl)-5-cyclopentyl-2,3-dihydro-oxazolo[3,2-a]pyrimidin-7-one;
(S)-2-(4-cyclohexyl-phenoxymethyl)-5-isobutyl-2,3-dihydro-oxazolo[3,2-a]pyrimidin-7-one;
(S)-2-(4-cyclohexyl-phenoxymethyl)-5-fluoromethyl-2,3-dihydro-oxazolo[3,2-a]pyrimidin-7-one;
(S)-2-(4-cyclohexyl-phenoxymethyl)-5-methoxymethyl-2,3-dihydro-oxazolo[3,2-a]pyrimidin-7-one;

(S)-2-(4-cyclohexyl-phenoxymethyl)-5-(1-fluoro-1-methyl-ethyl)-2,3-dihydro-oxazolo[3,2-a]pyrimidin-7-one;
(S)-5-fluoromethyl-2-[4-(3,3,5,5-tetramethyl-cyclohexyl)-phenoxymethyl]-2,3-dihydro-oxazolo[3,2-a]pyrimidin-7-one;
(S)-2-(4-bicyclo[3.3.1]non-9-yl-phenoxymethyl)-5-methoxymethyl-2,3-dihydro-oxazolo[3,2-a]pyrimidin-7-one;
(S)-2-(4-bicyclo[3.3.1]non-9-yl-phenoxymethyl)-5-methyl-2,3-dihydro-oxazolo[3,2-a]pyrimidin-7-one;
(S)-2-(4-bicyclo[3.3.1]non-9-yl-phenoxymethyl)-5-butyl-2,3-dihydro-oxazolo[3,2-a]pyrimidin-7-one;
(S)-2-(4-bicyclo[3.3.1]non-9-yl-phenoxymethyl)-5-cyclopentyl-2,3-dihydro-oxazolo[3,2-a]pyrimidin-7one;
(S)-5-methyl-2-[4-(1,1,3,3-tetramethyl-butyl)-phenoxymethyl]-2,3-dihydro-oxazolo[3,2-a]pyrimidin-7-one;
(S)-5-ethyl-2-[4-(1,1,3,3-tetramethyl-butyl)-phenoxymethyl]-2,3-dihydro-oxazolo[3,2-a]pyrimidin-7-one;
(S)-5-fluoromethyl-2-[4-(1,1,3,3-tetramethyl-butyl)-phenoxymethyl]-2,3-dihydro-oxazolo[3,2-a]pyrimidin-7-one;
(S)-5-methoxymethyl-2-[4-(1,1,3,3-tetramethyl-butyl)-phenoxymethyl]-2,3-dihydro-oxazolo[3,2-a]pyrimidin-7-one;
(S)-2-(4-cyclohexyl-phenoxymethyl)-5-ethoxymethyl-2,3-dihydro-oxazolo[3,2-a]pyrimidin-7-one;
(S)-2-[4-(4-isopropyl-phenoxy)-phenoxymethyl]-2,3-dihydro-oxazolo[3,2-a]pyrimidin-7-one;
(S)-2-(4-bicyclo[3.3.1]non-9-yl-phenoxymethyl)-5-cyclopropyl-2,3-dihydro-oxazolo[3,2-a]pyrimidin-7-one;
(S)-2-(4-bicyclo[3.3.1]non-9-yl-phenoxymethyl)-5-isobutyl-2,3-dihydro-oxazolo[3,2-a]pyrimidin-7-one; and
(S)-2-(4-cyclohexyl-phenoxymethyl)-5-ethoxy-2,3-dihydro-oxazolo[3,2-a]pyrimidin-7-one; ula (II) may be enumerated:

Again, all of the above enumerated compounds may exist in the form of a salt as described herein, all of which are part of this invention.

In another embodiment, a few other specific examples of stereospecific isomers within the scope of the compound of formula (II) without any limitation are the following:
2(R)-(4-bromo-phenoxymethyl)-2,3(R)-dihydro-oxazolo[3,2-a]pyrimidin-7-one;
2(R)-[4-(1,1,3,3-tetramethyl-butyl-phenoxymethyl]-2,3-dihydro-oxazolo[3,2-a]-pyrimidin-7-one;
2(R)-(4-tert-butyl-phenoxymethyl)-2,3-dihydro-oxazolo[3,2-a]pyrimidin-7-one; and
2(R)-(4-cyclohexyl-phenoxymethyl)-2,3-dihydro-oxazolo[3,2-a]pyrimidin-7-one.

Again, all of these compounds can exist in a variety of different salt forms as described herein and all of such salts form part of this invention.

In another embodiment, the compound of this invention can be represented by formula III:

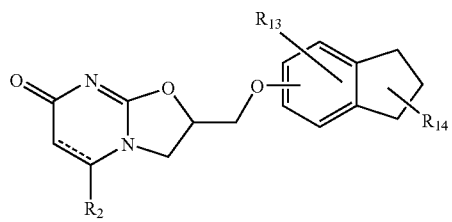

(III)

wherein:
----- is a double bond;
$R_2$ is hydrogen, $CF_3$, straight or branched $(C_1-C_{10})$alkyl, $(C_6,C_{10})$aryl or $(C_6,C_{10})$aryl$(C_1-C_4)$alkyl;
if $R_{13}$ is attached to the aromatic ring, then
$R_{13}$ is hydrogen, $CF_3$, $OCF_3$, fluorine, chlorine, bromine, $(C_1-C_4)$alkyl, $(C_3-C_6)$cycloalkyl or $(C_1-C_4)$alkoxy;
if $R_{13}$ and $R_{14}$ are both attached to the saturated ring, then
$R_{13}$ and $R_{14}$ are the same or different and independently of each other chosen from hydrogen, $(C_1-C_4)$alkyl or phenyl$(CR_9R_{10})_m$; or
$R_{13}$ and $R_{14}$ taken together with the carbon atom or carbon atoms to which they are attached form a substituted or unsubstituted $C_3-C_6$ carbocyclic ring; and
wherein
m is 0 or 1;
$R_9$ and $R_{10}$ are the same or different and independently of each other chosen from hydrogen or $(C_1-C_4)$alkyl.

As noted above, the substituents on some of the groups listed for $R_{13}$ and $R_{14}$ can be the same as the ones listed for $R_{13}$ and $R_{14}$ or any of the suitable art recognized substituents can be used as described herein. For instance, said substituents are selected from the group consisting of halogen, straight or branched chain $(C_1-C_{10})$alkyl and phenyl. The compound of formula (III) can also present in the form of a salt. Additionally, the compound of formula (III) can be present as a specific enantiomer, stereoisomer or a tautomer or as a racemic mixture; all such forms are part of this invention.

As a specific example of the compound of formula (III) without any limitation, the following compound is enumerated:
2-(indan-5-yloxymethyl)-2,3-dihydro-oxazolo[3,2-a]pyrimidin-7-one.

The above compound can present in the form of a salt or as an enantiomer, stereoisomer or a tautomer or as a racemic mixture.

In another embodiment of this invention, the compound of this invention can be represented by formula IV:

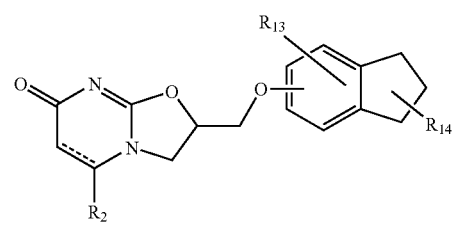

(IV)

wherein:
----- is a double bond;
$R_2$ is hydrogen, $CF_3$, straight or branched $(C_1-C_{10})$alkyl, $(C_6,C_{10})$aryl or $(C_6,C_{10})$aryl$(C_1-C_4)$alkyl;
if $R_{13}$ is attached to the aromatic ring, then
$R_{13}$ is hydrogen, $CF_3$, $OCF_3$, fluorine, chlorine, bromine, $(C_1-C_4)$alkyl, $(C_3-C_6)$cycloalkyl or $(C_1-C_4)$alkoxy;
if $R_{13}$ and $R_{14}$ are both attached to the saturated ring, then
$R_{13}$ and $R_{14}$ are the same or different and independently of each other chosen from hydrogen, $(C_1-C_4)$alkyl or phenyl$(CR_9R_{10})_m$; or
$R_{13}$ and $R_{14}$ taken together with the carbon atom or carbon atoms to which they are attached form a substituted or unsubstituted $C_3-C_6$ carbocyclic ring; and
wherein
m is 0 or 1;
$R_9$ and $R_{10}$ are the same or different and independently of each other chosen from hydrogen or $(C_1-C_4)$alkyl.

The substituents on some of the groups listed for $R_{13}$ and $R_{14}$ can be the same as the ones listed for $R_{13}$ and $R_{14}$ or any of the suitable art recognized substituents can also be used as described herein. For instance, said substituents are selected from the group consisting of halogen, straight or branched chain ($C_1$-$C_{10}$)alkyl and phenyl. The compound of formula (IV) can also present in the form of a salt. Additionally, the compound of formula (IV) can be present as a specific enantiomer, stereoisomer or a tautomer or as a racemic mixture; all such forms are part of this invention.

As a specific example of the compound of formula (IV) without any limitation, the following compound is enumerated:

2-(5,6,7,8-tetrahydro-naphthalen-2-yloxymethyl)-2,3-dihydro-oxazolo[3,2-a]pyrimidin-7-one.

The above compound can present in the form of a salt or as an enantiomer, stereoisomer or a tautomer or as a racemic mixture.

In yet another embodiment, the compound of this invention is represented by the formula V:

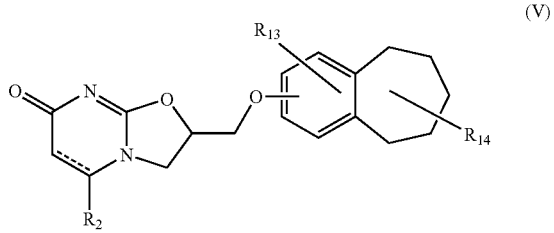

(V)

wherein:
- - - - - is a double bond;
$R_2$ is hydrogen, $CF_3$, straight or branched ($C_1$-$C_{10}$)alkyl, ($C_6$,$C_{10}$)aryl or ($C_6$,$C_{10}$)aryl($C_1$-$C_4$)alkyl;
if $R_{13}$ is attached to the aromatic ring, then
$R_{13}$ is hydrogen, $CF_3$, $OCF_3$, fluorine, chlorine, bromine, ($C_1$-$C_4$)alkyl, ($C_3$-$C_6$)cycloalkyl or ($C_1$-$C_4$)alkoxy;
if $R_{13}$ and $R_{14}$ are both attached to the saturated ring, then
$R_{13}$ and $R_{14}$ are the same or different and independently of each other chosen from hydrogen, ($C_1$-$C_4$)alkyl or phenyl($CR_9R_{10}$)$_m$; or
$R_{13}$ and $R_{14}$ taken together with the carbon atom or carbon atoms to which they are attached form a substituted or unsubstituted $C_3$-$C_6$ carbocyclic ring; and
wherein
m is 0 or 1;
$R_9$ and $R_{10}$ are the same or different and independently of each other chosen from hydrogen or ($C_1$-$C_4$)alkyl.

The substituents on some of the groups listed for $R_{13}$ and $R_{14}$ can be the same as the ones listed for $R_{13}$ and $R_{14}$ or any of the suitable art recognized substituents can also be used as described herein. For instance, said substituents are selected from the group consisting of halogen, straight or branched chain ($C_1$-$C_{10}$)alkyl and phenyl. The compound of formula (V) can also present in the form of a salt. Additionally, the compound of formula (V) can be present as a specific enantiomer, stereoisomer or a tautomer or as a racemic mixture; all such forms are part of this invention.

In another embodiment, the compound of this invention is represented by formula VI:

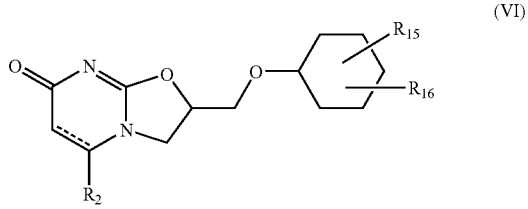

(VI)

wherein:
- - - - - is a double bond;
$R_2$ is hydrogen, $CF_3$, straight or branched ($C_1$-$C_{10}$)alkyl, ($C_6$,$C_{10}$)aryl or ($C_6$,$C_{10}$)aryl($C_1$-$C_4$)alkyl;

$R_{15}$ and $R_{16}$ are the same or different and independently of each other selected from the group consisting of hydrogen, fluorine, straight or branched chain ($C_1$-$C_{20}$)alkyl, substituted or unsubstituted ($C_3$-$C_{10}$)cycloalkyl ($CR_9R_{10}$)$_m$, substituted or unsubstituted ($C_6$,$C_{10}$)aryl ($CR_9R_{10}$)$_m$, substituted or unsubstituted ($C_8$-$C_{13}$)bicyclic, substituted or unsubstituted adamantyl, substituted or unsubstituted indanyl, substituted or unsubstituted tetralinyl, substituted or unsubstituted benzocycloheptyl, straight or branched chain ($C_1$-$C_{20}$)alkoxy, substituted or unsubstituted piperidinyl($CR_9R_{10}$)$_m$, substituted or unsubstituted piperazinyl($CR_9R_{10}$)$_m$, substituted or unsubstituted ($C_6$, $C_{10}$)aryloxy and substituted or unsubstituted heteroaryloxy; and wherein
m is 0 or 1;
$R_9$ and $R_{10}$ are the same or different and independently of each other chosen from hydrogen or ($C_1$-$C_4$)alkyl.

The substituents on some of the groups listed for $R_{15}$ and $R_{16}$ can be the same as the ones listed for $R_{15}$ and $R_{16}$ or any of the suitable art recognized substituents can also be used as described herein. For instance, said substituents are selected from the group consisting of halogen, straight or branched chain ($C_1$-$C_{10}$)alkyl and phenyl. The compound of formula (VI) can also present in the form of a salt. Additionally, the compound of formula (VI) can be present as a specific enantiomer, stereoisomer or a tautomer or as a racemic mixture; all such forms are part of this invention.

As a specific example of the compound of formula (VI) without any limitation, the following compound is enumerated:

2-(4-tert-butyl-cyclohexyloxymethyl)-2,3-dihydro-oxazolo[3,2-a]pyrimidin-7-one.

The above compound can present in the form of a salt or as an enantiomer, stereoisomer or a tautomer or as a racemic mixture.

In an embodiment, the compound of this invention is represented by the formula VII:

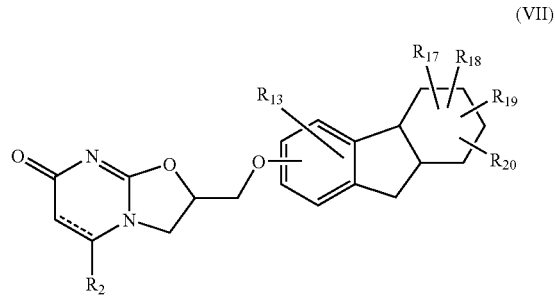

(VII)

wherein:
- - - - - is a double bond;
$R_2$ is hydrogen, $CF_3$, straight or branched ($C_1$-$C_{10}$)alkyl, ($C_6$,$C_{10}$)aryl or ($C_6$,$C_{10}$)aryl($C_1$-$C_4$)alkyl;
if $R_{13}$ is attached to the aromatic ring, then
$R_{13}$ is hydrogen, $CF_3$, $OCF_3$, fluorine, chlorine, bromine, ($C_1$-$C_4$)alkyl, ($C_3$-$C_6$)cycloalkyl or ($C_1$-$C_4$)alkoxy;
if $R_{13}$ is attached to the saturated ring, then
$R_{13}$ is chosen from hydrogen, ($C_1$-$C_4$)alkyl or phenyl ($CR_9R_{10}$)$_m$; and wherein
m is 0 or 1;
$R_9$ and $R_{10}$ are the same or different and independently of each other chosen from hydrogen or ($C_1$-$C_4$)alkyl; and
$R_{17}$, $R_{18}$, $R_{19}$ and $R_{20}$ are the same or different and independently selected from hydrogen or ($C_1$-$C_4$)alkyl.

The compound of formula (VII) can also present in the form of a salt. Additionally, the compound of formula (VII) can be present as a specific enantiomer, stereoisomer or a tautomer or as a racemic mixture; all such forms are part of this invention.

As a specific example of the compound of formula (VII) without any limitation, the following compounds are enumerated:

(S)-2-(5,6,7,8,8a,9-hexahydro-4bH-fluoren-2-yloxymethyl)-2,3-dihydro-oxazolo[3,2-a]pyrimidin-7-one; and
(S)-2-(5,6,7,8,8a,9-hexahydro-4bH-fluoren-2-phenoxymethyl)-5-ethyl-2,3-dihydro-oxazolo[3,2-a]pyrimidin-7-one.

The above compounds can present in the form of a salt or as an enantiomer, stereoisomer or a tautomer or as a racemic mixture.

In yet another embodiment of this invention, the compound of formula (I) is having the following substituents:
- - - - - is a double bond;
p is 1;
n is 0;
X and Y are oxygen;
$R_1$, $R_3$, $R_4$ and $R_5$ are hydrogen;
$R_2$ is hydrogen, $CF_3$, straight or branched $(C_1-C_{10})$alkyl, $(C_6,C_{10})$aryl or $(C_6,C_{10})$aryl$(C_1-C_4)$alkyl;
$R_8$ is selected from the group consisting of substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, substituted or unsubstituted tetrahydrodibenzofuranyl and substituted or unsubstituted hexahydrodibenzofuranyl; wherein
said substituents are selected from the group consisting of $CF_3$, $OCF_3$, fluorine, chlorine, bromine, CN, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$ and substituted or unsubstituted tetrahydropyranyl$(CR_9R_{10})_m$; wherein
m is 0 or 1;
$R_9$ and $R_{10}$ are the same or different and independently of each other chosen from hydrogen or $(C_1-C_4)$alkyl; or
$R_9$ and $R_{10}$ taken together with the carbon atom to which they are attached form a substituted or unsubstituted $C_3-C_8$ ring.

The compound of formula (I) of this embodiment can also present in the form of a salt. Additionally, the compound of formula (I) of this embodiment can be present as a specific enantiomer, stereoisomer or a tautomer or as a racemic mixture; all such forms are part of this invention.

As specific examples of the compound of formula (I) of this embodiment, without any limitation, the following compounds are enumerated:

2-(1H-indol-5-yloxymethyl)-2,3-dihydro-oxazolo[3,2-a]pyrimidin-7-one;
(S)-2-(6-cyclohexyl-pyridin-3-yloxymethyl)-2,3-dihydro-oxazolo[3,2-a]pyrimidin-7-one;
(S)-2-(benzothiazol-2-yloxymethyl)-2,3-dihydro-oxazolo[3,2a]pyrimidin-7-one; (S)-2-(6-tert-butyl-benzothiazol-2-yloxymethyl)-2,3-dihydro-oxazolo[3,2-a]pyrimidin-7-one;
(S)-2-(2,5-diphenyl-thiazol-4-yloxymethyl)-2,3-dihydro-oxazolo[3,2-a]pyrimidin-7-one;
2-(5a,6,7,8,9,9a-hexahydro-dibenzofuran-3-yl-oxymethyl)-2,3-dihydro-oxazolo[3,2-a]pyrimidin-7-one;
2-(6,7,8,9-tetrahydro-dibenzofuran-3-yl-oxymethyl)-2,3-dihydro-oxazolo[3,2-a]pyrimidin-7-one;
(S)-2-(benzo[b]thiophen-6-yloxymethyl)-2,3-dihydro-oxazolo[3,2-a]pyrimidin-7-one;
2-(2-p-tolyl-benzo[b]thiophen-6-yloxymethyl)-2,3-dihydro-oxazolo[3,2-a]pyrimidin-7-one;
2-[2-(4-ethyl-phenyl)-benzo[b]thiophen-6-yloxymethyl]-2,3-dihydro-oxazolo[3,2-a]pyrimidin-7-one;
2-[2-(4-isopropyl-phenyl)-benzo[b]thiophen-6-yloxymethyl]-2,3-dihydro-oxazolo[3,2-a]pyrimidin-7-one;
2-[2-(4-propyl-phenyl)-benzo[b]thiophen-6-yloxymethyl]-2,3-dihydro-oxazolo[3,2-a]-pyrimidin-7-one;
2-[2-(4-tert-butyl-phenyl)-benzo[b]thiophen-6-yloxymethyl]-2,3-dihydro-oxazolo[3,2-a]pyrimidin-7-one;
2-[2-(2-chloro-pyridin-4-yl)-benzo[b]thiophen-6-yloxymethyl]-2,3-dihydro-oxazolo[3,2-a]pyrimidin-7-one.

As already noted above, where possible the above compounds can present in the form of a salt or as an enantiomer, stereoisomer or a tautomer or as a racemic mixture.

In another embodiment of this invention, the compound of formula (I) is having the following substituents:
- - - - - is a double bond;
p is 0 or 1;
n is 0 or 1;
Y is oxygen or
X is oxygen or $NR_{21}$, wherein $R_{21}$ is hydrogen;
$R_1$, $R_3$, $R_4$, $R_5$, $R_6$ and $R_7$ are hydrogen;
$R_2$ is hydrogen, $CF_3$, straight or branched $(C_1-C_{10})$alkyl, $(C_6,C_{10})$aryl or $(C_6,C_{10})$aryl$(C_1-C_4)$alkyl;
$R_8$ is selected from the group consisting of substituted or unsubstituted phenyl, substituted or unsubstituted indanyl, substituted or unsubstituted tetralinyl, substituted or unsubstituted benzocycloheptanyl, substituted or unsubstituted hexahydrofluorenyl and substituted or unsubstituted cyclohexyl; wherein said substituents are selected from the group consisting of $CF_3$, $OCF_3$, fluorine, chlorine, bromine, CN, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$ and substituted or unsubstituted tetrahydropyranyl$(CR_9R_{10})_m$; wherein m is an integer from 0 to 3;

$R_9$ and $R_{10}$ are the same or different and independently of each other chosen from hydrogen or $(C_1$-$C_4)$alkyl; or $R_9$ and $R_{10}$ taken together with the carbon atom to which they are attached form a substituted or unsubstituted $C_3$-$C_8$ ring.

The compound of formula (I) of this embodiment can also present in the form of a salt. Additionally, the compound of formula (I) of this embodiment can be present as a specific enantiomer, stereoisomer or a tautomer or as a racemic mixture; all such forms are part of this invention.

As specific examples of the compound of formula (I) of this embodiment, without any limitation, the following compounds are enumerated:

2-benzyloxymethyl-2,3-dihydro-oxazolo[3,2-a]pyrimidin-7-one;

3-(4-tert-butyl-benzyloxymethyl)-2,3-dihydro-oxazolo[3,2-a]pyrimidin-7-one;

(S)-2-benzyloxymethyl-2,3-dihydro-oxazolo[3,2-a]pyrimidin-7-one;

2-[2-(4-cyclohexyl-phenyl)-ethyl]-2,3-dihydro-oxazolo[3,2-a]pyrimidin-7-one; and 2-[(4-cyclohexyl-phenylamino)-methyl]-2,3-dihydro-oxazolo[3,2-a]pyrimidin-7-one.

As already noted above, where possible the above compounds can present in the form of a salt or as an enantiomer, stereoisomer or a tautomer or as a racemic mixture.

Finally, in another embodiment of this invention, the compound of formula (I) is having the following substituents:

═══ is a double bond;

p is 1;

n is 0;

X is sulfur;

Y is oxygen;

$R_1$, $R_3$, $R_4$ and $R_5$ are hydrogen;

$R_2$ is hydrogen, $CF_3$, straight or branched $(C_1$-$C_{10})$alkyl, $(C_6,C_{10})$aryl or $(C_6,C_{10})$aryl$(C_1$-$C_4)$alkyl;

$R_8$ is selected from the group consisting of substituted or unsubstituted phenyl, substituted or unsubstituted indanyl, substituted or unsubstituted tetralinyl, substituted or unsubstituted benzocycloheptanyl, substituted or unsubstituted hexahydrofluorenyl and substituted or unsubstituted cyclohexyl; wherein said substituents are selected from the group consisting of $CF_3$, $OCF_3$, fluorine, chlorine, bromine, CN, straight or branched chain $(C_1$-$C_{20})$alkyl, $(C_1$-$C_4)$alkylsulfonyl, substituted or unsubstituted $(C_3$-$C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3$-$C_8)$cycloalkyl, substituted or unsubstituted $(C_8$-$C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1$-$C_{20})$alkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$ and substituted or unsubstituted tetrahydropyranyl$(CR_9R_{10})_m$; wherein m is an integer from 0 to 3;

$R_9$ and $R_{10}$ are the same or different and independently of each other chosen from hydrogen or $(C_1$-$C_4)$alkyl; or $R_9$ and $R_{10}$ taken together with the carbon atom to which they are attached form a substituted or unsubstituted $C_3$-$C_8$ ring.

The compound of formula (I) of this embodiment can also present in the form of a salt. Additionally, the compound of formula (I) of this embodiment can be present as a specific enantiomer, stereoisomer or a tautomer or as a racemic mixture; all such forms are part of this invention.

As a specific example of the compound of formula (I) of this embodiment, without any limitation, the following compound is enumerated:

2-(4-tert-butyl-phenylsulfanylmethyl)-2,3-dihydro-oxazolo[3,2-a]pyrimidin-7-one.

As already noted above, the above compound can present in the form of a salt or as an enantiomer, stereoisomer or a tautomer or as a racemic mixture.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein.

More specifically, the compounds disclosed herein can be synthesized according to the following procedures of Schemes A-C, wherein n, p, X, Y, $R_1$, $R_2$, $R_3$, $R_4$, $R_5$, $R_6$, $R_7$ and $R_8$ are as defined for Formula I unless otherwise indicated. Schemes G and H illustrate other approaches to the synthesis of compounds of formula I where for simplicity some of the substituents are shown as hydrogen. Several of the intermediates used in the preparation of the compound of formula (I) are known and can be prepared in accordance with the procedures known to one skilled in the art. A few other intermediates are novel, which can either be prepared in accordance with the procedures described herein (Schemes D-F) or by any of the procedures known in the art.

Scheme A illustrates a procedure for the preparation of a compound of formula (I) wherein p is 1, $R_1$ is hydrogen, ═══ is a double bond, and X and Y are oxygen. As noted, the starting alcohol of formula (VIII) is either available in the art or can be made by a variety of synthetic procedures, a few of which are described in detail below in Schemes D-F.

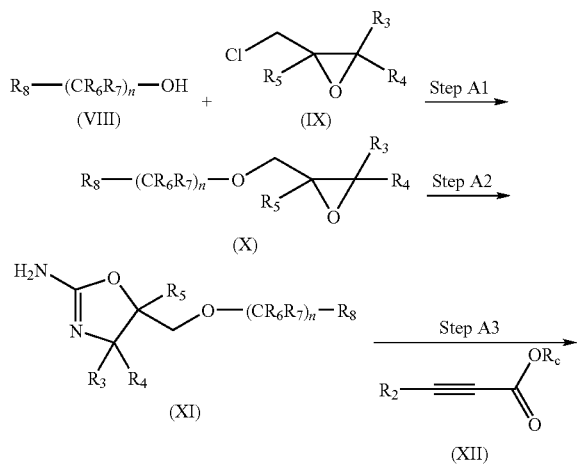

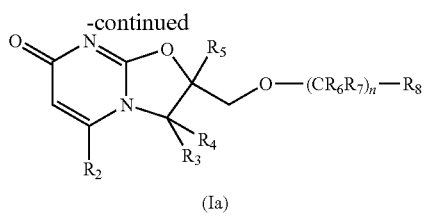

(Ia)

In Step A1, Scheme A, the alcohol, VIII is reacted with epichlorohydrin of formula (IX) in a suitable solvent and reaction conditions. In general, the reaction can be affected in the presence of a suitable base. Examples of bases include carbonate salts of alkaline metals such as lithium carbonate, sodium carbonate, potassium carbonate and cesium carbonate as well as alkali metal hydroxides such as lithium hydroxide, sodium hydroxide, potassium hydroxide and cesium hydroxide. However, other bases such as carbonate salts of alkaline earth metals such as barium carbonate or any other suitable base or a mixture of bases can be employed in this reaction. The reaction can be carried out in any of the organic solvents, such as acetone, methyl ethyl ketone, acetonitrile, dimethylformamide (DMF), dimethyl sulfoxide (DMSO), dimethyl acetamide (DMAC), and the like, or a mixture of solvents as listed herein. The reaction can also be carried out using water as a solvent. The reaction is generally carried out at ambient and/or super-ambient temperatures including the reflux temperature of the solvent. Generally, the reaction is carried out in the temperature range of from about ambient temperature to about 150° C. depending upon the boiling point of the solvent and/or solvent mixture employed. It should further be noted that nucleophilic addition reactions as illustrated in Step A1, Scheme A can more conveniently be carried out with an alcohol of formula (VIII) and an oxirane of formula (IX) wherein $R_3$, $R_4$ and $R_5$ are hydrogen. However, one skilled in the art readily appreciates that similar reactions with other substituents as disclosed herein can be carried out using various modifications that are available in the art and/or using other procedures known in the art.

In Scheme A, Step A2, the compound of formula (X) is reacted with a suitable cyanamide compound to form an oxazolylamine of formula (XI) in a suitable solvent. Any of the known cyanamide compounds that react with an epoxide to form oxazolylamines can be employed in this reaction. Suitable cyanamides for this purpose include without any limitation, sodium hydrogen cyanamide, lithium hydrogen cyanamide, potassium hydrogen cyanamide, cesium hydrogen cyanamide, and the like. The reaction can generally be carried out in alcoholic solvents such as methanol, ethanol, isopropanol and the like or a mixture thereof The reaction is further carrier out at a suitable temperature, for example, at about ambient to super-ambient temperatures.

In Scheme A, Step A3, the oxazolylamine of formula (XI) is finally reacted with an α,β-unsaturated alkynoic ester of formula (XII), wherein $R_c$ is $(C_1-C_4)$alkyl, to form the compound of formula (Ia) wherein p is 1, $R_1$ is hydrogen, ----- is a double bond, and X and Y are O. This reaction can again be carried out using any of the procedures known to one skilled in the art. Typically, such an addition reaction is carried out in a suitable alcoholic solvent such as methanol, ethanol or isopropanol or a mixture thereof. Such addition reactions can also be carried out using α,β-unsaturated alkynoic ester of formula (XII) itself as the solvent. The reaction is generally carried out at ambient to super-ambient temperature conditions. More generally, the reaction is carried out at the reflux temperature of the solvent. However, super-ambient temperatures involving the microwave oven can also be employed to carry out this reaction at a temperature ranging from about 100° C. to about 200° C. Various other compounds of formula (I) can similarly be prepared using appropriate starting materials. For instance, a compound of formula (I) wherein X is sulfur can be prepared starting with corresponding mercapto compound of formula (VIII). Similarly a compound of formula (I) wherein Y is sulfur can be prepared by employing thio-α,β-unsaturated alkynoic acid ester.

Scheme B illustrates the preparation of a stereospecific compound of formula (Ib). Thus in accordance with Scheme B, compounds of formula (I) wherein p is 1, X and Y are oxygen, $R_1$, $R_3$, $R_4$ and $R_5$ are hydrogen are prepared using stereospecific reaction conditions. First, the stereospecific oxirane of formula (Xa) is prepared starting from a stereospecific oxirane of formula (IXa). Again as illustrated, such stereospecific reactions can more conveniently be carried out using alcohols of formula (VIII) wherein n=0, and oxiranes of formula (IXa). In Step B1, Scheme B, (S)-enantiomer of oxirane of formula (Xa) can be formed starting from (R)-enantiomer of oxirane of formula (IXa) in a stereospecific substitution reaction by reacting it with an alcohol of formula (VIII). Generally, such stereospecific substitution reactions result in an enantiomeric ratio of from about 60:40 to 70:30. However, it has now been surprisingly found that enantiomeric ratio in excess of about 99:1 can be formed using a suitable solvent such as, acetone at a reaction temperature in the range of from about 40° C. to about 50° C. The enantiomeric purity of the compounds is measured by chiral high performance liquid chromatography (HPLC) or by any other known literature methods. The (R)-enantiomer of formula (X) can similarly be formed starting from the (S)-enantiomer of formula (IX). The stereospecific (S)-enantiomeric oxirane of the formula (Xa) thus obtained can then be converted to stereospecific (S)-enantiomeric compound of formula (Ib) following the procedures as outlined above in Scheme A by first forming the stereospecific (S)-enantiomeric oxazolylamine of formula (XIa) in Step B2, which is subsequently converted to compound of formula (Ib) in Step B3 by reaction with a suitable α,β-alkynoic acid ester or formula (XII), wherein $R_c$ is $(C_1-C_4)$alkyl.

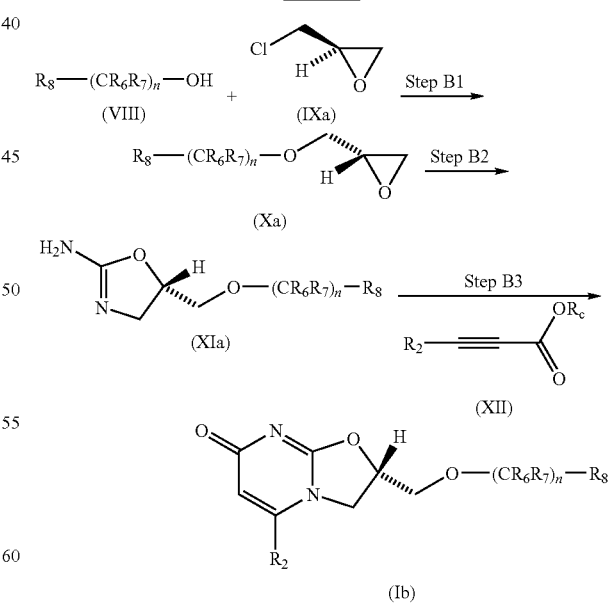

Scheme C illustrates a preparation of compound of formula (Ic) wherein ----- is a single bond. The oxazolylamine of formula (XI) formed in Step A2 of Scheme A is reacted with α,β-unsaturated alkenoic acid ester of formula (XIII), wherein $R_c$ is $(C_1-C_4)$alkyl, to form a compound of formula (Ic). This reaction can be carried out by any of the procedures known in the literature. In general, such reactions are carried out in an alcoholic solvent as described hereinabove in Scheme A, Step A3. Again, as noted above, the α,β-unsaturated alkenoic acid ester of formula (XIII) itself can be used as a solvent.

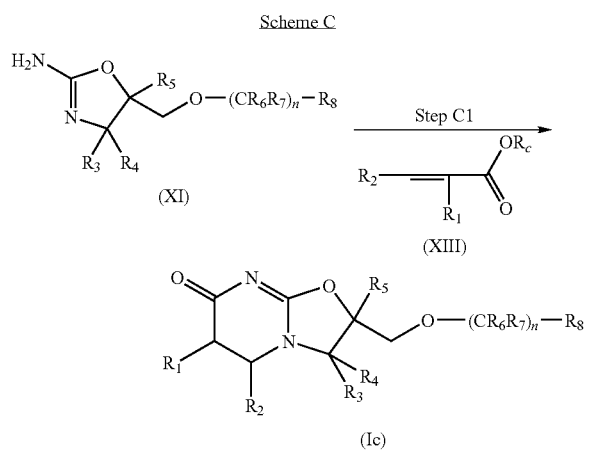

Finally, Schemes D through F illustrate preparation of a few of the starting alcohols in which n is 0 and $R_8$ is a substituted phenyl. Thus, Schemes D through F describe syntheses of a variety of phenols that can be used as starting alcohols of formula (VIII).

For instance, Scheme D illustrates preparation of phenols of formula (VIIIa) employing 4-benzyloxy-bromo-benzene as the starting material. In Step D1, Scheme D, 4-benzyloxy-bromo-benzene is first converted to a Grignard reagent by reacting with magnesium which is then reacted with a cyclic ketone of formula (XIV), where Z=CH$_2$ or oxygen and m=0, 1 or 2, to form a compound of formula (XV). The Grignard reaction is generally carried out in an ethereal solvent, such as tetrahydrofuran (THF) or diethyl ether. The Grignard reagent thus formed is then reacted with a cyclic ketone of formula (XIV), which results in an alcohol of formula (XV).

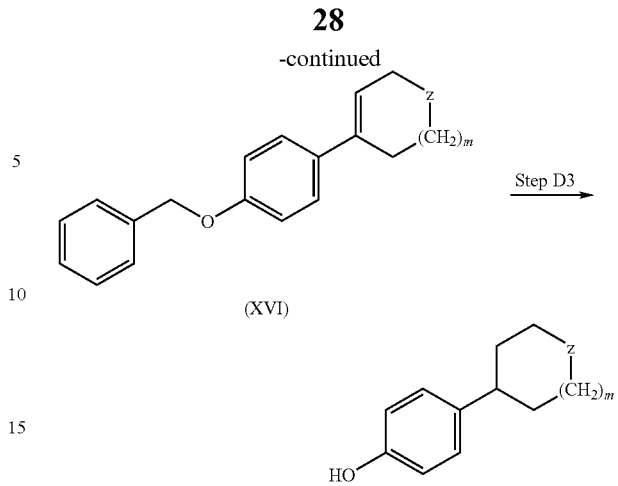

In Step D2, Scheme D, the compound of formula (XV) is subjected to a dehydration reaction under suitable reaction conditions to form a compound of formula (XVI). Such dehydration reactions are generally carried out in an alcoholic solvent such as ethanol in the presence of an acid catalyst such as hydrochloric acid. This reaction can be carried out at a reaction temperature in the range of from about sub-ambient to super-ambient temperatures. For instance, a temperature range of from about 30° C. to about 60° C. can be employed. Finally, in Step D3, Scheme D, the compound of formula (XVI) is subjected to reductive cleavage reaction to form the substituted phenolic compound of formula (VIIIa). The reductive cleavage reactions can be carried out using any of the known procedures in the art. For instance, such reductive cleavage can be effected by employing hydrogenation catalyst such as palladium on activated carbon in a hydrogen atmosphere.

Scheme E illustrates another preparative method for the preparation of a substituted phenolic compound of formula (VIIIb), which can also be used as a starting alcohol in the synthesis of compounds of formula (I). The phenolic compound of formula (VIIIb) is primarily substituted with a nitrogen heterocycle, which can readily be synthesized by an electrophilic substitution of anisole under acidic conditions as shown in Scheme E.

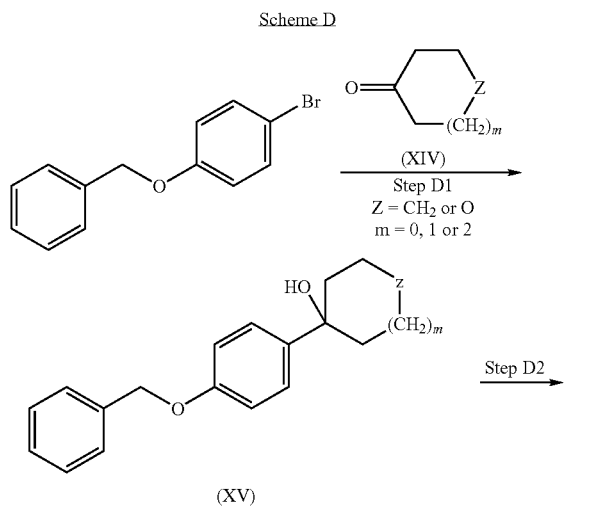

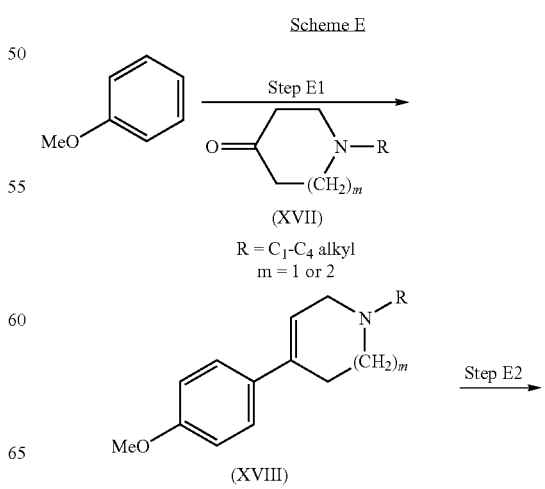

-continued

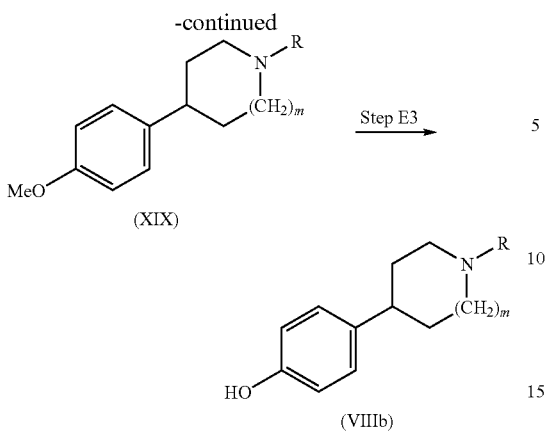

In Step E1, Scheme E, anisole is subjected to an electrophilic substitution reaction with an oxo-nitrogen heterocycle of formula (XVII), where R is $C_1$-$C_4$ alkyl and m=1 or 2. Any of the known electrophilic substitution reaction conditions can be employed in this step. For example, anisole is reacted with compound of formula (XVII) in the presence of hydrochloric acid to obtain compound of formula (XVIII), which in turn is subjected to hydrogenation reaction to form compound of formula (XIX). For instance, such an hydrogenation reaction can be carried out catalytically using palladium on activated carbon in an hydrogen atmosphere. Finally, the compound of formula (XIX) is subjected to demethylation reaction to form free phenolic compound of formula (VIIIb). Various known dealkylation, preferably, demethylation reaction conditions can be employed for this purpose. One such example include reacting compound of formula (XIX) with an acid such as hydrobromic acid to form compound of formula (VIIIb).

Finally, Scheme F illustrates a preparation of a phenolic compound of formula (VIIIc). In this illustration, in Step F1, Scheme F, a series of phenolic compounds of formula (VIIIc) can be prepared by employing an alcohol of formula (XX), which is reacted with phenol in the presence of a suitable acid catalyst, such as p-toluenesulfonic acid to form phenolic compound of formula (VIIIc). As illustrated herein, the substituents $R_d$, $R_e$ and $R_f$ are any of the feasible substituents as described herein.

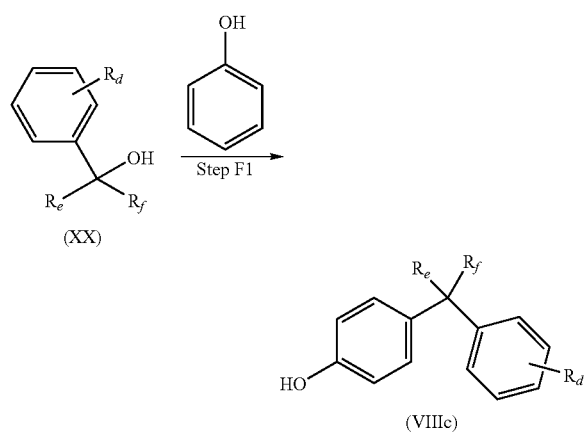

Scheme G illustrates another way of preparing compounds of formula (I) of this invention under stereospecific reaction conditions, i.e., substantially under enantioselective reaction conditions. That is under conditions which allow the formation of the compound of formula (I) with high retention of configuration of the optical center.

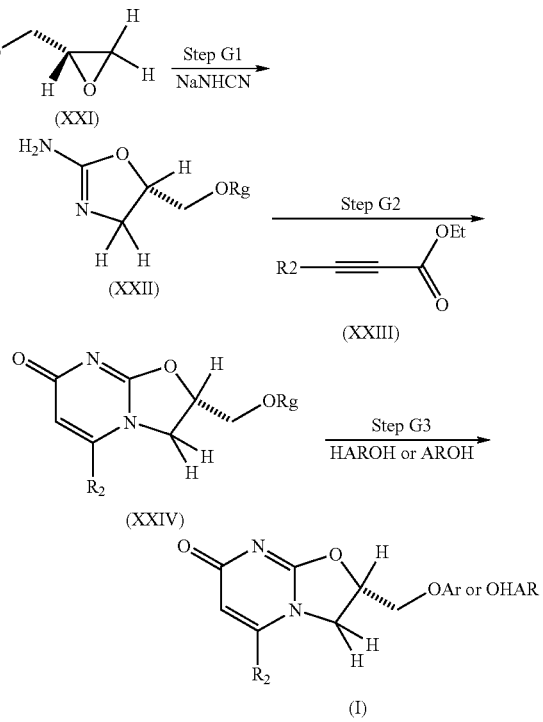

In Scheme G, step G1, compound of formula (XXI) is reacted with sodium cyanamide to form a compound of formula (XXII), wherein Rg is a substituted or unsubstituted arylsulfonyl group, such as substituted or unsubstituted phenylsulfonyl, e.g., a p-tosyl group, and the like. This reaction can be carried out using any of the methods known to one skilled in the art. Typically, such reactions are carried out in alcoholic solvents such as methanol at room temperature to obtain the corresponding dihydrooxazolylamine of formula (XXII).

In Scheme G, step G2, compound of formula (XXII) is reacted with an alkyl alkynoic acid ester of formula (XXIII) to form compound of formula (XXIV). Again, such reactions can be carried out using any of the methods known to one skilled in the art. Typically, such reactions can be carried out at the reflux temperature of the solvent, but other reaction conditions can also be employed depending upon the type of starting compounds (XXII) and (XXIII).

Finally, in Scheme G, step, G3 the compound of formula (XXIV) is reacted with a suitable hydroxy compound of formula ArOH, wherein Ar is a substituted or unsubstituted aryl, such as substituted or unsubstituted phenyl or a molecule of formula HAROH, wherein HAR is substituted or unsubstituted heteroaryl, such as substituted or unsubstituted benzothiophene. Such substitution reactions are generally carried out in an aprotic polar solvent, such as DMF or acetonitrile and in the presence of a suitable base such as alkali carbonates for example cesium carbonate or an organic base such as triethylamine. Alternatively a compound of formula (XXIV) in an aprotic solvent such as DMF or acetonitrile/dichloromethane/DMSO can be treated with a mixture of sodium hydride and ArOH or HAROH in a suitable solvent such as acetonitrile or DMF. The reaction temperatures can be sub-ambient to ambient to super-ambient, but typically the reaction is carried out under ambient to moderately higher temperatures in the range of 30 to 60° C.

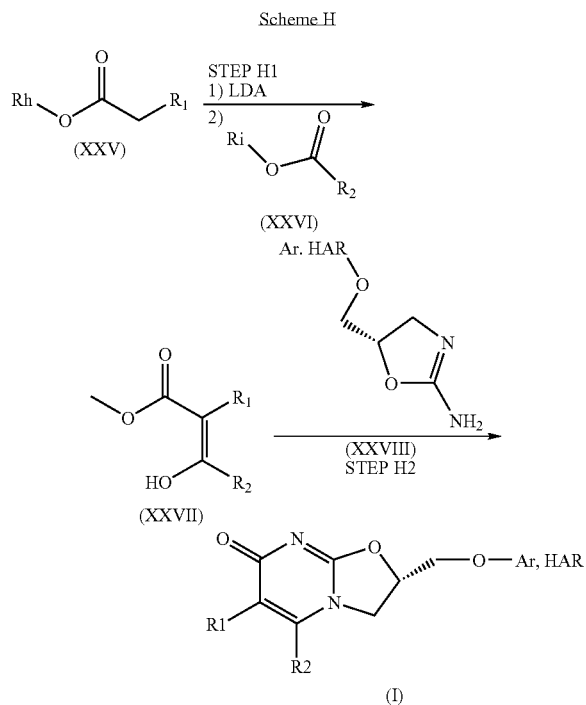

Scheme H

Scheme H illustrates another method of making compounds of formula (I) under stereospecific reaction conditions, i.e., substantially under enantioselective reaction conditions. That is under conditions which allow the formation of the compound of formula (I) with high retention of configuration of the optical center. In Scheme H, step H1, an ester of formula (XXV) is reacted first with LDA and then condensed with another ester of formula (XXVI) to form a compound of formula (XXVII). In formulae (XXV) and (XXVI), Rh and Ri are independently lower alkyl, preferably $C_1$-$C_4$alkyl, for example methyl, ethyl, n-propyl or n-butyl. This condensation reaction can be carried out using any of the methods known in the art. More typically, such reactions are carried out under inert atmospheres at around sub-ambient temperatures, such as −78° C. to ambient reaction temperatures in a suitable non-polar organic solvents, such as hexane, THF and the like.

In Scheme H, step H2, the compound of formula (XXVII) is then reacted with dihydrooxazolylamine of formula (XXVIII) to form compound of formula (I) with substituents as shown in Scheme H. All of the substituents defined for $R_1$ and $R_2$ may be made in accordance with this scheme, however, it is more preferred for compounds of formula (I) wherein $R_1$ is alkyl, mono- or di-fluoroalkyl or alkoxyalkyl and $R_2$ is hydrogen, alkyl, mono- or di-fluoroalkyl, arylalkyl or alkoxyalkyl. Ar and HAR are respectively substituted or unsubstituted aryl or substituted or unsubstituted heteroaryl as defined hereinabove.

In another aspect of this embodiment, this invention also relates to a method of modulating one or more metabotropic glutamate receptor functions in a patient requiring such treatment. Such a method involves administering an effective amount of a compound of formula (I) or a pharmaceutically acceptable salt, an enantiomer, a stereoisomer or a tautomer thereof or a racemic mixture thereof.

In a further embodiment, this invention also involves a method of treating a specific disease, a disorder or a condition using an effective amount of a compound of formula (I) of this invention. Specific diseases that can be treated using the compounds of formula (I) of this invention include, without any limitation, neurological or psychiatric disorders.

As used herein "psychiatric disorders" shall have the same meaning as "psychotic disorder" as defined in Diagnostic and Statistical Manual of Mental Disorders, 4th Ed., ("DSM-IV") American Psychiatric Association, 1995, incorporated herein by reference. The essential feature of brief psychotic disorder is a disturbance that involves the sudden onset of at least one of the following positive psychotic symptoms: delusions, hallucinations, disorganized speech, (e.g., frequent derailment or incoherence), or grossly disorganized or catatonic behavior (Criterion A). An episode of the disturbance lasts at least one day but less than one month, and the individual eventually has a full return to the premorbid level of functioning (Criterion B). The disturbance is not better accounted for by a mood disorder with psychotic features, by schizoaffective disorder, or by schizophrenia and is not due to the direct physiological effects of a substance (e.g., hallucinogen) or a general medical condition (e.g., subdural hematoma) (Criterion C). It should further be noted that a skilled artisan recognizes that there are alternative nomenclatures, nosologies, and classification systems for neurological and psychiatric disorders described herein and that these systems evolve with medical scientific progress.

It is also recognized that one skilled in the art may affect the neurological and psychiatric disorders by treating a patient presently afflicted with the disorders or by prophylactically treating a patient afflicted with the disorders with an effective amount of the compound of formula (I) of this invention. Thus, the terms "treatment" and "treating" are intended to refer to all processes wherein there may be a slowing, interrupting, arresting, controlling, or stopping of the progression of the neurological and psychiatric disorders described herein, but does not necessarily indicate a total elimination of all disorder symptoms, and is intended to include prophylactic treatment of such neurological and psychiatric disorders.

In a further embodiment of this invention, specific diseases that can be treated using the compounds of formula (I) of this invention include without any limitation: anxiety, migraine, schizophrenia, epilepsy and pain.

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease involving the effects of metabotropic glutamate receptor functions. That is, the compounds of the present invention are modulators of metabotropic glutamate receptors (mGluR), particularly, mGluR2, and may be effectively administered to ameliorate any disease state which is mediated all or in part by mGluR2.

All of the various embodiments of the compounds used in the methods of this invention as disclosed herein can be used in the method of treating various disease states as described herein. As stated herein, the compounds used in the method of this invention are capable of modulating the effects of mGluR2 and thereby alleviating the effects and/or conditions caused due to the activity of mGluR2. In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal, intracerebroventricular (icy) or topical route.

Finally, in yet another embodiment of this invention, there is also provided a pharmaceutical composition comprising a pharmaceutically acceptable carrier and a compound of formula (I) of this invention, including enantiomers, stereoisomers, and tautomers of said compound and pharmaceutically acceptable salts, solvates or derivatives thereof, with said compound having the general structure shown in formula I as described herein.

As described herein, the pharmaceutical compositions of this invention feature modulation of mGluR2 and thus are useful in treating any disease, condition or a disorder involving the effects of mGluR2 in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of formula (I) of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal, intracerebroventricular (icy) or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES

General

Reactions generally are run under a nitrogen atmosphere. Solvents are dried over sodium or magnesium sulfate and are evaporated under vacuum on a rotary evaporator. TLC analyses are performed with EM Science silica gel 60 F254 plates with visualization by UV irradiation wherever possible. Flash chromatography is performed using Isco prepacked silica gel cartridges. The $^1$H NMR spectra are run at 300 MHz on a Gemini 300 or Varian VXR 300 spectrometer and are determined in a deuterated solvent, such as DMSO-$d_6$ or CDCl$_3$ unless otherwise noted. Chemical shifts values are indicated in parts per million (ppm) with reference to tetramethylsilane (TMS) as the internal standard. The LC/MS are run on a Micromass Platform LCZ.

As used in the examples and preparations that follow, the terms used therein shall have the meanings indicated: "kg" refers to kilograms, "g" refers to grams, "mg" refers to milligrams, "µg" refers to micrograms, "pg" refers to picograms, "lb" refers to pounds, "oz" refers to ounces, "mol" refers to moles, "mmol" refers to millimoles, "µmole" refers to micromoles, "nmole" refers to nanomoles, "L" refers to liters, "mL" or "ml" refers to milliliters, "µL" refers to microliters, "gal" refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "THF" refers to tetrahydrofuran, "DMF" refers to dimethylformamide, "NMP" refers to 1-methyl-2-pyrrolidinone, "EtOH" refers to ethyl alcohol, "MeOH" refers to methyl alcohol, "EtOAc" refers to ethyl acetate; "brine" refers to a saturated aqueous sodium chloride solution, "M" refers to molar, "mM" refers to millimolar, "µM" refers to micromolar, "nM" refers to nanomolar, "N" refers to normal, "TLC" refers to thin layer chromatography, "HPLC" refers to high performance liquid chromatography, "i.p." refers to intraperitoneally, "i.v." refers to intravenously; anhyd=anhydrous; aq=aqueous; min=minute; mins=minutes; h or hr=hour; d=day; psi=pounds per square inch; atm=atmosphere; sat.=saturated; s=singlet, d=doublet; t=triplet; q=quartet; m=multiplet; dd=doublet of doublets; br=broad; LC=liquid chromatograph; MS=mass spectrograph; ESI=electrospray ionization; CI=chemical ionization; RT=retention time; M=molecular ion. Optical rotations $[\alpha]_D^{25}$ were measured using a Perkin Elmer polarimeter model 341 with a sodium lamp, D line (589 nm), path length 100 mm at 25° C. temperature at a concentration and solvent as specified in the respective examples below.

Example 1

(S)-2-(4-tert-Butyl-phenoxymethyl)-2,3-dihydro-oxazolo[3,2-a]pyrimidin-7-one

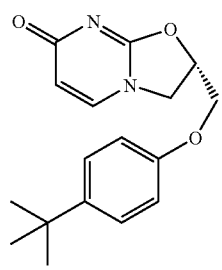 [SMILES: CC(C)(C)c1ccc(OC[C@@H]2Cn3ccc(=O)nc3O2)cc1]

Step 1: 2-(4-tert-Butyl-phenoxymethyl)-oxirane

To a mixture of (R)-epichlorohydrin (12.4 g, 134 mmol) and 4-tert-butylphenol (10.0 g, 66.8 mmol) in acetone (50 ml) was added potassium carbonate (9.24 g, 66.8 mmol). The mixture was stirred at 45° C. for 96 hours. The reaction mixture was then concentrated to remove acetone. The residue was partitioned between ethyl acetate and water and extracted twice with ethyl acetate. The organic phases were combined and washed with water, brine, dried over sodium sulfate and concentrated under vacuum. The resulting residue was purified by flash chromatography (silica, methylene chloride/heptane) to give 9.18 g (67%) of (S)-2-(4-tert-butyl-phenoxymethyl)oxirane.

$C_{13}H_{18}O_2$ (206.28), LCMS (ESI): 248.17 (M$^+$+H+ CH$_3$CN).

$^1$H NMR (CDCl$_3$, 300 MHz), δ 7.31 (d, 2H), 6.86 (d, 2H), 4.18 (dd, 1H), 3.97 (dd, 1H), 3.34 (m, 1H), 2.90 (t, 1H), 2.75 (dd, 1H), 1.27 (s, 9H).

Step 2: (S)-5-(4-tert-Butylphenoxymethyl)-4,5-dihydro-oxazol-2-ylamine

To a vigorously stirred solution of sodium hydrogen cyanamide (2.92 g, 44.5 mmol) in methanol (40 mL) was added dropwise (S)-2-(4-tert-butylphenoxymethyl)-oxirane (9.18 g, 44.5 mmol). The reaction mixture was stirred at room temperature overnight after which the reaction mixture was concentrated to remove methanol. Anhydrous diethyl ether (150 mL) was added. The resulting white precipitate was filtered through celite and the filtrate was concentrated. The residue was purified by flash chromatography (silica, 7N NH$_3$ in methanol/methylene chloride) to give 4.53 g (41%) of (S)-5-(4-tert-butyl-phenoxymethyl)-(4,5-dihydro-oxazol-2-yl)amine.

$C_{14}H_{20}N_2O_2$ (248.33), LCMS (ESI): 249.17 (M$^+$+H).

$^1$H NMR (CDCl$_3$, 300 MHz), δ 7.31 (d, 2H), 6.86 (d, 2H), 4.91 (m, 1H), 4.0 (v. br., 2H), 4.04 (AB-m, 2H), 3.92 (dd, 1H), 3.61 (dd, 1H), 1.29 (s, 9H).

Step 3: (S)-2-(4-tert-Butyl-phenoxymethyl)-2,3-dihydro-oxazolo[3,2-a]pyrimidin-7-one To a solution of (S)-5-(4-tert-butyl-phenoxymethyl)-4,5-dihydro-oxazol-2-ylamine (4.53 g, 18.3 mmol) in ethanol (35 mL) was added ethyl propiolate (2.32 g, 23.7 mmol). The reaction mixture was stirred at reflux for 6 hours. The mixture was stirred at 30° C. for a few minutes and subsequently cooled to room temperature. The resulting crystals were collected and washed twice with hexane. The solid was dried under high vacuum at 65° C. for 18 hours to afford 2.8 g (50%) of (S)-2-(4-tert-butyl-phenoxymethyl)-2,3-dihydro-oxazolo[3,2-a]pyrimidin-7-one. $[\alpha]_D^{25}$ –54.04 (c 0.503, CHCl$_3$).

$C_{17}H_{20}N_2O_3$ (300.36), LCMS (ESI): 301.15 (M$^+$+H).

$^1$H NMR (CDCl$_3$, 300 MHz) δ 7.31 (d, 2H), 7.24 (d, 1H), 6.81 (d, 2H), 6.09 (d, 1H), 5.27 (m, 1H), 4.21-4.41 (m, 4H), 1.29 (s, 9H).

Example 2

2-(4-Fluoro-phenoxymethyl)-2,3-dihydro-oxazolo[3,2-a]pyrimidin-7-one

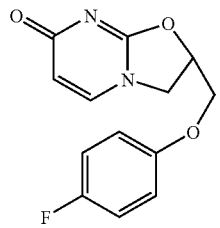 [SMILES: O=c1ccn2c(n1)OC(COc1ccc(F)cc1)C2]

Step 1: 2-(4-Fluoro-phenoxymethyl)-oxirane

To a mixture of epichlorohydrin (9.8 g, 106 mmol) and 4-fluorophenol (2.38 g, 21.2 mmol) in acetonitrile (40 ml) was added cesium carbonate (6.9 g, 21.2 mmol). The mixture was heated at reflux for 3 hours. The reaction mixture was cooled, poured into water (100 mL) and extracted twice with EtOAc. The organic phases were combined and washed with water, brine, dried (Na$_2$SO$_4$), concentrated and dried under high vacuum overnight to give the product as an oil (3.44 g, 96%).

$C_9H_9FO_2$ (168.05), LCMS (ESI): 210.10(M$^-$+H+CH$_3$CN)

$^1$H NMR (CDCl$_3$, 300 MHz), δ 6.93-7.02(m, 2H), 6.83-6.91 (m, 2H), 4.21 (dd, 1H), 3.92 (dd, 1H), 3.35 (m, 1H), 2.92 (t, 1H), 2.75 (dd, 1H).

Step 2: 5-(4-Fluoro-phenoxymethyl)-4,5-dihydro-oxazol-2-ylamine

To a vigorously stirred solution of sodium hydrogen cyanamide (0.64 g, 10.0 mmol) in methanol (10 mL) was added dropwise 2-(4-fluoro-phenoxymethyl)-oxirane (1.68 g, 10 mmol) after which the reaction mixture was stirred at room temperature overnight. The reaction mixture was concentrated to remove methanol. Anhydrous diethyl ether (50 mL) was added after which the resulting white precipitate was removed by filtration through celite and the filtrate concentrated. The residue was purified by flash chromatography (silica, 7N NH$_3$ in methanol/methylene chloride) to give 0.77 g (37%) of 5-(4-fluorophenoxymethyl)-(4,5-dihydro-oxazol-2-yl)amine.

C$_{10}$H$_{11}$FN$_2$O$_2$ (210.08), LCMS (ESI): 211.10 (M$^+$+H).
$^1$H NMR (CDCl$_3$, 300 MHz), δ 6.93-7.03 (m, 2H), 6.82-6.91 (m, 2H), 4.91 (m, 1H), 4.2 (v. br., 2H), 4.02 (AB-m, 2H), 3.93 (dd, 1H), 3.61 (dd, 1H).

Step 3: 2-(4-Fluoro-phenoxymethyl)-2,3-dihydro-oxazolo[3,2-a]pyrimidin-7-one To a solution of 5-(4-fluoro-phenoxymethyl)-4,5-dihydro-oxazol-2-ylamine (4.20 g, 2.00 mmol) in ethanol (8 mL) was added ethyl propiolate (0.25 g, 2.60 mmol). The reaction mixture was stirred at reflux for 6 hours. The mixture was stirred at 30° C. for a few minutes after which it was cooled to room temperature. The resulting crystals were collected and washed twice with hexane. The solid was dried under high vacuum at 65° C. for 18 hours to afford 0.23 g (50%) of 2-(4-fluorophenoxymethyl)-2,3-dihydro-oxazolo[3,2-a]pyrimidin-7-one.

C$_{13}$H$_{11}$FN$_2$O$_3$ (262.07), LCMS (ESI): 263.08 (M$^+$+H).
$^1$H NMR (CDCl$_3$, 300 MHz) δ 7.25 (d, 1H), 6.99 (m, 2H), 6.83 (m, 2H), 6.09 (d, 1H), 5.28 (m, 1H), 4.19-4.43 (m, 4H)

Example 3

2-(4-tert-Butyl-phenylsulfanylmethyl)-2,3-dihydro-oxazolo[3,2-a]pyrimidin-7-one

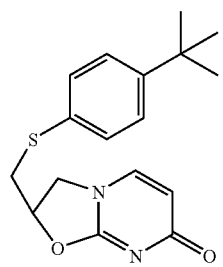 [SMILES: CC(C)(C)c1ccc(SCC2Cn3ccc(=O)nc3O2)cc1]

The title compound was prepared from 4-tert-butyl-benzenethiol and epichlorohydrin according to the method employed for the synthesis of Example 2.

C$_{17}$H$_{20}$N$_2$O$_2$S (316.12), LCMS (ESI): 317.15 (M$^+$+H).
$^1$H NMR (DMSO-d$_6$, 300 MHz) δ 7.70 (d, 1H), 7.37 (s, 4H), 5.79 (d, 1H), 5.07 (m, 1H), 4.35 (t, 1H), 3.99 (dd, 1H), 3.46 (AB-m, 2H), 1.28 (s, 9H).

Example 4

2-(4-tert-Butyl-cyclohexyloxymethyl)-2,3-dihydro-oxazolo[3,2-a]pyrimidin-7-one

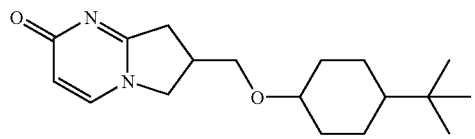 [SMILES: CC(C)(C)C1CCC(OCC2Cc3nc(=O)ccn3C2)CC1]

Step 1: 2-(4-tert-Butyl-cyclohexyloxymethyl)-oxirane

Epichlorohydrin (10.60 g, 111 mmol) and tricaprylmethylammonium chloride (aliquat 336, 0.5 g) were dissolved in cyclohexane (45 mL). 4-tert-Butylcyclohexanol (4.34 g, 27.8 mmol) was added and the reaction mixture was diluted with an aqueous solution of sodium hydroxide (50% in H$_2$O, 7.5 mL). The two phase system was heated to 90° C. under vigorous stirring for 5 hours. The mixture was diluted with water (300 mL) and extracted twice with hexane, and subsequently with ethyl acetate. The combined organic extracts were washed with dilute NH$_4$Cl, water, dried (Na$_2$SO$_4$) and concentrated to give a yellowish soft solid (6.10 g) which was used without further purification.

C$_{13}$H$_{24}$O$_2$ (212.17), LCMS (ESI): 254.24 (M$^+$+H+CH$_3$CN).

Step 2: 5-(4-tert-Butyl-cyclohexyloxymethyl)-4,5-dihydro-oxazol-2-ylamine

The title compound was prepared from 2-(4-tert-butyl-cyclohexyloxymethyl)-oxirane according to the procedure employed for the preparation of compound in Step 2 of Example 1.

C$_{14}$H$_{26}$N$_2$O$_2$ (254.19), LCMS (ESI): 255.18 (M$^+$+H).
$^1$H NMR (CDCl$_3$, 300 MHz), δ 4.69 (m, 1H), 3.86 (v. br., 2H), 3.80 (dd, 1H), 3.62 (dd, 1H), 3.46 (AB-m, 2H), 3.19 (m, 1H), 2.06 (br., 2H), 1.80 (br., 2H), 0.86-1.38 (m, 5H), 0.85 (s, 9H).

Step 3: 2-(4-tert-Butyl-cyclohexyloxymethyl)-2,3-dihydro-oxazolo[3,2-a]pyrimidin-7-one The title compound was prepared from 5-(4-tert-butyl-cyclohexyloxymethyl)-4,5-dihydro-oxazol-2-ylamine according to the procedure employed for the preparation of compound in Step 3 of Example 1.

C$_{17}$H$_{26}$N$_2$O$_3$ (306.13), LCMS (ESI): 307.19 (M$^+$+H).
$^1$H NMR (CDCl$_3$, 300 MHz), δ 7.20 (d, 1H), 6.05 (d, 1H), 5.04 (m, 1H), 4.19 (AB-m, 2H), 3.78 (AB-m, 2H), 3.23 (m, 1H), 1.99 (m, 2H), 1.78 (m, 2H), 0.91-1.18 (m, 5H), 0.86 (s, 9H).

Example 5

2-[4-(4,4-(Dimethyl)-cyclohexyl)-phenoxymethyl]-2,3-dihydro-oxazolo[3,2-a]pyrimidin-7-one

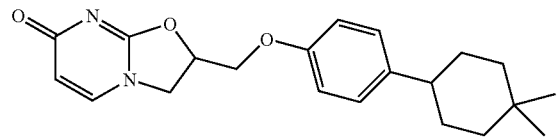 [SMILES: CC1(C)CCC(c2ccc(OCC3Cn4ccc(=O)nc4O3)cc2)CC1]

Step 1: 4,4-Dimethyl-cyclohexanone

To 0.1 g of palladium on activated carbon (10%) was added a solution of 4,4-dimethylcyclohex-2-enone (6.23 g, 50 mmol) in petroleum ether. This mixture was stirred under 1 atmosphere of hydrogen for 20 hours. After filtration through celite, the solvent was removed under reduced pressure to afford a white solid (5.7 g, 92%).

$C_8H_{14}O$ (126.10), LCMS (ESI): 127.11(M$^+$+H).
$^1$H NMR (CDCl$_3$, 300 MHz), δ 2.35 (t, 4H), 1.68 (t, 4H), 1.16 (s, 6H).

Step 2:
1-(4-Benzyloxyphenyl)-4,4-dimethyl-cyclohexanol

In a 250 mL round-bottomed flask was placed magnesium turnings (1.85 g, 76.1 mmol), which were stirred under vacuum without solvent overnight. To the turnings was added anhydrous THF (10 mL) and 4-benzyloxybromobenzene (10.0 g, 38.0 mmol) in anhydrous THF (40 ml) over 15 min. After the reaction was complete, the resulting gray slurry was stirred for 2 h at 60° C. To the slurry, cooled in an ice-water bath, was added 4,4-dimethyl-cyclohexanone (3.36 g, 26.6 mmol) in THF (15 mL). The reaction mixture was stirred for 1 hour at room temperature after which the solvent was removed under reduced pressure. The residue was partitioned between EtOAc/saturated NH$_4$Cl. The mixture was extracted twice with EtOAc. The organic phases were combined, dried (Na$_2$SO$_4$) and concentrated. The residue was purified via column chromatography on silica gel (eluting with 10-40% ethyl acetate/hexanes) to give 4.14 g (50%) of 1-(4-benzyloxy-phenyl)-4,4-dimethylcyclohexanol.
$C_{21}H_{26}O_2$ (310.19), LCMS (ESI): 293.18 (M$^+$+H–H$_2$O).
$^1$H NMR (CDCl$_3$, 300 MHz), δ 7.28-7.46 (m, 7H), 6.92 (d, 2H), 5.97 (br. s, 1H), 5.06 (s, 2H), 2.39 (br. s, 2H), 1.97 (br, S, 2H), 1.48-1.55 (m, 2H) 0.95 (s, 6H).

Step 3: 1-Benzyloxy-4-(4,4-dimethylcyclohex-1-enyl)-benzene 1-(4-Benzyloxyphenyl)-4,4-dimethyl-cyclohexanol (4.14 g, 13.3 mmol) was dissolved in ethanol (80 mL) by stirring after which concentrated hydrochloric acid (8 ml) was added. This stirred mixture was heated to 50° C. for 1.5 hours. The solvent was removed under reduced pressure. The residue was basified with ammonium hydroxide, extracted three times with EtOAc and the organic extracts combined and concentrated to afford 1-benzyloxy-4-(4,4-dimethylcyclohex-1-enyl)-benzene as a white solid (3.98 g, 99%).
$C_{21}H_{24}O$ (292.42), LCMS (ESI): 293.21(M+H).
$^1$H NMR (CDCl$_3$, 300 MHz), δ 7.28-7.46 (m, 7H), 6.92 (d, 2H), 5.97 (br. s, 1H), 5.06 (s, 2H), 2.39 (m, 2H), 1.97 (m, 2H), 1.48-1.55 (m, 2H), 0.95 (s, 6H).

Step 4: 4-(4,4-Dimethylcyclohexyl)-phenol (Scheme 4)

To 0.20 g of palladium on activated carbon (10%) was added a solution of 1-benzyloxy-4-(4,4-dimethylcyclohex-1-enyl)benzene (3.98 g, 13.3 mmol) in ethanol (80 mL)/THF (40 mL)/water (96 mL). The mixture was hydrogenated at 50 psi at room temperature overnight. The mixture was filtered through celite and the filtrate concentrated to a solid (2.71 g, 99%).
$C_{14}H_{20}O$ (204.15), LCMS (CI): 204.11(M$^+$).
$^1$H NMR (CDCl$_3$, 300 MHz), δ 7.09 (d, 2H), 6.67 (d, 2H), 4.61 (s, 1H), 2.35 (m, 1H), 1.42-1.70 (m, 6H), 1.29-1.37 (m, 2H), 0.96 (s, 3H), 0.95 (s, 3H).

Step 5: 2-[4-(4,4-Dimethyl-cyclohexyl)-phenoxymethyl]-oxirane

The title compound was prepared from 4-(4,4-dimethylcyclohexyl)-phenol and epichlorohydrin according to the procedures employed for the preparation of the compound in Step 1 of Example 2.
$C_{17}H_{24}O_2$ (260.17), LCMS (ESI): 261.20 (M$^+$+H).
$^1$H NMR (CDCl$_3$, 300 MHz), δ 7.15 (d, 2H), 6.85 (d, 2H), 4.18 (dd, 1H), 3.96 (dd, 1H), 3.34 (m, 1H), 2.90 (t, 1H), 2.75 (dd, 1H), 2.36 (m, 1H), 1.42-1.71 (m, 6H), 1.24-1.39 (m, 2H), 0.97 (s, 3H), 0.95 (s, 3H).

Step 6: 5-[4-(4,4-Dimethyl-cyclohexyl)-phenoxymethyl]-4,5-dihydro-oxazol-2-ylamine The title compound was prepared from 2-[4-(4,4-dimethyl-cyclohexyl)-phenoxymethyl]-oxirane and sodium hydrogen cyanamide according to the procedures employed for the preparation of the compound in Step 2 of Example 1.
$C_{18}H_{26}N_2O_2$ (302.19), LCMS (ESI): 303.21 (M$^+$+H).
$^1$H NMR (CDCl$_3$, 300 MHz), δ 7.15 (d, 2H), 6.86 (d, 2H), 4.92 (m, 1H), 4.04 (AB-m, 2H), 3.92 (dd, 1H), 3.61 (dd, 1H), 2.36 (m, 1H), 1.9 (v. br.), 1.43-1.72 (m, 6H), 1.24-1.38 (m, 2H), 0.97 (s, 3H), 0.95 (s, 3H).

Step 7: 2-[4-(4,4-(Dimethyl)-cyclohexyl)-phenoxymethyl]-2,3-dihydro-oxazolo[3,2-a]pyrimidin-7-one The title compound was prepared from 5-[4-(4,4-dimethyl-cyclohexyl)-phenoxymethyl]-4,5-dihydro-oxazol-2-ylamine according to the procedures employed in Step 3 of Example 1.
$C_{16}H_{25}NO$ (354.19), LCMS (ESI): 355.18 (M$^+$+H).
$^1$H NMR (DMSO-d$_6$, 300 MHz), δ 7.76 (d, 1H), 7.17 (d, 1H), 6.85 (d, 2H), 5.82 (d, 1H), 5.32 (m, 1H), 4.38 (t, 1H), 4.29 (AB-m, 2H), 4.09 (dd, 1H), 2.35 (m, 1H), 1.21-1.60 (m, 8H), 0.96 (s, 3H), 0.93 (s, 3H)

Example 6

2-[4-(Tetrahydropyran-4-yl)-phenoxymethyl]-2,3-dihydro-oxazolo[3,2-a]pyrimidin-7-one

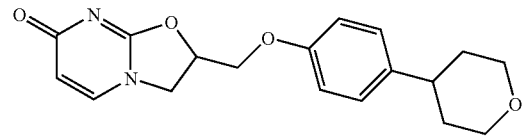 [SMILES: O=c1ccn2c(n1)OC(COc1ccc(C3CCOCC3)cc1)C2]

Step 1:
4-(4-Oxiranylmethoxy-phenyl)-tetrahydropyran

The title compound was prepared from 4-(tetrahydropyran-4-yl)-phenol and epichlorohydrin according to the procedures employed for the preparation of the compound in Step 1 of Example 2.
$C_{14}H_{18}O_3$ (234.13), LCMS (ESI): 257.15 (M$^+$+Na).
$^1$H NMR (CDCl$_3$, 300 MHz), δ 7.14 (d, 2H), 6.88 (d, 2H), 4.20 (dd, 1H), 4.01-4.13 (m, 2H), 3.96 (dd, 1H), 3.45-3.60 (m, 2H), 3.34 (m, 1H), 2.90 (t, 1H), 2.75 (dd, 1H), 2.70 (m, 1H), 1.71-1.78 (m, 4H).

Step 2: 5-[4-(Tetrahydropyran-4-yl)-phenoxymethyl]-4,5-dihydro-oxazol-2-ylamine

The title compound was prepared from 4-(4-oxiranylmethoxy-phenyl)-tetrahydropyran and sodium hydrogen cyanamide according to the procedures employed for the preparation of the compound in Step 2 of Example 1.
$C_{15}H_{20}N_2O_3$ (276.15), LCMS (ESI): 277.10 (M$^+$+H).

¹H NMR (CDCl₃, 300 MHz), δ 7.15 (d, 2H), 6.88 (d, 2H), 4.91 (m, 1H), 3.97-4.13 (m, 4H), 3.92 (dd, 1H), 3.7 (v. br., 2H), 3.45-3.64 (m, 3H), 2.70 (m, 1H), 1.66-1.86 (m, 4H).

Step 3: 2-[4-(Tetrahydropyran-4-yl)-phenoxymethyl]-2,3-dihydro-oxazolo[3,2-a]-pyrimidin-7-one The title compound was prepared from 5-[4-(tetrahydropyran-4-yl)-phenoxymethyl]-4,5-dihydro-oxazol-2-ylamine according to the procedures employed for the preparation of Example 1 in Step 3 of Example 1.

C₁₈H₂₀N₂O₄ (328.14), LCMS (ESI): 329.17 (M⁺+H).
¹H NMR (CDCl₃, 300 MHz), δ 7.24 (d, 1H), 7.15 (d, 2H), 6.83 (d, 2H), 6.10 (d, 1H), 5.27 (m, 1H), 4.22-4.20 (m, 4H), 4.07 (d, 2H), 3.52 (m, 2H), 2.71 (m, 1H), 1.69-1.85 (m, 4H).

Example 7

2-Benzyloxymethyl-2,3-dihydro-oxazolo[3,2-a]pyrimidin-7-one

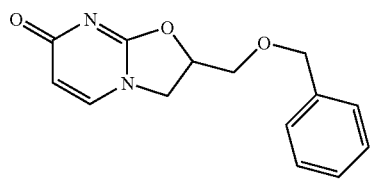 [SMILES: O=c1ccn2c(n1)OC(COCc1ccccc1)C2]

Step 1: 2-Benzyloxymethyl-oxirane

A mixture of 50% w/w aqueous potassium hydroxide (30 mL), epichlorohydrin (157 mmol, 20 mL) and tetrabutylammonium bromide (2.35 mmol, 0.75 g) was vigorously stirred at room temperature and cooled in an ice bath. Benzyl alcohol (96.0 mmol, 10 ml) was added dropwise, while maintaining the reaction temperature at about 10° C. by cooling the reaction mixture in an ice bath. The reaction mixture was then allowed to stir at room temperature overnight after which it was poured onto ice/water, and the aqueous phase extracted with diethyl ether. The organic phases were combined and washed with brine to neutrality and dried (Na₂SO₄). The solution was concentrated under reduced pressure. The residue was purified by flash chromatography (silica, 2-10% ethyl acetate/heptane) to give 14.8 g (94%) of 2-benzyloxymethyl-oxirane.

C₁₀H₁₂O₂ (164.21), LCMS (ESI): 165.10 (M+H).
¹H NMR (CDCl₃), 300 MHz), δ 7.26-7.38 (m, 5H), 4.59 (q, 2H), 3.77 (dd, 1H), 3.45 (dd, 1H), 3.19 (m, 1H), 2.80 (t, 1H), 2.63 (dd, 1H).

Step 2: 5-Benzyloxymethyl-4,5-dihydro-oxazol-2-ylamine

The title compound was prepared from 2-benzyloxymethyl-oxirane and sodium hydrogen cyanamide according to the procedures employed for the preparation of the compound in Step 2 of Example 1.

C₁₁H₁₄N₂O₂ (206.10), LCMS (ESI): 207.08 (M⁺+H).
¹H NMR (CDCl₃), 300 MHz), δ 7.26-7.40 (m, 5H), 4.74 (m, 1H), 4.49-4.66 (m, 2H), 3.81 (m, 1H), 3.35-3.63 (m, 3H), 3.5 (v. br., 2H)

Step 3: 2-Benzyloxymethyl-2,3-dihydro-oxazolo[3,2-a]pyrimidin-7-one

The title compound was prepared from 5-benzyloxymethyl-4,5-dihydro-oxazol-2-ylamine according to the procedure employed for Step 3 of Example 1.

C₁₄H₁₄N₂O₃ (258.20), LCMS (ESI): 259.08 (M⁺+H).
¹H NMR (CDCl₃), 300 MHz), δ 7.25-7.40 (m, 5H), 7.18 (d, 1H), 6.04 (d, 1H), 5.07 (m, 1H), 4.59 (q, 2H), 4.20 (AB-m, 2H), 3.78 (AB-m, 2H),

Example 8

2-(4-tert-Butyl-benzyloxymethyl)-2,3-dihydro-oxazolo[3,2-a]pyrimidin-7-one

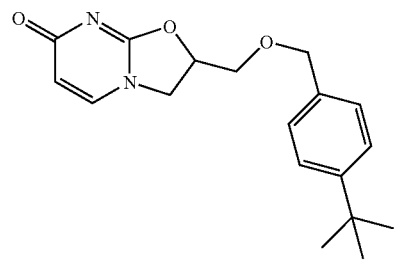 [SMILES: CC(C)(C)c1ccc(COCC2Cn3ccc(=O)nc3O2)cc1]

Step 1: 2-(4-tert-Butyl-benzyloxymethyl)-oxirane

The title compound was prepared from 4-(tert-butyl)-benzyl alcohol and epichlorohydrin according to the procedures employed for the preparation of the compound in Step 1 of Example 2.

C₁₄H₂₀O₂ (220.15), LCMS (ESI): 262.18 (M⁺+H+CH₃CN).
¹H NMR (CDCl₃), 300 MHz), δ 7.38 (d, 2H), 7.28 (d, 2H), 4.49-4.61 (q, 2H), 3.75 (dd, 1H), 3.45 (dd, 1H), 3.18 (m, 1H), 2.80 (t, 1H), 2.62 (dd, 1H), 1.32 (s, 9H).

Step 2: 5-(4-tert-Butyl-benzyloxymethyl)-4,5-dihydro-oxazol-2-ylamine

The title compound was prepared from 2-(4-tert-butyl-benzyloxymethyl)-oxirane and sodium hydrogen cyanamide according to the procedures employed for the preparation of the compound in Step 2 of Example 1.

C₁₅H₂₂N₂O₂ (262.17), 263.18 (M⁺+H).
¹H NMR (CDCl₃), 300 MHz), δ 7.38 (d, 2H), 7.27 (dd, 2H), 4.73 (m, 1H), 4.50-4.61 (m, 2H), 3.80 (dd, 1H), 3.56 (AB-m, 2H), 3.45 (dd, 1H), 3.1 (v.br., 2H), 1.32 (s, 9H).

Step 3: 2-(4-tert-Butyl-benzyloxymethyl)-2,3-dihydro-oxazolo[3,2-a]pyrimidin-7-one The title compound was prepared from 5-(4-tert-butyl-benzyloxymethyl)-4,5-dihydro-oxazol-2-ylamine according to the procedures employed in Step 3 of Example 1.

C₁₈H₂₂N₂O₃ (314.16), LCMS (ESI): 315.17 (M⁺+H).

¹H NMR (CDCl₃), 300 MHz), δ 7.38 (d, 2H), 7.23 (d, 1H), 7.18 (d, 2H), 6.06 (d, 1H), 5.05 (m, 1H), 4.56 (q, 2H), 4.18 (m, 2H), 3.82 (dd, 1H), 3.72 (dd, 1H), 1.30 (s, 9H)

Example 9

2-[4-(1,2,2,6,6-Pentamethyl-piperidin-4-yl)-phenoxymethyl]-2,3-dihydro-oxazolo[3,2-a]pyrimidin-7-one

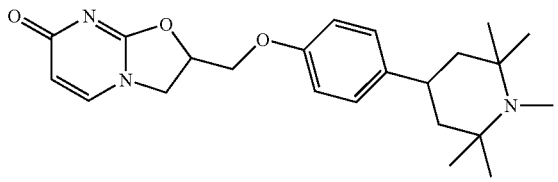 [SMILES: CN1C(C)(C)CC(c2ccc(OCC3Cn4ccc(=O)nc4O3)cc2)CC1(C)C]

Step 1: 4-(1,2,2,6,6-Pentamethyl-1,2,3,6-tetrahydropyridin-4-yl)-phenol 1,2,2,6,6-Pentamethyl-piperidin-4-one (8.64 g, 50.00 mmol) and phenol (4.98 g, 53.00 mmol) were melted together at 60° C. in a 100 mL round bottomed flask after which 13.5 mL of concentrated hydrochloric acid was added dropwise. The yellow solution was stirred at 70° C. for 24 hours. The mixture was poured into a beaker containing ice. Ammonium hydroxide was added carefully while stirring until the pH reached 7~8. The mixture was extracted with EtOAc five times. The organic phases were combined, dried (Na₂SO₄) and concentrated. The residue was purified by chromatography on a silica gel column, eluting with 7N NH₃ in methanol/dichloromethane to give 4-(1,2,2,6,6-pentamethyl-1,2,3,6-tetrahydropyridin-4-yl)-phenol (4.11 g, 34%).

C₁₆H₂₃NO (245.37), LCMS (ESI): 246.20(M⁺+H).
¹H NMR(CDCl₃, 300 MHz), δ 7.27 (d, 2H)), 6.79 (d, 2H), 5.73 (s, 1H), 3.45 (s, 1H), 2.31-2.37 (m, 5H), 1.20 (s, 6H), 1.15 (s, 6H).

Step 2: 4-(1,2,2,6,6-Pentamethyl-piperidin-4-yl)-phenol

To 0.33 g of palladium on activated carbon (10%) was added a solution of 4-(1,2,2,6,6-pentamethyl-1,2,3,6-tetrahydro-pyridin-4-yl)-phenol (3.27 g, 13.3 mmol) in methanol (100 mL). This mixture was stirred at room temperature under H₂ (1 atm) for 2 hours. The catalyst was filtered and the filtrate concentrated. The residue was purified by chromatography on silica gel (eluting with 7N NH₃ in methanol/dichloromethane) to give 4-(1,2,2,6,6-pentamethyl-piperidin-4-yl)-phenol (2 g 60%) as a white foam.

C₁₆H₂₅NO (247.38), LCMS (ESI): 248.21(M⁺+H).
¹H NMR (CDCl₃, 300 MHz), δ 7.11 (d, 2H), 6.77 (d, 2H), 2.88 (m, 1H), 2.30 (s, 3H), 1.54-1.69 (m, 4H), 1.17 (s, 6H), 1.10 (s, 6H).

Step 3: 1,2,2,6,6-Pentamethyl-4-(4-oxiranylmethoxy-phenyl)-piperidine

The title compound was prepared from 4-(1,2,2,6,6-pentamethyl-piperidin-4-yl)-phenol and epichlorohydrin according to the procedures employed for the preparation of the compound in Step 1 of Example 2.

C₁₉H₂₉NO₂ (303.21), 304.23 (M⁺+H).
¹H NMR (CDCl₃, 300 MHz), δ 7.16 (d, 2H), 6.86 (d, 2H), 4.18 (dd, 1H), 3.96 (dd, 1H), 3.34 (m, 1H), 2.90 (m, 2H), 2.75 (dd, 1H), 2.30 (s, 3H), 1.50-1.68 (m, 4H), 1.16 (s, 6H), 1.10 (s, 6H).

Step 4: 5-[4-(1,2,2,6,6-Pentamethyl-piperidin-4-yl)-phenoxymethyl]-4,5-dihydro-oxazol-2-ylamine The title compound was prepared from 1,2,2,6,6-pentamethyl-4-(4-oxiranylmethoxy-phenyl)-piperidine and sodium hydrogen cyanamide according to the procedures employed for the preparation of the compound in Step 2 of Example 1.

C₂₀H₃₁N₃O₂ (345.24), 346.27 (M⁺+H).
¹H NMR (CDCl₃, 300 MHz), δ 7.16 (d, 2H), 6.87 (d, 2H), 4.91 (m, 1H), 4.2 (v. br., 2H), 4.04 (AB-m, 2H), 3.93 (dd, 1H), 3.60 (dd, 1H), 2.89 (m, 1H), 2.30 (s, 3H), 1.53-1.68 (m, 4H), 1.17 (s, 6H), 1.10 (s, 6H).

Step 5: 2-[4-(1,2,2,6,6-Pentamethyl-piperidin-4-yl)-phenoxymethyl]-2,3-dihydro-oxazolo[3,2-a]pyrimidin-7-one The title compound was prepared from 5-[4-(1,2,2,6,6-pentamethyl-piperidin-4-yl)-phenoxymethyl]-4,5-dihydro-oxazol-2-ylamine employing the procedure of Step 3, Example 1.

C₂₃H₃₁N₃O₃ (397.23), LCMS (ESI): 398.26 (M⁺+H).
¹H NMR (CDCl₃, 300 MHz), δ 7.24 (d, 1H), 7.18 (d, 2H), 6.82 (d, 2H), 6.09 (d, 1H), 6.27 (m, 1H), 4.20-4.41 (m, 4H), 2.89 (m, 1H), 2.30 (s, 3H), 1.52-1.69 (m, 4H), 1.17 (s, 6H), 1.10 (s, 6H).

Example 10

2-(4-(1-Phenyl)-cyclohexyl)-phenoxymethyl)-2,3-dihydro-oxazolo[3,2-a]pyrimidin-7-one

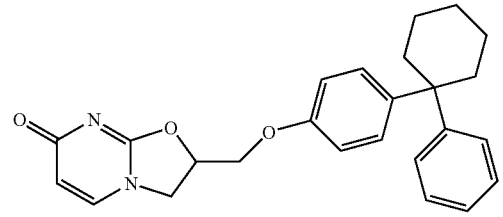 [SMILES: O=c1ccn2c(n1)OC(COc1ccc(C3(c4ccccc4)CCCCC3)cc1)C2]

Step 1: 4-(1'-(Phenyl)cyclohexyl)phenol

A mixture of 5 g (28.4 mmol) of 1-phenyl-1-cyclohexanol, 5.35 g (56.8 mmol) of phenol and 250 mg (1.32 mmol) of toluenesulfonic acid monohydrate was stirred at 85° C. under nitrogen atmosphere for 4 hours. The material was allowed to cool to room temperature, diluted with ethyl acetate, washed with saturated sodium bicarbonate, water and brine. The resulting solution was dried (Na₂SO₄), filtered and concentrated to a white solid which was heated under high vacuum to remove residual phenol. The resulting residue was purified by flash chromatography on silica gel, eluting with methanol/dichloromethane to provide 5.64 g (22.4 mmol) of 4-(1'-(phenyl)cyclohexyl)phenol.

C₁₈H₂₀O (252.15), LCMS (CI): 252.22 (M⁺).
¹H NMR (CDCl₃, 300 MHz), δ 7.25 (m, 5H), 7.13 (m., 2H), 6.73 (m, 2H), 4.55 (s, 1H), 2.24 (m, 4H), 1.55 (br s, 6H).

Step 2: 2-(4-(1-Phenyl)-cyclohexyl)-phenoxymethyl)-2,3-dihydro-oxazolo[3,2-a]pyrimidin-7-one The title compound was prepared from 4-(1'-(phenyl)cyclohexyl)phenol employing the three step procedures used to prepare Example 2.

C$_{25}$H$_{26}$N$_2$O$_3$ (402.50), LCMS (ESI): 403.21 (M+H).
$^1$H NMR (CDCl$_3$, 300 MHz), 7.76 (d, 1H), 7.22-7.29 (m, 6H), 7.10 (m, 1H), 6.82 (d, 2H), 5.81 (d, 1H), 5.30 (m, 1H), 4.38 (t, 1H), 4.23-4.31 (m, 2H), 4.09 (q, 1H), 2.17-2.28 (br s, 4H), 1.38-1.50 (br s, 6H).

Example 11

2-(4-Cyclohexyl-phenoxymethyl)-5-methyl-2,3-dihydro-oxazolo[3,2-a]pyrimidin-7-one

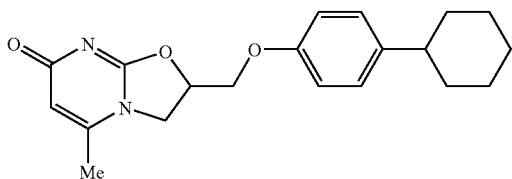 [SMILES: Cc1cc(=O)nc2n1CC(COc1ccc(C3CCCCC3)cc1)O2]

Step 1: 2-(4-Cyclohexyl-phenoxymethyl)-oxirane

The title compound was prepared from 4-cyclohexylphenol and epichlorohydrin employing the procedure in Step 1 of Example 2.

C$_{15}$H$_{20}$O$_2$ (232.15), LCMS (ESI): 274.18 (M$^+$+H+CH$_3$CN)
$^1$H NMR (CDCl$_3$, 300 MHz), 7.12 (d, 2H), 6.85 (d, 2H), 4.17 (dd, 1H), 3.96 (dd, 1H), 3.34 (m, 1H), 2.89 (t, 1H), 2.74 (dd, 1H), 2.44 (m, 1H), 1.78-1.85 (m, 5H), 1.31-1.43 (m, 5H).

Step 2: 5-(4-Cyclohexyl-phenoxymethyl)-4,5-dihydro-oxazol-2-ylamine

The title compound was prepared from 2-(4-cyclohexyl-phenoxymethyl)-oxirane employing the procedure in Step 2 of Example 1.

C$_{16}$H$_{22}$N$_2$O$_2$ (274.17), LCMS (ESI): 275.16 (M$^+$+H)
$^1$H NMR (CDCl$_3$, 300 MHz), 7.13 (d, 2H), 6.85 (dd, 2H), 4.91 (m, 1H), 4.2 (v. br., 2H), 4.05 (AB-m, 2H), 3.91 (dd, 1H), 3.61 (dd, 1H), 2.45 (br.s, 1H), 1.17-1.93 (m, 10H).

Step 3: 2-(4-Cyclohexyl-phenoxymethyl)-5-methyl-2,3-dihydro-oxazolo[3,2-a]pyrimidin-7-one To a solution of 5-(4-cyclohexyl-phenoxymethyl)-4,5-dihydro-oxazol-2-ylamine (300 mg, 1.095 mmol) in ethanol (6 mL) was added ethyl 2-butynoate (246 mg, 2.19 mmol). The reaction mixture was heated in a microwave oven at 150° C. for 30 min, then at 160° C. for 20 min, and at 170° C. for 30 min. Solvent was removed under vacuum, and the residue purified via flash column chromatography (silica gel, 1-18% EtOH/CH$_2$Cl$_2$) to afford 190 mg of 2-(4-cyclohexyl-phenoxymethyl)-5-methyl-2,3-dihydro-oxazolo[3,2-a]pyrimidin-7-one as a white solid.

C$_{20}$H$_{24}$N$_2$O$_3$ (340.43), LCMS (ESI): 341.2 (MH$^+$).
$^1$H NMR (300 MHz, DMSO-d$_6$): δ 7.15 (2H, d), 6.86 (2H, d), 5.68 (1H, s), 5.28 (1H, m), 4.11-4.44 (4H, m), 2.43 (1H, m), 2.19 (3H, s), 1.65-1.80 (5H, m), 1.16-1.40 (5H, m).

Example 12

2-(4-Cyclohexyl-phenoxymethyl)-5-ethyl-2,3-dihydro-oxazolo[3,2-a]pyrimidin-7-one

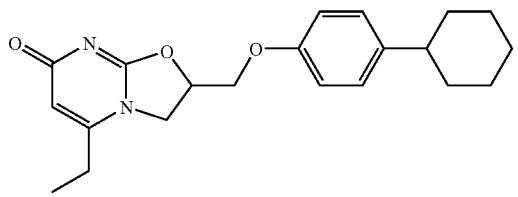 [SMILES: CCc1cc(=O)nc2n1CC(COc1ccc(C3CCCCC3)cc1)O2]

To a solution of 5-(4-cyclohexyl-phenoxymethyl)-4,5-dihydro-oxazol-2-ylamine (300 mg, 1.095 mmol) in ethanol (6 mL) was added ethyl 2-pentynoate (276 mg, 2.19 mmol). The reaction mixture was heated in a microwave oven at 170° C. for 70 min. The solvent was removed under vacuum, and the residue purified via flash column chromatography (silica gel, 1-12% EtOH/CH$_2$Cl$_2$) to afford 153 mg of 2-(4-cyclohexyl-phenoxymethyl)-5-ethyl-2,3-dihydro-oxazolo[3,2-a]pyrimidin-7-one as a slightly yellow solid.

C$_{21}$H$_{26}$N$_2$O$_3$ (354.45), LCMS (ESI): 355.2 (MH$^+$).
$^1$H NMR (300 MHz, DMSO-d$_6$): δ 7.14 (2H, d), 6.85 (2H, d), 5.63 (1H, s), 5.28 (1H, m), 4.10-4.44 (4H, m), 2.46 (3H, m), 1.65-1.80 (5H, m), 1.20-1.40 (5H, m), 1.14 (3H, t).

Example 13

(S)-2-(4-Cyclohexyl-phenoxymethyl)-5-ethyl-2,3-dihydro-oxazolo[3,2-a]pyrimidin-7-one

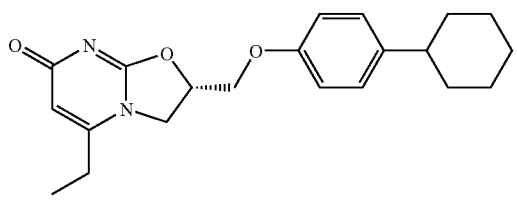 [SMILES: CCc1cc(=O)nc2n1C[C@@H](COc1ccc(C3CCCCC3)cc1)O2]

To a solution of (S)-5-(4-cyclohexyl-phenoxymethyl)-4,5-dihydro-oxazol-2-ylamine (1.0 g, 3.64 mmol), prepared in accordance with the procedures as set forth in Steps 1 and 2 of Example 1 and starting from R-epichlorohydrin and 4-cyclohexylphenol, in ethanol (18.2 mL) was added ethyl 2-pentynoate (0.92 g, 7.28 mmol). The reaction mixture was heated at reflux for 14 hrs and then gradually cooled to room temperature. The resulting crystalline solid was isolated by filtration, washed with heptane 3 times, and dried under vacuum to afford 560 mg of (S)-2-(4-cyclohexyl-phenoxymethyl)-5-ethyl-2,3-dihydro-oxazolo[3,2-a]pyrimidin-7-one as a white solid. $[\alpha]_D^{25}$ −27.96 (c 0.526, CHCl$_3$).

C$_{21}$H$_{26}$N$_2$O$_3$ (354.45), LCMS (ESI): 355.23 (MH$^+$).

$^1$H NMR (300 MHz, DMSO-d$_6$): δ 7.14 (2H, d), 6.85 (2H, d), 5.63 (1H, s), 5.29 (1H, m), 4.10-4.44 (4H, m), 2.46 (3H, m), 1.65-1.80 (5H, m), 1.20-1.40 (5H, m), 1.14 (3H, t).

Example 14

2-(4-Cyclohexyl-phenoxymethyl)-5-trifluoromethyl-2,3-dihydro-oxazolo[3,2-a]pyrimidin-7-one

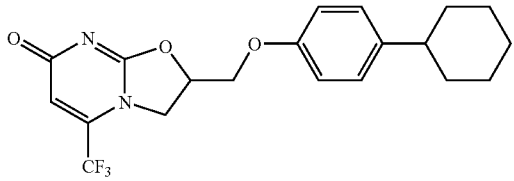 [SMILES: O=c1cc(C(F)(F)F)n2c(n1)OC(COc1ccc(C3CCCCC3)cc1)C2]

To a solution of 5-(4-cyclohexyl-phenoxymethyl)-4,5-dihydro-oxazol-2-ylamine (165 mg, 0.602 mmol) in ethanol (6 mL) was added ethyl 4,4,4-trifluoro-2-butynoate (100 mg, 0.602 mmol). The reaction mixture was heated in a microwave oven at 170° C. for 30 mins. Solvent was removed under vacuum, and the residue purified via flash column chromatography (silica gel, 1-10% EtOH/CH$_2$Cl$_2$) to afford 60 mg of 2-(4-cyclohexyl-phenoxymethyl)-5-trifluoromethyl-2,3-dihydro-oxazolo[3,2-a]pyrimidin-7-one as an off-white solid.

C$_{20}$H$_{21}$F$_3$N$_2$O$_3$ (394.40), LCMS (ESI): 395.16 (MH$^+$).

$^1$H NMR (300 MHz, DMSO-d$_6$): δ 7.15 (2H, d), 6.85 (2H, d), 6.46 (1H, s), 5.40 (1H, m), 4.14-4.51 (4H, m), 2.43 (1H, m), 1.65-1.80 (5H, m), 1.16-1.42 (5H, m).

Example 15

2-(4-Cyclohexyl-phenoxymethyl)-2,3,5,6-tetrahydro-oxazolo[3,2-a]pyrimidin-7-one

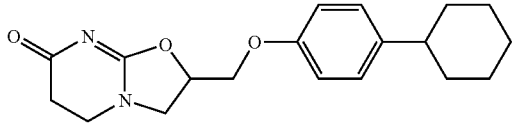

To a solution of 5-(4-cyclohexyl-phenoxymethyl)-4,5-dihydro-oxazol-2-ylamine (350 mg, 1.28 mmol) in ethanol (6 mL) was added ethyl acrylate (255.8 mg, 2.56 mmol). The reaction mixture was heated in a microwave oven at 150° C. for 40 min. The solvent was removed under vacuum, and the residue purified via flash column chromatography (silica gel, 0.5-12% EtOH/CH$_2$Cl$_2$) to afford an oil, which was dissolved in a small amount of methylene chloride and to which was then added heptane. A white solid precipitated to afford 110 mg of 2-(4-cyclohexyl-phenoxymethyl)-2,3,5,6-tetrahydro-oxazolo[3,2-a]pyrimidin-7-one.

C$_{19}$H$_{24}$N$_2$O$_3$ (328.41), LCMS (ESI): 329.17 (MH$^+$).

$^1$H NMR (300 MHz, DMSO-d$_6$): δ 7.15 (2H, d), 6.89 (2H, d), 5.16 (1H, m), 4.22 (2H, ddd), 3.86 (1H, t), 3.55 (1H, dd), 3.48 (2H, t), 2.44 (3H, m), 1.65-1.84 (5H, m), 1.14-1.44 (5H, m).

Example 16

2-(4-tert-Butyl-phenoxymethyl)-2,3,5,6-tetrahydro-oxazolo[3,2-a]pyrimidin-7-one

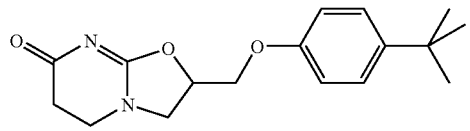 [SMILES: CC(C)(C)c1ccc(OCC2CN3CCC(=O)N=C3O2)cc1]

Steps 1 and 2: 5-(4-tert-Butyl-phenoxymethyl)-4,5-dihydro-oxazol-2-ylamine

The title compound was prepared from 4-tert-butylphenol employing the procedures in Steps 1 and 2 of Example 2.

Step 3: 2-(4-tert-butyl-phenoxymethyl)-2,3,5,6-tetrahydro-oxazolo[3,2-a]pyrimidin-7-one To a solution of 5-(4-tert-butyl-phenoxymethyl)-4,5-dihydro-oxazol-2-ylamine (520 mg, 2.10 mmol) in ethanol (10 mL) was added ethyl acrylate (273.3 mg, 2.73 mmol). The reaction mixture was heated in a microwave oven at 130° C. for 10 min, then at 140° C. for 10 min, and finally at 150° C. for 30 min. Solvent was removed under vacuum, and the residual solid washed with small amount of EtOH to afford 195 mg of 2-(4-tert-butyl-phenoxymethyl)-2,3,5,6-tetrahydro-oxazolo[3,2-a]pyrimidin-7-one as a white solid.

C$_{17}$H$_{22}$N$_2$O$_3$ (302.38), LCMS (ESI): 303.17 (MH$^+$).

$^1$H NMR (300 MHz, DMSO-d$_6$): δ 7.32 (2H, d), 6.90 (2H, d), 5.17 (1H, m), 4.23 (2H, m), 3.87 (1H, t), 3.45-3.58 (3H, m), 2.45 (2H, t), 1.25 (9H, s).

Example 17

(S)-2-(4-Piperidin-1-yl-phenoxymethyl)-2,3-dihydro-oxazolo[3,2-a]pyrimidin-7-one

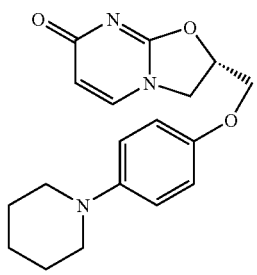 [SMILES: O=c1ccn2c(n1)O[C@H](COc1ccc(N3CCCCC3)cc1)C2]

Step 1: 4-Piperidin-1-yl-phenol

The title compound was prepared in accordance with the procedures described in S. Urgaonkar, et al., Adv. Synth. Catal. 2004, 346, 611-616, and employing 4-bromophenol and piperidine as the starting materials in the presence of palladium acetate and lithium bis(trimethylsilyl)amide.

C$_{11}$H$_{15}$NO (177.11), LCMS (ESI): 178.13(M$^+$+H).

$^1$H NMR (CDCl$_3$, 300 MHz), δ 6.86 (d, 2H), 6.74 (d, 2H), 4.43 (s, 1H), 3.01 (m, 4H), 1.72 (m, 4H), 1.55 (m, 2H).

Steps 2 to 4: (S)-2-(4-Piperidin-1-yl-phenoxymethyl)-2,3-dihydro-oxazolo[3,2-a]pyrimidin-7-one The title compound was prepared from 4-piperidin-1-yl-phenol employing the procedures in Steps 1 through 3 of Example 1. $[\alpha]_D^{25}$ −40.47 (c 0.502, CHCl$_3$).

$C_{18}H_{21}N_3O_3$ (327.15), LCMS (ESI): 328.14 (M$^+$+H).

$^1$H NMR (CDCl$_3$, 300 MHz), δ 7.24 (d, 1H), 6.90 (d, 2H), 6.79 (d, 2H), 6.10 (d, 1H), 5.25 (m, 1H), 4.20-4.38 (m, 4H), 3.04 (t, 4H), 1.71 (m, 4H), 1.57(m, 2H).

Example 18

(S)-2-[4-(3,3-Dimethyl-cyclohexyl)-phenoxymethyl]-2,3-dihydro-oxazolo[3,2-a]pyrimidin-7-one

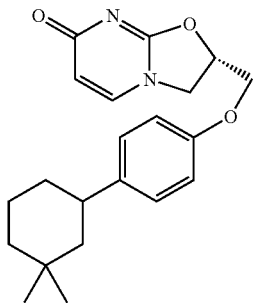 [SMILES: CC1(C)CCCC(c2ccc(OC[C@@H]3Cn4ccc(=O)nc4O3)cc2)C1]

Step 1: 3,3-Dimethyl-cyclohexanone

First, 3-methyl-cyclohexenone was prepared in accordance with the procedures of Jirgensons et. al., *Euro. J. Med. Chem.* 35 (2000) 555-565. Then, 3-methyl-cyclohexenone was reacted with methyl magnesium iodide in the presence of cuprous chloride in diethyl ether to obtain the title compound.

Step 2: 1-(4-Benzyloxy-phenyl)-3,3-dimethyl-cyclohexanol

In a RB flask (250 mL) was placed magnesium turnings (2.08 g, 85.9 mmol), which were stirred under vacuum without solvent overnight. To the stirred magnesium turnings was added anhydrous THF (10 mL). To the resulting mixture at 50° C. was added several drops of dibromoethane, followed by 4-benzyloxybromobenzene (11.8 g, 42.9 mmol) in 40 ml of THF. After addition was complete, the reaction mixture was heated at 60° C. for 3 hours until a brownish-grey slurry was formed. The reaction mixture was cooled in an ice-bath and 3,3-dimethyl-cyclohexanone (3.87 g, 30.67 mmol) in THF (15 mL) was added dropwise. The reaction mixture was stirred at room temperature for one hour. The solvent was removed under reduced pressure. The residue was partitioned between EtOAc/aqueous NH$_4$Cl. The aqueous phase was extracted three times with EtOAc. The organic phase was combined and dried (Na$_2$SO$_4$). Silica gel chromatography (EtOAc/heptane) provided 5.08 g of 1-(4-benzyloxy-phenyl)-3,3-dimethyl-cyclohexanol as a white solid.

$C_{21}H_{26}O_2$ (310.19), LCMS (ESI): 293.17(M$^+$+H−H$_2$O).

Step 3: 1-Benzyloxy-4-(3,3-dimethyl-cyclohex-1-enyl)-benzene 1-(4-Benzyloxy-phenyl)-3,3-dimethyl-cyclohexanol (5.08 g, 16.4 mmol) was dissolved in EtOH (80 mL) after which concentrated hydrochloric acid (8 mL) was added. This mixture was stirred at 50° C. for 1.5 hours. The solvent was removed under reduced pressure. Water (15 mL) was added. The mixture was basified with aqueous ammonia and extracted three times with EtOAc. The organic phase was dried and concentrated to provide the title compound as a yellow solid 4.43 g as a mixture of isomers.

$C_{21}H_{24}O$ (292.18), LCMS (ESI): 293.22 (M$^+$+H).

Step 4: 4-(3,3-Dimethyl-cyclohexyl)-phenol

To 1-benzyloxy-4-(3,3-dimethyl-cyclohex-1-enyl)-benzene (4.3 g, 16.4 mmol) in MeOH (50 mL) and EtOAc (50 mL) was added 10% Pd/C (0.67 g) under N$_2$. This mixture was stirred under H$_2$ (1 atm) overnight. The reaction mixture was filtered through celite. The filtrate was concentrated to give the title compound as a white solid (3.43 g).

$C_{14}H_{20}O$ (204.15), LCMS (CI): 204.15(M$^+$).

$^1$H NMR (CDCl$_3$, 300 MHz), δ 7.07 (d, 2H), 6.75 (d, 2H), 4.60 (s, 1H), 2.63 (m, 1H), 1.09-1.88 (m, 8H), 0.99 (s, 3H), 0.94 (s, 3H).

Steps 5 to 7: (S)-2-[4-(3,3-Dimethyl-cyclohexyl)-phenoxymethyl]-2,3-dihydro-oxazolo[3,2-a]pyrimidin-7-one The title compound was prepared from 4-(3,3-dimethyl-cyclohexyl)-phenol and R-epichlorohydrin employing the procedures in Steps 1 through 3 of Example 1. $[\alpha]_D^{25}$ −48.48 (c 0.503, CHCl$_3$).

$C_{21}H_{26}N_2O_3$ (354.19), LCMS (ESI): 355.23 (M$^+$+H).

$^1$H NMR (CDCl$_3$, 300 MHz), δ 7.24 (d, 1H), 7.13 (d, 2H), 6.80 (d, 2H), 6.08 (d, 1H), 5.27 (m, 1H), 4.20-4.41 (m, 4H), 2.66 (m, 1H), 1.11-1.90 (m, 8H), 0.99 (s, 3H), 0.95 (s, 3H).

Example 19

(S)-2-(5,6,7,8,8a,9-Hexahydro-4bH-fluoren-2-yloxymethyl)-2,3-dihydro-oxazolo[3,2-a]pyrimidin-7-one

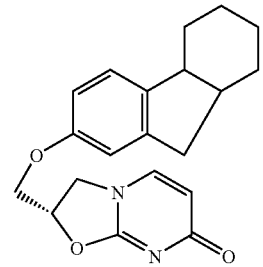 [SMILES: O=c1ccn2c(n1)O[C@H](COc1ccc3c(c1)CC1CCCCC31)C2]

Step 1: 5,6,7,8,8a,9-Hexahydro-4bH-fluoren-2-ol

2-[1-(3-Methoxy-phenyl)-meth-(Z)-ylidene]-cyclohexanone was prepared in accordance with the procedure of Baltzly et. al., *Journal of the American Chemical Society* (1955), 77, 624-8, which was subsequently hydrogenated (Pd/C, EtOH, H$_2$ 1 atm) to form 2-(3-methoxy-benzyl)-cyclohexanone.

2-(3-Methoxy-benzyl)-cyclohexanone was converted to 7-methoxy-2,3,4,9-tetrahydro-1H-fluorene in accordance with the procedure of U.S. Pat. No. 3,743,663, followed by hydrogenation (Pd/C, MeOH/EtOH, H$_2$, 1 atm) to obtain 7-methoxy-2,3,4,4a,9,9a-hexahydro-1H-fluorene.

To 7-methoxy-2,3,4,4a,9,9a-hexahydro-1H-fluorene (1.95 g, 9.65 mmol) in CH$_2$Cl$_2$ (20 mL) was added BBr$_3$ (1M in CH$_2$Cl$_2$, 24 mmol) dropwise at 0° C. This mixture was stirred at 0° C. for one hour. The reaction mixture was then quenched with MeOH (5 mL). Aqueous sodium hydrogen carbonate (10 mL) was added. The reaction mixture was stirred at room temperature overnight. The reaction mixture was extracted with CH$_2$Cl$_2$. The organic phase was washed with brine, dried (Na$_2$SO$_4$) and concentrated. Silica gel chromatography (EtOAc/heptane) provided 1.48 g of 5,6,7,8,8a,9-hexahydro-4bH-fluoren-2-ol.

C$_{13}$H$_{16}$O (188.12), LCMS (ESI): 189.14 (M$^+$+H).
$^1$H NMR (CDCl$_3$, 300 MHz), δ 7.00 (d, 1H), 6.72 (s, 1H), 6.62 (d, 1H), 4.50 (s, 1H), 3.02 (q, 1H), 2.79 (AB-m, 1H), 2.52 (AB-m, 1H), 2.42 (m, 1H), 1.77 (m, 2H), 1.16-1.62 (m, 6H).

Steps 2 to 4: (S)-2-(5,6,7,8,8a,9-Hexahydro-4bH-fluoren-2-yloxymethyl)-2,3-dihydro-oxazolo[3,2-a]pyrimidin-7-one The title compound was prepared from 5,6,7,8,8a,9-hexahydro-4bH-fluoren-2-ol and R-epichlorohydrin employing the procedures in Steps 1 through 3 of Example 1. [α]$_D^{25}$ −48.40 (c 0.5, CHCl$_3$).

C$_{20}$H$_{22}$N$_2$O$_3$ (338.16), LCMS (ESI): 339.18 (M$^+$+H).
$^1$H NMR (CDCl$_3$, 300 MHz), δ 7.25 (d, 1H), 7.05 (d, 1H), 6.77 (s, 1H), 6.67 (d, 1H), 6.08 (d, 1H), 5.27 (m, 1H), 4.20-4.42 (m, 4H), 3.04 (q, 1H), 2.82 (dd, AB-m), 2.54 (1H, AB-m), 2.44 (m, 1H), 1.13-1.86 (m, 8H).

Example 20

(S)-2-(4-Bicyclo[3.3.1]non-9-yl-phenoxymethyl)-2,3-dihydro-oxazolo[3,2-a]pyrimidin-7-one

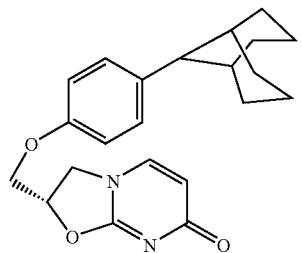 [SMILES: O=c1ccn2c(n1)O[C@H](COc1ccc(C3C4CCCC3CCC4)cc1)C2]

Step 1: 9-(4-Benzyloxy-phenyl)-bicyclo[3.3.1]nonane 9-(4-Benzyloxy-phenyl)-bicyclo[3.3.1]nonan-9-ol (4.7 g, 14.57 mmol) (prepared in accordance with the procedures set forth in Step 2 of Example 18) was dissolved in EtOH (150 mL) after which concentrated hydrochloric acid (15 mL) was added. This mixture was stirred at 50° C. overnight. The solvent was removed under reduced pressure. Water (50 mL) was added. The mixture was basified with aqueous ammonia and extracted three times with EtOAc. The organic phase was dried and concentrated to provide the title compound (5.5 g).

$^1$H NMR (CDCl$_3$, 300 MHz), δ 7.28-7.49 (s, 7H), 6.95 (d, 2H), 5.06 (s, 2H), 2.74 (br.s, 1H), 2.38 (b.s, 2H), 1.36-2.08 (m, 12H).

Step 2: 4-Bicyclo[3.3.1]non-9-yl-phenol

To 9-(4-benzyloxy-phenyl)-bicyclo[3.3.1]nonane (4.4 g, 14.6 mmol) in MeOH (100 mL) and EtOAc (100 mL) (warmed to 40° C. to facilitate dissolution, then cooled to room temperature) was added 10% Pd/C (0.5 g) under N$_2$. This mixture was stirred under H$_2$ (1 atm) overnight. The reaction mixture was then filtered through celite. The filtrate was concentrated to give the title compound as a solid.(3.1 g).

C$_{15}$H$_{20}$O (216.15), LCMS (CI): 216.17 (M$^+$).
$^1$H NMR (DMSO-d$_6$, 300 MHz), δ 9.11 (s, 1H), 7.14 (d, 2H), 6.72 (d, 2H), 2.62 (s, 1H), 2.13 (b.s, 2H), 1.24-2.06 (m, 12H).

Steps 2 to 4: (S)-2-(4-Bicyclo[3.3.1]non-9-yl-phenoxymethyl)-2,3-dihydro-oxazolo[3,2-a]pyrimidin-7-one The title compound was prepared from 4-bicyclo[3.3.1]non-9-yl-phenol and R-epichlorohydrin employing the procedures in Steps 1 through 3 of Example 1. [α]$_D^{25}$ −43.56 (c 0.5, CHCl$_3$).

C$_{22}$H$_{26}$N$_2$O$_3$ (366.19), LCMS (ESI): 367.16(M$^+$+H).
$^1$H NMR (CDCl$_3$, 300 MHz), δ 7.77 (d, 1H), 7.27 (d, 2H), 6.90 (d, 2H), 5.83 (d, 1H), 5.33 (m, 1H), 4.23-4.43 (m, 3H), 4.10 (AB-m, 1H) 2.68 (br.s, 1H), 2.37 (br.s, 2H), 1.26-2.06 (m, 12H).

Example 21

(S)-2-(6-Cyclohexyl-pyridin-3-yloxymethyl)-2,3-dihydro-oxazolo[3,2-a]pyrimidin-7-one

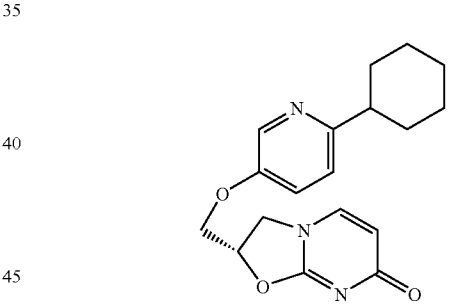

Step 1: 6-(1-Hydroxy-cyclohexyl)-pyridin-3-ol

To a solution of 6-bromo-pyridin-3-ol (5.0 g, 28.7 mmol) in anhydrous THF (75 mL) and anhydrous toluene (40 mL) at −78° C. was added n-butyllithium (2.5 M in hexane, 28.73 mmol). The mixture was stirred for 20 min. A solution of sec-butyllithium (1.4 M in cyclohexane, 43.1 mmol) was added dropwise and the mixture stirred at −78° C. for 1 hour. To the mixture was added cyclohexanone (4.23 g, 43.1 mmol) in THF (25 mL) at −78° C. and the mixture stirred at −78° C. for 1 hour. Saturated NaH$_2$PO$_4$ solution (10 mL) was slowly added to the mixture and the mixture then warmed to room temperature. Water (300 mL) was added. The reaction mixture was neutralized with hydrochloric acid (2N), and the mixture extracted three times with EtOAc. The organic layer was washed with brine and dried (Na$_2$SO$_4$). Silica gel chromatography (EtOAc/heptane) provided 2.63 g of the title compound. C$_{11}$H$_{15}$NO$_2$ (193.11), LCMS (ESI): 194.09 (M$^+$+H).

Step 2: 6-Cyclohex-1-enyl-pyridin-3-ol

To a suspension of 6-(1-hydroxy-cyclohexyl)-pyridin-3-ol (2.5 g, 12.9 mmol) in toluene (130 mL) was added p-toluenesulfonic acid monohydrate (8.12 g, 42.7 mmol). The mixture was refluxed with azeotropic removal of water for 2 hours. The reaction mixture was cooled to room temperature, neutralized with aqueous NaHCO$_3$ and extracted three times with EtOAc. The organic phase was washed with brine, dried (Na$_2$SO$_4$), passed through a silica gel pad and concentrated to provide the title compound as a solid (2.2 g).

C$_{11}$H$_{13}$NO (175.09), LCMS (ESI): 176.07 (M$^+$+H).

Step 3: 6-Cyclohexyl-pyridin-3-ol

To a solution of 6-cyclohex-1-enyl-pyridin-3-ol (2.2 g, 12.6 mmol) in methanol (45 ml) was added 10% Pd/C (0.22 g) under N$_2$. This mixture was stirred under hydrogen (1 atm) for 3 h. The reaction mixture was filtered through celite. The filtrate was concentrated to a solid (2.2 g) to provide the title compound.

C$_{11}$H$_{15}$NO (177.11), LCMS (ESI): 178.10 (M$^+$+H).
$^1$H NMR (CDCl$_3$, 300 MHz), δ 8.17 (d, 1H), 7.23 (dd, 1H), 7.09 (s, 1H), 2.63 (m, 1H), 1.68-1.97 (m, 5H), 1.15-1.56 (m, 5H).

Steps 4 to 6: (S)-2-(6-Cyclohexyl-pyridin-3-yloxymethyl)-2,3-dihydro-oxazolo[3,2-a]pyrimidin-7-one The title compound was prepared from 6-cyclohexyl-pyridin-3-ol and R-epichlorohydrin employing the procedures as set forth in Steps 1 through 3 of Example 1, with the exception of maintaining the reaction temperature at 50° C., rather than ethanol reflux as used in Step 3, Example 1. [α]$_D^{25}$ −28.00 (c 0.5, CHCl$_3$).

C$_{18}$H$_{21}$N$_3$O$_3$ (327.15), LCMS (ESI): 328.17 (M$^+$+H).
$^1$H NMR(CDCl$_3$, 300 MHz), δ 8.21(d, 1H), 7.04-7.24 (m, 3H), 6.10 (d, 1H), 5.30 (m, 1H), 4.24-4.42 (m, 4H), 2.65 (br.s, 1H), 1.19-1.95 (m, 10H).

Example 22

(S)-2-(4-Cyclohexyl-3-methyl-phenoxymethyl)-2,3-dihydro-oxazolo[3,2-a]pyrimidin-7-one

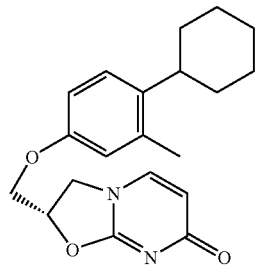 [SMILES: Cc1cc(OC[C@@H]2Cn3ccc(=O)nc3O2)ccc1C1CCCCC1]

Step 1: 4-Cyclohexyl-3-methyl-phenol (S)-Cyclohexyl-4-methoxy-2-methyl-benzene was prepared in two steps by a Suzuki coupling of 2-methyl-4-methoxyphenyl-1-boronic acid and cyclohexenol triflate following the procedures of Carmen et. al., Synlett 2005, No. 10, pp 1601-1605, to obtain 1-cyclohexenyl-4-methoxy-2-methyl-benzene, which was subsequently hydrogenated to form 1-cyclohexyl-4-methoxy-2-methyl-benzene.

To 1-cyclohexyl-4-methoxy-2-methyl-benzene (2.04 g, 10.0 mmol) in CH$_2$Cl$_2$ (20 mL) was added BBr$_3$ (1 M in CH$_2$Cl$_2$, 25 mmol) dropwise at 0° C. This mixture was stirred at 0° C. for two hours. The reaction mixture was then quenched with MeOH (5 mL), followed by addition of aqueous sodium hydrogen carbonate (10 mL). The reaction mixture was stirred at room temperature for three hours, then extracted with CH$_2$Cl$_2$ three times. The organic phase was washed with brine, dried (Na$_2$SO$_4$) and concentrated. Silica gel chromatography (EtOAc/heptane) provided 1.6 g of the title compound.

C$_{13}$H$_{18}$O (190.13), LCMS (ESI): 191.15(M$^-$+H).
$^1$H NMR (CDCl$_3$, 300 MHz), δ 7.06 (d, 1H), 6.64 (d, 1H), 6.62 (s, 1H), 4.51 (s, 1H), 2.62 (m, 1H), 2.28 (s, 3H), 1.20-1.89 (m, 10H).

Steps 2 to 4: (S)-2-(4-Cyclohexyl-3-methyl-phenoxymethyl)-2,3-dihydro-oxazolo[3,2-a]pyrimidin-7-one The title compound was prepared from 4-cyclohexyl-3-methyl-phenol and R-epichlorohydrin employing the procedures as set forth in Steps 1 through 3 of Example 1.
[α]$_D^{25}$ −51.00 (c 0.5, CHCl$_3$).
C$_{20}$H$_{24}$N$_2$O$_3$ (340.17), LCMS (ESI): 341.16 (M$^+$+H).
$^1$H NMR (CDCl$_3$, 300 MHz), δ 7.23 (d, 1H), 7.13 (d, 1H), 6.68 (d, 1H), 6.67 (s, 1H), 6.09 (d, 1H), 5.26 (m, 1H), 4.20-4.38 (m, 4H), 2.63 (br.s, 1H), 2.30 (s, 3H), 1.24-1.91 (m, 10H).

Example 23

(S)-2-(4-Cyclohexyloxy-phenoxymethyl)-2,3-dihydro-oxazolo[3,2-a]pyrimidin-7-one

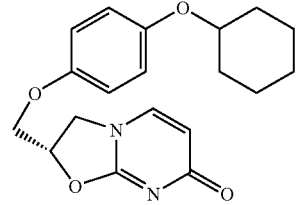 [SMILES: O=c1ccn2c(n1)O[C@H](COc1ccc(OC3CCCCC3)cc1)C2]

Step 1: 4-Cyclohexyloxy-phenol

To 1-cyclohexyloxy-4-methoxy-benzene (2.06 g, 10 mmol), prepared in accordance with the procedure of He, et. al., J. Am. Chem. Soc., 2005, 127, 6966, in DMF (20 mL) was added sodium ethanethiolate (1.15 g, 11 mmol). The reaction mixture was stirred at reflux for two hours. The reaction mixture was then cooled to room temperature. Water (5 mL) was added after which the mixture was neutralized with hydrochloric acid (2N). Ethyl acetate (200 mL) was then added and the organic phase washed with water three times, brine twice, and dried (Na$_2$SO$_4$). Silica gel chromatography (EtOAc/heptane) provided 0.88 g of the title compound.

C$_{12}$H$_{16}$O$_2$ (192.11), LCMS (ESI): 193.13 (M$^+$+H).
$^1$H NMR (CDCl$_3$, 300 MHz), δ 6.77 (q, 4H), 4.41 (s, 1H), 4.08 (m, 1H), 1.97 (m, 2 H), 1.78 (m, 2H), 1.22-1.62 (m, 6H).

Steps 2 to 4: (S)-2-(4-Cyclohexyloxy-phenoxymethyl)-2,3-dihydro-oxazolo[3,2-a]pyrimidin-7-one The title compound was prepared from 4-cyclohexyloxy-phenol and R-epichlorohydrin employing the procedures as set forth in Steps 1 through 3 of Example 1. [α]$_D^{25}$ −33.21 (c 0.557, CHCl$_3$).
C$_{19}$H$_{22}$N$_2$O$_4$ (342.15), LCMS (ESI): 343.17 (M$^+$+H).

Example 24

(S)-2-[4-(4,4-Difluoro-cyclohexyl)-phenoxymethyl]-2,3-dihydro-oxazolo[3,2-a]pyrimidin-7-one

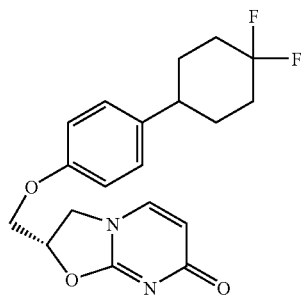 [SMILES: O=c1ccn2c(n1)O[C@H](COc1ccc(C3CCC(F)(F)CC3)cc1)C2]

Step 1: 4-(4,4-Difluoro-cyclohexyl)-phenol

To a solution of 4-(4-hydroxy-phenyl)-cyclohexanone (5 g, 26.3 mmol) was added bis(2-methoxyethyl)amino)sulfurtriflouride (29.1 g, 131 mmol) under nitrogen in a plastic bottle. The reaction mixture was stirred at room temperature for 48 hours. EtOH (14 drops) was added, and the reaction mixture allowed to stir for an additional 24 hours. The reaction mixture was poured into water (140 mL) and the aqueous layer extracted twice with dichloromethane. The organic phase was washed with brine and dried ($Na_2SO_4$). Silica gel chromatography afforded the title compound (2.8 g).

$C_{12}H_{14}F_2O$ (212.10), LCMS (CI): 212.09 ($M^+$).
$^1$H NMR (CDCl$_3$, 300 MHz), δ 7.09 (d, 2H), 6.77 (d, 2H), 4.57 (s, 1H), 2.54 (m, 1H), 2.18 (m, 2H), 1.67-1.97 (m, 6H).

Steps 2 to 4: (S)-2-[4-(4,4-Difluoro-cyclohexyl)-phenoxymethyl]-2,3-dihydro-oxazolo[3,2-a]pyrimidin-7-one The title compound was prepared from 4-(4,4-difluoro-cyclohexyl)-phenol and R-epichlorohydrin employing the procedures as set forth in Steps 1 through 3 of Example 1.

$C_{19}H_{20}F_2N_2O_3$ (362.14), LCMS (ESI): 363.15 ($M^+$+H).
$^1$H NMR (DMSO-d$_6$, 300 MHz), δ 7.76 (d, 1H), 7.18 (d, 2H), 6.88 (d, 2H), 5.82 (d, 1H), 5.33 (br.s, 1H), 4.22-4.43 (m, 3H), 4.09 (AB-m, 1H), 2.68 (b.s, 1H), 1.55-2.15 (m, 8H).

Example 25

(S)-2-(4-1,3-Dioxinan-2-yl-phenoxymethyl)-2,3-dihydro-oxazolo[3,2-a]pyrimidin-7-one

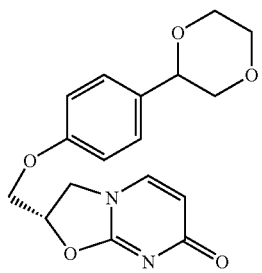 [SMILES: O=c1ccn2c(n1)O[C@H](COc1ccc(C3COCCO3)cc1)C2]

Step 1: 4-1,3-Dioxinan-2-yl-phenol

The title compound was prepared in accordance with the procedures as described in Gopinath et al., J. Org. Chem. 2002, 67, 5842-5845.

$C_{10}H_{12}O_3$ (180.07), LCMS (ESI): 181.09 ($M^+$+H).
$^1$H NMR (CDCl$_3$, 300 MHz), δ 7.34 (d, 2H), 6.77(d, 2H), 5.45 (s, 1H), 4.25 (m, 2H), 3.98 (t, 2H), 3.73 (q, 1H), 2.21 (m, 1H), 1.92(m, 1H).

Steps 2 to 4: (S)-2-(4-1,3-Dioxinan-2-yl-phenoxymethyl)-2,3-dihydro-oxazolo[3,2-a]pyrimidin-7-one The title compound was prepared from 4-1,3-dioxinan-2-yl-phenol and R-epichlorohydrin employing the procedures as set forth in Steps 1 through 3 of Example 1.

$[\alpha]_D^{25}$ −57.00 (c 0.553, CHCl$_3$).
$C_{17}H_{18}N_2O_5$ (330.34), LCMS (ESI): 331.08 ($M^+$+H).
$^1$H NMR (DMSO-d$_6$, 300 MHz), δ 7.76 (d, 1H), 7.32 (d, 2H), 6.91(d, 2H), 5.82 (d, 1H), 5.44 (s, 1H), 5.33 (br.s, 1H), 4.26-4.43 (m, 3H), 4.07-4.15 (m, 3H), 3.91 (m, 2H), 1.89-2.06 (m, 1H) 1.42 (d, 1H).

Example 26

2(S)-(4-Bromo-phenoxymethyl)-2,3(S)-dihydro-oxazolo[3,2-a]pyrimidin-7-one

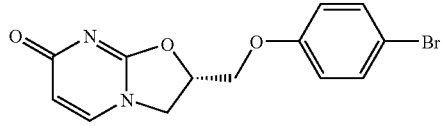 [SMILES: O=c1ccn2c(n1)O[C@H](COc1ccc(Br)cc1)C2]

Step 1: (S)-2-(4-Bromo-phenoxymethyl)-oxirane

The title compound was prepared from 4-bromophenol and R-epichlorohydrin employing the procedures as set forth in Step 1 of Example 1.

$C_9H_9BrO_2$ (227.97), LCMS (ESI): 270.06 ($M^+$+H+$CH_3CN$).
$^1$H NMR (CDCl$_3$, 300 MHz), δ 7.35 (d, 2H), 6.80 (d, 2H), 4.22 (dd, 1H), 3.92 (dd, 1H), 3.35 (m, 1H), 2.91 (t, 1H), 2.76 (dd, 1H).

Step 2: (S)-5-(4-Bromo-phenoxymethyl)-4,5-dihydro-oxazol-2-ylamine

The title compound was prepared from (S)-2-(4-bromo-phenoxymethyl)-oxirane employing the procedures as set forth in Step 2 of Example 1.

$C_{10}H_{11}BrN_2O_2$ (270), LCMS (ESI): 271.03 ($M^+$+H).
$^1$H NMR (CDCl$_3$, 300 MHz), δ 7.39 (d, 2H), 6.81 (d, 2H), 4.91 (m, 1H), 4.2 (v. br., 2H), 4.03 (AB-m, 2H), 3.94 (dd, 1H), 3.61 (dd, 1H).

Step 3: 2(S)-(4-Bromo-phenoxymethyl)-2,3(S)-dihydro-oxazolo[3,2-a]pyrimidin-7-one The title compound was prepared from (S)-5-(4-bromo-phenoxymethyl)-4,5-dihydro-oxazol-2-ylamine employing the procedures as set forth in Step 3 of Example 1.

$C_{13}H_{11}BrN_2O_3$ (321.99), LCMS (ESI): 323.01 ($M^+$+H).
$^1$H NMR (DMSO-d$_6$, 300 MHz), δ 7.75 (d, 2H), 7.48 (d, 1H), 6.93 (d, 2H), 5.81 (d, 1H), 5.32 (m, 1H), 4.24-4.44 (m, 3H), 4.10 (dd, 1H).

Example 27

2(S)-[4-(1,1,3,3-Tetramethyl-butyl)-phenoxymethyl]-2,3-dihydro-oxazolo[3,2-a]pyrimidin-7-one

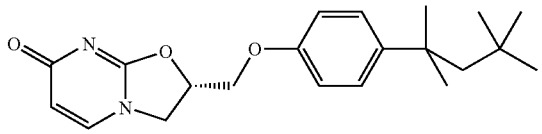

Step 1: (S)-2-(4-(1,1,3,3-Tetramethyl-butyl)-phenoxymethyl)-oxirane

The title compound was prepared from 4-(1,1,3,3-tetramethyl-butyl)-phenol and R-epichlorohydrin employing the procedures as set forth in Step 1 of Example 1.

$C_{17}H_{26}O_2$ (262.19), LCMS (ESI): 304.23 (M$^+$+H+CH$_3$CN).

$^1$H NMR (CDCl$_3$, 300 MHz), δ 7.28 (d, 2H), 6.84 (d, 2H), 4.19 (dd, 1H), 3.98 (dd, 1H), 3.36 (m, 1H), 2.90 (t, 1H), 2.76 (dd, 1H), 1.71 (s, 2H), 1.35 (s, 6H), 0.72 (s, 9H).

Step 2: (S)-5-(4-(1,1,3,3-Tetramethyl-butyl)-phenoxymethyl)-4,5-dihydro-oxazol-2-ylamine The title compound was prepared from (S)-2-(4-(1,1,3,3-tetramethyl-butyl)-phenoxymethyl)-oxirane employing the procedures as set forth in Step 2 of Example 1.

$C_{18}H_{28}N_2O_2$ (304.22), LCMS (ESI): 305.2 (M$^+$+H).

$^1$H NMR (CDCl$_3$, 300 MHz), δ 7.25 (d, 2H), 6.86 (d, 2H), 4.92 (m, 1H), 4.04 (AB-m, 2H), 3.92 (dd, 1H), 3.62 (dd, 1H), 2.19 (v. br., 2H), 1.70 (s, 2H), 1.34 (s, 6H), 0.71 (s, 9H).

Step 3: 2(S)-[4-(1,1,3,3-Tetramethyl-butyl)-phenoxymethyl]-2,3-dihydro-oxazolo[3,2-a]pyrimidin-7-one The title compound was prepared from (S)-5-(4-(1,1,3,3-tetramethyl-butyl)-phenoxymethyl)-4,5-dihydro-oxazol-2-ylamine employing the procedures as set forth in Step 3 of Example 1. [α]$_D^{25}$ –43.52 (c 0.551, CHCl$_3$).

$C_{21}H_{28}N_2O_3$ (356.21), LCMS (ESI): 357.18 (M$^+$+H).

$^1$H NMR (CDCl$_3$, 300 MHz), δ 7.28(d, 2H), 7.22 (s, 1H), 6.79 (d, 2H), 6.10 (d, 1H), 5.26 (m, 1H), 4.22-4.39 (m, 4H), 1.70 (s, 2H), 1.34 (s, 6H), 0.70 (s, 9H).

Example 28

2(S)-(4-Cyclohexyl-phenoxymethyl)-2,3-dihydro-oxazolo[3,2-a]pyrimidin-7-one

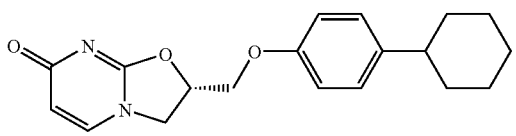 [SMILES: O=c1ccn2c(n1)O[C@H](COc1ccc(C3CCCCC3)cc1)C2]

Step 1: (S)-2-(4-Cyclohexyl-phenoxymethyl)-oxirane

The title compound was prepared from 4-cyclohexyl-phenol and R-epichlorohydrin employing the procedures as set forth in Step 1 of Example 1.

$C_{15}H_{20}O_2$ (232.15), LCMS (ESI): 274.19 (M$^+$+H+CH$_3$CN).

$^1$H NMR (CDCl$_3$, 300 MHz), δ 7.12 (d, 2H), 6.85 (d, 2H), 4.17 (dd, 1H), 3.96 (dd, 1H), 3.34 (m, 1H), 2.89 (t, 1H), 2.74 (dd, 1H), 2.44 (m, 1H), 1.78-1.85 (m, 5H), 1.31-1.43 (m, 5H).

Step 2: (S)-5-(4-Cyclohexyl-phenoxymethyl)-4,5-dihydro-oxazol-2-ylamine

The title compound was prepared from (S)-2-(4-cyclohexyl-phenoxymethyl)-oxirane employing the procedures as set forth in Step 2 of Example 1.

$C_{16}H_{22}N_2O_2$ (274.17), LCMS (ESI): 275.16 (M$^+$+H).

$^1$H NMR (CDCl$_3$, 300 MHz), δ 7.13 (d, 2H), 6.85 (dd, 2H), 4.91 (m, 1H), 4.2 (v. br., 2H), 4.05 (AB-m, 2H), 3.91 (dd, 1H), 3.61 (dd, 1H), 2.45 (br.s, 1H), 1.17-1.93 (m, 10H).

Step 3: 2(S)-(4-Cyclohexyl-phenoxymethyl)-2,3-dihydro-oxazolo[3,2-a]pyrimidin-7-one The title compound was prepared from (S)-5-(4-cyclohexyl-phenoxymethyl)-4,5-dihydro-oxazol-2-ylamine employing the procedures as set forth in Step 3 of Example 1.

[α]$_D^{25}$ –56.40 (c 0.5, CHCl$_3$).

$C_{19}H_{22}N_2O_3$ (326.16), LCMS (ESI): 327.16 (M$^+$+H).

$^1$H NMR (CDCl$_3$, 300 MHz), δ 7.23 (d, 1H), 7.14(d, 2H), 6.80 (d, 2H), 6.10 (d, 1H), 5.26 (m, 1H), 4.22-4.38 (m, 4H), 2.45 (br.s, 1H), 1.70-1.88 (m, 5H), 1.32-1.43 (m, 5H).

Example 29

(S)-2-(4-Trifluoromethyl-phenoxy-phenoxymethyl)-2,3-dihydro-oxazolo[3,2-a]pyrimidin-7-one

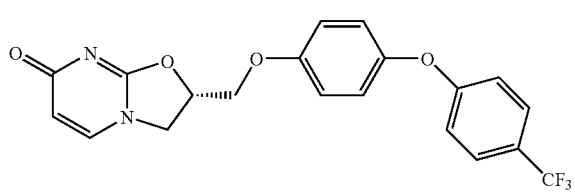 [SMILES: O=c1ccn2c(n1)O[C@H](COc1ccc(Oc3ccc(C(F)(F)F)cc3)cc1)C2]

The title compound was prepared from 4-(4-trifluoromethyl-phenoxy)-phenol and R-epichlorohydrin employing the procedures as set forth in Steps 1 through 3 of Example 1.

[α]$_D^{25}$ –31.20 (c 0.5, CHCl$_3$).

$C_{20}H_{15}F_3N_2O_4$ (404.10), LCMS (ESI): 405.09 (M$^+$+H).

$^1$H NMR (CDCl$_3$, 300 MHz), δ 7.55 (d, 2H), 7.26 (d, 1H), 7.00 (m, 4H), 6.90 (d, 2H), 6.11 (d, 1H), 5.29 (br.s, 1H), 4.24-4.44 (m, 4H).

Example 30

(S)-2-(4-Phenoxy-phenoxymethyl)-2,3-dihydro-oxazolo[3,2-a]pyrimidin-7-one

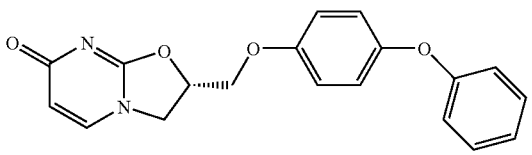 [SMILES: O=c1ccn2c(n1)O[C@H](COc1ccc(Oc3ccccc3)cc1)C2]

The title compound was prepared from 4-phenoxy-phenol and R-epichlorohydrin employing the procedures as set forth in Steps 1 through 3 of Example 1. $[\alpha]_D^{25}$ −0.60 (c 0.503, DMSO).
$C_{19}H_{16}N_2O_4$, LCMS (ESI): 337.11 (M⁻+H).
$^1$H NMR (DMSO-$d_6$, 300 MHz), δ 7.76 (d, 1H), 7.35 (d, 2H), 7.07 (t, 1H), 6.99 (s, 4H), 6.92 (d, 2H), 5.82 (d, 1H), 5.34 (br.s, 1H), 4.25-4.45 (m, 3H), 4.12 (AB-m, 1H).

Example 31

(S)-2-(Benzothiazol-2-yloxymethyl)-2,3-dihydro-oxazolo[3,2a]pyrimidin-7-one

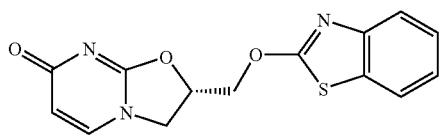 [SMILES: O=c1ccn2c(n1)O[C@H](COc1nc3ccccc3s1)C2]

The title compound was prepared from benzothiazol-2-ol and R-epichlorohydrin employing the procedures as set forth in Steps 1 through 3 of Example 1. $[\alpha]_D^{25}$ −45.80 (c 0.5, DMSO).
$C_{14}H_{11}N_3O_3S$ (301.05), LCMS (ESI): 302.06 (M⁺+H).
$^1$H NMR (DMSO-$d_6$, 300 MHz), δ 7.74 (d, 1H), 7.69 (d, 1H), 7.53 (d, 1H), 7.40 (t, 1H), 7.24 (t, 1H), 5.80 (d, 1H), 5.30 (br.s, 1H), 4.30-4.58 (m, 3H), 4.08 (AB-m, 1H).

Example 32

(S)-2-[4-(2-Oxo-pyrrolidin-1-yl)-phenoxymethyl]-2,3-dihydro-oxazolo[3,2-a]pyrimidin-7-one

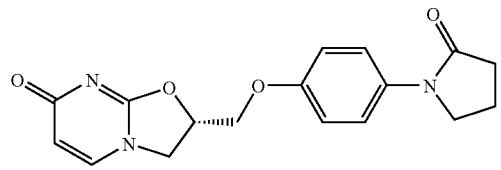 [SMILES: O=C1CCCN1c1ccc(OC[C@@H]2Cn3ccc(=O)nc3O2)cc1]

The title compound was prepared from 4-(2-oxo-pyrrolidin-1-yl)-phenol and R-epichlorohydrin employing the procedures as set forth in Steps 1 through 3 of Example 1.
$[\alpha]_D^{25}$ −9.47 (c 0.507, DMSO).
$C_{17}H_{17}N_3O_4$ (327.12), LCMS (ESI): 328.16 (M⁺+H).
$^1$H NMR (DMSO-$d_6$, 300 MHz), δ 7.76 (d, 1H), 7.57 (d, 2H), 6.95 (d, 2H), 5.82 (d, 1H), 5.33 (br.s, 1H), 4.24-4.44 (m, 3H), 4.11 (AB-m, 1H), 3.79 (t, 2H), 2.46 (t, 2H), 2.04 (m, 2H).

Example 33

(S)-2-(2,5-Diphenyl-thiazol-4-yloxymethyl)-2,3-dihydro-oxazolo[3,2-a]pyrimidin-7-one

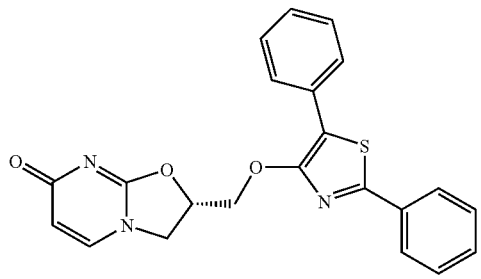 [SMILES: O=c1ccn2c(n1)O[C@H](COc1nc(-c3ccccc3)sc1-c1ccccc1)C2]

The title compound was prepared from 2,5-diphenyl-thiazol-4-ol and R-epichlorohydrin employing the procedures as set forth in Steps 1 through 3 of Example 1.
$[\alpha]_D^{25}$ +39.93 (c 0.503, DMSO).
$C_{22}H_{17}N_3O_3S$ (403.10), LCMS (ESI): 404.08 (M⁺+H).
$^1$H NMR (DMSO-$d_6$, 300 MHz), δ 7.95 (m, 2H), 7.78 (d, 1H), 7.52 (m, 5H), 7.32 (m, 2H), 7.25 (d, 1H), 5.86 (d, 1H), 5.46 (br.s, 1H), 4.83 (b.s, 2H), 4.46 (t, 1H), 4.27 (AB-m, 1H).

Example 34

(S)-2-(4-tert-Butoxy-phenoxymethyl)-2,3-dihydro-oxazolo[3,2-a]pyrimidin-7-one

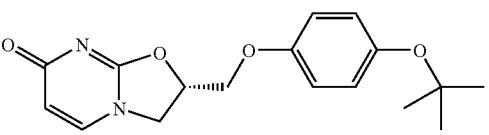 [SMILES: CC(C)(C)Oc1ccc(OC[C@@H]2Cn3ccc(=O)nc3O2)cc1]

The title compound was prepared from 4-tert-butoxy-phenol and R-epichlorohydrin employing the procedures as set forth in Steps 1 through 3 of Example 1. $[\alpha]_D^{25}$ −45.05 (c 0.5, CHCl₃).
$C_{17}H_{20}N_2O_4$ (316.14), LCMS (ESI): 317.11 (M⁺+H).
$^1$H NMR (DMSO-$d_6$, 300 MHz), δ 7.76 (d, 1H), 6.87 (m, 4H), 5.82 (d, 1H), 5.31 (br.s, 1H), 4.21-4.43 (m, 3H), 4.11 (AB-m, 1H), 1.23 (s, 9H).

Example 35

(S)-2-(4-Pentafluorosulfur-phenoxymethyl)-2,3-dihydro-oxazolo[3,2a]pyrimidin-7-one

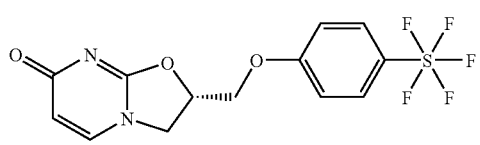

The title compound was prepared from 4-pentafluorosulfur-phenol and R-epichlorohydrin employing the procedures as set forth in Steps 1 through 3 of Example 1.
$C_{13}H_{11}F_5N_2O_3S$ (370.04), LCMS (ESI): 371.02 (M⁺+H).

¹H NMR (DMSO-d₆, 300 MHz), δ 7.85 (d, 2H), 7.77 (d, 1H), 7.13 (d, 2H), 5.83 (d, 1H), 5.37 (br.s, 1H), 4.39-4.49 (m, 3H), 4.12 (m, 1H).

Example 36

2-[4-(4-tert-Butyl-cyclohexyl)-phenoxymethyl]-2,3-dihydro-oxazolo[3,2-a]pyrimidin-7-one

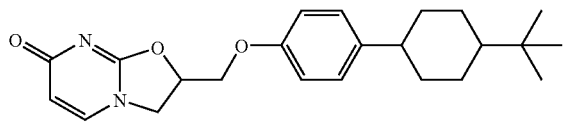 [SMILES: CC(C)(C)C1CCC(c2ccc(OCC3Cn4ccc(=O)nc4O3)cc2)CC1]

Step 1: [4-(4-tert-Butyl-cyclohexyl)-phenoxymethyl]-oxirane

The title compound was prepared as a 65:35 mixture of two isomers starting from 4-tert-butyl-cyclohexyl-phenol and epichlorohydrin employing the procedures as set forth in Step 1 of Example 2.

$C_{19}H_{28}O_2$ (288.20), LCMS (ESI): 330.28 (M⁺+H+CH₃CN).

Step 2: 5-[4-(4-tert-Butyl-cyclohexyl)-phenoxymethyl]-4,5-dihydro-oxazol-2-ylamine The title compound was prepared as a 65:35 mixture of two isomers from [4-(4-tert-butyl-cyclohexyl)-phenoxymethyl]-oxirane employing the procedures as set forth in Step 2 of Example 1.

$C_{20}H_{30}N_2O_2$ (330.23), LCMS (ESI): 331.25 (M⁺+H).

Step 3: 2-[4-(4-tert-Butyl-cyclohexyl)-phenoxymethyl]-2,3-dihydro-oxazolo[3,2-a]pyrimidin-7-one The title compound was prepared from 5-[4-(4-tert-butyl-cyclohexyl)-phenoxymethyl]-4,5-dihydro-oxazol-2-ylamine employing the procedures as set forth in Step 3 of Example 1.

$C_{23}H_{30}N_2O_3$ (382.22), LCMS (ESI): 383.25 (M⁺+H)
¹H NMR (CDCl₃, 300 MHz), δ 7.24 (d, 1H), 7.15 (d, 2H), 6.81 (d, 1H), 6.10 (d, 1H), 5.26 (m, 1H), 4.21-4.41 (m, 4H), 2.86 (q, 1H), 1.21 (d, 6H).

Example 37

2-(3,4-Dimethyl-phenoxymethyl)-2,3-dihydro-oxazolo[3,2-a]pyrimidin-7-one

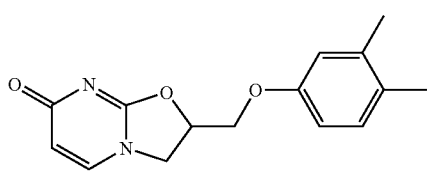 [SMILES: Cc1ccc(OCC2Cn3ccc(=O)nc3O2)cc1C]

Step 1: 2-(3,4-Dimethyl-phenoxymethyl)-oxirane

The title compound was prepared from 3,4-dimethyl-phenol and epichlorohydrin employing the procedures as set forth in Step 1 of Example 2.

$C_{11}H_{14}O_2$ (178.09), LCMS (ESI): 220.14 (M⁺+H+CH₃CN).

¹H NMR (CDCl₃, 300 MHz), δ 7.03 (d, 1H), 6.74 (d, 1H), 6.66 (dd, 1H), 4.17 (dd, 1H), 3.95 (dd, 1H), 3.34 (m, 1H), 2.89 (t, 1H)), 2.74 (dd, 1H), 2.23 (s, 3H), 2.19(s, 3H).

Step 2: 5-(3,4-Dimethyl-phenoxymethyl)-4,5-dihydro-oxazol-2-ylamine

The title compound was prepared from 2-(3,4-dimethyl-phenoxymethyl)-oxirane employing the procedures as set forth in Step 2 of Example 1.

$C_{12}H_{16}N_2O_2$ (220.12), LCMS (ESI): 221.10 (M⁺+H).

¹H NMR (CDCl₃, 300 MHz), δ 7.03 (d, 1H), 6.74 (s, 1H), 6.66 (d, 1H), 4.90 (m, 1H), 4.2 (v. br., 2H), 4.03 (AB-m, 2H), 3.92 (dd, 1H), 3.60 (dd, 1H), 2.23 (s, 3H), 2.19 (s, 3H).

Step 3: 2-(3,4-Dimethyl-phenoxymethyl)-2,3-dihydro-oxazolo[3,2-a]pyrimidin-7-one The title compound was prepared from 5-(3,4-dimethyl-phenoxymethyl)-4,5-dihydro-oxazol-2-ylamine employing the procedures as set forth in Step 3 of Example 1.

$C_{15}H_{16}N_2O_3$ (272.11), LCMS (ESI): 273.13 (M⁺+H).

¹H NMR (DMSO-d₆, 300 MHz), δ 7.75 (d, 1H), 7.04 (d, 1H), 6.75 (s, 1H), 6.66 (d, 1H), 5.82 (d, 1H), 5.31 (m, 1H), 4.38 (t, 1H), 4.26 (AB-m, 2H), 4.09 (dd, 1H), 2.18 (s, 3H), 2.14 (s, 3H).

Example 38

2-(4-Isopropyl-phenoxymethyl)-2,3-dihydro-oxazolo[3,2-a]pyrimidin-7-one

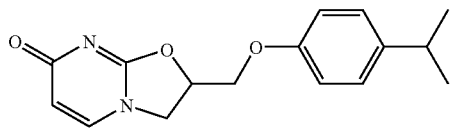 [SMILES: CC(C)c1ccc(OCC2Cn3ccc(=O)nc3O2)cc1]

Step 1: 2-(4-Isopropyl-phenoxymethyl)-oxirane

The title compound was prepared from 4-isopropyl-phenol and epichlorohydrin employing the procedures as set forth in Step 1 of Example 2.

$C_{12}H_{16}O_2$ (192.11), LCMS (ESI): 234.16 (M⁺+H+CH₃CN).

¹H NMR (CDCl₃, 300 MHz), δ 7.15 (d, 2H), 6.86 (d, 2H), 4.19 (dd, 1H), 3.97 (dd, 1H), 3.35 (m, 1H), 2.83-2.94 (m, 2H)), 2.78 (dd, 1H), 1.24 (d, 6H).

Step 2: 5-(4-Isopropyl-phenoxymethyl)-4,5-dihydro-oxazol-2-ylamine

The title compound was prepared from 2-(4-isopropyl-phenoxymethyl)-oxirane employing the procedures as set forth in Step 2 of Example 1.

$C_{13}H_{18}N_2O_2$ (234.13), LCMS (ESI): 235.16 (M⁺+H).

$^1$H NMR (CDCl$_3$, 300 MHz), δ 7.15 (d, 2H), 6.86 (d, 2H), 4.93 (m, 1H), 4.2 (v. br., 2H), 4.04 (AB-m, 2H), 3.92 (dd, 1H), 3.60 (dd, 1H), 2.86 (q, 1H), 1.22 (d, 6H).

Step 3: 2-(4-Isopropyl-phenoxymethyl)-2,3-dihydro-oxazolo[3,2-a]pyrimidin-7-one

The title compound was prepared from 5-(4-isopropyl-phenoxymethyl)-4,5-dihydro-oxazol-2-ylamine employing the procedures as set forth in Step 3 of Example 1.

C$_{16}$H$_{18}$N$_2$O$_3$ (286.13), LCMS (ESI): 287.14 (M$^+$+H).

$^1$H NMR (CDCl$_3$, 300 MHz), δ 7.24 (d, 1H), 7.15 (d, 2H), 6.81(d, 2H), 6.10 (d, 1H), 5.26 (m, 1H), 4.21-4.41 (m, 4H), 2.86 (q, 1H), 1.21 (d, 6H).

Example 39

2-(3-tert-Butyl-phenoxymethyl)-2,3-dihydro-oxazolo[3,2-a]pyrimidin-7-one

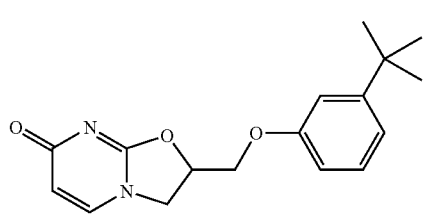 [SMILES: CC(C)(C)c1cccc(OCC2Cn3ccc(=O)nc3O2)c1]

Step 1: 2-(3-tert-Butyl-phenoxymethyl)-oxirane

The title compound was prepared from 3-tert-butyl-phenol and epichlorohydrin employing the procedures as set forth in Step 1 of Example 2.

C$_{13}$H$_{18}$O$_2$ (206.13), LCMS (ESI): 248.17 (M$^+$+H+CH$_3$CN).

$^1$H NMR (CDCl$_3$, 300 MHz), δ 7.22 (d, 1H), 6.97-7.03 (m, 2H), 6.72 (dd, 1H), 4.21 (dd, 1H), 3.99 (dd, 1H), 3.38 (m, 1H), 2.92 (t, 1H), 2.78 (dd, 1H), 1.31 (s, 9H).

Step 2: 5-(3-tert-Butyl-phenoxymethyl)-4,5-dihydro-oxazol-2-ylamine

The title compound was prepared from 2-(3-tert-butyl-phenoxymethyl)-oxirane employing the procedures as set forth in Step 2 of Example 1.

C$_{14}$H$_{20}$N$_2$O$_2$ (248.15), LCMS (ESI): 249.17 (M$^+$+H).

$^1$H NMR (CDCl$_3$, 300 MHz), δ 7.22 (d, 1H), 7.02 (d, 1H), 6.98 (s, 1H), 6.72 (d, 1H), 4.93 (m, 1H), 4.2 (v. br., 2H), 4.06 (AB-m, 2H), 3.94 (dd, 1H), 3.62 (dd, 1H), 1.35 (s, 9H).

Step 3: 2-(3-tert-Butyl-phenoxymethyl)-2,3-dihydro-oxazolo[3,2-a]pyrimidin-7-one The title compound was prepared from 5-(3-tert-butyl-phenoxymethyl)-4,5-dihydro-oxazol-2-ylamine employing the procedures as set forth in Step 3 of Example 1.

C$_{17}$H$_{20}$N$_2$O$_3$ (286.13), LCMS (ESI): 301.15 (M$^+$+H).

$^1$H NMR (CDCl$_3$, 300 MHz), δ 7.20-7.27 (m, 2H), 7.06 (d, 1H), 6.90 (s, 1H), 6.69 (d, 1H), 6.10 (d, 1H), 5.29 (m, 1H), 4.23-4.42 (m, 4H), 1.30 (s, 9H).

Example 40

2-(4-Chloro-phenoxymethyl)-2,3-dihydro-oxazolo[3,2-a]pyrimidin-7-one

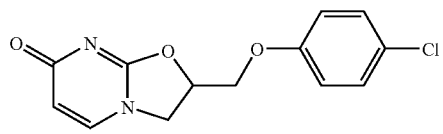

Step 1: 2-(4-Chloro-phenoxymethyl)-oxirane

The title compound was prepared from 4-chlorophenol and epichlorohydrin employing the procedures as set forth in Step 1 of Example 2.

C$_9$H$_9$ClO$_2$ (184.02), LCMS (ESI): 226.07 (M$^+$+H+CH$_3$CN).

$^1$H NMR (CDCl$_3$, 300 MHz), δ 7.25 (d, 2H), 6.86 (d, 2H), 4.22 (dd, 1H), 3.92 (dd, 1H), 3.35 (m, 1H), 2.91 (t, 1H), 2.78 (dd, 1H).

Step 2: 5-(4-Choloro-phenoxymethyl)-4,5-dihydro-oxazol-2-ylamine

The title compound was prepared from 2-(4-chloro-phenoxymethyl)-oxirane employing the procedures as set forth in Step 2 of Example 1.

C$_{10}$H$_{11}$ClN$_2$O$_2$ (226.05), LCMS (ESI): 227.06 (M$^+$+H).

$^1$H NMR (CDCl$_3$, 300 MHz), δ 7.24 (d, 2H), 6.85 (d, 2H), 4.91 (m, 1H), 4.2 (v. br. 2H) 4.03 (AB-m, 2H), 3.93 (dd, 1H), 3.61(dd, 1H).

Step 3: 2-(4-Chloro-phenoxymethyl)-2,3-dihydro-oxazolo[3,2-a]pyrimidin-7-one

The title compound was prepared from 5-(4-chloro-phenoxymethyl)-4,5-dihydro-oxazol-2-ylamine employing the procedures as set forth in Step 3 of Example 1.

C$_{13}$H$_{11}$ClN$_2$O$_3$ (278.05), LCMS (ESI): 279.06 (M$^+$+H).

$^1$H NMR (CDCl$_3$, 300 MHz), δ 7.22-7.30 (m, 3H), 6.81 (d, 2H), 6.09 (d, 1H), 5.28 (m, 1H), 4.20-4.44 (m, 4H).

Example 41

2-(4-Bromo-phenoxymethyl)-2,3-dihydro-oxazolo[3,2-a]pyrimidin-7-one

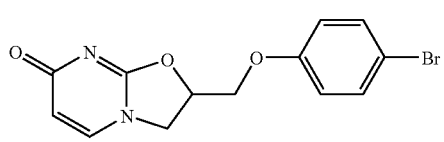

Step 1: 2-(4-Bromo-phenoxymethyl)-oxirane

The title compound was prepared from 4-bromophenol and epichlorohydrin employing the procedures as set forth in Step 1 of Example 2.

C₉H₉BrO₂ (227.97), LCMS (ESI): 270.03 (M⁺+H+ CH₃CN).
¹H NMR (CDCl₃, 300 MHz), δ 7.25 (d, 2H), 6.85 (d, 2H), 4.22 (dd, 1H), 3.92 (dd, 1H), 3.35 (m, 1H), 2.91 (t, 1H), 2.76 (dd, 1H).

Step 2: 5-(4-Bromo-phenoxymethyl)-4,5-dihydro-oxazol-2-ylamine

The title compound was prepared from 2-(4-bromo-phenoxymethyl)-oxirane employing the procedures as set forth in Step 2 of Example 1.
C₁₀H₁₁BrN₂O₂ (270), LCMS (ESI): 271.02 (M⁺+H).
¹H NMR (CDCl₃, 300 MHz), δ 7.39 (d, 2H), 6.81 (d, 2H), 4.91 (m, 1H), 4.2 (v. br., 2H), 4.03 (AB-m, 2H), 3.94 (dd, 1H), 3.61 (dd, 1H).

Step 3: 2-(4-Bromo-phenoxymethyl)-2,3-dihydro-oxazolo[3,2-a]pyrimidin-7-one

The title compound was prepared from 5-(4-bromo-phenoxymethyl)-4,5-dihydro-oxazol-2-ylamine employing the procedures as set forth in Step 3 of Example 1.
C₁₃H₁₁BrN₂O₃ (321.99), LCMS (ESI): 323.01 (M⁺+H).
¹H NMR (CDCl₃, 300 MHz), δ 7.40 (d, 2H), 7.25 (d, 1H), 6.77 (d, 2H), 6.09 (d, 1H), 5.28 (m, 1H), 4.20-4.44 (m, 4H).

Example 42

2-(4-Trifluoromethyl-phenoxymethyl)-2,3-dihydro-oxazolo[3,2-a]pyrimidin-7-one

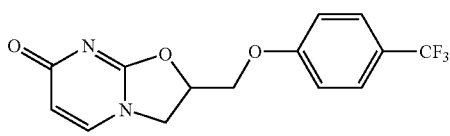

Step 1: 2-(4-Trifluoromethyl-phenoxymethyl)-oxirane

The title compound was prepared from 4-trifluromethyl-phenol and epichlorohydrin employing the procedures as set forth in Step 1 of Example 2.
¹H NMR (CDCl₃, 300 MHz), δ 7.25 (d, 2H), 6.68 (d, 2H), 4.22 (dd, 1H), 3.91 (dd, 1H), 3.35 (m, 1H), 2.91 (t, 1H), 2.76 (dd, 1H).

Step 2: 5-(4-Trifluoromethyl-phenoxymethyl)-4,5-dihydro-oxazol-2-ylamine

The title compound was prepared from 2-(4-trifluoromethyl-phenoxymethyl)-oxirane employing the procedures as set forth in Step 2 of Example 1.
C₁₁H₁₁F₃N₂O₂ (260.07), LCMS (ESI): 261.08 (M⁺+H).
¹H NMR (CDCl₃, 300 MHz), δ 7.56 (d, 2H), 6.99 (d, 2H), 4.94 (m, 1H), 4.2 (v. br., 2H), 4.11 (AB-m, 2H), 3.96 (dd, 1H), 3.64 (dd, 1H).

Step 3: 2-(4-Trifluoromethyl-phenoxymethyl)-2,3-dihydro-oxazolo[3,2-a]pyrimidin-7-one The title compound was prepared from 5-(4-trifluoromethyl-phenoxymethyl)-4,5-dihydro-oxazol-2-ylamine employing the procedures as set forth in Step 3 of Example 1.

C₁₄H₁₁F₃N₂O₃ (312.07), LCMS (ESI): 313.07 (M⁺+H).
¹H NMR (CDCl₃, 300 MHz), δ 7.57 (d, 2H), 7.26 (d, 1H), 6.96 (d, 2H), 6.10 (d, 1H), 5.33 (m, 1H), 4.27-4.46 (m, 4H).

Example 43

2-(2-Chloro-4-(1,1-dimethyl-propyl)-phenoxymethyl)-2,3-dihydro-oxazolo[3,2-a]pyrimidin-7-one

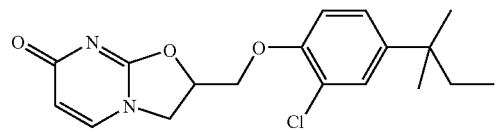 [SMILES: CCC(C)(C)c1ccc(OCC2Cn3ccc(=O)nc3O2)c(Cl)c1]

Step 1: 2-(2-Chloro-4-(1,1-dimethyl-propyl)-phenoxymethyl)-oxirane

The title compound was prepared from 2-chloro-4-(1,1-dimethyl-propyl)-phenol and epichlorohydrin employing the procedures as set forth in Step 1 of Example 2.
C₁₄H₁₉ClO₂ (254.11), LCMS (ESI): 296.13 (M⁺+H+ CH₃CN).
¹H NMR (CDCl₃, 300 MHz), δ 7.31 (s, 1H), 7.14 (d, 1H), 6.89 (d, 1H), 4.26 (dd, 1H), 4.05 (dd, 1H), 3.38 (m, 1H), 2.91 (t, 1H), 2.81 (dd, 1H), 1.59 (m, 2H), 1.24 (s, 6H), 0.67 (t, 3H).

Step 2: 5-(2-Chloro-4-(1,1-dimethyl-propyl)-phenoxymethyl)-4,5-dihydro-oxazol-2-ylamine The title compound was prepared from 2-(2-chloro-4-(1,1-dimethyl-propyl)-phenoxymethyl)-oxirane employing the procedures as set forth in Step 2 of Example 1.
C₁₅H₂₁ClN₂O₂ (296.13), LCMS (ESI): 297.42 (M⁺+H).

Step 3: 2-(2-Chloro-4-(1,1-dimethyl-propyl)-phenoxymethyl)-2,3-dihydro-oxazolo[3,2-a]pyrimidin-7-one The title compound was prepared from 5-(2-chloro-4-(1,1-dimethyl-propyl)-phenoxymethyl)-4,5-dihydro-oxazol-2-ylamine employing the procedures as set forth in Step 3 of Example 1.
C₁₈H₂₁ClN₂O₃ (348.12), LCMS (ESI): 349.12 (M⁺+H).
¹H NMR (CDCl₃, 300 MHz), δ 7.28 (d, 2H), 7.16 (d, 1H), 6.87 (d, 1H), 6.08 (d, 1H), 5.29 (m, 1H), 4.34-4.47 (m, 3H), 4.26 (dd, 1H), 1.53-1.65 (m, 2H), 1.24 (s, 6H), 0.66 (t, 3H).

Example 44

2-(Biphenyl-4-oxymethyl)-2,3-dihydro-oxazolo[3,2-a]pyrimidin-7-one

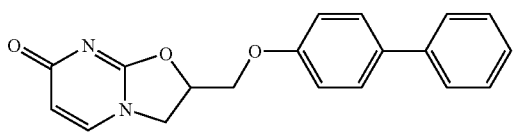 [SMILES: O=c1ccn2c(n1)OC(COc1ccc(-c3ccccc3)cc1)C2]

Step 1: 2-(Biphenyl-4-oxymethyl)-oxirane

The title compound was prepared from 4-biphenol and epichlorohydrin employing the procedures as set forth in Step 1 of Example 2.

$C_{15}H_{14}O_2$ (226.09), LCMS (ESI): 268.15 (M$^+$+H+ CH$_3$CN).

$^1$H NMR (CDCl$_3$, 300 MHz), δ 7.49-7.58 (m, 3H), 7.42 (t, 2H), 7.26-7.34 (m, 2H), 7.01 (d, 2H), 4.26 (dd, 1H), 4.02 (dd, 1H), 3.39 (m, 1H), 2.93 (t, 1H), 2.79 (dd, 1H).

Step 2: 5-(Biphenyl-4-oxymethyl)-4,5-dihydro-oxazol-2-ylamine

The title compound was prepared from 2-(biphenyl-4-oxymethyl)-oxirane employing the procedures as set forth in Step 2 of Example 1.

$C_{16}H_{16}N_2O_2$ (268.12), LCMS (ESI): 269.10 (M$^+$+H).

$^1$H NMR (CDCl$_3$, 300 MHz), δ 7.26-7.58 (m, 7H), 6.99 (d, 2H), 4.95 (m, 1H), 4.2 (v. br., 2H), 4.10 (AB-m, 2H), 3.95 (dd, 1H), 3.64 (dd, 1H).

Step 3: 2-(Biphenyl-4-oxymethyl)-2,3-dihydro-oxazolo[3,2-a]pyrimidin-7-one

The title compound was prepared from 5-(biphenyl-4-oxymethyl)-4,5-dihydro-oxazol-2-ylamine employing the procedures as set forth in Step 3 of Example 1.

$C_{19}H_{16}N_2O_3$ (320.11), LCMS (ESI): 321.15 (M$^+$+H).

$^1$H NMR (DMSO-d$_6$, 300 MHz), δ 7.78 (d, 1H), 7.26 (d, 4H), 7.42 (t, 2H), 7.32 (t, 1H), 7.04 (d, 2H), 5.84 (d, 1H), 5.36 (m, 1H), 4.32-4.47 (m, 3H), 4.13 (dd, 1H).

Example 45

2-(5,6,7,8-Tetrahydro-naphthalen-2-yloxymethyl)-2,3-dihydro-oxazolo[3,2-a]pyrimidin-7-one

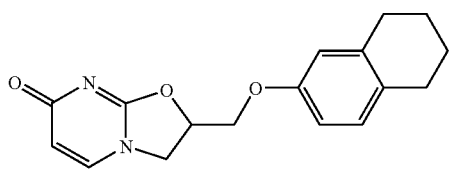 [SMILES: O=c1ccn2c(n1)OC(COc1ccc3c(c1)CCCC3)C2]

Step 1: 2-(5,6,7,8-Tetrahydro-naphthalen-2-yloxymethyl)-oxirane

The title compound was prepared from 5,6,7,8-tetrahydro-naphthalen-2-ol and epichlorohydrin employing the procedures as set forth in Step 1 of Example 2.

$C_{13}H_{16}O_2$ (204.11), LCMS (ESI): 246.1 (M$^+$+H+ CH$_3$CN).

$^1$H NMR (CDCl$_3$, 300 MHz), δ 6.97 (d, 1H), 6.69 (d, 1H), 6.62 (s, 1H), 4.16 (dd, 1H), 3.95 (dd, 1H), 3.33 (m, 1H), 2.89 (t, 1H), 2.64-2.76 (m, 5H), 1.76 (br. s, 4H).

Step 2: 5-(5,6,7,8-Tetrahydro-naphthalen-2-yloxymethyl)-4,5-dihydro-oxazol-2-ylamine The title compound was prepared from 2-(5,6,7,8-tetrahydro-naphthalen-2-yloxymethyl)-oxirane employing the procedures as set forth in Step 2 of Example 1.

$C_{14}H_{18}N_2O_2$ (246.13), LCMS (ESI): 247.13 (M$^+$+H).

$^1$H NMR (CDCl$_3$, 300 MHz), δ 6.97 (d, 1H), 6.68 (d, 1H), 6.63 (s, 1H), 4.92 (m, 1H), 4.2 (v. br., 2H), 4.00 (AB-m, 2H), 3.92 (dd, 1H), 3.60 (dd, 1H), 2.71 (m, 4H), 1.78 (br. s, 4H).

Step 3: 2-(5,6,7,8-Tetrahydro-naphthalen-2-yloxymethyl)-2,3-dihydro-oxazolo[3,2-a]pyrimidin-7-one The title compound was prepared from 5-(5,6,7,8-tetrahydro-naphthalen-2-yloxymethyl)-4,5-dihydro-oxazol-2-ylamine employing the procedures as set forth in Step 3 of Example 1.

$C_{17}H_{18}N_2O_3$ (298.13), LCMS (ESI): 299.13 (M$^+$+H).

$^1$H NMR (CDCl$_3$, 300 MHz), δ 7.24 (d, 1H), 6.98 (d, 1H), 6.62 (d, 1H), 6.58 (s, 1H), 6.08 (d, 1H), 5.25 (m, 1H), 4.18-4.40 (m, 4H), 2.71 (m, 4H), 1.77 (m, 4H).

Example 46

2-(4-(1,1-Dimethyl-propyl-phenoxymethyl)-2,3-dihydro-oxazolo[3,2-a]pyrimidin-7-one

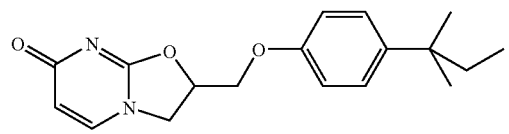 [SMILES: CCC(C)(C)c1ccc(OCC2Cn3ccc(=O)nc3O2)cc1]

Step 1: 2-(4-(1,1-Dimethyl-propyl)-phenoxymethyl)-oxidant

The title compound was prepared from 4-(1,1-dimethyl-propyl)-phenol and epichlorohydrin employing the procedures as set forth in Step 1 of Example 2.

$C_{14}H_{20}O_2$ (220.15), LCMS (ESI): 262.23 (M$^+$+H+ CH$_3$CN).

$^1$H NMR (CDCl$_3$, 300 MHz), δ 7.23 (d, 2H), 6.86 (d, 2H), 4.18 (dd, 1H), 3.97 (dd, 1H), 3.34 (m, 1H), 2.90 (t, 1H), 2.75 (dd, 1H), 1.61 (m, 2H), 1.26 (s, 6H), 0.67 (t, 3H).

Step 2: 5-(4-(1,1-Dimethyl-propyl)-phenoxymethyl)-4,5-dihydro-oxazol-2-ylamine The title compound was prepared from 2-(4-(1,1-dimethyl-propyl)-phenoxymethyl)-oxirane employing the procedures as set forth in Step 2 of Example 1.

$C_{15}H_{22}N_2O_2$ (262.17), LCMS (ESI): 263.15 (M$^+$+H).

$^1$H NMR (CDCl$_3$, 300 MHz), δ 7.23 (d, 2H), 6.86 (d, 2H), 4.92 (m, 1H), 4.05 (AB-m, 2H), 3.92 (dd, 1H), 3.61 (dd, 1H), 3.0 (v. br., 2H), 1.61 (dd, 2H), 1.25 (s, 6H), 0.67 (t, 3H).

Step 3: 2-(4-(1,1-Dimethyl-propyl)-phenoxymethyl)-2,3-dihydro-oxazolo[3,2-a]pyrimidin-7-one The title compound was prepared from 5-(4-(1,1-dimethyl-propyl)-phenoxymethyl)-4,5-dihydro-oxazol-2-ylamine employing the procedures as set forth in Step 3 of Example 1.

$C_{18}H_{22}N_2O_3$ (314.16), LCMS (ESI): 315.15 (M$^+$+H).

¹H NMR (CDCl₃, 300 MHz), δ 7.25(d, 2H), 7.23 (s, 1H), 6.81 (d, 2H), 6.08 (d, 1H), 5.27 (m, 1H), 4.22-4.40 (m, 4H), 1.55-1.65 (m, 2H), 1.25 (s, 6H), 0.66 (t, 3H).

Example 47

2-(4-Cyclopentyl-phenoxymethyl)-2,3-dihydro-oxazolo[3,2-a]pyrimidin-7-one

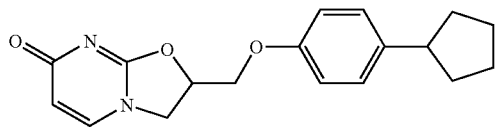 [SMILES: O=c1ccn2c(n1)OC(COc1ccc(C3CCCC3)cc1)C2]

Step 1: 2-(4-Cyclopentyl-phenoxymethyl)-oxirane

The title compound was prepared from 4-cyclopentyl-phenol and epichlorohydrin employing the procedures as set forth in Step 1 of Example 2.

C₁₄H₁₈O₂ (218.13), LCMS (ESI): 260 (M⁺H+CH₃CN).
¹H NMR (CDCl₃, 300 MHz), δ 7.17 (d, 2H), 6.86 (d, 2H), 4.17 (dd, 1H), 3.97 (dd, 1H), 3.35 (m, 1H), 2.85-3.00 (m, 2H), 2.75 (dd, 1H), 1.97-2.10 (m, 2H), 1.47-1.83 (m, 6H).

Step 2: 5-(4-Cyclopentyl-phenoxymethyl)-4,5-dihydro-oxazol-2-ylamine

The title compound was prepared from 2-(4-cyclopentyl-phenoxymethyl)-oxirane employing the procedures as set forth in Step 2 of Example 1.

C₁₅H₂₀N₂O₂ (260.15), LCMS (ESI): 261.6 (M⁺+H).
¹H NMR (CDCl₃, 300 MHz), δ 7.17 (d, 2H), 6.85 (d, 2H), 4.92 (m, 1H), 4.03 (AB-m, 2H), 3.91 (dd, 1H), 3.61 (dd, 1H), 3.4 (v. br., 2H), 2.93 (m, 1H), 2.03 (br. s, 2H), 1.44-1.86 (m, 6H).

Step 3: 2-(4-Cyclopentyl-phenoxymethyl)-2,3-dihydro-oxazolo[3,2-a]pyrimidin-7-one The title compound was prepared from 5-(4-cyclopentyl-phenoxymethyl)-4,5-dihydro-oxazol-2-ylamine employing the procedures as set forth in Step 3 of Example 1.

C₁₈H₂₀N₂O₃ (312.14), LCMS (ESI): 313.17 (M⁺+H).
¹H NMR (DMSO-d₆, 300 MHz), δ 7.75 (d, 1H), 7.16 (d, 2H), 6.85 (d, 2H), 5.82 (d, 1H), 5.31 (m, 1H), 4.39 (t, 1H), 4.29 (AB-m, 2H), 4.09 (dd, 1H), 2.91(m, 1H), 1.97 (m, 2H), 1.38-1.79 (m, 6H).

Example 48

2-(4-(1,1,3,3-Tetramethyl-butyl)-phenoxymethyl)-2,3-dihydro-oxazolo[3,2-a]pyrimidin-7-one

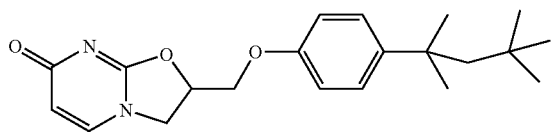 [SMILES: CC(C)(C)CC(C)(C)c1ccc(OCC2Cn3ccc(=O)nc3O2)cc1]

Step 1: 2-(4-(1,1,3,3-Tetramethyl-butyl)-phenoxymethyl)-oxirane

The title compound was prepared from 4-(1,1,3,3-tetramethyl-butyl)-phenol and epichlorohydrin employing the procedures as set forth in Step 1 of Example 2.

C₁₇H₂₆O₂ (262.19), LCMS (ESI): 304.3 (M⁺H+CH₃CN).
¹H NMR (CDCl₃, 300 MHz), δ 7.28 (d, 2H), 6.84 (d, 2H), 4.19 (dd, 1H), 3.98 (dd, 1H), 3.36 (m, 1H), 2.90 (t, 1H), 2.76 (dd, 1H), 1.71 (s, 2H), 1.35 (s, 6H), 0.72 (s, 9H).

Step 2: 5-(4-(1,1,3,3-Tetramethyl-butyl)-phenoxymethyl)-4,5-dihydro-oxazol-2-ylamine The title compound was prepared from 2-(4-(1,1,3,3-tetramethyl-butyl) -phenoxymethyl)-oxirane employing the procedures as set forth in Step 2 of Example 1.

C₁₈H₂₈N₂O₂ (304.22), LCMS (ESI): 305.2 (M⁺+H).
¹H NMR (CDCl₃, 300 MHz), δ 7.25 (d, 2H), 6.83 (d, 2H), 4.92 (m, 1H), 4.04 (AB-m, 2H), 3.9 (v. br., 2H), 3.92 (dd, 1H), 3.62 (dd, 1H), 1.70 (s, 2H), 1.34 (s, 6H), 0.71 (s, 9H).

Step 3: 2-(4-(1,1,3,3-Tetramethyl-butyl)-phenoxymethyl)-2,3-dihydro-oxazolo[3,2-a]pyrimidin-7-one The title compound was prepared from 5-(4-(1,1,3,3-tetramethyl-butyl) -phenoxymethyl)-4,5-dihydro-oxazol-2-ylamine employing the procedures as set forth in Step 3 of Example 1.

C₂₁H₂₈N₂O₃ (356.21), LCMS (ESI): 357.18 (M⁺+H).
¹H NMR (CDCl₃, 300 MHz), δ 7.28(d, 2H), 7.22 (s, 1H), 6.79 (d, 2H), 6.10 (d, 1H), 5.26 (m, 1H), 4.22-4.39 (m, 4H), 1.70 (s, 2H), 1.34 (s, 6H), 0.70 (s, 9H).

Example 49

2-(4-Tricyclo[3.3.1.13,7]decan-2-yl-phenoxymethyl)-2,3-dihydro-oxazolo[3,2-a]pyrimidin-7-one

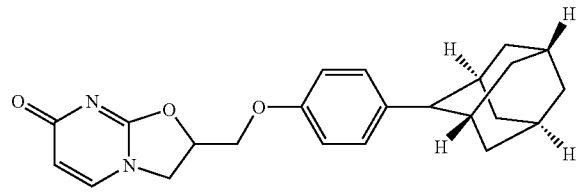 [SMILES: O=c1ccn2c(n1)OC(COc1ccc(C3[C@H]4C[C@@H]5C[C@@H](C[C@H]3C5)C4)cc1)C2]

Step 1:
2-(4-Tricyclo[3.3.1.13,7]decan-2-yl-phenoxymethyl)-oxirane

The title compound was prepared from 4-tricyclo[3.3.1.13,7]decan-2-yl-phenol and epichlorohydrin employing the procedures as set forth in Step 1 of Example 2.

C₁₉H₂₄O₂ (284.18), LCMS (ESI): 326.27 (M⁺H+CH₃CN).
¹H NMR (CDCl₃, 300 MHz), δ 7.27 (d, 2H), 6.87 (d, 2H), 4.16 (dd, 1H), 3.97 (dd, 1H), 3.34 (m, 1H), 2.89 (t, 1H), 2.74 (dd, 1H), 2.02-2.11 (m, 3H), 1.85-1.91 (m, 6H), 1.72-1.79 (m, 6H).

Step 2: 5-(4-Tricyclo[3.3.1.1³,⁷]decan-2-yl-phenoxymethyl)-4,5-dihydro-oxazol-2-ylamine The title compound was prepared from 2-(4-tricyclo[3.3.1.1³,⁷]decan-2-yl-phenoxymethyl)-oxirane employing the procedures as set forth in Step 2 of Example 1.
$C_{20}H_{26}N_2O_2$ (326.2), LCMS (ESI): 327.19 (M⁺+H).
¹H NMR (DMSO-$d_6$, 300 MHz), δ 7.25 (d, 2H), 6.87 (d, 2H), 5.88 (br., s, 2H), 4.74 (m, 1H), 3.89-4.05 (m, 3H), 3.69 (dd, 1H), 2.04 (br., s, 3H), 1.82 (br., s, 6H), 1.72 (br., s, 6H).

Step 3: 2-(4-Tricyclo[3.3.1.1³,⁷]decan-2-yl-phenoxymethyl)-2,3-dihydro-oxazolo[3,2-a]pyrimidin-7-one The title compound was prepared from 5-(4-tricyclo[3.3.1.1³,⁷]decan-2-yl-phenoxymethyl)-4,5-dihydro-oxazol-2-ylamine employing the procedures as set forth in Step 3 of Example 1.
$C_{23}H_{26}N_2O_3$ (378.48), LCMS (ESI): 379.18 (M⁺+H).
¹H NMR (DMSO-$d_6$, 300 MHz), δ 7.76 (d, 1H), 7.27 (d, 2H), 6.87 (d, 2H), 5.82 (d, 1H), 5.32 (m, 1H), 4.39 (t, 1H), 4.29 (AB-m, 2H), 4.09 (dd, 1H), 2.04(br.s, 3H), 1.82 (br.s, 6H), 1.72 (br.s, 6H).

Example 50

2-(4-(1-Methyl-1-phenyl-ethyl)-phenoxymethyl)-2,3-dihydro-oxazolo[3,2-a]pyrimidin-7-one

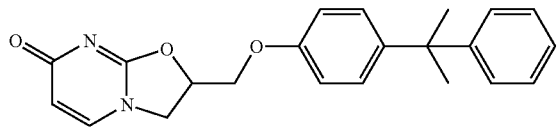 [SMILES: CC(C)(c1ccccc1)c1ccc(OCC2Cn3ccc(=O)nc3O2)cc1]

Step 1: 2-(4-(1-Methyl-1-phenyl-ethyl)-phenoxymethyl)-oxirane

The title compound was prepared from 4-(1-methyl-1-phenyl-ethyl)-phenol and epichlorohydrin employing the procedures as set forth in Step 1 of Example 2.
$C_{18}H_{20}O_2$ (268.15), LCMS (ESI): 310.23 (M⁺+H+CH₃CN).
¹H NMR (CDCl₃, 300 MHz), δ 7.12-7.28 (m, 7H), 6.82 (d, 2H), 4.17 (dd, 1H), 3.95 (dd, 1H), 3.33 (m, 1H), 2.88 (t, 1H), 2.73 (dd, 1H), 1.66 (s, 6H).

Step 2: 5-(4-(1-Methyl-1-phenyl-ethyl)-phenoxymethyl)-4,5-dihydro-oxazol-2-ylamine The title compound was prepared from 2-(4-(1-methyl-1-phenyl-ethyl)-phenoxymethyl)-oxirane employing the procedures as set forth in Step 2 of Example 1.
$C_{19}H_{22}N_2O_2$ (310.17), LCMS (ESI): 311.14 (M⁺+H).
¹H NMR (CDCl₃, 300 MHz), δ 7.21-7.24 (m, 4H), 7.14 (dd, 3H), 6.81 (dd, 2H), 4.92 (m, 1H), 4.0 (v. br., 2H), 4.04 (AB-m, 2H), 3.90 (dd, 1H), 3.59 (dd, 1H), 1.66 (s, 6H).

Step 3: 2-(4-(1-Methyl-1-phenyl-ethyl)-phenoxymethyl)-2,3-dihydro-oxazolo[3,2-a]pyrimidin-7-one The title compound was prepared from 5-(4-(1-methyl-1-phenyl-ethyl)-phenoxymethyl)-4,5-dihydro-oxazol-2-ylamine employing the procedures as set forth in Step 3 of Example 1.
$C_{22}H_{22}N_2O_3$ (362.16), LCMS (ESI): 363.15 (M⁺+H).
¹H NMR (CDCl₃, 300 MHz), δ 7.14-7.25 (m, 8H), 6.78 (d, 2H), 6.10 (d, 1H), 5.26 (m, 1H), 4.20-4.38 (m, 4H), 1.66 (s, 6H).

Example 51

2-(4-tert-Butyl-2-methyl-phenoxymethyl)-2,3-dihydro-oxazolo[3,2-a]pyrimidin-7-one

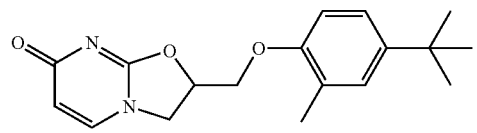 [SMILES: Cc1cc(C(C)(C)C)ccc1OCC1Cn2ccc(=O)nc2O1]

Step 1: 2-(4-tert-Butyl-2-methyl-phenoxymethyl)-oxirane

The title compound was prepared from 4-tert-butyl-2-methyl-phenol and epichlorohydrin employing the procedures as set forth in Step 1 of Example 2.
$C_{14}H_{20}O_2$ (220.15), LCMS (ESI): 262.23 (M⁺H+CH₃CN).
¹H NMR (CDCl₃, 300 MHz), δ 7.11-7.18 (m, 2H), 6.74 (d, 1H), 4.19 (dd, 1H), 3.97 (dd, 1H), 3.35 (m, 1H), 2.89 (t, 1H), 2.77 (dd, 1H), 2.25 (s, 3H), 1.29 (s, 9H).

Step 2: 5-(4-tert-Butyl-2-methyl-phenoxymethyl)-4,5-dihydro-oxazol-2-ylamine The title compound was prepared from 2-(4-tert-butyl-2-methyl-phenoxymethyl)-oxirane employing the procedures as set forth in Step 2 of Example 1.
$C_{15}H_{22}N_2O_2$ (262.17), LCMS (ESI): 263.14 (M⁺+H).
¹H NMR (CDCl₃, 300 MHz), δ 7.16 (s, 1H), 7.13 (d, 1H), 6.73 (dd, 1H), 4.91 (m, 1H), 4.04 (AB-m, 2H), 3.92 (dd, 1H), 3.7 (v. br., 2H), 3.66 (dd, 1H), 2.24 (s, 3H), 1.29 (s, 9H).

Step 3: 2-(4-tert-Butyl-2-methyl-phenoxymethyl)-2,3-dihydro-oxazolo[3,2-a]pyrimidin-7-one The title compound was prepared from 5-(4-tert-butyl-2-methyl-phenoxymethyl)-4,5-dihydro-oxazol-2-ylamine employing the procedures as set forth in Step 3 of Example 1.
$C_{18}H_{22}N_2O_3$ (314.16), LCMS (ESI): 315.14 (M⁺+H).
¹H NMR (CDCl₃, 300 MHz), δ 7.24 (d, 1H), 7.13-7.19 (m, 2H), 6.71 (d, 1H), 6.09 (d, 1H), 5.29 (m, 1H), 4.40 (t, 1H), 4.27-4.35 (m, 2H), 4.21 (dd, 1H), 2.05(s, 3H), 1.28 (s, 9H).

Example 52

2-(2,4-Di-tert-butyl-phenoxymethyl)-2,3-dihydro-oxazolo[3,2-a]pyrimidin-7-one

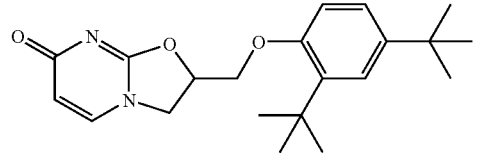 [SMILES: CC(C)(C)c1ccc(OCC2Cn3ccc(=O)nc3O2)c(C(C)(C)C)c1]

Step 1: 2-(2,4-Di-tert-butyl-phenoxymethyl)-oxirane

The title compound was prepared from 2,4-di-tert-butyl-phenol and epichlorohydrin employing the procedures as set forth in Step 1 of Example 2.

$C_{17}H_{26}O_2$ (262.19), LCMS (ESI): 304.27 ($M^+H+CH_3CN$).

$^1H$ NMR (CDCl$_3$, 300 MHz), δ 7.33 (s, 1H), 7.16 (d, 1H), 6.76 (d, 1H), 4.21(dd, 1H), 4.00 (dd, 1H), 3.39 (m, 1H), 2.91 (t, 1H), 2.78 (dd, 1H), 1.41 (s, 9H), 1.30 (s, 9H).

Step 2: 5-(2,4-Di-tert-butyl-phenoxymethyl)-4,5-dihydro-oxazol-2-ylamine

The title compound was prepared from 2-(2,4-di-tert-butyl-phenoxymethyl)-oxirane employing the procedures as set forth in Step 2 of Example 1.

$C_{18}H_{28}N_2O_2$ (304.22), LCMS (ESI): 305.2 ($M^++H$).

$^1H$ NMR (CDCl$_3$, 300 MHz), δ 7.34 (s, 1H), 7.17 (dd, 1H), 6.77 (m, 1H), 4.94 (m, 1H), 3.87-4.15 (m, 3H), 3.8 (v. br., 2H), 3.68 (dd, 1H), 1.38 (s, 9H), 1.30 (s, 9H).

Step 3: 2-(2,4-Di-tert-butyl-phenoxymethyl)-2,3-dihydro-oxazolo[3,2-a]pyrimidin-7-one The title compound was prepared from 5-(2,4-di-tert-butyl-phenoxymethyl)-4,5-dihydro-oxazol-2-ylamine employing the procedures as set forth in Step 3 of Example 1.

$C_{21}H_{28}N_2O_3$ (356.21), LCMS (ESI): 357.19 ($M^++H$).

$^1H$ NMR (CDCl$_3$, 300 MHz), δ 7.34 (d, 1H), 7.22 (d, 1H), 7.19 (d, 1H), 6.78 (d, 1H), 6.10 (d, 1H), 5.34 (m, 1H), 4.24-4.47 (m, 4H), 1.30 (s, 9H), 1.27 (s, 9H).

Example 53

2-(3,4-Difluoro-phenoxymethyl)-2,3-dihydro-oxazolo[3,2-a]pyrimidin-7-one

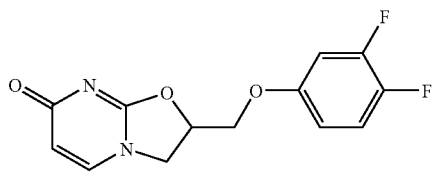 [SMILES: O=c1ccn2c(n1)OC(COc1ccc(F)c(F)c1)C2]

Step 1: 2-(3,4-Difluoro-phenoxymethyl)-oxirane

The title compound was prepared from 3,4-difluoro-phenol and epichlorohydrin employing the procedures as set forth in Step 1 of Example 2.

$C_9H_8F_2O_2$ (186.04), LCMS (ESI): 228.09 ($M^+H+CH_3CN$).

$^1H$ NMR (CDCl$_3$, 300 MHz), δ 7.15-7.00 (m, 1H), 6.72-6.81 (m, 1H), 6.59-6.67(m, 1H), 4.21 (dd, 1H), 3.88 (dd, 1H), 3.34 (m, 1H), 2.92 (t, 1H), 2.75 (dd, 1H).

Step 2: 5-(3,4-Difluoro-phenoxymethyl)-4,5-dihydro-oxazol-2-ylamine

The title compound was prepared from 2-(3,4-difluoro-phenoxymethyl)-oxirane employing the procedures as set forth in Step 2 of Example 1.

$C_{10}H_{10}F_2N_2O_2$ (228.07), LCMS (ESI): 229.1 ($M^++H$).

$^1H$ NMR (CDCl$_3$, 300 MHz), δ 7.07 (q, 1H), 6.75 (m, 1H), 6.62 (m, 1H), 4.89 (m, 1H), 4.6 (v. br., 2H), 4.00 (AB-m, 2H), 3.92 (dd, 1H), 3.59 (dd, 1H).

Step 3: 2-(3,4-Difluoro-phenoxymethyl)-2,3-dihydro-oxazolo[3,2-a]pyrimidin-7-one The title compound was prepared from 5-(3,4-difluoro-phenoxymethyl)-4,5-dihydro-oxazol-2-ylamine employing the procedures as set forth in Step 3 of Example 1.

$C_{13}H_{10}F_2N_2O_3$ (280.06), LCMS (ESI): 281.09 ($M^++H$).

$^1H$ NMR(DMSO-d$_6$, 300 MHz), δ 7.76 (d, 1H), 7.38 (q, 1H), 7.13 (m, 1H), 6.80 (m, 1H), 5.82(d, 1H), 5.32 (m, 1H), 4.26-4.44 (m, 3H), 4.08 (dd, 1H).

Example 54

2-(3,4-Dimethoxy-phenoxymethyl)-2,3-dihydro-oxazolo[3,2-a]pyrimidin-7-one

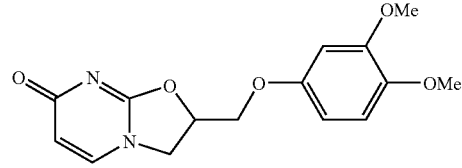 [SMILES: COc1ccc(OCC2Cn3ccc(=O)nc3O2)cc1OC]

Step 1: 2-(3,4-Dimethoxy-phenoxymethyl)-oxirane

The title compound was prepared from 3,4-dimethoxy-phenol and epichlorohydrin employing the procedures as set forth in Step 1 of Example 2.

$C_{11}H_{14}O_4$ (210.08), LCMS (ESI): 211.09 ($M^++H$).

$^1H$ NMR (CDCl$_3$, 300 MHz), δ 6.78 (d, 1H), 6.58 (s, 1H), 6.41 (d, 1H), 4.19 (dd, 1H), 3.93 (dd, 1H), 3.86 (s, 3H), 3.83 (s, 3H), 3.35 (m, 1H), 2.91 (t, 1H)), 2.75 (dd, 1H).

Step 2: 5-(3,4-Dimethoxy-phenoxymethyl)-4,5-dihydro-oxazol-2-ylamine

The title compound was prepared from 2-(3,4-dimethoxy-phenoxymethyl)-oxirane employing the procedures as set forth in Step 2 of Example 1.

$C_{12}H_{16}N_2O_4$ (252.11), LCMS (ESI): 253.1 ($M^++H$).

$^1H$ NMR (CDCl$_3$, 300 MHz), δ 6.77 (d, 1H), 6.56 (s, 1H), 6.40 (d, 1H), 4.89 (m, 1H), 4.2 (v. br., 2H), 3.82-4.16 (m, 3H), 3.85 (s, 3H), 3.84 (s, 3H), 3.62 (dd, 1H).

Step 3: 2-(3,4-Dimethoxy-phenoxymethyl)-2,3-dihydro-oxazolo[3,2-a]pyrimidin-7-one The title compound was prepared from 5-(3,4-dimethoxy-phenoxymethyl)-4,5-dihydro-oxazol-2-ylamine employing the procedures as set forth in Step 3 of Example 1.

$C_{15}H_{16}N_2O_5$ (304.11), LCMS (ESI): 305.15 ($M^++H$).

¹H NMR (DMSO-d₆, 300 MHz), δ 7.76 (d, 1H), 6.86 (d, 1H), 6.58 (d, 1H), 6.46 (dd, 1H), 5.82 (d, 1H), 5.31 (m, 1H), 4.39 (t, 1H), 4.27 (AB-m, 2H), 4.10 (dd, 1H), 3.73 (s, 3H), 3.69 (s, 3H).

Example 55

2-(4-Trifluoromethoxy-phenoxymethyl)-2,3-dihydro-oxazolo[3,2-a]pyrimidin-7-one

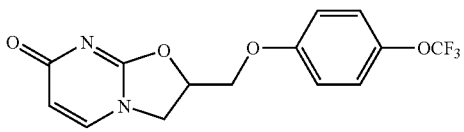 [SMILES: O=c1ccn2c(n1)OC(COc1ccc(OC(F)(F)F)cc1)C2]

Step 1:
2-(4-Trifluoromethoxy-phenoxymethyl)-oxirane

The title compound was prepared from 4-trifluoromethoxy-phenol and epichlorohydrin employing the procedures as set forth in Step 1 of Example 2.
$C_{10}H_9F_3O_3$ (234.05), LCMS (ESI): 276.1 (M⁺H+ CH₃CN).
¹H NMR (CDCl₃, 300 MHz), δ 7.15 (d, 2H), 6.91 (d, 2H), 4.23 (dd, 1H), 3.94 (dd, 1H), 3.35 (m, 1H), 2.92 (t, 1H), 2.76 (dd, 1H).

Step 2: 5-(4-Trifluoromethoxy-phenoxymethyl)-4,5-dihydro-oxazol-2-ylamine

The title compound was prepared from 2-(4-trifluoromethoxy-phenoxymethyl)-oxirane employing the procedures as set forth in Step 2 of Example 1.
$C_{11}H_{11}F_3N_2O_3$ (276.07), LCMS (ESI): 277.1 (M⁺+H).
¹H NMR (CDCl₃, 300 MHz), δ 7.15 (d, 2H), 6.91 (d, 2H), 4.91 (m, 1H), 4.2 (v..br., 2H), 4.05 (AB-m, 2H), 3.94 (dd, 1H), 3.61 (dd, 1H).

Step 3: 2-(4-Trifluoromethoxy-phenoxymethyl)-2,3-dihydro-oxazolo[3,2-a]pyrimidin-7-one The title compound was prepared from 5-(4-trifluoromethoxy-phenoxymethyl)-4,5-dihydro-oxazol-2-ylamine employing the procedures as set forth in Step 3 of Example 1.
$C_{14}H_{11}F_3N_2O_4$ (328.07), LCMS (ESI): 329.1 (M⁺+H).
¹H NMR (DMSO-d₆, 300 MHz), δ 7.76 (d, 1H), 7.32 (d, 2H), 7.05 (d, 2H), 5.82 (d, 1H), 5.34 (m, 1H), 4.29-4.45 (m, 3H), 4.11(dd, 1H).

Example 56

2-(4-Methanesulfonyl-phenoxymethyl)-2,3-dihydro-oxazolo[3,2-a]pyrimidin-7-one

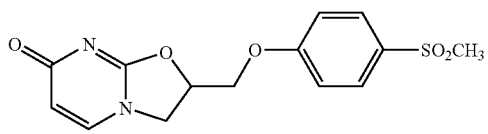 [SMILES: CS(=O)(=O)c1ccc(OCC2Cn3ccc(=O)nc3O2)cc1]

Step 1:
2-(4-Methanesulfonyl-phenoxymethyl)-oxirane

The title compound was prepared from 4-methanesulfonyl-phenol and epichlorohydrin employing the procedures as set forth in Step 1 of Example 2.
$C_{10}H_{12}O_4S$ (228.04), LCMS (ESI): 270.1 (M⁺H+ CH₃CN).
¹H NMR (CDCl₃, 300 MHz), δ 7.87 (d, 2H), 7.05 (d, 2H), 4.36 (dd, 1H), 4.00 (dd, 1H), 3.38 (m, 1H), 3.03 (s, 3H), 2.94 (t, 1H), 2.78 (dd, 1H).

Step 2: 5-(4-Methanesulfonyl-phenoxymethyl)-4,5-dihydro-oxazol-2-ylamine

The title compound was prepared from 2-(4-methanesulfonyl-phenoxymethyl)-oxirane employing the procedures as set forth in Step 2 of Example 1.
$C_{11}H_{14}N_2O_4S$ (270.06), LCMS (ESI): 271.1 (M⁺+H).
¹H NMR (CDCl₃, 300 MHz), δ 7.89 (d, 2H), 7.05 (d, 2H), 4.97 (m, 1H), 4.14 (AB-m, 2H), 3.97 (dd, 1H), 3.65 (dd, 1H), 3.05 (s, 3H), 1.7 (v. br., 2H).

Step 3: 2-(4-Methanesulfonyl-phenoxymethyl)-2,3-dihydro-oxazolo[3,2-a]pyrimidin-7-one The title compound was prepared from 5-(4-methanesulfonyl-phenoxymethyl)-4,5-dihydro-oxazol-2-ylamine employing the procedures as set forth in Step 3 of Example 1.
$C_{14}H_{14}N_2O_5S$ (322.06), LCMS (ESI): 323.11 (M⁺+H).
¹H NMR (DMSO-d₆, 300 MHz), δ 7.86 (d, 2H), 7.77 (d, 1H), 7.18 (d, 2H), 5.83 (d, 1H), 5.36 (m, 1H), 4.33-4.54 (m, 3H), 4.11 (dd, 1H), 3.16 (s, 3H).

Example 57

2-(3-Trifluoromethoxy-phenoxymethyl)-2,3-dihydro-oxazolo[3,2-a]pyrimidin-7-one

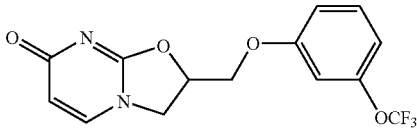

Step 1:
2-(3-Trifluoromethoxy-phenoxymethyl)-oxirane

The title compound was prepared from 3-trifluoromethoxy-phenol and epichlorohydrin employing the procedures as set forth in Step 1 of Example 2.
$C_{10}H_9F_3O_3$ (234.05), LCMS (ESI): 276.1 (M⁺H+ CH₃CN).
¹H NMR (CDCl₃, 300 MHz), δ 7.27-7.33 (m, 1H), 6.77-6.89 (m, 3H), 4.25 (dd, 1H), 3.94 (dd, 1H), 3.35 (m, 1H), 2.92 (t, 1H) 2.76 (dd, 1H).

Step 2: 5-(3-Trifluoromethoxy-phenoxymethyl)-4,5-dihydro-oxazol-2-ylamine

The title compound was prepared from 2-(3-trifluoromethoxy-phenoxymethyl)-oxirane employing the procedures as set forth in Step 2 of Example 1.
$C_{11}H_{11}F_3N_2O_3$ (276.07), LCMS (ESI): 277.1 (M⁺+H).

¹H NMR (CDCl₃, 300 MHz), δ 7.29 (t, 1H), 6.77-6.90 (m, 3H), 4.92 (m, 1H), 4.5 (v.br., 2H), 4.06 (AB-m, 2H), 3.94 (dd, 1H), 3.61(dd, 1H).

Step 3: 2-(3-Trifluoromethoxy-phenoxymethyl)-2,3-dihydro-oxazolo[3,2-a]pyrimidin-7-one The title compound was prepared from 5-(3-trifluoromethoxy-phenoxymethyl)-4,5-dihydro-oxazol-2-ylamine employing the procedures as set forth in Step 3 of Example 1.

$C_{14}H_{11}F_3N_2O_4$ (328.07), LCMS (ESI): 329.08 (M⁺+H).

¹H NMR (DMSO-D₆, 300 MHz), δ 7.76 (d, 1H), 7.44 (t, 1H), 6.95-7.05 (m, 3H), 5.83 (d, 1H), 5.34 (m, 1H), 4.32-4.46 (m, 3H), 4.11 (dd, 1 H).

Example 58

2-(1H-Indol-5-yloxymethyl)-2,3-dihydro-oxazolo[3,2-a]pyrimidin-7-one

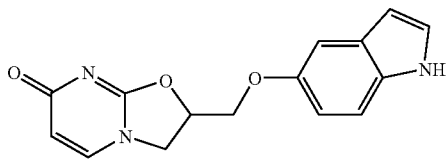 [SMILES: O=c1ccn2c(n1)OC(COc1ccc3[nH]ccc3c1)C2]

Step 1: 5-Oxiranylmethoxy-1H-indole

The title compound was prepared from 5-hydroxyindole and epichlorohydrin employing the procedures as set forth in Step 1 of Example 2.

$C_{11}H_{11}NO_2$ (189.07), LCMS (ESI): 190.1 (M⁺+H).

¹H NMR (CDCl₃, 300 MHz), δ 8.10 (br. s, 1H), 7.10-7.31 (m, 3H), 6.90 (dd, 1H), 6.48 (s, 1H), 4.24 (dd, 1H), 4.03 (dd, 1H), 3.39 (m, 1H), 2.91 (t, 1H), 2.78 (dd, 1H).

Step 2: 5-(1H-Indol-5-yloxymethyl)-4,5-dihydro-oxazol-2-ylamine

The title compound was prepared from 5-oxiranylmethoxy-1H-indole employing the procedures as set forth in Step 2 of Example 1.

$C_{12}H_{13}N_3O_2$ (231.1), LCMS (ESI): 232.1 (M⁺+H).

¹H NMR (CDCl₃, 300 MHz), δ 9.4 (v..br., 1H), 7.31 (d, 1H), 7.20 (d, 1H), 7.10 (d, 1H), 6.84 (dd, 1H), 6.42 (d, 1H), 4.95 (m, 1H), 4.6 (v..br., 2H), 4.09 (AB-m, 2H), 3.92 (dd, 1H), 3.62 (dd, 1H).

Step 3: 2-(1H-Indol-5-yloxymethyl)-2,3-dihydro-oxazolo[3,2-a]pyrimidin-7-one

The title compound was prepared from 5-(1H-indol-5-yloxymethyl)-4,5-dihydro-oxazol-2-ylamine employing the procedures as set forth in Step 3 of Example 1.

$C_{15}H_{13}N_3O_3$ (283.09), LCMS (ESI): 284.09 (M⁺+H).

¹H NMR (DMSO-d₆, 300 MHz), δ 10.96 (s, 1H), 7.77 (d, 1H), 7.24-7.32 (m, 2H), 7.08 (d, 1H), 6.71 (dd, 1H), 6.34 (s, 1H), 5.82 (d, 1H), 5.34 (m, 1H), 4.40 (t, 1H), 4.30 (AB-m, 2H), 4.14 (dd, 1H).

Example 59

2-(4-Isopropyl-3-methyl-phenoxymethyl)-2,3-dihydro-oxazolo[3,2-a]pyrimidin-7-one

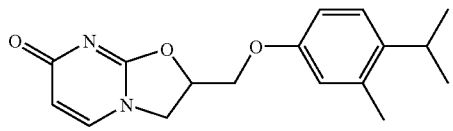 [SMILES: Cc1cc(OCC2Cn3ccc(=O)nc3O2)ccc1C(C)C]

Step 1: 2-(4-Isopropyl-3-methyl-phenoxymethyl)-oxirane

The title compound was prepared from 4-isopropyl-3-methyl-phenol and epichlorohydrin employing the procedures as set forth in Step 1 of Example 2.

$C_{13}H_{18}O_2$ (206.13), LCMS (ESI): 248.19 (M⁺H+CH₃CN).

¹H NMR (CDCl₃, 300 MHz), δ 7.14 (d, 1H), 6.74 (d, 1H), 6.72 (s, 1H), 4.16 (dd, 1H), 3.96 (dd, 1H), 3.33 (m, 1H), 3.07 (m, 1H), 2.89 (t, 1H), 2.74 (dd, 1H), 2.31 (s, 3H), 1.19 (d, 6 H).

Step 2: 5-(4-Isopropyl-3-methyl-phenoxymethyl)-4,5-dihydro-oxazol-2-ylamine

The title compound was prepared from 2-(4-isopropyl-3-methyl-phenoxymethyl)-oxirane employing the procedures as set forth in Step 2 of Example 1.

$C_{14}H_{20}N_2O_2$ (248.15), LCMS (ESI): 249.14 (M⁺+H).

¹H NMR (CDCl₃, 300 MHz), δ 7.14 (d, 1H), 6.74 (d, 1H), 6.72 (s, 1H), 4.90 (m, 1H), 4.01 (AB-m, 2H), 4.0 (v. br., 2H), 3.92 (dd, 1H), 3.60 (dd, 1H), 3.07 (q, 1H), 2.30 (s, 3H), 1.90 (d, 6H).

Step 3: 2-(4-Isopropyl-3-methyl-phenoxymethyl)-2,3-dihydro-oxazolo[3,2-a]pyrimidin-7-one The title compound was prepared from 5-(4-isopropyl-3-methyl-phenoxymethyl) -4,5-dihydro-oxazol-2-ylamine employing the procedures as set forth in Step 3 of Example 1.

$C_{17}H_{20}N_2O_3$ (300.15), LCMS (ESI): 301.13 (M⁺+H).

¹H NMR (CDCl₃, 300 MHz), δ 7.23 (d, 1H), 7.15 (d, 1H), 6.63-6.72 (m, 2H), 6.10 (d, 1H), 5.25 (m, 1H), 4.20-4.38 (m, 4H), 3.07 (m, 1H), 2.30 (s, 3H), 1.19 (d, 6H).

Example 60

2-(3,4-Dichloro-phenoxymethyl)-2,3-dihydro-oxazolo[3,2-a]pyrimidin-7-one

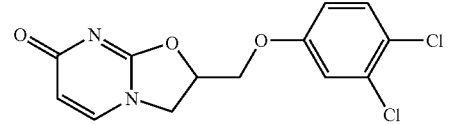 [SMILES: O=c1ccn2c(n1)OC(COc1ccc(Cl)c(Cl)c1)C2]

Step 1: 2-(3,4-Dichloro-phenoxymethyl)-oxirane

The title compound was prepared from 3,4-dichloro-phenol and epichlorohydrin employing the procedures as set forth in Step 1 of Example 2.

$C_9H_8Cl_2O_2$ (217.99), LCMS (ESI): 260.07 (M$^+$H+CH$_3$CN).
$^1$H NMR (CDCl$_3$, 300 MHz), δ 7.32 (d, 1H), 7.03 (s, 1H), 6.79 (d, 1H), 4.23 (dd, 1H), 3.89 (dd, 1H), 3.33 (m, 1H), 2.92 (t, 1H), 2.75 (dd, 1H).

Step 2: 5-(3,4-Dichloro-phenoxymethyl)-4,5-dihydro-oxazol-2-ylamine

The title compound was prepared from 2-(3,4-dichloro-phenoxymethyl)-oxirane employing the procedures as set forth in Step 2 of Example 1.
$C_{10}H_{10}Cl_2N_2O_2$ (260.01), LCMS (ESI): 261.01 (M$^-$+H).

Step 3: 2-(3,4-Dichloro-phenoxymethyl)-2,3-dihydro-oxazolo[3,2-a]pyrimidin-7-one The title compound was prepared from 5-(3,4-dichloro-phenoxymethyl)-4,5-dihydro-oxazol-2-ylamine employing the procedures as set forth in Step 3 of Example 1.
$C_{13}H_{10}Cl_2N_2O_3$ (312.01), LCMS (ESI): 313 (M$^+$+H).
$^1$H NMR (CDCl$_3$, 300 MHz), δ 7.36 (d, 1H), 7.23 (d, 1H), 7.00 (d, 1H), 6.75 (dd, 1H), 6.11 (d, 1H), 5.28 (m, 1H), 4.20-4.43 (m, 4H).

Example 61

2-(4-(1-Phenyl-ethyl)-phenoxymethyl)-2,3-dihydro-oxazolo[3,2-a]pyrimidin-7-one

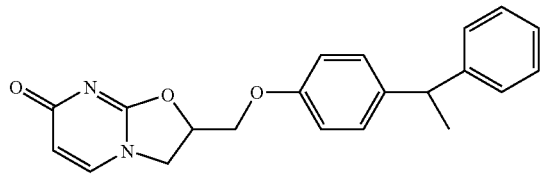 [SMILES: CC(c1ccccc1)c1ccc(OCC2Cn3ccc(=O)nc3O2)cc1]

Step 1:
2-(4-(1-Phenyl-ethyl)-phenoxymethyl)-oxirane

The title compound was prepared from 4-(1-phenyl-ethyl)-phenol and epichlorohydrin employing the procedures as set forth in Step 1 of Example 2.
$C_{17}H_{18}O_2$ (254.13), LCMS (ESI): 296.16 (M$^+$H+CH$_3$CN).
$^1$H NMR (CDCl$_3$, 300 MHz), δ 7.07-7.35 (m, 7H), 6.85 (d, 2H), 4.04-4.21 (m, 2H), 3.94 (dd, 1H), 3.33 (m, 1H), 2.89 (t, 1H), 2.74 (dd, 1H), 1.61 (d, 3H).

Step 2: 5-(4-(1-Phenyl-ethyl)-phenoxymethyl)-4,5-dihydro-oxazol-2-ylamine

The title compound was prepared from 2-(4-(1-phenyl-ethyl)-phenoxymethyl)-oxirane employing the procedures as set forth in Step 2 of Example 1.
$C_{18}H_{20}N_2O_2$ (296.15), LCMS (ESI): 297.43 (M$^+$+H).

Step 3: 2-(4-(1-Phenyl-ethyl)-phenoxymethyl)-2,3-dihydro-oxazolo[3,2-a]pyrimidin-7-one The title compound was prepared from 5-(4-(1-phenyl-ethyl)-phenoxymethyl)-4,5-dihydro-oxazol-2-ylamine employing the procedures as set forth in Step 3 of Example 1.
$C_{21}H_{20}N_2O_3$ (348.15), LCMS (ESI): 349.14 (M$^+$+H).

$^1$H NMR (CDCl$_3$, 300 MHz), δ 7.12-7.31 (m, 8H), 6.79 (d, 2H), 6.09 (d, 1H), 5.25 (m, 1H), 4.19-4.38 (m, 4H), 4.11 (q, 1H), 1.61 (d, 3H).

Example 62

2-(4-Indan-1-yl-phenoxymethyl)-2,3-dihydro-oxazolo[3,2-a]pyrimidin-7-one

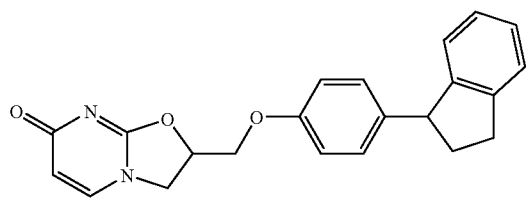 [SMILES: O=c1ccn2c(n1)OC(COc1ccc(C3CCc4ccccc43)cc1)C2]

Step 1: 2-(4-Indan-1-yl-phenoxymethyl)-oxirane

The title compound was prepared from 4-indan-1-yl-phenol and epichlorohydrin employing the procedures as set forth in Step 1 of Example 2.
$C_{18}H_{18}O_2$ (266.13), LCMS (ESI): 308.16 (M$^+$H+CH$_3$CN).
$^1$H NMR (CDCl$_3$, 300 MHz), δ 7.23-7.30 (m, 1H), 7.06-7.21 (m, 4H), 6.93 (d, 1H), 6.86 (d, 2H), 4.28 (t, 1H), 4.19 (dd, 1H), 3.96 (dd, 1H), 3.34 (m, 1H), 2.86-3.06 (m, 3H), 2.76 (dd, 1H), 2.49-2.61 (m, 1H), 1.93-2.09 (m, 1H).

Step 2: 5-(4-Indan-1-yl-phenoxymethyl)-4,5-dihydro-oxazol-2-ylamine

The title compound was prepared from 2-(4-indan-1-yl-phenoxymethyl)-oxirane employing the procedures as set forth in Step 2 of Example 1.
$C_{19}H_{20}N_2O_2$ (308.15), LCMS (ESI): 309.45 (M$^+$+H).

Step 3: 2-(4-Indan-1-yl-phenoxymethyl)-2,3-dihydro-oxazolo[3,2-a]pyrimidin-7-one The title compound was prepared from 5-(4-indan-1-yl-phenoxymethyl)-4,5-dihydro-oxazol-2-ylamine employing the procedures as set forth in Step 3 of Example 1.
$C_{22}H_{20}N_2O_3$ (360.15), LCMS (ESI): 361.15 (M$^+$+H).
$^1$H NMR (CDCl$_3$, 300 MHz), δ 7.29 (d, 2H), 7.24 (d, 2H), 7.11 (d, 2H), 6.91 (d, 1H), 6.82 (d, 2H), 6.09 (d, 1H), 5.28 (m, 1H), 4.22-4.41(m, 5H), 2.98(m, 2H), 2.55 (m, 1H), 1.99 (m, 1H).

Example 63

2-(Indan-5-yl-oxymethyl)-2,3-dihydro-oxazolo[3,2-a]pyrimidin-7-one

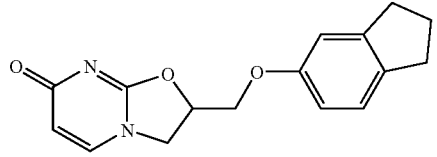 [SMILES: O=c1ccn2c(n1)OC(COc1ccc3c(c1)CCC3)C2]

Step 1: 2-(Indan-5-yl-oxymethyl)-oxirane

The title compound was prepared from 5-indanol and epichlorohydrin employing the procedures as set forth in Step 1 of Example 2.

$C_{12}H_{14}O_2$ (190.09), LCMS (ESI): 232.12 (M$^+$H+ CH$_3$CN).
$^1$H NMR (CDCl$_3$, 300 MHz), δ 7.10 (d, 1H), 6.80 (s, 1H), 6.70 (d, 1H), 4.17 (dd, 1H), 3.95 (dd, 1H), 3.33 (m, 1H), 2.78-2.93 (m, 5H), 2.74 (m, 1H), 2.07 (t, 2H).

Step 2: 5-(Indan-5-yloxymethyl)-4,5-dihydro-oxazol-2-ylamine

The title compound was prepared from 2-(indan-5-yl-oxymethyl)-oxirane employing the procedures as set forth in Step 2 of Example 1.

$C_{13}H_{16}N_2O_2$ (232.12), LCMS (ESI): 233.11 (M$^+$+H).
$^1$H NMR (CDCl$_3$, 300 MHz), δ 7.12 (d, 1H), 6.81 (s, 1H), 6.70 (d, 1H), 4.91 (m, 1H), 4.2 (v. br., 2H), 4.04 (AB-m, 2H), 3.91 (dd, 1H), 3.62 (dd, 1H), 2.85 (br. s, 4H), 2.07 (m, 2H).

Step 3: 2-(Indan-5-yl-oxymethyl)-2,3-dihydro-oxazolo[3,2-a]pyrimidin-7-one

The title compound was prepared from 5-(indan-5-yloxymethyl)-4,5-dihydro-oxazol-2-ylamine employing the procedures as set forth in Step 3 of Example 1.

$C_{16}H_{16}N_2O_3$ (284.11), LCMS (ESI): 285.12 (M$^+$+H).
$^1$H NMR (CDCl$_3$, 300 MHz), δ 7.24 (d, 1H), 7.12 (d, 1H), 6.76 (s, 1H), 6.65 (d, 1H), 6.09 (d, 1H), 5.26 (m, 1H), 4.19-4.41(m, 4H), 2.85 (q, 4H), 2.08 (q, 2H).

Example 64

2-(4-Imidazol-1-yl-phenoxymethyl)-2,3-dihydro-oxazolo[3,2-a]pyrimidin-7-one

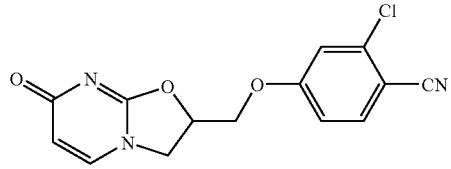

Step 1: 1-(4-Oxiranylmethoxy-phenyl)-1H-imidazole

The title compound was prepared from 4-imidazol-1-yl-phenol and epichlorohydrin employing the procedures as set forth in Step 1 of Example 2.

$C_{12}H_{12}N_2O_2$ (216.08), LCMS (ESI): 217.09 (M$^+$H+ CH$_3$CN).
$^1$H NMR (CDCl$_3$, 300 MHz), δ 7.76 (s, 1H), 7.23-7.33 (m, 2H), 7.19 (d, 2H), 7.01 (d, 2H), 4.29 (dd, 1H), 3.97 (dd, 1H), 3.37 (m, 1H), 2.93 (t, 1H), 2.77 (dd, 1H).

Step 2: 5-(4-Imidazol-1-yl-phenoxymethyl)-4,5-dihydro-oxazol-2-ylamine

The title compound was prepared from 1-(4-oxiranyl-methoxy-phenyl)-1H-imidazole employing the procedures as set forth in Step 2 of Example 1.

$C_{13}H_{14}N_4O_2$ (258.11), LCMS (ESI): 259.12 (M$^+$+H).
$^1$H NMR (CDCl$_3$, 300 MHz), δ 7.76 (s, 1H), 7.31 (d, 2H), 7.20 (d, 2H), 7.01 (d, 2H), 4.94 (m, 1H), 4.10 (AB-m, 2H), 3.96 (dd, 1H), 3.65 (dd, 1H), 2.5 (v. br., 2H).

Step 3: 2-(4-Imidazol-1-yl-phenoxymethyl)-2,3-dihydro-oxazolo[3,2-a]pyrimidin-7-one The title compound was prepared from 5-(4-imidazol-1-yl-phenoxymethyl)-4,5-dihydro-oxazol-2-ylamine employing the procedures as set forth in Step 3 of Example 1.

$C_{16}H_{14}N_4O_3$ (310.1), LCMS (ESI): 311.1 (M$^+$+H).
$^1$H NMR (CDCl$_3$, 300 MHz), δ 7.76 (s, 1H), 7.31 (t, 3H), 7.20 (d, 2H), 6.98 (d, 2H), 6.10 (d, 1H), 5.33 (m, 1H), 4.28-4.47 (m, 4H).

Example 65

2-Chloro-4-(7-oxo-2,3-dihydro-7H-oxazolo[3,2-a]pyrimidin-2-ylmethoxy)-benzonitrile

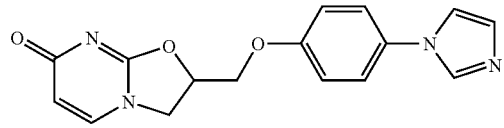 [SMILES: O=c1ccn2c(n1)OC(COc1ccc(-n3ccnc3)cc1)C2]

Step 1: 2-Chloro-4-oxiranylmethoxy-benzonitrile

The title compound was prepared from 2-chloro-4-hydroxy-benzonitrile and epichlorohydrin employing the procedures as set forth in Step 1 of Example 2.

$C_{10}H_8ClNO_2$ (209.02), LCMS (ESI): 210.05 (M$^+$+H).
$^1$H NMR (CDCl$_3$, 300 MHz), δ 7.58 (d, 1H), 7.06 (d, 1H), 6.91 (dd, 1H), 4.35 (dd, 1H), 3.96 (dd, 1H), 3.36 (m, 1H), 2.94 (t, 1H), 2.76 (dd, 1H).

Step 2: 4-(2-Amino-4,5-dihydro-oxazol-5-ylmethoxy)-2-chloro-benzonitrile

The title compound was prepared from 2-chloro-4-oxiranylmethoxy-benzonitrile employing the procedures as set forth in Step 2 of Example 1.

$C_{11}H_{10}ClN_3O_2$ (251.05), LCMS (ESI): 252.07 (M$^+$+H).
$^1$H NMR (CDCl$_3$, 300 MHz), δ 7.59 (d, 1H), 7.06 (d, 1H), 6.90 (dd, 1H), 4.92 (m, 1H), 4.11 (AB-m, 2H), 3.95 (dd, 1H), 3.6 (v. br., 2H), 3.63 (dd, 1H).

Step 3: 2-Chloro-4-(7-oxo-2,3-dihydro-7H-oxazolo[3,2-a]pyrimidin-2-ylmethoxy)-benzonitrile The title compound was prepared from 4-(2-amino-4,5-dihydro-oxazol-5-ylmethoxy)-2-chloro-benzonitrile employing the procedures as set forth in Step 3 of Example 1.

$C_{14}H_{10}ClN_3O_3$ (303.04), LCMS (ESI): 304.06 (M$^+$+H).

$^1$H NMR (DMSO-d$_6$, 300 MHz), δ 7.92 (d, 1H), 7.76(d, 1H), 7.41(d, 1H), 7.13(dd, 1H), 5.82 (d, 1H), 5.36 (m, 1H), 4.35-4.57 (m, 3H), 4.04-4.12 (m, 1H).

Example 66

2(R)-[4-(1,1,3,3-Tetramethyl-butyl)-phenoxymethyl]-2,3-dihydro-oxazolo[3,2-a]pyrimidin-7-one

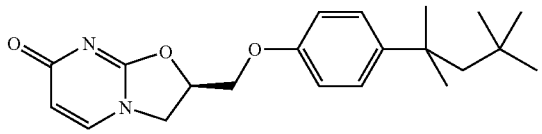 [SMILES: CC(C)(C)CC(C)(C)c1ccc(OC[C@H]2Cn3ccc(=O)nc3O2)cc1]

Step 1: (R)-2-(4-(1,1,3,3-Tetramethyl-butyl)-phenoxymethyl)-oxirane

The title compound was prepared from 4-(1,1,3,3-tetramethyl-butyl)-phenol and S-epichlorohydrin employing the procedures as set forth in Step 1 of Example 1.

$C_{17}H_{26}O_2$ (262.19), LCMS (ESI): 304.23 (M$^+$H+CH$_3$CN).
$^1$H NMR (CDCl$_3$, 300 MHz), δ 7.28 (d, 2H), 6.84 (d, 2H), 4.19 (dd, 1H), 3.98 (dd, 1H), 3.36 (m, 1H), 2.90 (t, 1H), 2.76 (dd, 1H), 1.71 (s, 2H), 1.35 (s, 6H), 0.72 (s, 9H).

Step 2: (R)-5-(4-(1,1,3,3-Tetramethyl-butyl)-phenoxymethyl)-4,5-dihydro-oxazol-2-ylamine The title compound was prepared from (R)-2-(4-(1,1,3,3-tetramethyl-butyl) -phenoxymethyl)-oxirane employing the procedures as set forth in Step 2 of Example 1.

$C_{18}H_{28}N_2O_2$ (304.22), LCMS (ESI): 305.2 (M$^+$+H).
$^1$H NMR (CDCl$_3$, 300 MHz), δ 7.25 (d, 2H), 6.83 (d, 2H), 4.92 (m, 1H), 4.04 (AB-m, 2H), 3.9 (v.br., 2H), 3.92 (dd, 1H), 3.62 (dd, 1H), 1.70 (s, 2H), 1.34 (s, 6H), 0.71 (s, 9H).

Step 3: 2(R)-[4-(1,1,3,3-Tetramethyl-butyl)-phenoxymethyl]-2,3-dihydro-oxazolo[3,2-a]pyrimidin-7-one The title compound was prepared from (R)-5-(4-(1,1,3,3-tetramethyl-butyl) -phenoxymethyl)-4,5-dihydro-oxazol-2-ylamine employing the procedures as set forth in Step 3 of Example 1. [α]$_D^{25}$ −45.23 (c 0.489, CHCl$_3$).

$C_{21}H_{28}N_2O_3$ (356.21), LCMS (ESI): 357.18 (M$^+$+H).
$^1$H NMR (CDCl$_3$, 300 MHz), δ 7.28 (d, 2H), 7.22 (s, 1H), 6.79 (d, 2H), 6.10 (d, 1H), 5.26 (m, 1H), 4.22-4.39 (m, 4H), 1.70 (s, 2H), 1.34 (s, 6H), 0.70 (s, 9H).

Example 67

2(R)-(4-tert-butyl-phenoxymethyl)-2,3-dihydro-oxazolo[3,2-a]pyrimidin-7-one

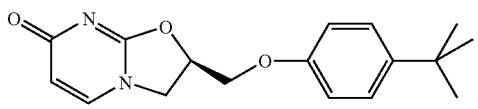

Step 1: (R)-2-(4-tert-butyl-phenoxymethyl)-oxirane

The title compound was prepared from 4-tert-butyl-phenol and S-epichlorohydrin employing the procedures as set forth in Step 1 of Example 1.

$C_{13}H_{18}O_2$ (206.13), LCMS (ESI): 248.18 (M$^+$H+CH$_3$CN).
$^1$H NMR (CDCl$_3$, 300 MHz), δ 7.30 (d, 2H), 6.86 (d, 2H), 4.18 (dd, 1H), 3.97 (dd, 1H), 3.34 (m, 1H), 2.90 (t, 1H), 2.75 (dd, 1H), 1.30 (s, 9H).

Step 2: (R)-5-(4-tert-Butyl-phenoxymethyl)-4,5-dihydro-oxazol-2-ylamine

The title compound was prepared from (R)-2-(4-tert-butyl-phenoxymethyl)-oxirane employing the procedures as set forth in Step 2 of Example 1.

$C_{14}H_{20}N_2O_2$ (248.15), LCMS (ESI): 249.13 (M$^+$+H).
$^1$H NMR (CDCl$_3$, 300 MHz), δ 7.32 (d, 2H), 6.86 (d, 2H), 4.92 (m, 1H), 4.05 (AB-m, 2H), 3.92 (dd, 1H), 3.61 (dd, 1H), 1.96 (v. br., 2H), 1.30 (s, 9H).

Step 3: 2(R)-(4-tert-Butyl-phenoxymethyl)-2,3-dihydro-oxazolo[3,2-a]pyrimidin-7-one The title compound was prepared from (R)-5-(4-tert-butyl-phenoxymethyl)-4,5-dihydro-oxazol-2-ylamine employing the procedures as set forth in Step 3 of Example 1. [α]$_D^{25}$ + 52.20 (c 0.5, CHCl$_3$).

$C_{17}H_{20}N_2O_3$ (300.14), LCMS (ESI): 301.13 (M$^+$+H).
$^1$H NMR (CDCl$_3$, 300 MHz) δ 7.31 (d, 2H), 7.24 (d, 1H), 6.82 (d, 2H), 6.09 (d, 1H), 5.28 (m, 1H), 4.23-4.42 (m, 4H), 1.30 (s, 9H).

Example 68

2(R)-(4-Cyclohexyl-phenoxymethyl)-2,3-dihydro-oxazolo[3,2-a]pyrimidin-7-one

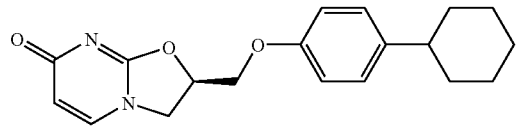

Step 1: (R)-2-(4-Cyclohexyl-phenoxymethyl)-oxirane

The title compound was prepared from 4-cyclohexyl-phenol and S-epichlorohydrin employing the procedures as set forth in Step 1 of Example 1.

$C_{15}H_{20}O_2$ (232.15), LCMS (ESI): 274.18 (M$^+$H+CH$_3$CN).
$^1$H NMR (CDCl$_3$, 300 MHz), δ 7.12 (d, 2H), 6.85 (d, 2H), 4.17 (dd, 1H), 3.96 (dd, 1H), 3.34 (m, 1H), 2.89 (t, 1H), 2.74 (dd, 1H), 2.44 (m, 1H), 1.78-1.85 (m, 5H), 1.31-1.43 (m, 5H).

Step 2: (R)-5-(4-Cyclohexyl-phenoxymethyl)-4,5-dihydro-oxazol-2-ylamine

The title compound was prepared from (R)-2-(4-cyclohexyl-phenoxymethyl)-oxirane employing the procedures as set forth in Step 2 of Example 1.

$C_{16}H_{22}N_2O_2$ (274.17), LCMS (ESI): 275.16 (M$^+$+H).

¹H NMR (CDCl₃, 300 MHz), δ 7.13 (d, 2H), 6.85 (dd, 2H), 4.91 (m, 1H), 4.2 (v. br., 2H), 4.05 (AB-m, 2H), 3.91 (dd, 1H), 3.61 (dd, 1H), 2.45 (br.s, 1H), 1.17-1.93 (m, 10H).

Step 3: 2(R)-(4-Cyclohexyl-phenoxymethyl)-2,3-dihydro-oxazolo[3,2-a]pyrimidin-7-one The title compound was prepared from (R)-5-(4-cyclohexyl-phenoxymethyl)-4,5-dihydro-oxazol-2-ylamine employing the procedures as set forth in Step 3 of Example 1. $[\alpha]_D^{25}$ +52.40 (c 0.5, CHCl₃).

$C_{19}H_{22}N_2O_3$ (326.16), LCMS (ESI): 327.16 (M⁺+H).

¹H NMR (CDCl₃, 300 MHz), δ 7.23 (d, 1H), 7.14(d, 2H), 6.80 (d, 2H), 6.10 (d, 1H), 5.26 (m, 1H), 4.22-4.38 (m, 4H), 2.45 (br.s, 1H), 1.70-1.88 (m, 5H), 1.32-1.43 (m, 5H).

Example 69

(S)-2-(4-Bicyclo[3.3.1]non-9-yl-phenoxymethyl)-5-ethyl-2,3-dihydro-oxazolo[3,2-a]pyrimidin-7-one

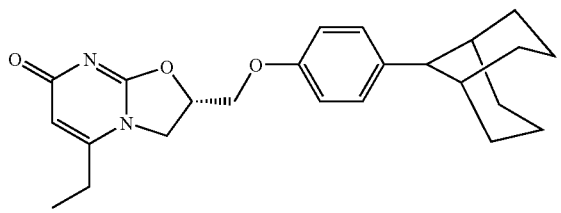 [SMILES: CCc1cc(=O)nc2n1C[C@@H](COc1ccc(C3C4CCCC3CCC4)cc1)O2]

To a solution of (S)-5-(4-bicyclo[3.3.1]non-9-yl-phenoxymethyl)-4,5-dihydro-oxazol-2-ylamine (0.26 g, 0.828 mmol), prepared in accordance with the procedures as set forth in Steps 1 and 2 of Example 1 and starting from R-epichlorohydrin and 4-bicyclo[3.3.1]non-9-yl phenol (prepared with the same procedure as set forth in steps 1 and 2 of Example 20), in ethanol (5 mL) was added ethyl 2-pentynoate (0.157 g, 1.24 mmol). The reaction mixture was heated at reflux for 14 hrs and then cooled to room temperature. The reaction mixture was concentrated and loaded onto a silica gel column, and eluted with 4-6% methanol/methylene chloride to afford 120 mg of (S)-2-(4-bicyclo[3.3.1]non-9-yl-phenoxymethyl)-5-ethyl-2,3-dihydro-oxazolo[3,2-a]pyrimidin-7-one. $[\alpha]_D^{25}$ −36.89 (c 0.501, CHCl₃).

$C_{24}H_{30}N_2O_3$ (394.22), LCMS (ESI): 395.19 (MH⁺).

¹H NMR (300 MHz, CDCl₃): δ 7.29 (d, 2H), 6.84 (d, 2H), 5.89 (s, 1H), 5.25 (m, 1H), 4.23-4.38 (m, 4H), 2.73 (br.s, 1H), 2.49 (q, 2H), 2.38 (br.s, 2H), 1.34-2.07 (m, 12H), 1.28 (t, 3H).

Example 70

(2S,6R)-2-(4-Cyclohexyl-phenoxymethyl)-6-methyl-2,3,5,6-tetrahydro-oxazolo[3,2-a]pyrimidin-7-one

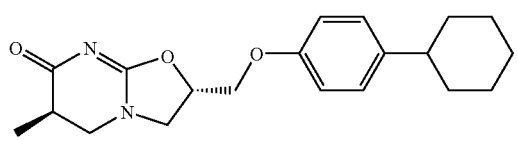 [SMILES: C[C@@H]1CN2C[C@@H](COc3ccc(C4CCCCC4)cc3)OC2=NC1=O]

(2S,6S)-2-(4-Cyclohexyl-phenoxymethyl)-6-methyl-2,3,5,6-tetrahydro-oxazolo[3,2-a]pyrimidin-7-one

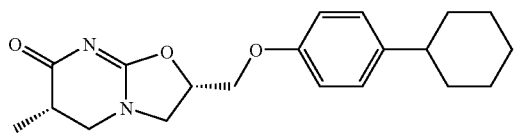 [SMILES: C[C@H]1CN2C[C@@H](COc3ccc(C4CCCCC4)cc3)OC2=NC1=O]

A mixture of (S)-5-(4-cyclohexyl-phenoxymethyl)-4,5-dihydro-oxazol-2-ylamine (0.85 g, 3.09 mmol), prepared in accordance with the procedures as set forth in Steps 1 and 2 of Example 1 and starting from R-epichlorohydrin and 4-cyclohexylphenol, and methyl methacrylate (3.72 g, 37.15 mmol) stabilized with hydroquinone was heated at 90° C. for 14 hrs. The reaction mixture was concentrated and loaded onto a silica gel column, eluted with 2-6% isopropanol/methylene chloride to afford (2S,6R)-2-(4-cyclohexyl-phenoxymethyl)-6-methyl-2,3,5,6-tetrahydro-oxazolo[3,2-a]pyrimidin-7-one and (2S,6S)-2-(4-cyclohexyl-phenoxymethyl)-6-methyl-2,3,5,6-tetrahydro-oxazolo[3,2-a]pyrimidin-7-one (total 0.79 g).

(2S,6R)-2-(4-Cyclohexyl-phenoxymethyl)-6-methyl-2,3,5,6-tetrahydro-oxazolo[3,2-a]pyrimidin-7-one. $[\alpha]_D^{25}$ + 78.40 (c 0.5, DMSO).

$C_{20}H_{26}N_2O_3$ (342.19), LCMS (ESI): 343.20 (MH⁺).

¹H NMR (300 MHz, DMSO-d₆): δ 7.18 (2H, d), 6.85 (2H, d), 5.16 (1H, m), 4.23 (1H, dd), 4.18 (1H, dd), 3.85 (1H, dd), 3.59 (2H, m), 3.13 (1H, dd), 2.50 (1H, ddq), 2.42 (1H, m), 1.65-1.82 (5H, m), 1.20-1.40 (5H, m), 1.06 (3H, d).

(2S,6S)-2-(4-Cyclohexyl-phenoxymethyl)-6-methyl-2,3,5,6-tetrahydro-oxazolo[3,2-a]pyrimidin-7-one. $[\alpha]_D^{25}$ + 102.29 (c 0.503, DMSO).

$C_{20}H_{26}N_2O_3$ (342.19), LCMS (ESI): 343.18 (MH⁺).

¹H NMR (300 MHz, DMSO-d₆): δ 7.18 (2H, d), 6.85 (2H, d), 5.16 (1H, m), 4.26 (1H, dd), 4.17 (1H, dd), 3.90 (1H, dd), 3.59 (2H, m), 3.13 (1H, dd), 2.50 (1H, ddq), 2.43 (1H, m), 1.65-1.82 (5H, m), 1.20-1.40 (5H, m), 1.06 (3H, d).

Example 71

(S)-2-(4-Cyclohexyl-phenoxymethyl)-6-methyl-2,3-dihydro-oxazolo[3,2-a]pyrimidin-7-one

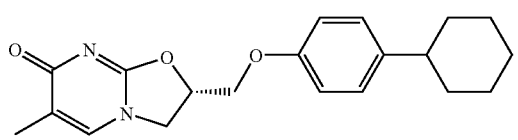

To a solution of (2S,6S)-2-(4-cyclohexyl-phenoxymethyl)-6-methyl-2,3,5,6-tetrahydro-oxazolo[3,2-a]pyrimidin-7-one (38 mg, 0.111 mmol) in toluene (3 ml) was added 96 mg (1.11 mmol) of manganese(IV) oxide. The reaction mixture was heated at 110° C. overnight. The reaction mixture was filtered and the filtrate concentrated and loaded onto a silica gel column, and eluted with 2-7% isopropanol/methylene chloride to afford 8 mg of (S)-2-(4-cyclohexyl-phenoxymethyl)-6-methyl-2,3-dihydro-oxazolo[3,2-a]pyrimidin-7-one.

$C_{20}H_{24}N_2O_3$ (340.17), LCMS (ESI): 341.20 (MH⁺).

$^1$H NMR (300 MHz, CDCl$_3$): δ 7.13 (2H, d), 7.12 (1H, s), 6.80 (2H, d), 5.22 (1H, m), 4.22-4.36 (4H, m), 2.45 (1H, m), 2.01 (3H, s), 1.69-1.88 (5H, m), 1.33-1.44 (5H, m).

Example 72

(S)-5-ethyl-2-(5,6,7,8,8a,9-hexahydro-4bH-flouren-2-yloxymethyl)-2,3-dihydro-oxazolo[3,2-a]pyrimidin-7-one.

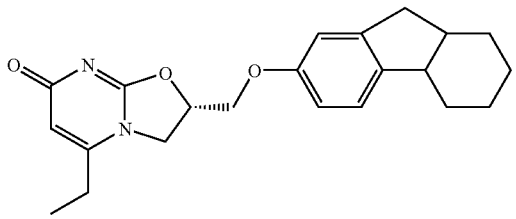 [SMILES: CCc1cc(=O)nc2n1C[C@@H](COc1ccc3c(c1)CC1CCCCC31)O2]

To a solution of (S)-5-(5,6,7,8,8a,9-hexahydro-4bH-fluoren-2-yloxymethyl)-4,5-dihydro-oxazol-2-ylamine (16 mg, 0.055 mmol), prepared in accordance with the procedures in Steps 1 and 2 of Example 1 and starting from R-epichlorohydrin and 5,6,7,8,8a,9-hexahydro-4bH-fluoren-2-ol (prepared by the same procedure as in Step 1 of Example 19), in ethanol (2 mL) was added ethyl 2-pentynoate (4.2 mg, 0.065 mmol). The reaction mixture was heated at reflux for 14 hrs and then cooled to room temperature. The reaction mixture was concentrated and then loaded onto a silica gel column, and eluted with 2-6% methanol/methylene chloride to afford 8 mg of (S)-5-ethyl-2-(5,6,7,8,8a,9-hexahydro-4bH-fluoren-2-yloxymethyl)-2,3-dihydro-oxazolo[3,2-a]pyrimidin-7-one.

C$_{22}$H$_{26}$N$_2$O$_3$ (366.19), LCMS (ESI): 367.21 (MH$^+$).
$^1$H NMR (300 MHz, CDCl$_3$): δ 6.36 (d, 1H), 6.07 (s, 1H), 6.97 (d, 1H), 5.21 (s, 1H), 4.52 (m, 1H), 3.50-3.68 (m, 4H), 2.34 (m, 1H), 2.12 (dd, 1H), 1.62-1.91 (m, 4H), 0.49-1.15 (m, 11H).

Example 73

(2S,6R)-2-(4-Cyclohexyl-phenoxymethyl)-6-ethyl-2,3,5,6-tetrahydro-oxazolo[3,2-a]pyrimidin-7-one

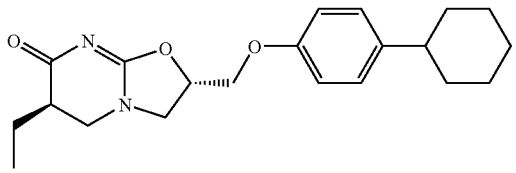 [SMILES: CC[C@@H]1CN2C[C@@H](COc3ccc(C4CCCCC4)cc3)OC2=NC1=O]

(2S,6S)-2-(4-Cyclohexyl-phenoxymethyl)-6-ethyl-2,3,5,6-tetrahydro-oxazolo[3,2-a]pyrimidin-7-one

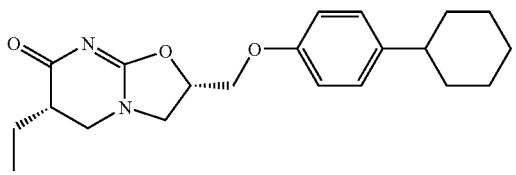

A solution of (S)-5-(4-cyclohexyl-phenoxymethyl)-4,5-dihydro-oxazol-2-ylamine (0.85 g, 3.09 mmol), prepared in accordance with the procedures in Steps 1 and 2 of Example 1 and starting from R-epichlorohydrin and 4-cyclohexylphenol, and ethyl ethylacrylate (1.0 g, 7.57 mmol) in n-butanol (2 ml) was heated at 90° C. for 18 hrs. The reaction mixture was concentrated and loaded onto a silica gel column, and eluted with 2-6% isopropanol/methylene chloride to afford (2S,6R)-2-(4-cyclohexyl-phenoxymethyl)-6-ethyl-2,3,5,6-tetrahydro-oxazolo[3,2-a]pyrimidin-7-one (0.24 g) and (2S,6S)-2-(4-cyclohexyl-phenoxymethyl)-6-ethyl-2,3,5,6-tetrahydro-oxazolo[3,2-a]pyrimidin-7-one (0.34 g).

(2S,6R)-2-(4-Cyclohexyl-phenoxymethyl)-6-ethyl-2,3,5,6-tetrahydro-oxazolo[3,2-a]pyrimidin-7-one. [α]$_D^{25}$ +32.12 (c 0.504, DMSO).
C$_{21}$H$_{28}$N$_2$O$_3$ (356.20), LCMS (ESI): 357.23 (MH$^+$).
$^1$H NMR (300 MHz, DMSO-d$_6$): δ 7.18 (2H, d), 6.85 (2H, d), 5.16 (1H, m), 4.24 (1H, dd), 4.18 (1H, dd), 3.86 (1H, dd), 3.58 (2H, m), 3.22 (1H, dd), 2.43 (1H, m), 2.31 (1H, m), 1.65-1.82 (6H, m), 1.28-1.40 (5H, m), 1.21 (1H, m), 0.89 (3H, t).

(2S,6S)-2-(4-Cyclohexyl-phenoxymethyl)-6-ethyl-2,3,5,6-tetrahydro-oxazolo[3,2-a]pyrimidin-7-one
C$_{21}$H$_{28}$N$_2$O$_3$ (356.20), LCMS (ESI): 357.23 (MH$^+$).
$^1$H NMR (300 MHz, DMSO-d$_6$): δ 7.18 (2H, d), 6.85 (2H, d), 5.16 (1H, m), 4.26 (1H, dd), 4.17 (1H, dd), 3.90 (1H, dd), 3.57 (2H, m), 3.22 (1H, dd), 2.43 (1H, m), 2.31 (1H, m), 1.65-1.82 (6H, m), 1.28-1.46 (5H, m), 1.21 (1H, m), 0.89 (3H, t).

Example 74

(S)-2-[4-(3,3,5,5-Tetramethyl-cyclohexyl)-phenoxymethyl]-2,3-dihydro-oxazolo[3,2-a]pyrimidin-7-one

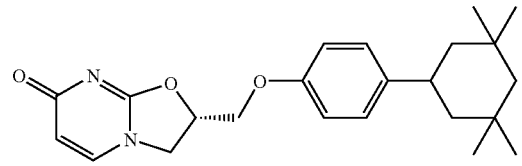 [SMILES: CC1(C)CC(c2ccc(OC[C@@H]3Cn4ccc(=O)nc4O3)cc2)CC(C)(C)C1]

Step 1: 4-(3,3,5,5-Tetramethyl-cyclohexyl)-phenol

To 10% Pd/C (0.17 g) under N$_2$ was added 1-benzyloxy-4-(3,3,5,5-tetramethyl-cyclohex-1-enyl)-benzene (1.7 g, 5.3 mmol), prepared by a substantially similar procedure to that of Step 1 of Example 18, in MeOH (15 mL) and EtOAc (15 mL). This mixture was stirred under H$_2$ (1 atm) overnight. The reaction mixture was filtered through celite. The filtrate was concentrated to give the title compound as a white solid (1.19 g).

C$_{16}$H$_{24}$O (232.18), LCMS (CI): 232.15(M$^+$).
$^1$H NMR (CDCl$_3$, 300 MHz): 7.10 (d, 2H), 6.76 (d, 2H), 4.55 (s, 1H), 2.80 (m, 1H), 1.54 (m, 2H), 1.11-1.34 (m, 4H), 1.08 (s, 6H), 0.92 (s, 6H).

Steps 2 to 4: (S)-2-[4-(3,3,5,5-Tetramethyl-cyclohexyl)-phenoxymethyl]-2,3-dihydro-oxazolo[3,2-a]pyrimidin-7-one The title compound was prepared from 4-(3,3,5,5-tetramethyl-cyclohexyl)-phenol and R-epichlorohydrin employing the procedures in Steps 1 through 3 of Example 1.

C$_{23}$H$_{30}$N$_2$O$_3$ (382.23), LCMS (ESI): 383.23 (M$^+$+H).
$^1$H NMR (DMSO-d$_6$, 300 MHz), 7.76 (d, 1H), 7.16 (d, 2H), 6.85 (d, 2H), 5.82 (d, 1H), 5.32 (b.s, 1H), 4.24-4.44 (m, 3H), 4.09 (AB-m, 1H), 2.70-2.87 (m, 1H), 1.44 (d, 2H), 1.10-1.30 (m, 4H), 1.06 (s, 6H), 0.90 (s, 6H).

Example 75

(S)-2-(6-tert-Butyl-benzothiazol-2-yloxymethyl)-2,3-dihydro-oxazolo[3,2-a]pyrimidin-7-one

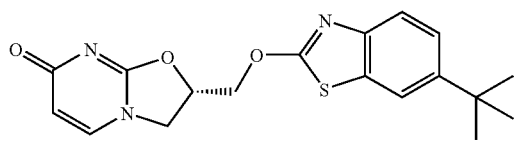 [SMILES: CC(C)(C)c1ccc2nc(OC[C@@H]3Cn4ccc(=O)nc4O3)sc2c1]

The title compound was prepared from 5-tert-butyl-benzothiazol-2-ol and R-epichlorohydrin employing the procedures in Steps 1 through 3 of Example 1. $[\alpha]_D^{25}$ +6.08 (c 0.51, CHCl$_3$).

C$_{18}$H$_{19}$N$_3$O$_3$S (357.12), LCMS (ESI): 358.02 (M$^+$+H).

$^1$H NMR (DMSO-d$_6$, 300 MHz), 7.74 (m, 2H), 7.43 (d, 2H), 5.81 (d, 1H), 5.28 (b.s, 1H), 4.26-4.55 (m, 3H), 4.08 (AB-m, 1H), 1.30 (s, 9H).

Example 76

(S)-2-(4-Cyclohexyl-phenoxymethyl)-5-propyl-2,3-dihydro-oxazolo[3,2-a]pyrimidin-7-one

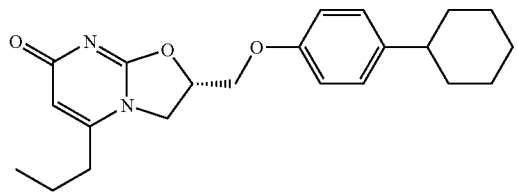 [SMILES: CCCc1cc(=O)nc2n1C[C@@H](COc1ccc(C3CCCCC3)cc1)O2]

(S)-5-(4-Cyclohexyl-phenoxymethyl)-4,5-dihydro-oxazol-2-ylamine (0.37 g, 1.35 mmol), prepared in accordance with the procedures in Steps 1 and 2 of Example 1 and starting from R-epichlorohydrin and 4-cyclohexylphenol, was dissolved in ethanol (6 mL). Methyl 2-hexynoate (0.34 g, 2.70 mmol) was then added and the reaction mixture was heated at reflux for 24 hrs and then cooled to room temperature. The resulting crystalline solid was isolated by filtration, washed with heptane 3 times, and dried under vacuum to afford 135 mg (27% yield) of (S)-2-(4-cyclohexyl-phenoxymethyl)-5-propyl-2,3-dihydro-oxazolo[3,2-a]pyrimidin-7-one as a white solid.

C$_{22}$H$_{28}$N$_2$O$_3$ (368.48), LC/MS (ESI): 369.21 (MH$^+$)

$^1$H NMR (300 MHz, DMSO-d$_6$): δ 7.14 (2H, d), 6.84 (2H, d), 5.63 (1H, s), 5.29 (1H, m), 4.11-4.44 (4H, m), 2.45 (3H, m), 1.64-1.80 (5H, m), 1.55-1.64 (2H, m), 1.16-1.42 (5H, m), 0.96 (3H, t).

Example 77

(S)-2-(4-Cyclohexyl-phenoxymethyl)-5-phenyl-2,3-dihydro-oxazolo[3,2-a]pyrimidin-7-one

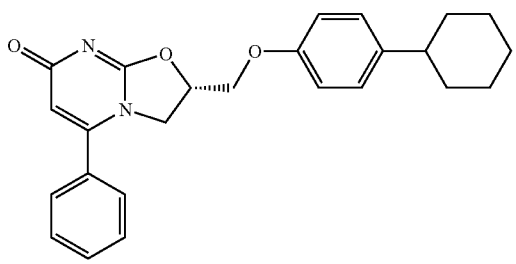 [SMILES: O=c1cc(-c2ccccc2)n2c(n1)O[C@H](COc1ccc(C3CCCCC3)cc1)C2]

The title compound was prepared from (S)-5-(4-cyclohexyl-phenoxymethyl)-4,5-dihydro-oxazol-2-ylamine and ethyl phenylpropiolate employing the procedure described in Example 76. $[\alpha]_D^{25}$ +100.26 (c 0.507, DMSO).

C$_{25}$H$_{26}$N$_2$O$_3$ (402.50), LC/MS (ESI): 403.19 (MH$^+$)

$^1$H NMR (300 MHz, DMSO-d$_6$): δ 7.56 (5H, m), 7.14 (2H, d), 6.84 (2H, d), 5.84 (1H, s), 5.25 (1H, m), 4.21-4.38 (3H, m), 3.97 (1H, m), 2.43 (1H, m), 1.65-1.80 (5H, m), 1.15-1.42 (5H, m).

Example 78

(S)-2-[4-(4-tert-Butyl-phenoxy)-phenoxymethyl]-2,3-dihydro-oxazolo[3,2-a]pyrimidin-7-one

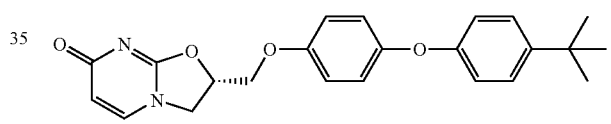

The title compound was prepared from 4-(4-tert-butylphenoxy)-phenol (prepared in accordance with the procedures of Yeager, et. al., *Synthesis*. 1991, 63-68) and R-epichlorohydrin employing the procedures set forth in Steps 1 through 3 of Example 1. $[\alpha]_D^{25}$ −35.00 (c 0.571, CHCl$_3$).

C$_{23}$H$_{24}$N$_2$O$_4$ (392.17), LCMS (ESI): 393.15 (M$^+$+H).

$^1$H NMR (DMSO-d$_6$, 300 MHz), δ 7.76 (d, 1H), 7.35 (d, 2H), 6.97 (s, 4H), 6.85 (d, 2H), 5.82 (d, 1H), 5.32 (br.s, 1H), 4.24-4.43 (m, 3H), 4.11 (AB-m, 1H), 1.27 (s, 9H).

Example 79

(S)-2-(4-Cyclohexyl-phenoxymethyl)-7-oxo-2,3-dihydro-7H-oxazolo[3,2-a]pyrimidine-5-carboxylic acid ethyl ester

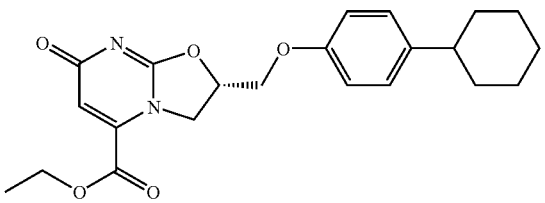 [SMILES: CCOC(=O)c1cc(=O)nc2n1C[C@@H](COc1ccc(C3CCCCC3)cc1)O2]

To a solution of (S)-5-(4-cyclohexyl-phenoxymethyl)-4,5-dihydro-oxazol-2-ylamine (0.5 g, 1.82 mmol), prepared in accordance with the procedures described in Steps 1 and 2 of Example 1 and starting from R-epichlorohydrin and 4-cyclohexylphenol, in ethanol (10 mL) was added diethyl acetylenedicarboxylate (0.39 g, 2.29 mmol). The reaction mixture was heated at reflux for 14 hours and then stored in a freezer overnight. The reaction mixture was warmed to room temperature. The resulting crystalline solid was isolated by centrifugation and dried under vacuum at 60° C. to afford 427 mg of (S)-2-(4-cyclohexyl-phenoxymethyl)-7-oxo-2,3-dihydro-7H-oxazolo[3,2-a]pyrimidine-5-carboxylic acid ethyl ester. $[\alpha]_D^{25}$ −16.15 (c 0.52, $CHCl_3$).

$C_{22}H_{26}N_2O_5$ (398.18), LCMS (ESI): 399.20 ($M^+$+H)
$^1$H NMR ($CDCl_3$, 300 MHz), δ 7.13 (2H, d), 6.80 (3H, m), 5.21 (1H, m), 4.62-4.78 (2H, m), 4.39 (2H, q), 4.20-4.33 (2H, m), 2.45 (br.s, 1H), 1.67-1.88 (m, 5H), 1.18-1.43 (8H, m).

Example 80

(S)-2-[4-(4-Cyclohexyl-phenoxy)-phenoxymethyl]-2,3-dihydro-oxazolo[3,2-a]pyrimidin-7-one

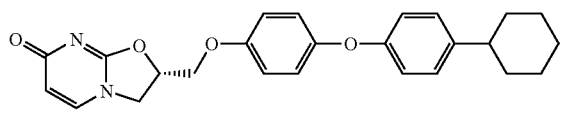

The title compound was prepared from 4-(4-cyclohexylphenoxy)-phenol (prepared in accordance with the procedures of Yeager, et. al., *Synthesis.* 1991, 63-68) and R-epichlorohydrin employing the procedures as set forth in Steps 1 through 3 of Example 1. $[\alpha]_D^{25}$ −33.76 (c 0.563, $CHCl_3$).

$C_{25}H_{26}N_2O_4$ (418.18), LCMS (ESI): 419.20 ($M^+$+H).
$^1$H NMR (DMSO-$d_6$, 300 MHz), δ 7.76 (d, 1H), 7.17 (d, 2H), 6.97 (s, 4H), 6.83 (d, 2H), 5.82 (d, 1H), 5.34 (br.s, 1H), 4.23-4.46 (m, 3H), 4.12 (AB-m, 1H), 2.42 (m, 1H), 1.66-1.84 (m, 5H), 1.14-1.43 (m, 5H).

Example 81

(S)-2-(4-Cyclohexyl-phenoxymethyl)-6-ethyl-2,3-dihydro-oxazolo[3,2-a]pyrimidin-7-one

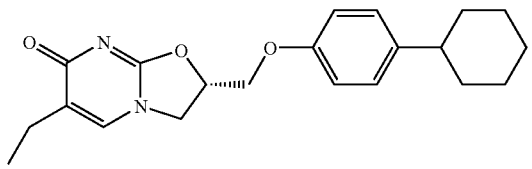 [SMILES: CCc1cn2c(nc1=O)O[C@H](COc1ccc(C3CCCCC3)cc1)C2]

To a solution of (2S,6R)-2-(4-cyclohexyl-phenoxymethyl)-6-ethyl-2,3,5,6-tetrahydro-oxazolo[3,2-a]pyrimidin-7-one (108 mg, 0.41 mmol) in toluene (2 ml) was added manganese(IV) oxide (360 mg, 4.1 mmol). The reaction mixture was heated at reflux for three days. The reaction mixture was filtered without cooling and the filtrate concentrated and loaded on a silica gel column. The column was eluted with 2-7% isopropanol/methylene chloride to afford 8 mg of (S)-2-(4-cyclohexyl-phenoxymethyl)-6-ethyl-2,3-dihydro-oxazolo[3,2-a]pyrimidin-7-one. $[\alpha]_D^{25}$ −22.40 (c 0.5, $CHCl_3$).

$C_{21}H_{26}N_2O_3$ (354.19), LCMS (ESI): 355.21 ($MH^+$).
$^1$H NMR (300 MHz, $CDCl_3$): δ 7.13 (2H, d), 7.04 (1H, s), 6.81 (2H, d), 5.23 (1H, m), 4.19-4.39 (4H, m), 2.40-2.53 (3H, m), 1.67-1.87 (5H, m), 1.13-1.42 (8H, m).

Example 82

(S)-5-Ethyl-2-[4-(3,3,5,5-tetramethyl-cyclohexyl)-phenoxymethyl]-2,3-dihydro-oxazolo[3,2-a]pyrimidin-7-one

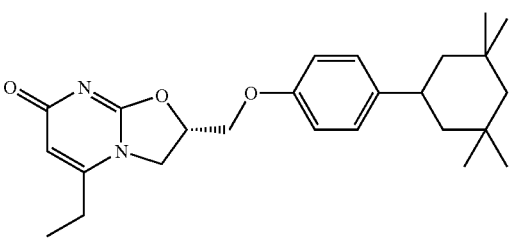 [SMILES: CCc1cc(=O)nc2n1C[C@@H](COc1ccc(C3CC(C)(C)CC(C)(C)C3)cc1)O2]

To a solution of 5-[4-(3,3,5,5-tetramethyl-cyclohexyl)-phenoxymethyl]-4,5-dihydro-oxazol-2-ylamine (0.15 g, 0.454 mmol), prepared in accordance with the procedures described in Steps 1 and 2 of Example 1 and starting from R-epichlorohydrin and 4-(3,3,5,5-tetramethyl-cyclohexyl)-phenol (prepared using the same procedure as in step 1 of Example 74), in ethanol (5 mL) was added ethyl 2-pentynoate (0.086 g, 0.681 mmol). The reaction mixture was heated at reflux for 14 hrs and then cooled to room temperature. The reaction mixture was concentrated, loaded onto a silica gel column, and eluted with 4% methanol/methylene chloride to afford 23 mg of (S)-5-ethyl-2-[4-(3,3,5,5-tetramethyl-cyclohexyl)-phenoxymethyl]-2,3-dihydro-oxazolo[3,2-a]pyrimidin-7-one.

$C_{25}H_{34}N_2O_3$ (410.26), LCMS (ESI): 411.25 ($MH^+$).
$^1$H NMR (300 MHz, $CDCl_3$): 7.15 (d, 2H), 6.81 (d, 2H), 5.89 (s, 1H), 5.22 (b.s, 1H), 4.20-4.38 (m, 4H), 2.18 (m, 1H), 2.50 (q, 2H), 1.55 (m, 2H) 1.11-1.35 (m, 7H), 1.08 (s, 6H), 0.93 (s, 6H)

Example 83

(S)-2-(4-Cyclohexyl-3-isopropyl-phenoxymethyl)-2,3-dihydro-oxazolo[3,2-a]pyrimidin-7-one

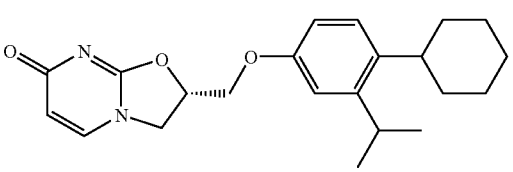 [SMILES: CC(C)c1cc(OC[C@@H]2Cn3ccc(=O)nc3O2)ccc1C1CCCCC1]

Steps 1 and 2:
1-cyclohexyl-4-methoxy-2-isopropyl-benzene

1-Bromo-2-isopropyl-4-methoxy-benzene was prepared in accordance with the procedures of Konishi et. al., *Bull. Chem. Soc. Jpn.*, 1989, 62, 591-593. To a solution of 1-bromo-2-isopropyl-4-methoxy-benzene (4.5 g, 19.7 mmol) was added BuLi (1.6M in hexane, 14.8 mL, 23.7 mmol) at −78° C. The reaction mixture was stirred at −78° C. for 40 min, followed by addition of B(O-iPr)$_3$ dropwise. The resulting mixture was stirred at −78° C. for 2 hours, then warmed to room temperature overnight. The reaction mixture was quenched with HCl (1N) and extracted with diethyl ether three times. The organic phase was washed with water, brine and dried (Na$_2$SO$_4$). Silica gel chromatography (10-30%EtOAc/heptane) provided 2.3 g of 4-methoxy-2-isopropyl-phenylboronic acid.

Cyclohexyl-4-methoxy-2-isopropyl-benzene was prepared in two steps by a Suzuki coupling of 4-methoxy-2-isopropyl-phenylboronic acid and cyclohexenol triflate following the procedures of Carmen et. al., *Synlett* 2005, No. 10, pp 1601-1605, to obtain 1-cyclohex-1-enyl-2-isopropyl-4-methoxy-benzene, which was subsequently hydrogenated (Pd/C, H$_2$, MeOH) to form 1-cyclohexyl-4-methoxy-2-isopropyl-benzene.

C$_{16}$H$_{24}$O (232.18), LCMS (EI): 232.17(M$^+$).
$^1$H NMR (CDCl$_3$, 300 MHz), δ 7.15 (d, 1H), 6.81 (d, 1H), 6.70 (dd, 1H), 3.79 (s, 3H), 3.22 (quin, 1H), 2.72 (br. s, 1H), 1.67-1.92 (m, 5H), 1.27-1.48 (m, 5H), 1.23 (d, 6H).

Step 3: 4-Cyclohexyl-3-isopropyl-phenol

To 1-cyclohexyl-4-methoxy-2-isopropyl-benzene (2.09 g, 9.0 mmol) in CH$_2$Cl$_2$ (20 mL) was added BBr$_3$ (1 M in CH$_2$Cl$_2$, 22.5 mmol) dropwise at 0° C. This mixture was stirred at 0° C. for two hours. The reaction mixture was then quenched with MeOH (5 mL), after which aqueous sodium hydrogen carbonate (10 mL) was added. The reaction mixture was stirred at room temperature for one hour and extracted with CH$_2$Cl$_2$ three times. The organic phase was washed with brine, dried (Na$_2$SO$_4$) and concentrated. Silica gel chromatography (0-2% EtOAc/heptane) provided 2.36 g of the title compound.

C$_{15}$H$_{22}$O (218.16), LCMS (ESI): 219.18 (M$^+$+H).
$^1$H NMR (CDCl$_3$, 300 MHz), δ 7.09 (d, 1H), 6.73 (d, 1H), 6.62 (d, 1H), 4.47 (s, 1H), 3.20 (quin, 1H), 2.72 (br. s, 1H), 1.63-1.92 (m, 5H), 1.12-1.48 (m, 5H), 1.21 (d, 6H).

Steps 4 to 6: (S)-2-(4-Cyclohexyl-3-isopropyl-phenoxymethyl)-2,3-dihydro-oxazolo[3,2-a]pyrimidin-7-one The title compound was prepared from 4-cyclohexyl-3-isopropyl-phenol and R-epichlorohydrin employing the procedures as set forth in Steps 1 through 3 of Example 1. [α]$_D^{25}$ −54.00 (c 0.5, CHCl$_3$).

C$_{22}$H$_{28}$N$_2$O$_3$ (368.20), LCMS (ESI): 369.23 (M$^+$+H).
$^1$H NMR (CDCl$_3$, 300 MHz), δ 7.26 (d, 1H), 7.15 (d, 1H), 6.76 (d, 1H), 6.67 (dd, 1H), 6.10 (d, 1H), 5.28 (m, 1H), 4.18-4.44 (m, 4H), 3.22 (quin, 1H), 2.74 (br. s, 1H), 1.67-1.89 (m, 5H), 1.20-1.50 (m, 5H), 1.21 (d, 6H).

Example 84

(S)-2-(4-Cyclohexyl-3-ethyl-phenoxymethyl)-2,3-dihydro-oxazolo[3,2-a]pyrimidin-7-one

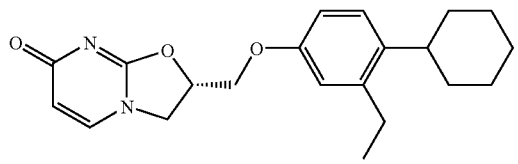 [SMILES: CCc1cc(OC[C@@H]2Cn3ccc(=O)nc3O2)ccc1C1CCCCC1]

Step 1: 4-Cyclohexyl-3-ethyl-phenol

4-Cyclohexyl-3-ethyl-phenol was prepared by employing the procedures in step 1 through 3 of Example 83.
C$_{14}$H$_{20}$O (204.15), LCMS (ESI): 205.17 (M$^+$+H).
$^1$H NMR (CDCl$_3$, 300 MHz), δ 7.08 (d, 1H), 6.64 (m, 2H), 4.51 (s, 1H), 2.62 (m, 3H), 1.68-1.90 (m, 5H), 1.17-1.50 (m, 5H), 1.19 (t, 3H).

Step 2 to 4: (S)-2-(4-Cyclohexyl-3-ethyl-phenoxymethyl)-2,3-dihydro-oxazolo[3,2-a]pyrimidin-7-one The title compound was prepared from 4-cyclohexyl-3-ethyl-phenol and R-epichlorohydrin employing the procedures as set forth in Steps 1 through 3 of Example 1. [α]$_D^{25}$ −51.60 (c 0.5, CHCl$_3$).

C$_{21}$H$_{26}$N$_2$O$_3$ (354.19), LCMS (ESI): 355.19 (M$^+$+H).
$^1$H NMR (CDCl$_3$, 300 MHz), δ 7.24 (d, 1H), 7.15 (d, 1H), 6.64-6.73 (m, 2H), 6.08 (d, 1H), 5.27 (m, 1H), 4.18-4.43 (m, 4H), 2.58-2.74 (m, 3H), 1.63-1.93 (m, 5H), 1.20-1.50 (m, 5H), 1.19 (t, 3H).

Example 85

(S)-2-(4-Cyclohexyl-3,5-dimethyl-phenoxymethyl)-2,3-dihydro-oxazolo[3,2-a]pyrimidin-7-one

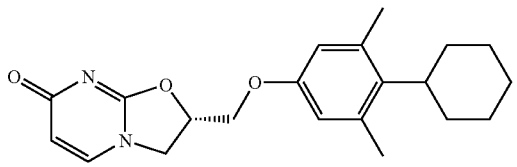 [SMILES: Cc1cc(OC[C@@H]2Cn3ccc(=O)nc3O2)cc(C)c1C1CCCCC1]

Step 1: 4-Cyclohexyl-3,5-dimethyl-phenol

4-Cyclohexyl-3,5-dimethyl-phenol was prepared in accordance with the procedures of Boisselet et. al., FR 1315008.
C$_{14}$H$_{20}$O (204.15), LCMS (ESI): 205.17 (M$^+$+H).
$^1$H NMR (CDCl$_3$, 300 MHz), δ 6.48 (s, 2H), 4.37 (s, 1H), 2.90 (m, 1H), 2.36 (br.s, 6H), 1.15-1.95 (m, 10H).

Step 2 to 4: (S)-2-(4-Cyclohexyl-3,5-dimethyl-phenoxymethyl)-2,3-dihydro-oxazolo[3,2-a]pyrimidin-7-one The title compound was prepared from 4-cyclohexyl-3,5-dimethyl-phenol and R-epichlorohydrin employing the procedures as set forth in Steps 1 through 3 of Example 1. [α]$_D^{25}$ −4.40 (c 0.5, DMSO).

C$_{21}$H$_{26}$N$_2$O$_3$ (354.19), LCMS (ESI): 355.19 (M$^+$+H).
$^1$H NMR (DMSO-D6, 300 MHz), δ 7.76 (d, 1H), 6.50 (br. s, 2H), 5.82 (d, 1H), 5.29 (m, 1H), 4.73 (t, 1H), 4.24 (m, 2H), 4.08 (m, 1H), 2.86 (m, 1H), 2.32(br. s, 6H), 1.22-1.89 (m, 10H).

Example 86

2-[3-Methyl-4-(3,3,5,5-tetramethyl-cyclohexyl)-phenoxymethyl]-2,3-dihydro-oxazolo[3,2-a]pyrimidin-7-one

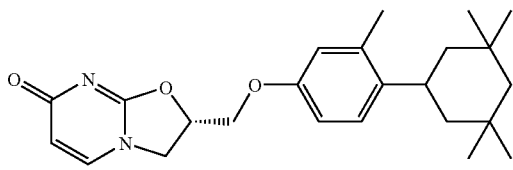

Step 1: 3-Methyl-4-(3,3,5,5-tetramethyl-cyclohexyl)-phenol

Trifluoro-methanesulfonic acid 3,3,5,5-tetramethyl-cyclohex-1-enyl ester was prepared in accordance with the procedures of Hanack et. al., *J. Heterocyclic Chem.* 1988, 25, pp 1237-1241. 4-Methoxy-2-methyl-1-(3,3,5,5-tetramethyl-cyclohex-1-enyl)-benzene was prepared in two steps by a Suzuki coupling of 4-methoxy-2-methyl-phenylboronic acid and trifluoro-methanesulfonic acid 3,3,5,5-tetramethyl-cyclohex-1-enyl ester following the procedures of Carmen et. al., *Synlett* 2005, No. 10, pp 1601-1605, to obtain 4-methoxy-2-methyl-1-(3,3,5,5-tetramethyl-cyclohex-1-enyl)-benzene, which was subsequently hydrogenated to form 1-cyclohexyl-4-methoxy-2-methyl-benzene.

To 1-cyclohexyl-4-methoxy-2-ethyl-benzene (1.86 g, 7.15 mmol) in $CH_2Cl_2$ (20 mL) was added $BBr_3$ (1 M in $CH_2Cl_2$, 17.88 mmol) dropwise at 0° C. This mixture was stirred at 0° C. for three hours. The reaction mixture was then quenched with MeOH (5 mL), after which aqueous sodium hydrogen carbonate (10 mL) was added. The reaction mixture was stirred at room temperature overnight and extracted with $CH_2Cl_2$ three times. The organic phase was washed with brine, dried ($Na_2SO_4$) and concentrated. Silica gel chromatography (EtOAc/heptane) provided 1.76 g of the title compound.

$C_{17}H_{26}O$ (246.19), LCMS (ESI): 247.22 ($M^+$+H).
$^1$H NMR ($CDCl_3$, 300 MHz), δ 7.07 (d, 1H), 6.64 (m, 2H), 4.43 (s, 1H), 3.03 (m, 1H), 2.30 (s, 3H), 1.12-1.51 (m, 6H), 1.10 (s, 6H), 0.93 (s, 6H).

Steps 2 to 4: 2-[3-M ethyl-4-(3,3,5,5-tetramethyl-cyclohexyl)-phenoxymethyl]-2,3-dihydro-oxazolo[3,2-a]pyrimidin-7-one The title compound was prepared from 3-methyl-4-(3,3,5,5-tetramethyl-cyclohexyl)-phenol and R-epichlorohydrin employing the procedures set forth in Steps 1 through 3 of Example 1. $[α]_D^{25}$ -43.00 (c 0.5, $CHCl_3$).

$C_{24}H_{32}N_2O_3$ (396.24), LCMS (ESI): 397.24 ($M^+$+H).
$^1$H NMR ($CDCl_3$, 300 MHz), δ 7.25 (d, 1H), 7.12 (d, 1H), 6.68 (m, 2H), 6.08 (d, 1H), 5.26 (m, 1H), 4.20-4.41 (m, 4H), 3.03 (m, 1H), 2.31 (s, 3H), 1.20-1.51 (m, 6H), 1.11 (s, 6H), 0.93 (s, 6H).

Example 87

(S)-2-(4-Cyclohexyl-phenoxymethyl)-6-isopropyl-2,3-dihydro-oxazolo[3,2-a]pyrimidin-7-one

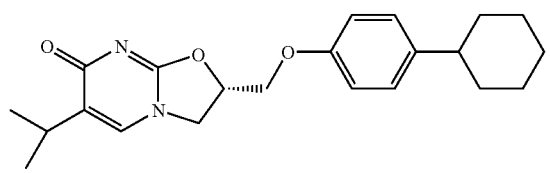 [SMILES: CC(C)c1cn2c(nc1=O)O[C@H](COc1ccc(C3CCCCC3)cc1)C2]

Step1: 2-Formyl-3-methyl-butyric acid ethyl ester

A solution of diisopropylamine (2.53 g, 25 mmol) in THF (25 mL) was treated with n-butyllithium (1.6M in hexane, 16 mL, 25.6 mmol) at room temperature under $N_2$. The resulting pale yellow solution was cooled to -78° C. A solution of 3-methyl-butyric acid ethyl ester (2.91 g, 22.31 mmol) in THF (7 mL) was added. Stirring was continued for a half hour at -78° C., after which ethyl formate (5.5 g, 75 mmol) was added. The reaction mixture was allowed to warm to room temperature and stirred for three hours under $N_2$. The reaction mixture was quenched with acetic acid (4.5 ml), diluted with diethyl ether, washed with water, brine, and dried ($Na_2SO_4$). Silica gel chromatography (methyl acetate/hexane) provided 3.2 g of the title compound as a mixture of isomers.

$C_8H_{14}O_3$ (158.09), LCMS (ESI): 159.11($M^+$+H).

Step 2: (S)-244-Cyclohexyl-phenoxymethyl)-6-isopropyl-2,3-dihydro-oxazolo[3,2-a]pyrimidin-7-one To a solution of (S)-5-(4-cyclohexyl-phenoxymethyl)-4,5-dihydro-oxazol-2-ylamine (0.48 g, 1.74 mmol) (prepared in accordance with the procedures described in Steps 1 and 2 of Example 1 and starting from R-epichlorohydrin and 4-cyclohexylphenol) in ethanol (16 mL) was added 2-formyl-3-methyl-butyric acid ethyl ester (0.33 g, 2.1 mmol). The reaction mixture was heated at reflux for 24 hours. It was then concentrated to remove solvent and loaded on silica gel column. Chromatography with (1-5%) 2-propanol/methylene chloride gave 0.144 g of the title compound. $[α]_D^{25}$ -15.80 (c 0.5, $CHCl_3$).

$C_{22}H_{28}N_2O_3$ (368.20), LCMS (ESI): 369.24 ($M^+$+H).
$^1$H NMR ($CDCl_3$, 300 MHz), δ 7.13 (d, 2H), 7.00 (s, 1H), 6.81 (d, 2H), 5.23 (m, 1H), 4.23-4.39 (m, 4H), 3.07 (quin, 1H), 2.45 (br.s, 1H), 1.69-1.93 (m, 5H), 1.26-1.46 (m, 5H), 1.18 (d, 3H), 1.15 (d, 3H).

Example 88

(S)-2-(4-Cyclohexyl-phenoxymethyl)-6-(2-methoxyethyl)-2,3-dihydro-oxazolo[3,2-a]pyrimidin-7-one

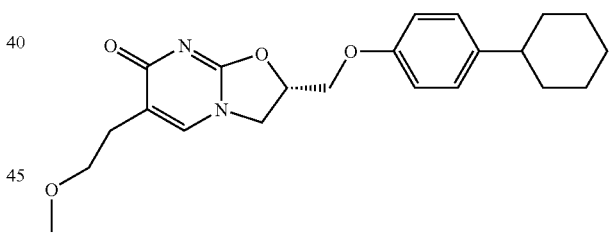

Step1: 2-Formyl-4-methoxy-butyric acid methyl ester

The title compound was prepared from 4-methoxy-butyric acid methyl ester and ethyl formate employing the procedure set forth in Step 1 of Example 87.

$C_7H_{12}O_4$ (160.07), LCMS (EI): 160.10 ($M^+$).

Step 2: 2-(4-Cyclohexyl-phenoxymethyl)-6-(2-methoxy-ethyl)-2,3-dihydro-oxazolo[3,2-a]pyrimidin-7-one The title compound was prepared from (S) -5-(4-cyclohexyl-phenoxy methyl)-4,5-dihydro-oxazol-2-ylamine and 2-formyl-4-methoxy-butyric acid methyl ester employing the procedure described in Step2 of Example 87. $[α]_D^{25}$ -19.00 (c 0.5, $CHCl_3$).

$C_{22}H_{28}N_2O_4$ (384.20), LCMS (ESI): 385.21 ($M^+$+H).

¹H NMR (CDCl₃, 300 MHz), δ 7.24 (s, 1H), 7.13 (d, 2H), 6.81 (d, 2H), 5.23 (m, 1H), 4.30 (m, 4H), 3.61 (t, 2H), 3.33 (s, 3H), 2.67 (t, 2H), 2.45 (br.s, 1H), 1.69-1.90 (m, 5H), 1.17-1.46 (m, 5H).

Example 89

(S)-2-(4-tert-Butyl-phenoxymethyl)-6-ethyl-2,3-dihydro-oxazolo[3,2-a]pyrimidin-7-one

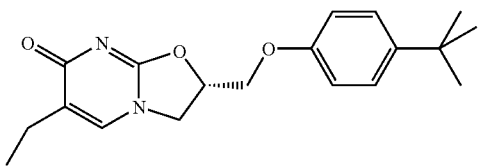 [SMILES: CCc1cn2c(nc1=O)O[C@H](COc1ccc(C(C)(C)C)cc1)C2]

Step1: 2-Formyl-butyric acid ethyl ester

The title compound was prepared from butyric acid ethyl ester and ethyl formate employing the procedure set forth in Step 1 of Example 87.
$C_7H_{12}O_3$ (144.07), LCMS (ESI): 145.08 (M⁺+H).

Step 2: 2-(4-tert-Butyl-phenoxymethyl)-6-ethyl-2,3-dihydro-oxazolo[3,2-a]pyrimidin-7-one The title compound was prepared from (S)-5-(4-tert-butyl-phenoxymethyl)-4,5-dihydro-oxazol-2-ylamine and 2-formyl-butyric acid ethyl ester employing the procedure described in Step2 of Example 87. $[\alpha]_D^{25}$ −31.20 (c 0.5, CHCl₃).
$C_{19}H_{24}N_2O_3$ (328.17), LCMS (ESI): 329.14 (M⁻+H).
¹H NMR (CDCl₃, 300 MHz), δ 7.23 (d, 2H), 7.05 (s, 1H), 6.82 (d, 2H), 5.24 (m, 1H), 4.23-4.39 (m, 4H), 2.45 (q, 2H), 1.30 (s, 9H), 1.17 (t, 3H).

Example 90

(S)-2-(4-Cyclohexyl-phenoxymethyl)-5,6-diethyl-2,3-dihydro-oxazolo[3,2-a]pyrimidin-7-one

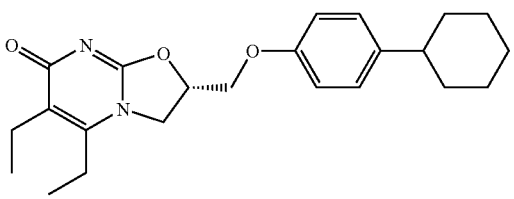 [SMILES: CCc1c(CC)n2c(nc1=O)O[C@H](COc1ccc(C3CCCCC3)cc1)C2]

Step1: 2-Ethyl-3-oxo-pentanoic acid ethyl ester

To a solution of 3-oxo-pentanoic acid ethyl ester (5.19 g, 36 mmol) in anhydrous EtOH (40 mL) was added NaOEt (21% wt. in EtOH, 11.7 mL, 36 mmol). he reaction mixture was heated to 80° C. Ethyl iodide (6.18 g, 39.6 mmol) was added dropwise at 80° C. Stirring was continued at 80° C. for 16 hours. The reaction mixture was concentrated and loaded onto a silica gel column and eluted with 1-2% EtOAc/heptane to give 4.38 g of the title compound.
$C_9H_{16}O_3$ (172.10), LCMS (ESI): 173.11(M⁻+H).

¹H NMR (CDCl₃, 300 MHz), δ 4.19 (q, 2H), 3.36 (t, 1H), 2.54 (m, 2H), 1.88 (quin, 2H), 1.27 (t, 3H), 1.07 (t, 3H), 0.92 (t, 3H).

Step2: 2-(4-Cyclohexyl-phenoxymethyl)-5,6-diethyl-2,3-dihydro-oxazolo[3,2-a]pyrimidin-7-one The title compound was prepared from (S)-5-(4-cyclohexyl-phenoxymethyl)-4,5-dihydro-oxazol-2-ylamine and 2-ethyl-3-oxo-pentanoic acid ethyl ester in accordance with the procedures of O.-S. Adetchessi, et. al., Tetrahedron, 61, (2005), 4453-4460. $[\alpha]_D^{25}$ −11.20 (c 0.5, CHCl₃).
$C_{23}H_{30}N_2O_3$ (382.22), LCMS (ESI): 383.25 (M⁺+H).
¹H NMR (CDCl₃, 300 MHz), δ 7.13 (d, 2H), 6.81 (d, 2H), 5.18 (m, 1H), 4.21-4.40 (m, 4H), 2.39-2.66 (m, 5H), 1.67-1.91 (m, 5H), 1.18-1.45 (m, 8H), 1.11(t, 3H).

Example 91

(S)-2-(5a,6,7,8,9,9a-Hexahydro-dibenzofuran-3-yl-oxymethyl)-2,3-dihydro-oxazolo[3,2-a]pyrimidin-7-one

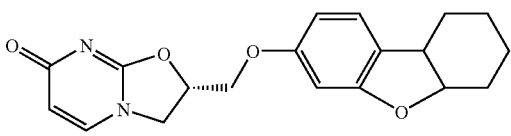

Step1: 7-Methoxy-1,2,3,4,4a,9b-hexahydro-dibenzofuran

A solution of AuCl₃ (0.303 g, 1.0 mmol) and AgOTf (0.770 g, 3.0 mmol) was stirred in anhydrous CH₂Cl₂ (150 mL) for 2 hours. 3-methoxy-phenol (2.48 g, 20 mmol) in CH₂Cl₂ (25 mL) was added, followed by addition of cyclohexadiene in CH₂Cl₂ (25 mL) at 40° C. over two hours. The reaction mixture was stirred at 40° C. overnight. The reaction mixture was passed through a silica gel plug. The filtrate was concentrated. The residue was purified by silica gel chromatography (5-30% CH₂Cl₂/heptane) to give 0.393 g of the title compound and 0.67 g of 7-methoxy-1,2,3,4-tetrahydro-dibenzofuran.
$C_{13}H_{16}O_2$ (204.11), LCMS (ESI): 205.11 (M⁺+H).
¹H NMR (CDCl₃, 300 MHz), δ 7.02 (d, 1H), 6.42 (m, 2H), 4.68 (q, 1H), 3.77 (s, 3H), 3.14 (q, 1H), 1.70-2.03 (m, 3H), 1.26-1.60 (m, 5H).
7-Methoxy-1,2,3,4-tetrahydro-dibenzofuran
$C_{13}H_{14}O_2$ (202.09), LCMS (CI): 203.11 (M⁺+H).
¹H NMR (CDCl₃, 300 MHz), δ 7.26 (d, 1H), 6.96 (d, 1H), 6.82 (dd, 1H), 3.83 (s, 3H), 2.71 (m, 2H), 2.58 (m, 2H), 1.87(m, 4H).

Step 2: 5 a,6,7,8,9,9a-Hexahydro-dibenzofuran-3-ol

To 7-methoxy-1,2,3,4,4a,9b-hexahydro-dibenzofuran (0.33 g, 1.61 mmol) in anhydrous DMF (10 mL) was added NaSEt (80%, 0.19 g, 1.78 mmol). The reaction mixture was stirred at reflux for 12 hours. The reaction mixture was cooled after which water (5 mL) was added. The mixture was neutralized with HCl (2 N) and EtOAc (100 mL) was added. The whole mixture was washed with water three times, brine twice and dried (Na₂SO₄). Silica gel chromatography (8-14% EtOAc/heptane) afforded the 0.36 g of the title compound.
$C_{12}H_{14}O_2$ (190.09), LCMS (ESI): 191.10 (M⁺+H).
¹H NMR (CDCl₃, 300 MHz), δ 6.96 (d, 1H), 6.33 (m, 2H), 4.67 (q, 1H), 4.61 (s, 1H), 3.12 (q, 1H), 1.22-2.03 (m, 8H).

Step 3: (S)-2-(5 a,6,7,8,9,9a-Hexahydro-dibenzofuran-3-yloxymethyl)-2,3-dihydro-oxazolo[3,2-a]pyrimidin-7-one The title compound was prepared from 5a,6,7,8,9,9a-hexahydro-dibenzofuran-3-ol and R-epichlorohydrin employing the procedures set forth in Steps 1 through 3 of Example 1. $[\alpha]_D^{25}$ −37.80 (c 0.5, CHCl$_3$).

$C_{19}H_{20}N_2O_4$ (340.14), LCMS (ESI): 341.15 (M$^+$+H).
$^1$H NMR (CDCl$_3$, 300 MHz), δ 7.24 (d, 1H), 7.01 (d, 1H), 6.36 (m, 2H), 6.08 (d, 1H), 5.26 (m, 1H), 4.68 (q, 1H), 4.18-4.40 (m, 4H), 3.14 (q, 1H), 1.34-1.95 (m, 8H).

Example 92

(S)-2-(6,7,8,9-Tetrahydro-dibenzofuran-3-yl-oxymethyl)-2,3-dihydro-oxazolo[3,2-a]pyrimidin-7-one

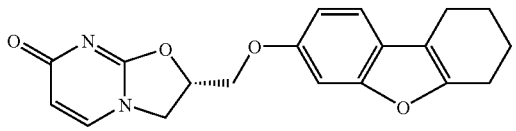 [SMILES: O=c1ccn2c(n1)O[C@H](COc1ccc3c4c(oc3c1)CCCC4)C2]

Step 1: 6,7,8,9-Tetrahydro-dibenzofuran-3-ol

The title compound was prepared from 7-methoxy-1,2,3,4-tetrahydro-dibenzofuran (prepared in Example 91, Step 1) employing the procedure as set forth in step 2 of Example 91.
$C_{12}H_{12}O_2$ (188.08), LCMS (CI): 189.08 (M$^+$+H).
$^1$H NMR (CDCl$_3$, 300 MHz), δ 7.23 (d, 1H), 6.90 (d, 1H), 6.72 (dd, 1H), 4.64 (s, 1H), 2.70 (m, 2H), 2.58 (m, 2H), 1.87 (m, 4H).

Step 2: 2-(6,7,8,9-Tetrahydro-dibenzofuran-3-yl-oxymethyl)-2,3-dihydro-oxazolo[3,2-a]pyrimidin-7-one The title compound was prepared from 6,7,8,9-tetrahydro-dibenzofuran-3-ol and R-epichlorohydrin employing the procedures set forth in Steps 1 through 3 of Example 1. $[\alpha]_D^{25}$ −45.40 (c 0.5, CHCl$_3$).
$C_{19}H_{18}N_2O_4$ (338.12), LCMS (ESI): 339.10 (M$^+$+H).
$^1$H NMR (CDCl$_3$, 300 MHz), δ 7.22-7.29 (m, 2H), 6.94 (d, 1H), 6.78 (dd, 1H), 6.10 (d, 1H), 5.29 (m, 1H), 4.25-4.42 (m, 4H), 2.71 (m, 2H), 2.58 (m, 2H) 1.77-1.97 (m, 4H).

Example 93

(S)-2-(4-Cyclohexyl-phenoxymethyl)-6-phenylsulfanyl-2,3-dihydro-oxazolo[3,2-a]pyrimidine-153,C7-one

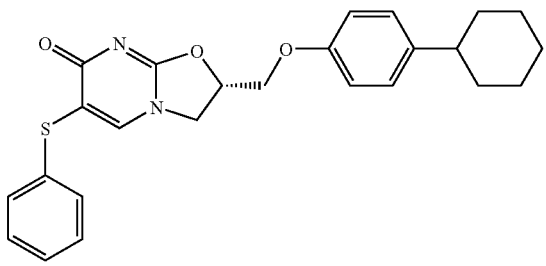 [SMILES: O=c1nc2n(cc1Sc1ccccc1)C[C@@H](COc1ccc(C3CCCCC3)cc1)O2]

To a solution of (S)-5-(4-cyclohexyl-phenoxymethyl)-4,5-dihydro-oxazol-2-yl-amine (0.92 g, 3.34 mmol) (prepared in accordance with the procedures set forth in Steps 1 and 2 of Example 1 and starting from R-epichlorohydrin and 4-cyclohexylphenol) in toluene (warm, 50 mL) was added 3-oxo-2-phenylsulfanyl-propionic acid ethyl ester (0.92 g, 6.68 mmol), prepared in accordance with the procedures of Lissavetzky, et. al., *Heterocycles, Vol.* 43, No. 4, 1996 pp 775-780. The reaction mixture was heated at 80° C. for 18 hours. The reaction mixture was concentrated and loaded onto silica gel column and eluted with 1-2% 2-propanol/CH$_2$Cl$_2$ to give 0.36 g of the title compound. $[\alpha]_D^{25}$ +80.40 (c 0.5, CHCl$_3$).
$C_{25}H_{26}N_2O_3S$ (434.16), LCMS (ESI): 435.17 (M$^+$+H).
$^1$H NMR (CDCl$_3$, 300 MHz), δ 7.51 (d, 2H), 7.37 (m, 3H), 7.12 (d, 2H), 6.81 (s, 1H), 6.78 (d, 2H), 5.23 (m, 1H), 4.16-4.32 (m, 4H), 2.44 (m, 1H), 1.70-1.88 (m, 5H) 1.16-1.50 (m, 5H).

Example 94

(S)-2-(4-Bicyclo[3.3.1]non-9-yl-phenoxymethyl)-5-fluoromethyl-2,3-dihydro-oxazolo[3,2-a]pyrimidin-7-one

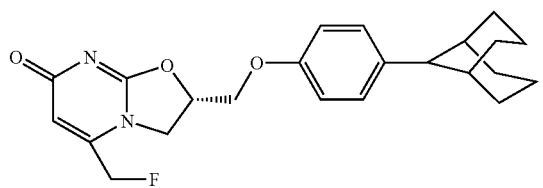 [SMILES: O=c1cc(CF)n2c(n1)O[C@H](COc1ccc(C3C4CCCC3CCC4)cc1)C2]

To a solution of (S)-5-(4-bicyclo[3.3.1]non-9-yl-phenoxymethyl)-4,5-dihydro-oxazol-2-yl-amine (1.1 g, 3.5 mmol) (prepared from 4-bicyclo[3.3.1]non-9-yl-phenol and R-epichlorohydrin employing the procedures in Steps 1 through 2 of Example 1) in t-butanol (13 mL) was added 0.82 g (0.63 mmol) of 4-fluoro-but-2-ynoic acid ethyl ester (prepared in accordance with the procedures as described in Poulter, *J Org Chem* 1981, 46, 1532). The reaction mixture was refluxed for 6 hours after which it was concentrated and loaded on silica gel column and eluted with 1-6% EtOH/CH$_2$Cl$_2$ to afford 0.31g of the title compound. $[\alpha]_D^{25}$ −26.00 (c 0.5, CHCl$_3$).
$C_{23}H_{27}FN_2O_3$ (398.20), LCMS (ESI): 399.21(MH$^+$).
$^1$H NMR (CDCl$_3$, 300 MHz), δ 7.28 (d, 2H), 6.85 (d, 2H), 6.07 (d, 1H), 5.28 (m, 1H), 5.20 (d, 2H), 4.42 (m, 2H), 4.31(AB-m, 2H), 2.73 (br. s, 1H), 2.38 (br. s, 2H), 1.34-2.03 (m, 12H).

Example 95

(S)-2-(4-tert-Butyl-phenoxymethyl)-5-methoxymethyl-2,3-dihydro-oxazolo[3,2-a]pyrimidin-7-one

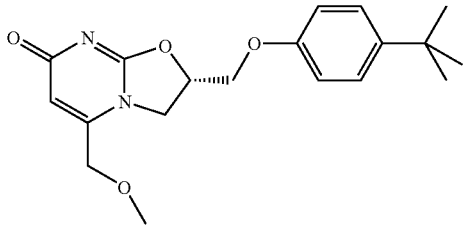 [SMILES: COCc1cc(=O)nc2n1C[C@@H](COc1ccc(C(C)(C)C)cc1)O2]

To a solution of (S)-5-(4-tert-butyl-phenoxymethyl)-4,5-dihydro-oxazol-2-yl-amine (2.3 g, 9.26 mmol) (prepared according to the procedures employed in Step 1 through 2 of Example 1) in ethanol (35 mL) was added 1.7 g (12.04 mmol) of 4-methoxy-but-2-ynoic acid ethyl ester (prepared in accordance with the procedures as described in Larock, *J Org Chem* 2002, 67, 9318). This mixture was stirred at reflux for 6 hours and cooled. The reaction mixture was concentrated and loaded onto a silica gel column. Chromatography with 1-10% EtOH/CH$_2$Cl$_2$ provided 2.22 g of the title compound. $[\alpha]_D^{25}$ −18.00 (c 0.5, CHCl$_3$)

C$_{19}$H$_{24}$N$_2$O$_4$ (344.17), LCMS (ESI): 345.18 (MH$^+$).

$^1$H NMR (CDCl$_3$, 300 MHz), δ 7.31 (d, 2H), 6.81 (d, 2H), 5.97 (s, 1H), 5.24 (m, 1H), 4.19-4.49 (m, 6H), 3.39 (s, 3H), 1.29 (s, 9H).

(S)-2-(4-tert-Butyl-phenoxymethyl)-5-fluoromethyl-2,3-dihydro-oxazolo[3,2-a]pyrimidin-7-one

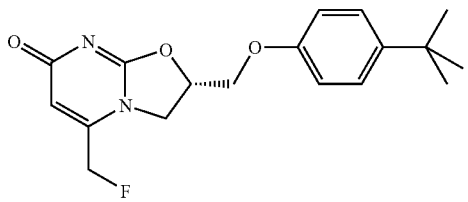 [SMILES: CC(C)(C)c1ccc(OC[C@@H]2Cn3c(CF)cc(=O)nc3O2)cc1]

The title compound was prepared from (S)-5-(4-tert-butyl-phenoxymethyl)-4,5-dihydro-oxazol-2-yl-amine and 4-fluoro-but-2-ynoic acid ethyl ester (prepared in accordance with the procedures as described in Poulter, *J Org Chem* 1981, 46, 1532) according to the procedures employed for the preparation of the compound in Example 98.

C$_{18}$H$_{21}$FN$_2$O$_3$ (332.15), LCMS (ESI): 333.17 (MH$^+$). $[\alpha]_D^{25}$ −34.80 (c 0.5, CHCl$_3$).

$^1$H NMR (CDCl$_3$, 300 MHz), δ 7.32 (d, 2H), 6.82 (d, 2H), 6.04 (d, 1H), 5.27 (m, 1H), 5.20(d, 2H), 4.20-4.49 (m, 4H), 1.29 (s, 9H).

Example 97

(S)-2-(4-tert-Butyl-phenoxymethyl)-5-ethyl-2,3-dihydro-oxazolo[3,2-a]pyrimidin-7-one

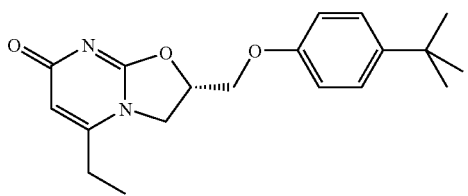 [SMILES: CCc1cc(=O)nc2n1C[C@@H](COc1ccc(C(C)(C)C)cc1)O2]

The title compound was prepared from (S)-5-(4-tert-butyl-phenoxymethyl)-4,5-dihydro-oxazol-2-yl-amine and ethyl 2-pentynoate according to the procedures employed for the preparation of the compound in Example 95. $[\alpha]_D^{25}$ −29.20 (c 0.5, CHCl$_3$)

C$_{19}$H$_{24}$N$_2$O$_3$ (328.17), LCMS (ESI): 329.19 (MH$^+$).

$^1$H NMR (CDCl$_3$, 300 MHz), δ 7.31 (d, 2H), 6.82 (d, 2H), 5.86 (s, 1H), 5.25 (m, 1H), 4.20-4.40 (m, 4H), 2.49(q, 2H), 1.29 (s, 9H), 1.27 (t, 3H).

Example 98

(S)-2-(4-Cyclohexyl-phenoxymethyl)-6-methylsulfanyl-2,3-dihydro-oxazolo[3,2-a]pyrimidin-7-one

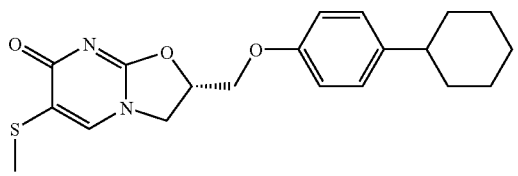 [SMILES: CSc1cn2c(nc1=O)O[C@H](COc1ccc(C3CCCCC3)cc1)C2]

To a solution of (S)-5-(4-cyclohexyl-phenoxymethyl)-4,5-dihydro-oxazol-2-ylamine (0.91 g, 3.34 mmol) (prepared in accordance with the procedures set forth in Steps 1 and 2 of Example 1 and starting from R-epichlorohydrin and 4-cyclohexylphenol) in toluene (50 mL) was added 3-hydroxy-2-methylsulfanyl-acrylic acid ethyl ester (1.08 g, 6.68 mmol) prepared in accordance with the procedures in Step 1 of Example 87 The reaction mixture was heated at 80° C. for 18 hours. The reaction mixture was concentrated and loaded onto a silica gel column and eluted with 0-5% 2-propanol/CH$_2$Cl$_2$ to afford 0.44 g of the title compound. $[\alpha]_D^{25}$ +18.24 (c 0.537, CHCl$_3$)

C$_{20}$H$_{24}$N$_2$O$_3$S (372.15), LCMS (ESI): 373.17 (MH$^+$).

$^1$H NMR (CDCl$_3$, 300 MHz), δ 7.13 (d, 2H), 7.02 (s, 1H), 6.81 (d, 2H), 5.27 (m, 1H), 4.21-4.44 (m, 4H), 2.44 (m, 1H), 2.35 (s, 3H), 1.20-1.92 (m, 10H).

Example 99

(S)-2-(4-Cyclohexyl-phenoxymethyl)-5-cyclopropyl-2,3-dihydro-oxazolo[3,2-a]pyrimidin-7-one

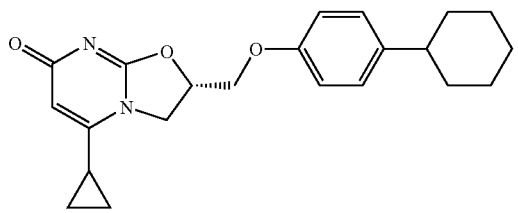 [SMILES: O=c1cc(C2CC2)n2c(n1)O[C@H](COc1ccc(C3CCCCC3)cc1)C2]

To a solution of (S)-5-(4-cyclohexyl-phenoxymethyl)-4,5-dihydro-oxazol-2-ylamine (0.5 g, 1.82 mmol), (see Example 28), in ethanol (5 mL) was added cyclopropyl-propynoic acid ethyl ester (0.377 g, 2.73 mmol) (prepared from ethynyl-cyclopropane and ethyl chloroformate in accordance with the procedures of G. Cai et al., *Tetrahedron*, 2006, 5697-5708). The reaction mixture was heated in a microwave oven at 170° C. for 30 min. The solvent was removed under vacuum, and the residue purified by flash column chromatography (silica gel, 2% 7N NH$_3$ in MeOH/CH$_2$Cl$_2$) to afford 0.635 g of (S)-2-(4-cyclohexyl-phenoxymethyl)-5-cyclopropyl-2,3-dihydro-oxazolo[3,2-a]pyrimidin-7-one as a white solid. $[\alpha]_D^{25}$ −13.40 (c 0.5, CHCl$_3$)

C$_{22}$H$_{26}$N$_2$O$_3$ (366.20), LCMS (ESI): 367.17(M$^+$+H).

$^1$H NMR (300 MHz, DMSO-d6): δ 7.17 (d, 2H), 6.87 (d, 2H), 5.49 (s, 1H), 5.32 (br., s, 1H), 4.52(t, 1H), 4.37-4.18 (m, 3H), 2.44 (m, 1H)1.89-1.64 (m, 6H), 1.46-1.11 (m, 5H), 0.96 (dd, 2H), 0.86-0.72 (m, 2H).

Example 100

(S)-2-(4-Cyclohexyl-phenoxymethyl)-5-hydroxymethyl-2,3-dihydro-oxazolo[3,2-a]pyrimidin-7-one

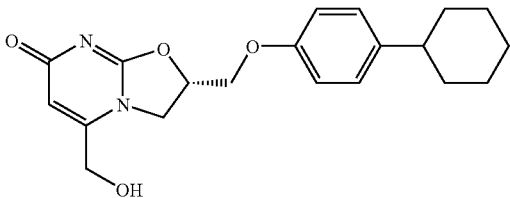 [SMILES: O=c1cc(CO)n2c(n1)O[C@H](COc1ccc(C3CCCCC3)cc1)C2]

The title compound was prepared from (S)-5-(4-cyclohexyl-phenoxymethyl)-4,5-dihydro-oxazol-2-ylamine and 4-hydroxy-but-2-ynoic acid ethyl ester (G. Cai et al., *Tetrahedron*, 2006, 5697-5708) employing the procedure described in Example 99. $[\alpha]_D^{25}$ +5.80 (c 0.5, DMSO)
$C_{20}H_{24}N_2O_4$ (356.17), LCMS (ESI): 357.16 (M$^+$+H)
$^1$H NMR (300 MHz, DMSO-d6): δ 7.14 (d, 2H), 6.86 (d, 2H), 5.77 (s, 1H), 5.68 (t, 1H), 5.32 (br., s, 1H), 4.46-4.09 (m, 6H), 2.43 (br, s, 1H) 1.85-1.66 (m, 5H), 1.42-1.11 (m, 5H)

Example 101

(S)-5-n-Butyl-2-(4-cyclohexyl-phenoxymethyl)-2,3-dihydro-oxazolo[3,2-a]pyrimidin-7-one

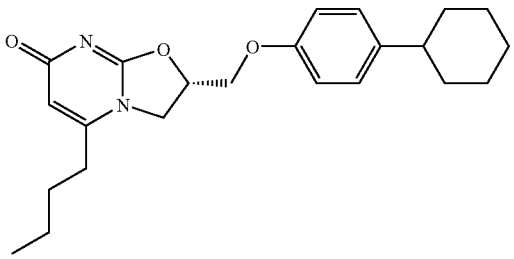 [SMILES: CCCCc1cc(=O)nc2n1C[C@@H](COc1ccc(C3CCCCC3)cc1)O2]

The title compound was prepared from (S)-5-(4-cyclohexyl-phenoxymethyl)-4,5-dihydro-oxazol-2-ylamine and hept-2-ynoic acid ethyl ester employing the procedure described in Example 99. $[\alpha]_D^{25}$ +8.40 (c 0.5, DMSO)
$C_{23}H_{30}N_2O_3$ (382.23), LCMS (ESI): 383.22 (M$^+$+H)
$^1$H NMR (300 MHz, CDCl$_3$): δ 7.17 (d, 2H), 6.80 (d, 2H), 5.87 (s, 1H), 5.21 (br., s, 1H), 4.30 (m, 4H), 2.44 (m, 3H), 1.93-1.17 (m, 14H), 0.96 (t, 3H).

Example 102

(S)-2-(4-Cyclohexyl-phenoxymethyl)-5-cyclopentyl-2,3-dihydro-oxazolo[3,2-a]pyrimidin-7-one

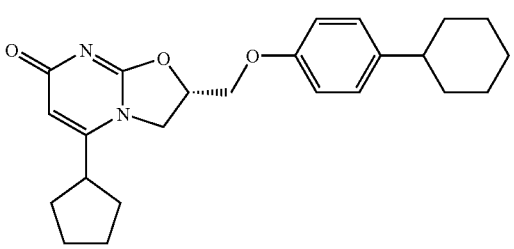 [SMILES: O=c1cc(C2CCCC2)n2c(n1)O[C@H](COc1ccc(C3CCCCC3)cc1)C2]

Step 1: Cyclopentyl-propynoic acid ethyl ester

The title compound was prepared from ethynyl-cyclopentane and ethyl chloroformate in accordance with the procedures of G. Cai et al., *Tetrahedron*, 2006, 5697-5708.

$C_{10}H_{14}O_2$ (166.10), LCMS (CI): 167.11 (M$^+$+H).
$^1$H NMR (300 MHz, CDCl$_3$): δ 4.21 (q, 2H), 2.74 (m, 1H), 2.03-1.49 (m, 8H), 1.30 (t, 3H).

Step 2: (S)-2-(4-Cyclohexyl-phenoxymethyl)-5-cyclopentyl-2,3-dihydro-oxazolo[3,2a]pyrimidin-7-one The title compound was prepared from (S)-5-(4-cyclohexyl-phenoxymethyl)-4,5-dihydro-oxazol-2-ylamine and cyclopentyl-propynoic acid ethyl ester employing the procedure described in Example 99. $[\alpha]_D^{25}$ −16.14 (c 0.551, CHCl$_3$)
$C_{24}H_{30}N_2O_3$ (394.23), LCMS (ESI): 395.24 (M$^+$+H).
$^1$H NMR (300 MHz, DMSO-d6): δ 7.14 (d, 2H), 6.84 (d, 2H), 5.66 (s, 1H), 5.29 (br., s, 1H), 4.45(t, 1H), 4.36-4.12 (m, 3H), 2.90 (m, 1H), 2.44(m, 1H), 2.04-1.11 (series of m, 18 H).

Example 103

(S)-5-Cyclohexyl-2-(4-cyclohexyl-phenoxymethyl)-2,3-dihydro-oxazolo[3,2-a]pyrimidin-7-one

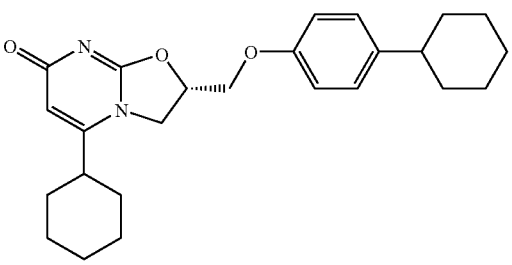 [SMILES: O=c1cc(C2CCCCC2)n2c(n1)O[C@H](COc1ccc(C3CCCCC3)cc1)C2]

The title compound was prepared from (S)-5-(4-cyclohexyl-phenoxymethyl)-4,5-dihydro-oxazol-2-ylamine and cyclohexyl-propynoic acid ethyl ester (see Example 103) employing the procedure described in Example 100. $[\alpha]_D^{25}$ +17.80 (c 0.5, DMSO)
$C_{25}H_{32}N_2O_3$ (408.24), LCMS (ESI):409.25 (M$^+$+H).
$^1$H NMR (300 MHz, DMSO-d$_6$): δ 7.14 (2H, d), 6.84 (2H, d), 5.61 (1H, s), 5.29 (1H, br., s), 4.45(t, 1H), 4.34-4.14 (m, 3H), 2.40 (2H, m), 1.95-1.61 (10H, m), 1.46-1.12 (10H, m).

Example 104

(S)-2-(4-Cyclohexyl-phenoxymethyl)-5-isobutyl-2,3-dihydro-oxazolo[3,2-a]pyrimidin-7-one

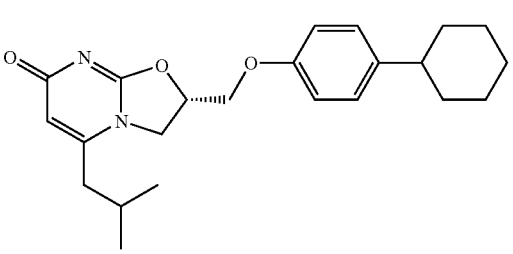 [SMILES: CC(C)Cc1cc(=O)nc2n1C[C@@H](COc1ccc(C3CCCCC3)cc1)O2]

Step 1: 5-Methyl-hex-2-ynoic acid ethyl ester

The title compound was prepared from 4-methyl-pent-1-yne and ethyl chloroformate in accordance with the procedures of G. Cai et al., *Tetrahedron*, 2006, (5697-5708).
$C_9H_{14}O_2$ (154.10), LCMS (CI): 155.11 (M$^+$+H).
$^1$H NMR (300 MHz, CDCl$_3$): δ 4.22 (q, 2H), 2.23 (d, 2H), 1.92 (m, 1H), 1.31 (t, 3H), 1.02 (d, 6H).

Step 2: (S)-2-(4-Cyclohexyl-phenoxymethyl)-5-isobutyl-2,3-dihydro-oxazolo[3,2-a]pyrimidin-7-one The title compound was prepared from (S)-5-(4-cyclohexyl-phenoxymethyl)-4,5-dihydro-oxazol-2-ylamine and 5-methyl-hex-2-ynoic acid ethyl ester (prepared from 4-methyl-pent-1-yne and ethyl chloroformate in accordance with the procedures of G. Cai et al., *Tetrahedron*, 2006, 5697-5708) employing the procedure described in Example 99. $[\alpha]_D^{25}$ −13.93 (c 0.546, CHCl$_3$)

$C_{23}H_{30}N_2O_3$ (382.23), LCMS (ESI): 383.24(M$^+$H).

$^1$H NMR (300 MHz, DMSO-d6): δ 7.14 (d, 2H), 6.84 (d, 2H), 5.66 (s, 1H), 5.27 (br., s, 1H), 4.41(t, 1H), 4.35-4.09 (m, 3H), 2.43(m, 1H), 2.35(d, 2H), 1.90 (m, 1H), 1.83-1.62 (m, 5H), 1.44-1.12 (m, 5H), 0.95 (d, 6 H).

Example 105

(S)-2-(4-Cyclohexyl-phenoxymethyl)-5-fluoromethyl-2,3-dihydro-oxazolo[3,2-a]pyrimidin-7-one

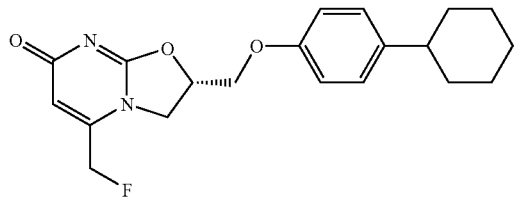 [SMILES: O=c1cc(CF)n2c(n1)O[C@H](COc1ccc(C3CCCCC3)cc1)C2]

To a solution of (S)-5-(4-cyclohexyl-phenoxymethyl)-4,5-dihydro-oxazol-2-ylamine (0.464 g, 1.69 mmol), (see Example 28) in ethanol (25 mL) was added 4-fluoro-but-2-ynoic acid ethyl ester (0.22 g, 1.69 mmol) (see Poulter, *J Org Chem* 1981, 46, 1532). The reaction mixture was heated at reflux for 14 hrs and then gradually cooled to room temperature. The solvent was removed under vacuum, and the residue purified by flash column chromatography (silica gel, 0-2% 7N NH$_3$ in MeOH /CH$_2$Cl$_2$) to afford 0.358g of (S)-2-(4-cyclohexyl-phenoxymethyl)-5-fluoromethyl-2,3-dihydro-oxazolo[3,2 a]-pyrimidin-7-one. $[\alpha]_D^{25}$ −28.20 (c 0.5, CHCl$_3$).

$C_{20}H_{23}FN_2O_3$ (358.17), LCMS (ESI): 359.17(M$^+$+H).

$^1$H NMR (300 MHz, DMSO-d6): δ 7.13 (d, 2H), 6.86 (d, 2H), 5.97 (d, 1H), 5.40 (d, 2H), 5.32 (br., s, 1H), 4.45(t, 1H), 4.36-4.12 (m, 3H), 2.43(m, 1H), 1.85-1.63 (m, 5H), 1.43-1.09 (m, 5H).

Example 106

(S)-2-(4-Cyclohexyl-phenoxymethyl)-5-methoxymethyl-2,3-dihydro-oxazolo[3,2-a]pyrimidin-7-one

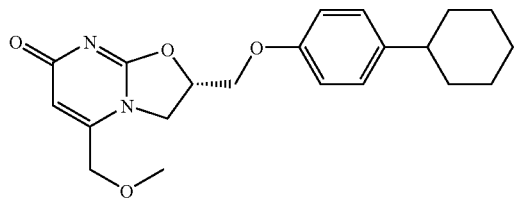 [SMILES: COCc1cc(=O)nc2n1C[C@@H](COc1ccc(C3CCCCC3)cc1)O2]

The title compound was prepared from (S)-5-(4-cyclohexyl-phenoxymethyl)-4,5-dihydro-oxazol-2-ylamine and 4-methoxy-but-2-ynoic acid ethyl ester (Larock, *J Org Chem* 2002, 67, 9318) employing the procedure described in Example 105. $[\alpha]_D^{25}$ −17.80 (c 0.5, CHCl$_3$).

$C_{21}H_{26}N_2O_4$ (370.19), LCMS (ESI): 371.19(M$^+$H).

$^1$H NMR (300 MHz, DMSO-d6): δ 7.13 (d, 2H), 6.88 (d, 2H), 5.85 (s, 1H), 5.31 (br., s, 1H), 4.47-4.08 (m, 6H), 3.32 (s, 3H), 2.43(m, 1H), 1.86-1.60 (m, 5H), 1.44-1.11 (m, 5H).

Example 107

(S)-2-(4-Cyclohexyl-phenoxymethyl)-5-(1-hydroxy-1-methyl-ethyl)-2,3-dihydro-oxazolo[3,2-a]pyrimidin-7-one

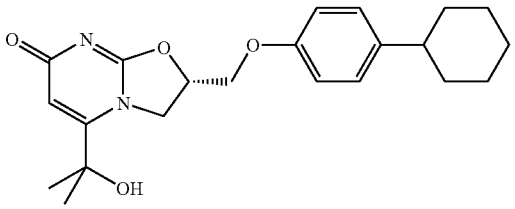 [SMILES: CC(C)(O)c1cc(=O)nc2n1C[C@@H](COc1ccc(C3CCCCC3)cc1)O2]

Step 1: 4,4-Dimethyl-5-trimethylsilanyloxy-pent-2-ynoic acid ethyl ester

The title compound was prepared from (2,2-dimethyl-but-3-ynyloxy)-trimethyl-silane and ethyl chloroformate in accordance with the procedures of G. Cai et al., *Tetrahedron*, 2006, (5697-5708).

$C_{11}H_{20}O_3Si$ (228.12), LCMS (ESI): 229.14 (M$^+$+H).

$^1$H NMR (300 MHz, CDCl$_3$): δ 4.24 (q, 2H), 1.54 (s, 6H), 1.32 (t, 3H), 0.22 (s, 9H).

Step 2: 4-Hydroxy-4-methyl-pent-2-ynoic acid ethyl ester

To a solution of 4-methyl-4-trimethylsilanyloxy-pent-2-ynoic acid ethyl ester (5.4 g, 23.7 mmol) in ethyl ether (50 mL) was added tetrabutylammonium fluoride (TBAF) (7.42 g, 28.4 mmol). The reaction mixture was stirred at room temperature for 2 hours, quenched with H$_2$O, and extracted with ethyl ether. The organic phase was washed with brine, dried (Na$_2$SO$_4$) and concentrated to afford 3.51 g of 4-hydroxy-4-methyl-pent-2-ynoic acid ethyl ester as yellow oil.

$C_8H_{12}O_3$ (156.08), LCMS (ESI): 157.09 (M$^+$+H).

$^1$H NMR (300 MHz, CDCl$_3$): δ 4.25 (q, 2H), 2.29 (s, 1H), 1.57 (s, 6H), 1.32 (t, 3H).

Step 3: (S)-2-(4-Cyclohexyl-phenoxymethyl)-5-(1-hydroxy-1-methyl-ethyl)-2,3-dihydro oxazolo[3,2-a]pyrimidin-7-one The title compound was prepared from (S)-5-(4-cyclohexyl-phenoxymethyl)-4,5-dihydro-oxazol-2-ylamine and 4-hydroxy-4-methyl-pent-2-ynoic acid ethyl ester employing the procedure described in Example 105.

$C_{22}H_{28}N_2O_4$ (384.21), LCMS (ESI): 385.20(M$^+$+H)

¹H NMR (300 MHz, DMSO-d6): δ 7.13 (d, 2H), 6.86 (d, 2H), 5.78 (s, 1H), 5.60 (s, 1H), 5.25 (br., s, 1H), 4.64 (m, 1H), 4.45-4.22 (m, 3H), 2.43(m, 1H), 1.84-1.62 (m, 5H), 1.46 (d, 6H), 1.40-1.15 (m, 5H)

Example 108

(S)-2-(4-Cyclohexyl-phenoxymethyl)-5-(2-hydroxy-ethyl)-2,3-dihydro-oxazolo[3,2-a]pyrimidin-7-one

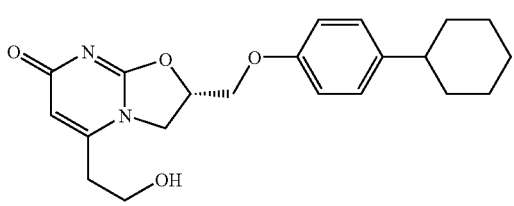 [SMILES: O=c1cc(CCO)n2c(n1)O[C@H](COc1ccc(C3CCCCC3)cc1)C2]

Step 1: 5-(Tetrahydro-pyran-2-yloxy)-pent-2-ynoic acid ethyl ester

The title compound was prepared from 2-but-3-ynyloxy-tetrahydro-pyran and ethyl chloroformate in accordance with the procedures of G. Cai et al., Tetrahedron, 2006, (5697-5708).

$C_{12}H_{18}O_4$ (226.12), LCMS (ESI): 227.14 (M⁺+H).

¹H NMR (300 MHz, CDCl₃): δ 4.65 (t, 1H), 4.22 (q, 2H), 3.87 (m, 2H), 3.62 (m,1H), 3.35 (m, 1H), 2.65 (t, 2H), 1.91-1.46 (m, 6H), 1.31 (t,3H).

Step 2: 5-Hydroxy-pent-2-ynoic acid ethyl ester

The title compound was prepared from 5-(tetrahydro-pyran-2-yloxy)-pent-2-ynoic acid ethyl ester employing p-toluenesulfonic acid in ethanol.

$C_7H_{10}O_3$ (142.06), LCMS (ESI): 143.01(M⁻+H).

¹H NMR (300 MHz, CDCl₃): δ 4.24 (q, 2H), 3.81 (q, 2H), 2.61 (t, 2H), 2.23 (br., s, 1H), 1.31 (t,3H).

Step 3: (S)-2-(4-Cyclohexyl-phenoxymethyl)-5-(2-hydroxy-ethyl)-2,3-dihydro-oxazolo[3,2-a]pyrimidin-7-one The title compound was prepared from (S)-5-(4-cyclohexyl-phenoxymethyl)-4,5-dihydro-oxazol-2-ylamine and 5-hydroxy-pent-2-ynoic acid ethyl ester employing the procedure described in Example 105. $[\alpha a]_D^{25}$ +6.40 (c 0.5, DMSO).

$C_{21}H_{26}N_2O_4$ (370.19), LCMS (ESI): 371.18 (M⁺+H).

¹H NMR (300 MHz, DMSO-d6): δ 7.13 (d, 2H), 6.86 (d, 2H), 5.71 (s, 1H), 5.27 (br., s, 1H), 4.94 (t, 1H), 4.45 (t, 1H), 4.35-4.13 (m, 3H), 3.68 (q, 2H), 2.62 (t, 2H), 2.43(m, 1H), 1.83-1.64 (m, 5H), 1.44-1.10 (m, 5H).

Example 109

(S)-2-(4-Cyclohexyl-phenoxymethyl)-5-(1-fluoro-1-methyl-ethyl)-2,3-dihydro-oxazolo[3,2-a]pyrimidin-7-one

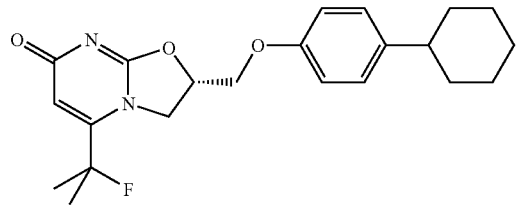 [SMILES: CC(C)(F)c1cc(=O)nc2n1C[C@@H](COc1ccc(C3CCCCC3)cc1)O2]

Step 1: 4-Fluoro-4-methyl-pent-2-ynoic acid ethyl ester

The title compound was prepared from 4-hydroxy-4-methyl-pent-2-ynoic acid ethyl ester (see Example 107) employing the procedure of Poulter (J Org Chem 1981, 46, 1532).

$C_8H_{11}FO_2$ (158.08), LCMS (ESI): 159.09 (M⁺+H)

¹H NMR (300 MHz, CDCl₃): δ 4.46 (q, 2H), 1.69 (d, 6H), 1.32 (t, 3H)

Step 2: (S)-2-(4-Cyclohexyl-phenoxymethyl)-5-(1-fluoro-1-methyl-ethyl)-2,3-dihydro-oxazolo-[3,2-a]pyrimidin-7-one The title compound was prepared from (S)-5-(4-cyclohexyl-phenoxymethyl)-4,5-dihydro-oxazol-2-ylamine and 4-fluoro-4-methyl-pent-2-ynoic acid ethyl ester employing the procedure described in Example 105. $[\alpha]_D^{25}$ −21.61 (c 0.56, CHCl₃).

$C_{22}H_{27}FN_2O_3$ (386.20), LCMS (ESI): 387.20 (M⁺+H).

¹H NMR (300 MHz, DMSO-d6): δ 7.13 (d, 2H), 6.84 (d, 2H), 5.91 (s, 1H), 5.28 (br., s, 1H), 4.53 (m, 1H), 4.29 (m, 3H), 2.43(m, 1H), 1.83-1.69 (m, 5H), 1.67 (d, 6H), 1.44-1.10 (m, 5H).

Example 110

(S)-5-Fluoromethyl-2-[4-(3,3,5,5-tetramethyl-cyclohexyl)-phenoxymethyl]-2,3-dihydro-oxazolo[3,2-a]pyrimidin-7-one

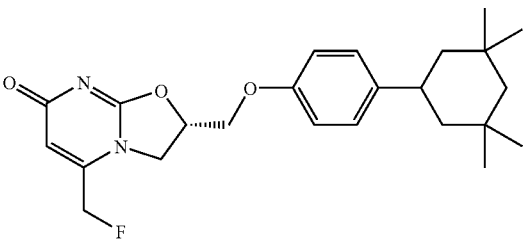 [SMILES: CC1(C)CC(c2ccc(OC[C@@H]3Cn4c(CF)cc(=O)nc4O3)cc2)CC(C)(C)C1]

Step 1: 4-(3,3,5,5-Tetramethyl-cyclohexyl)-phenol

The title compound was prepared from 4-methoxy-benzeneboronic acid and trifluoro-methanesulfonic acid 3,3,5,5- tetramethyl-cyclohex-1-enyl ester in accordance with the procedure described in Step 1, Example 86.

Step 2: (S)-5-Fluoromethyl-2-[4-(3,3,5,5-tetramethyl-cyclohexyl)-phenoxymethyl]-2,3-dihydro-oxazolo[3,2-a]pyrimidin-7-one The title compound was prepared from 5-[4-(3,3,5,5-tetramethyl-cyclohexyl)-phenoxymethyl]-4,5-dihydro-oxazol-2-ylamine (prepared from 4-(3,3,5,5-tetramethyl-cyclohexyl)-phenol and (R)-epichlorohydrin according to the procedures employed in Step 1 through 2 of Example 1) and 4-fluoro-but-2-ynoic acid ethyl ester (see Example 105) according to the procedures described in Example 95. $[\alpha]_D^{25}$ −21.40 (c 0.5, CHCl$_3$).

$C_{24}H_{31}FN_2O_3$ (414.23), LCMS (ESI): 415.25 (M$^+$+H).

$^1$H NMR (300 MHz, CDCl$_3$): δ 7.14 (d, 2H), 6.82 (d, 2H), 6.09 (d, 1H), 5.27 (m, 1H), 5.20 (d, 2H), 4.51-4.20 (m, 4H), 2.83(m, 1H), 1.52 (m, 2H), 1.35-1.11 (m, 4H), 1.08 (s, 6H), 0.92 (s, 6H).

Example 111

(S)-2-(4-Bicyclo[3.3.1]non-9-yl-phenoxymethyl)-5-methoxymethyl-2,3-dihydro-oxazolo[3,2-a]pyrimidin-7-one

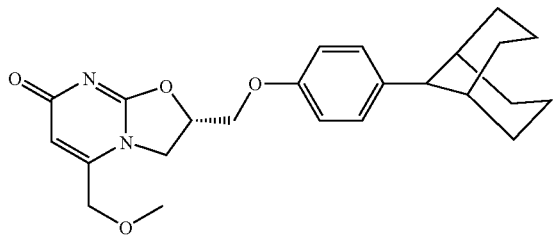 [SMILES: COCc1cc(=O)nc2n1C[C@@H](COc1ccc(C3C4CCCC3CCC4)cc1)O2]

The title compound was prepared from (S)-5-(4-bicyclo[3.3.1]non-9-yl-phenoxymethyl)-4,5-dihydro-oxazol-2-ylamine (see Example 20) and 4-methoxy-but-2-ynoic acid ethyl ester (see Example 106) employing the procedure described in Example 95. $[\alpha]_D^{25}$ −14.55 (c 0.495, CHCl$_3$).

$C_{24}H_{30}N_2O_4$ (410.22), LCMS (ESI): 411.21 (M$^+$+H).

$^1$H NMR (300 MHz, CDCl$_3$): δ 7.28 (d, 2H), 6.84 (d, 2H), 5.96 (s, 1H), 5.27 (m, 1H), 4.52-4.19 (m, 6H), 3.40 (s, 3H), 2.73(br., s, 1H), 2.37 (br., s, 2H), 2.09-1.33 (m, 12H).

Example 112

(S)-2-(4-Bicyclo[3.3.1]non-9-yl-phenoxymethyl)-5-methyl-2,3-dihydro-oxazolo[3,2-a]pyrimidin-7-one

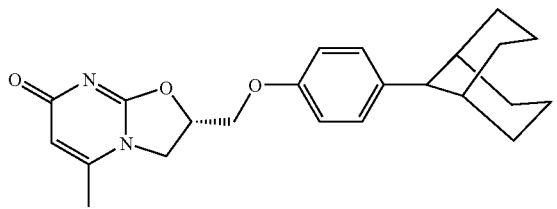 [SMILES: Cc1cc(=O)nc2n1C[C@@H](COc1ccc(C3C4CCCC3CCC4)cc1)O2]

The title compound was prepared from (S)-5-(4-bicyclo[3.3.1]non-9-yl-phenoxymethyl)-4,5-dihydro-oxazol-2-ylamine (see Example 20) and but-2-ynoic acid ethyl ester employing the procedure described in Example 95. $[\alpha]_D^{25}$ −33.80 (c 0.5, CHCl$_3$).

$C_{23}H_{28}N_2O_3$ (380.21), LCMS (ESI): 381.22 (M$^+$+H).

$^1$H NMR (300 MHz, CDCl$_3$): δ 7.28 (d, 2H), 6.86 (d, 2H), 5.89 (s, 1H), 5.26 (m, 1H), 4.42-4.21 (m, 4H), 2.73(br., s, 1H), 2.39 (br., s, 2H), 2.23 (s, 3H), 2.08-1.36 (m, 12H).

Example 113

(S)-2-(4-Bicyclo[3.3.1]non-9-yl-phenoxymethyl)-5-butyl-2,3-dihydro-oxazolo[3,2-a]pyrimidin-7-one

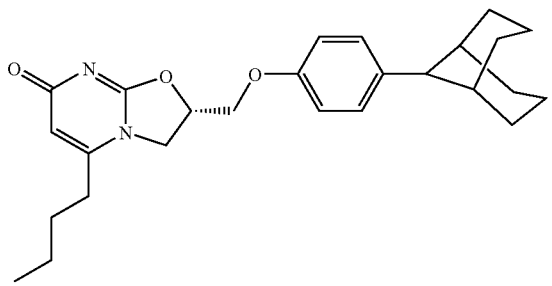 [SMILES: CCCCc1cc(=O)nc2n1C[C@@H](COc1ccc(C3C4CCCC3CCC4)cc1)O2]

The title compound was prepared from (S)-5-(4-bicyclo[3.3.1]non-9-yl-phenoxymethyl)-4,5-dihydro-oxazol-2-ylamine (see Example 20) and hept-2-ynoic acid ethyl ester employing the procedure described in Example 95. $[\alpha]_D^{25}$ −14.60 (c 0.5, CHCl$_3$).

$C_{26}H_{34}N_2O_3$ (422.27), LCMS (ESI): 423.22 (M$^+$+H)

$^1$H NMR (300 MHz, CDCl$_3$): δ 7.27 (d, 2H), 6.84 (d, 2H), 5.78 (s, 1H), 5.31 (m, 4.45 (m, 1H), 4.38-4.16 (m, 3H), 2.71(br., s, 1H), 2.39 (m, 4H), 2.08-1.30 (m, 16H), 0.95 (t, 3H)

Example 114

(S)-2-(4-Bicyclo[3.3.1]non-9-yl-phenoxymethyl)-5-cyclopentyl-2,3-dihydro-oxazolo[3,2-a]pyrimidin-7one

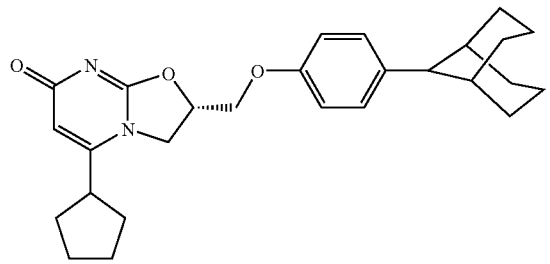 [SMILES: O=c1cc(C2CCCC2)n2c(n1)O[C@H](COc1ccc(C3C4CCCC3CCC4)cc1)C2]

The title compound was prepared from (S)-5-(4-bicyclo[3.3.1]non-9-yl-phenoxymethyl)-4,5-dihydro-oxazol-2-ylamine (see Example 20) and cyclopentyl-propynoic acid ethyl ester (see Example 102) employing the procedure described in Example 95. $[\alpha]_D^{25}$ −4.80 (c 0.5, CHCl$_3$).

$C_{27}H_{34}N_2O_3$ (434.26), LCMS (ESI): 435.27 (M$^+$+H).

$^1$H NMR (300 MHz, CDCl$_3$): δ 7.27 (d, 2H), 6.86 (d, 2H), 5.94 (s, 1H), 5.23 (m, 1H), 4.45-4.20 (m, 4H), 2.78(t, 1H), 2.77(br., s, 1H), 2.39 (br., s, 2H), 2.14-1.32 (series of m, 20H).

Example 115

(S)-5-Methyl-2-[4-(1,1,3,3-tetramethyl-butyl)-phenoxymethyl]-2,3-dihydro-oxazolo[3,2-a]pyrimidin-7-one

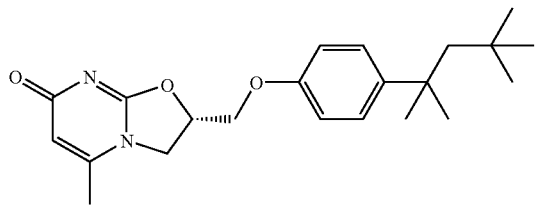 [SMILES: Cc1cc(=O)nc2n1C[C@@H](COc1ccc(C(C)(C)CC(C)(C)C)cc1)O2]

The title compound was prepared from (S)-5-(4-(1,1,3,3-tetramethyl-butyl) -phenoxymethyl)-4,5-dihydro-oxazol-2-ylamine (see Example 27) and but-2-ynoic acid ethyl ester employing the procedure described in Example 95. $[\alpha]_D^{25}$ −36.20 (c 0.5, CHCl$_3$).

$C_{22}H_{30}N_2O_3$ (370.23), LCMS (ESI): 371.20 (M$^+$+H)
1H NMR (300 MHz, CDCl$_3$): δ 7.28 (d, 2H), 6.80 (d, 2H), 5.87 (s, 1H), 5.24 (m, 4.41-4.22 (m, 4H), 2.24(s, 3H), 1.72(s, 2H), 1.33 (s, 6H), 0.71 (s, 9H)

Example 116

(S)-5-Ethyl-2-[4-(1,1,3,3-tetramethyl-butyl)-phenoxymethyl]-2,3-dihydro-oxazolo[3,2-a]pyrimidin-7-one

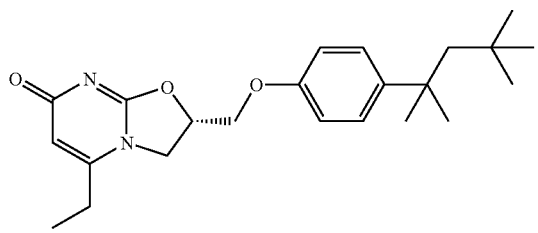 [SMILES: CCc1cc(=O)nc2n1C[C@@H](COc1ccc(C(C)(C)CC(C)(C)C)cc1)O2]

The title compound was prepared from (S)-5-(4-(1,1,3,3-tetramethyl-butyl) -phenoxymethyl)-4,5-dihydro-oxazol-2-ylamine (see Example 27) and pent-2-ynoic acid ethyl ester employing the procedure described in Example 95. $[\alpha]_D^{25}$ −21.00 (c 0.5, CHCl$_3$).

$C_{23}H_{32}N_2O_3$ (384.24), LCMS (ESI): 385.25 (M$^+$+H).
$^1$H NMR (300 MHz, CDCl$_3$): δ 7.28 (d, 2H), 6.80 (d, 2H), 5.90 (s, 1H), 5.22 (m, 1H), 4.35-4.20 (m, 4H), 2.50(q, 2H), 1.70(s, 2H), 1.34 (s, 6H), 1.28 (t, 3H), 0.70 (s, 9H).

Example 117

(S)-5-Fluoromethyl-2-[4-(1,1,3,3-tetramethyl-butyl)-phenoxymethyl]-2,3-dihydro-oxazolo[3,2-a]pyrimidin-7-one

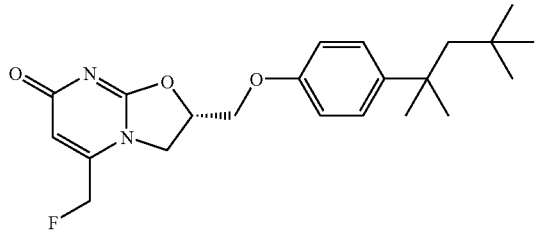 [SMILES: CC(C)(C)CC(C)(C)c1ccc(OC[C@@H]2Cn3c(CF)cc(=O)nc3O2)cc1]

The title compound was prepared from (S)-5-(4-(1,1,3,3-tetramethyl-butyl) -phenoxymethyl)-4,5-dihydro-oxazol-2-ylamine (see Example 27) and 4-fluoro-but-2-ynoic acid ethyl ester (see Example 105) employing the procedure described in Example 95. $[\alpha]_D^{25}$ −28.00 (c 0.5, CHCl$_3$).

$C_{22}H_{29}FN_2O_3$ (388.22), LCMS (ESI): 389.23 (M$^+$+H).
$^1$H NMR (300 MHz, CDCl$_3$): δ 7.28 (d, 2H), 6.80 (d, 2H), 6.07 (d, 1H), 5.29 (m, 1H), 5.21 (d, 2H), 4.51-4.20 (m, 4H), 1.70(s, 2H), 1.35 (s, 6H), 0.70 (s, 9H).

Example 118

(S)-5-Methoxymethyl-2-[4-(1,1,3,3-tetramethyl-butyl) -phenoxymethyl]-2,3-dihydro-oxazolo[3,2-a]pyrimidin-7-one

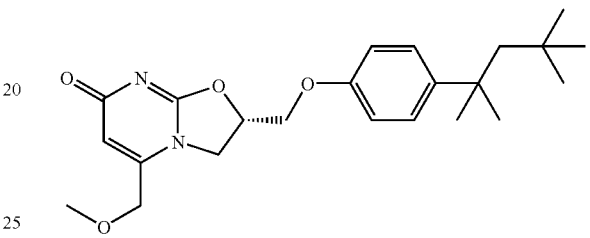

The title compound was prepared from (S)-5-(4-(1,1,3,3-tetramethyl-butyl) -phenoxymethyl)-4,5-dihydro-oxazol-2-ylamine (see Example 27) and 4-methoxy-but-2-ynoic acid ethyl ester (see Example 106) employing the procedure described in Example 95. $[\alpha]_D^{25}$ −14.80 (c 0.5, CHCl$_3$).

$C_{23}H_{32}N_2O_4$ (400.24), LCMS (ESI): 401.23 (M$^+$+H)
$^1$H NMR (300 MHz, CDCl$_3$): δ 7.28 (d, 2H), 6.79 (d, 2H), 5.98 (s, 1H), 5.24 (m, 1H), 4.49-4.22 (series of m, 6H), 3.40 (s, 3H), 1.70 (s, 2H), 1.34 (s, 6H), 0.72 (s, 9H)

Example 119

(S)-2-(4-Cyclohexyl-phenoxymethyl)-5-ethoxymethyl-2,3-dihydro-oxazolo[3,2-a]pyrimidin-7-one

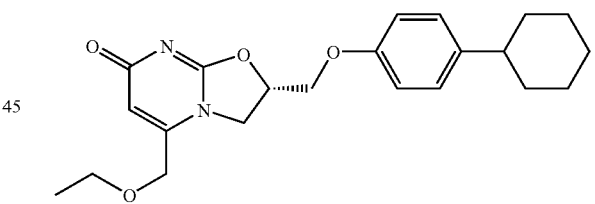

Step 1:
2-(4-Ethoxy-but-2-yn-yloxy)-tetrahydro-pyran

An oven dried 500 ml RBF was charged with NaH (60% in mineral oil) (1.41 g, 35.3 mmol) and suspended in DMF (100 mL). The mixture was cooled to 0° C. and 4-(tetrahydro-pyran-2-yloxy)-but-2-yn-1-ol (prepared in accordance with the procedures of Tamaru et al., *Bull. Chem. Soc. Jpn.*, 1995, 1689-1705) (6.0 g, 35.3 mmol) was added. The reaction mixture was allowed to reach room temperature and stirred for one hour. To the mixture was added iodoethane (20.8 g, 133 mmol). The reaction mixture was stirred for 3.5 hours at room temperature before being quenched with ice/H$_2$O and extracted with MeOAc. The organic phase was washed with brine, dried (Na$_2$SO$_4$) and concentrated. Silica gel chromatography (1-20% MeOAc/hexane) provided 4.71 g of 2-(4-ethoxy-but-2-ynyloxy)-tetrahydro-pyran as a clear oil.

$C_{11}H_{18}O_3$ (198.13), LCMS (ESI): 199.12(M$^+$+H).

¹H NMR (300 MHz, CDCl₃): δ 4.81 (t, 1H), 4.32 (q, 2H), 4.19 (s, 2H), 3.83 (m, 1H), 3.56 (m, 3H), 1.90-1.47 (m, 6H), 1.23 (t, 3H).

Step 2: 4-Ethoxy-but-2-yn-1-ol

To a solution of 2-(4-ethoxy-but-2-ynyloxy)-tetrahydropyran (0.5 g, 2.52 mmol) in methanol (10 mL) was added p-toluenesulfonic acid monohydrate (p-TSOH) (0.086 g, 0.454 mmol). The reaction mixture was stirred at room temperature for 3.5 hours. The reaction mixture was poured into aqueous sodium carbonate and extracted with methyl acetate. The organic layers were combined, dried (Na₂SO₄) and concentrated. Silica gel chromatography (1-10% MeOAc/hexane) provided 0.2 g of 4-ethoxy-but-2-yn-1-ol as a clear oil.

¹H NMR (300 MHz, CDCl₃): δ 4.32 (q, 2H), 4.18 (br., s, 2H), 3.58 (q, 2H), 2.25 (t, 1H), 1.24 (t, 3H).

Step 3: 4-Ethoxy-but-2-ynoic acid methyl ester

To a stirred solution of 4-ethoxy-but-2-yn-1-ol (1 g, 8.76 mmol) in acetone (26 mL) at 0° C. was added dropwise Jones reagent. The reaction mixture was stirred at room temperature for 3 hours. The reaction mixture was diluted with water and extracted with methyl acetate. The organic layers were combined, dried (Na₂SO₄), and concentrated. The resulting 4-ethoxy-but-2-ynoic acid was methylated (TMSCHN₂ (2 M), MeOH/toluene, room temperature, 3 hours) to afford 0.66 g of the title compound as a clear oil.

$C_7H_{10}O_3$ (142.06), LCMS (ESI): 143.07 (M⁺+H).
¹H NMR (300 MHz, CDCl₃): δ 4.27 (s, 2H), 3.79 (s, 3H), 3.60 (q, 2H), 1.24 (t, 3H).

Step 4: (S)-2-(4-Cyclohexyl-phenoxymethyl)-5-ethoxymethyl-2,3-dihydro-oxazolo[3,2-a]pyrimidin-7-one The title compound was prepared from (S)-5-(4-cyclohexyl-phenoxymethyl)-4,5-dihydro-oxazol-2-ylamine and 4-ethoxy-but-2-ynoic acid methyl ester employing the procedure described in Example 94. $[\alpha]_D^{25}$ −9.80 (c 0.5, CHCl₃).

$C_{22}H_{28}N_2O_4$ (384.21), LCMS (ESI): 385.17 (M⁺+H).
¹H NMR (300 MHz, CDCl₃): δ 7.15 (d, 2H), 6.81 (d, 2H), 6.00 (s, 1H), 5.22 (m, 1H) 4.48-4.17 (series of m, 6H), 3.56 (q, 2H), 2.44 (br., s, 1H), 1.93-1.69 (m, 5H), 1.51-1.31 (m, 5H), 1.22 (t, 3H).

Example 120

(S)-2-(4-Cyclohexyl-phenoxymethyl)-5-phenylsulfanylmethyl-2,3-dihydro-oxazolo[3,2-a]pyrimidin-7-one

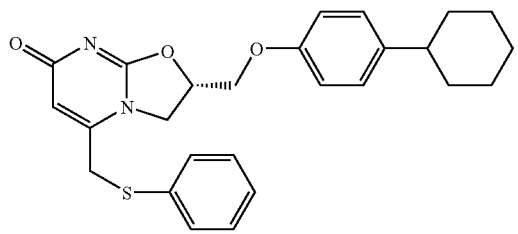 [SMILES: O=c1cc(CSc2ccccc2)n2c(n1)O[C@H](COc1ccc(C3CCCCC3)cc1)C2]

Step 1: 4-Phenylsulfanyl-but-2-ynoic acid ethyl ester

The title compound was prepared from prop-2-ynylsulfanyl-benzene and ethyl chloroformate in accordance with the procedures of G. Cai et al., *Tetrahedron*, 2006, (5697-5708).

$C_{12}H_{12}O_2S$ (220.06), LCMS (ESI): 221.06 (M⁺+H).
¹H NMR (300 MHz, CDCl₃): δ 7.48 (d, 2H), 7.33 (m, 3H), 4.21 (q, 2H), 3.70 (s, 2H), 1.30 (t, 3H).

Step 2: (S)-2-(4-Cyclohexyl-phenoxymethyl)-5-phenylsulfanylmethyl-2,3-dihydro-oxazolo[3,2-a]pyrimidin-7-one The title compound was prepared from (S)-5-(4-cyclohexyl-phenoxymethyl)-4,5-dihydro-oxazol-2-ylamine and 4-phenylsulfanyl-but-2-ynoic acid ethyl ester employing the procedure described in Example 94. $[\alpha]_D^{25}$ −19.40 (c 0.5, CHCl₃).

$C_{26}H_{28}N_2O_3S$ (448.18), LCMS (ESI): 449.19 (M⁺+H).
¹H NMR (300 MHz, CDCl₃): δ 7.32 (m, 5H), 7.12 (d, 2H), 6.83 (d, 2H), 5.52 (s, 1H), 5.26 (m, 1H), 4.51 (d, 2H), 4.27 (AB-m, 2H), 3.76 (s, 2H), 2.46 (br., s, 1H), 1.93-1.65 (m, 5H), 1.50-1.13 (m, 5H).

Example 121

(S)-2-[4-(4-Isopropyl-phenoxy)-phenoxymethyl]-2,3-dihydro-oxazolo[3,2-a]pyrimidin-7-one

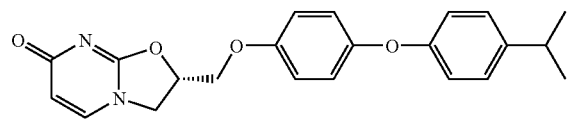 [SMILES: CC(C)c1ccc(Oc2ccc(OC[C@@H]3Cn4ccc(=O)nc4O3)cc2)cc1]

The title compound was prepared from 4-(4-isopropyl-phenoxy)-phenol (prepared in accordance with the procedures of Yeager, et. al., *Synthesis* 1991, 63-68) and R-epichlorohydrin employing the procedures described in Steps 1 through 3 of Example 1.

$C_{22}H_{22}N_2O_4$ (378.16), LCMS (ESI): 379.17 (M⁻+H)
¹H NMR (300 MHz, DMSO-d6), δ 7.76 (d, 1H), 7.21 (d, 2H), 6.98 (s, 4H), 6.86 (d, 2H), 5.83 (d, 1H), 5.33 (m, 1H), 4.47-4.26 (m, 3H), 4.11 (m, 1H), 2.87 (quin, 1H), 1.18 (d, 6H)

Example 122

(S)-2-(4'-Propyl-biphenyl-4-yloxymethyl)-2,3-dihydro-oxazolo[3,2-a]pyrimidin-7-one

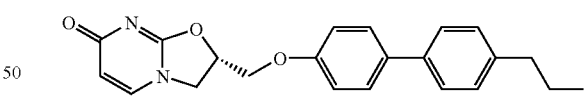

A mixture of (S)-2-(4-bromo-phenoxymethyl)-[3,2-a]pyrimidin-7-one (Example 26)(0.1 g, 0.31 mmol), 4-propylphenylboronic acid (0.1 g, 0.62 mmol), tetrakis(triphenylphosphine)palladium(0) (0.15 g, 0.62 mmol) and potassium carbonate (0.086 g, 0.62 mmol) in 25 ml of anhydrous tetrahydrofuran was heated under reflux for 18 hours. The mixture was filtered through celite and the filtrate was evaporated. The residue was purified by flash chromatography on silica gel using 9:1 methylene chloride:methanol and then 6:1 methylene chloride:methanol. The evaporated product fractions were combined and evaporated to provide the title compound as a solid (0.013 g, 12%). $[\alpha]_D^{25}$ +2.40 (c 0.5, DMSO).

$C_{22}H_{22}N_2O_3$ (362.41), LCMS (ESI): 363.17 (M⁺H).
¹H NMR (DMSO-d₆, 300 MHz) d 7.79 (d, 1H), 7.61 (d, 2H), 7.58 (d, 2H), 7.23 (d, 2H), 7.04 (d, 2H), 5.82 (d, 1H), 5.36 (m, 1H), 4.35-4.44 (m, 3H), 4.12-4.15 (m, 1H), 2.55 (t, 2H), 1.57 (q, 2H), 0.88 (t, 3H).

Example 123

(S)-2-(2',3'-Dimethyl-biphenyl-4-yloxymethyl)-2,3-dihydro-oxazolo[3,2-a]pyrimidin-7-one

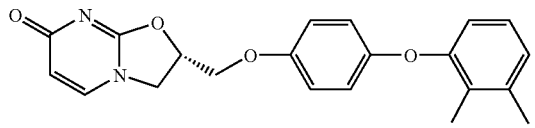 [SMILES: Cc1cccc(Oc2ccc(OC[C@@H]3Cn4ccc(=O)nc4O3)cc2)c1C]

A mixture of (S)-2-(4-bromo-phenoxymethyl)-[3,2-a]pyrimidin-7-one (0.4 g, 1.23 mmol), 2,3-dimethylphenylboronic acid (0.73 g, 4.9 mmol), tetrakis(triphenylphosphine)-palladium(0) (0.3 mmol) and sodium carbonate (4.9 mmol) in 30 ml of anhydrous ethylene glycol dimethyl ether was heated under reflux for 6 hours. The mixture was diluted with 10 ml of methanol and the mixture was filtered through celite. The filtrate was evaporated and the residue was purified by flash chromatography on silica gel using 100% methylene chloride and then 9:1 methylene chloride:methanol. The evaporated product residue was triturated with heptane and the insoluble material was collected to provide the title compound as a solid (0.07 g, 17%). $[\alpha]_D^{25}$ −46.48 (c 0.549, CHCl$_3$).

$C_{21}H_{20}N_2O_3$ (348.40), LCMS (ESI): 349.13 (M$^+$H).
$^1$H NMR (DMSO-d$_6$, 300 MHz), δ7.78 (d, 2H), 7.22 (d, 2H), 7.13 (m, 1H), 7.02 (m, 3H), 5.83 (d, 1H), 5.34 (m, 1H), 4.36-4.42 (m, 3H), 4.13-4.17 (m, 1H), 3.32 (s, 6H).

Example 124

(S)-2-(4'-tert-Butyl-biphenyl-4-yloxymethyl)-2,3-dihydro-oxazolo[3,2-a]pyrimidin-7-one

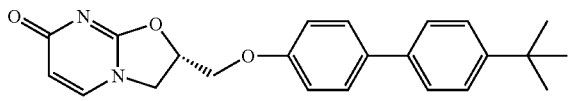 [SMILES: CC(C)(C)c1ccc(-c2ccc(OC[C@@H]3Cn4ccc(=O)nc4O3)cc2)cc1]

A mixture of (S)-2-(4-bromo-phenoxymethyl)-[3,2-a]pyrimidin-7-one(0.2 g, 0.62 mmol), 4-tert-butylphenylboronic acid (0.44 g, 2.5 mmol), tetrakis(triphenylphosphine)-palladium(0) (0.18 g, 0.16 mmol) and sodium carbonate (0.26 g, 2.5 mmol) in 30 ml of anhydrous ethylene glycol dimethyl ether was heated under reflux for 3 hours. The mixture was cooled and a combination of 4-tert-butylphenylboronic acid (0.22 g, 1.25 mmol), tetrakis(triphenylphosphine)palladium (0) (0.090 mg (0.08 mmol) and sodium carbonate (0.13 g, 1.25 mmol) was added in one portion. The mixture was again heated for an additional 2 hours. The mixture was diluted with 10 ml of methanol and was filtered through celite. The filtrate was evaporated and the residue was purified by flash chromatography on silica gel using 100% ethyl acetate and then 9:1 methylene chloride:methanol. The product residue was further purified by reverse phase HPLC using 10-100% (acetonitrile:0.1% trifluoroacetic acid) over 20 minutes to give the lyophilized title compound (0.03 g, 13%). $[\alpha]_D^{25}$ −5.40 (c 0.5, DMSO).

$C_{23}H_{24}N_2O_3$ (376.45), LCMS (ESI): 377.17 (M$^+$H).

$^1$H NMR (DMSO-d$_6$, 300 MHz), δ 7.78 (d, 1H), 7.52-7.57 (m, 4H), 7.43-7.46 (m, 2H), 7.01-7.04 (m, 2H), 5.83 (d, 1H), 5.38 (m, 1H), 4.36-4.41 (m, 3H), 4.12-4.15 (m, 1H), 1.31 (s, 9H).

Example 125

(S)-2-(4'-Ethoxy-biphenyl-4-yloxymethyl)-2,3-dihydro-oxazolo[3,2-a]pyrimidin-7-one

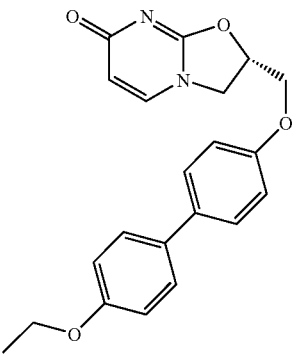 [SMILES: CCOc1ccc(-c2ccc(OC[C@@H]3Cn4ccc(=O)nc4O3)cc2)cc1]

A mixture of (S)-2-(4-bromo-phenoxymethyl)-[3,2-a]pyrimidin-7-one (0.4 g, 1.23 mmol), 4-ethoxyphenylboronic acid (0.82 g, 4.95 mmol), tetrakis(triphenylphosphine)-palladium(0) (0.34 g, 0.3 mmol) and sodium carbonate (0.52 g, 4.95 mmol) in 30 ml of anhydrous ethylene glycol dimethyl ether was heated under reflux for 3 hours. The mixture was cooled and a combination of 4-ethoxyphenylboronic acid (0.2 g, 1.1 mmol), tetrakis(triphenylphosphine)palladium(0) (0.085 g, 0.7 mmol) and sodium carbonate (0.12 g, 1.1 mmol) was added in one portion. The mixture was heated for an additional 1 hour. The mixture was diluted with 20 ml of methanol and was filtered through celite. The evaporated residue was purified by flash chromatography on silica gel using 100% methylene chloride then 95:5 methylene chloride:methanol and finally 9:1 methylene chloride:methanol. The evaporated product residue was dissolved in the minimum amount of hot methanol and was filtered. The filtrate was diluted with ether to precipitate the title compound (0.06 g, 13%).

$C_{21}H_{20}N_2O_4$ (364.40), LCMS (ESI): 365.17 (M$^+$H).
$^1$H NMR (DMSO-d$_6$, 300 MHz), δ 7.76 (d, 1H), 7.52-7.57 (m, 4H), 6.96-7.02 (m, 4H), 5.81 (d, 1H), 5.34-5.39 (m, 1H), 4.34-4.44 (m, 3H), 4.02-4.15 (m, 3H), 1.32 (t, 3H).

Example 126

(S)-2-(2'-Chloro-biphenyl-4-yloxymethyl)-2,3-dihydro-oxazolo[3,2-a]pyrimidin-7-one

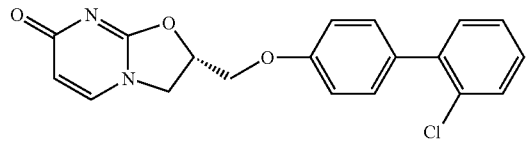

A mixture of (S)-2-(4-bromo-phenoxymethyl)-[3,2-a]pyrimidin-7-one (0.4 g, 1.23 mmol), 2-chlorophenylboronic acid (0.77 g, 4.95 mmol), tetrakis(triphenylphosphine)-palladium (0) (0.34 g, 0.3 mmol) and sodium carbonate (0.52 g, 4.95 mmol) in 25 ml of anhydrous ethylene glycol dimethyl ether was heated under reflux for 5 hours. The mixture was filtered through celite after dilution with 10 ml of methanol. The filtrate was evaporated and the residue was purified by flash chromatography on silica gel using 100% methylene chloride then 95:5 methylene chloride:methanol and finally 9:1 methylene chloride:methanol. The product fractions were combined and evaporated. The residue was treated with ethyl acetate and the solid which formed was collected to give the title compound (0.15 g, 35%).

$C_{19}H_{15}ClN_2O_3$ (354.79), LCMS (ESI): 355.12 ($M^+H$).

$^1$H NMR (DMSO-$d_6$, 300 MHz) δ 7.79 (d, 1H), 7.54 (d, 1H), 7.40 (m, 5H), 7.06 (d, 2H), 5.84 (d, 1H), 5.38 (m, 1H), 4.38-4.42 (m, 3H), 4.11-4.17 (m, 1H).

Example 127

2-(4-Cyclohexyl-phenoxymethyl)-2-methyl-2,3-dihydro-oxazolo[3,2-a]pyrimidin-7-one

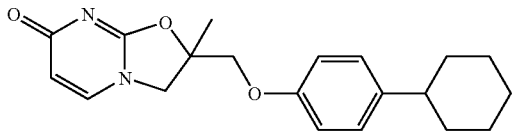 [SMILES: CC1(COc2ccc(C3CCCCC3)cc2)Cn2ccc(=O)nc2O1]

Step 1:
2-(4-cyclohexyl-phenoxymethyl)-2-methyl-oxirane

A solution of 2-choromethyl-2-methyl-oxirane (5.32 g, 50 mmol), in 50 ml of acetonitrile, was added to a refluxing mixture of 4-cyclohexylphenol (4.41 g, 25 mmol) and cesium carbonate (9.77 g, 30 mmol) in 50 ml of acetonitrile. The mixture was heated at reflux for 4 hours, cooled to room temperature, and concentrated in vacuo. The residue was partitioned between ethyl acetate and water, the layers were separated and the organic phase was extracted with brine. The organic phase was dried over 4 A molecular sieves, filtered, and concentrated in vacuo to yield 6.15 g of a colorless oil which slowly solidified to provide the title compound as a white solid.

$^1$H NMR (CDCl$_3$, 300 MHz), δ 7.13 (d, 2H), 6.82 (d, 2H), 3.95 (dd, 2H), 2.85 (d, 1H), 2.70 (d, 1H), 2.38-2.5 (m, 1H), 1.65-1.92 (m, 5H), 1.45 (s, 3H)1.15-1.55 (m, 5H).

Step 2: 5-(4-Cyclohexyl-phenoxymethyl)-5-methyl-oxazolidin-2-ylideneamine

Methanol (250 ml) and sodium hydrogen cyanamide (1.92 g, 30 mmol) were added to a flask containing 2-(4-cyclohexyl-phenoxymethyl)-2-methyl-oxirane (6.15 g, 25 mmol). The reaction mixture was stirred overnight at room temperature and then concentrated in vacuo. The residue was dissolved in methylene chloride and washed with water, then saturated potassium carbonate. The methylene chloride layer was dried over 4 A molecular sieves, filtered and concentrated in vacuo to yield 5.46 g of a white solid. The white solid was recrystallized from ether to yield 1.11 g of the title compound as white crystals. A second crop yielded 0.64 g of white crystals.

$^1$H NMR (CDCl$_3$, 300 MHz), δ 7.13 (d, 2H), 6.82 (d, 2H), 4.42 (br. s, 2H), 3.92 (dd, 2H), 3.75 (d, 1H), 3.50 (d, 1H), 2.38-2.5 (m, 1H), 1.65-1.92 (m, 5H), 1.50 (s, 3H), 1.15-1.48 (m, 5H).

Step3: 2-(4-Cyclohexyl-phenoxymethyl)-2-methyl-2,3-dihydro-oxazolo[3,2-a]pyrimidin-7-one A suspension of 5-(4-cyclohexyl-phenoxymethyl)-5-methyl-oxazolidin-2-ylideneamine (1.11 g, 3.85 mmol) in 15 ml of t-butanol was heated to 80° C. All of the suspension dissolved. Ethyl propiolate (0.51 ml, 5.0 mmol) was added followed by 5 ml of ethanol. The reaction mixture was heated at reflux for 8 hrs. An off-white precipitate gradually came out of the solution. The reaction was cooled to room temperature and the solid isolated by filtration and washed with ether to provide the title compound as a white solid. Yield 0.75 g.

$C_{20}H_{24}N_2O_3$ (340.43), LCMS (ESI): 341.17 ($M^+$+H).

$^1$H NMR (CDCl$_3$, 300 MHz) δ 7.22 (d, 1H), 7.14 (d, 2H), 6.77 (d, 2H), 6.05 (d, 1H), 4.37 (d, 1H), 4.14 (d, 1H), 4.02 (d, 1H), 3.98 (d, 1H), 2.35-2.52 (m, 1H), 1.72-1.90 (m, 5H), 1.71 (s, 3H), 1.15-1.45 (m, 5H).

Example 128

(S)-2-(Benzo[b]thiophen-6-yloxymethyl)-2,3-dihydro-oxazolo[3,2-a]pyrimidin-7-one

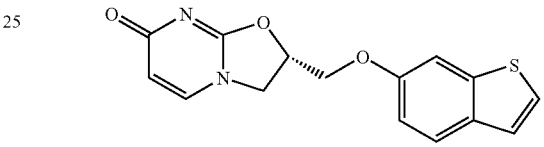

Step1: (S)-5-(toluene-4-sulfonic acid methyl)-(4,5-dihydro-oxazol-2-yl)amine

To a vigorously stirred solution of sodium hydrogen cyanamide (2.81 g, 43.8 mmol) in methanol (44 mL) was added dropwise (2S)-glycidyl tosylate (10 g, 43.8 mmol) in methanol. The reaction mixture was stirred at room temperature overnight after which the reaction mixture was concentrated to remove methanol. Ethyl acetate was added (150 mL) along with 50 ml of water. The contents were transferred to a separatory funnel, the organic layer was removed, dried over Na$_2$SO$_4$ and concentrated under vacuum to give 5.74 g (48%) of (S)-5-(toluene-4-sulfonic acid methyl)-(4,5-dihydro-oxazol-2-yl)amine. $^1$H NMR (CDCl$_3$, 300 MHz), δ 7.83 (d, 2H), 7.39 (d, 2H), 4.80-4.70 (m, 1H), 4.15-4.10 (m, 1H), 3.83 (dd, 1H), 3.09-2.99 (m, 2H), 2.46 (s, 3H).

Step 2: (S)-2-Toluene-4-sulfonic acid methyl-2,3-dihydro-oxazolo[3,2-a]pyrimidin-7-one To a solution of (S)-5-(toluene-4-sulfonic acid methyl)-(4,5-dihydro-oxazol-2-yl)amine (5.69 g, 21.1 mmol) in t-butanol (150 mL) and ethanol (50 mL) was added ethyl propiolate (2.14 mL, 21.1 mmol). The reaction mixture was stirred at reflux for 2.5 hours. The mixture was cooled to room temperature, concentrated under vacuum and purified by column chromatography on silica gel (200 g column, 45 mL/min, 4:1 ethyl acetate:heptanes to 10% methanol in dichloromethane). This afforded 2.15 g (32%) of (S)-2-toluene-4-sulfonic acid methyl-2,3-dihydro-oxazolo[3,2-a]pyrimidin-7-one.

$C_{14}H_{14}N_2O_5S$ (322.06), LCMS (ESI): 323.07 ($M^+$+H).

$^1$H NMR ((CD$_3$)$_2$SO, 300 MHz) δ 7.80 (d, 2H), 7.69 (d, 1H), 7.51 (d, 2H), 5.79 (d, 1H), 5.24-5.15 (m, 1H), 4.43-4.26 (m, 2H), 4.27 (t, 1H), 3.90 (dd, 1H), 2.05 (s, 3H).

Step 3: To a solution of (S)-2-toluene-4-sulfonic acid methyl-2,3-dihydro-oxazolo[3,2-a]pyrimidin-7-one (100 mg, 0.31 mmol) in dimethylformamide (3 mL) was added benzo[b]thiophen-6-ol (52 mg, 0.34 mmol) followed by cesium carbonate (112 mg, 0.34 mmol). The reaction mixture was stirred at room temperature for 18 hours. The mixture was concentrated under vacuum and purified by HPLC with a C18-10 μm SunFire column using a gradient ranging from 40% $CH_3CN/TFA$:60% $H_2O/TFA$ and ending with 100% $CH_3CN/TFA$. This afforded 56 mg (60%) of the title compound. OR $[α]_D$=11.20°.

$C_{15}H_{12}N_2O_3S$ (300.05), LCMS (ESI): 301.05 ($M^+$+H). $[α]_D^{25}$ −11.20 (c 0.5, DMSO).

$^1$H NMR (($CD_3$)$_2$SO, 300 MHz): δ 7.82-7.76 (m, 2H), 7.62 (d, 1H), 7.56 (d, 1H), 7.36 (d, 1H), 7.01 dd, 1H), 5.87 (d, 1H), 5.42-5.37 (m, 1H), 4.47-4.35 (m, 3H), 4.16 (dd, 1H).

Example 129

(S)-2-(4-Bicyclo[3.3.1]non-9-yl-phenoxymethyl)-5-cyclopropyl-2,3-dihydro-oxazolo[3,2-a]pyrimidin-7-one

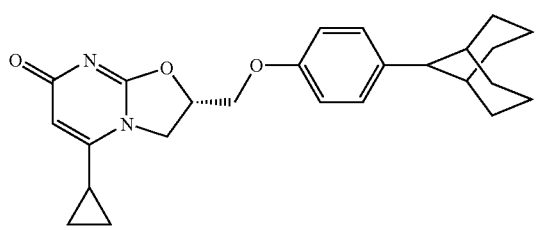 [SMILES: O=c1cc(C2CC2)n2c(n1)O[C@H](COc1ccc(C3C4CCCC3CCC4)cc1)C2]

To a solution of (S)-5-(4-bicyclo[3.3.1]non-9-yl-phenoxymethyl)-4,5-dihydro-oxazol-2-ylamine (0.7 g, 2.23 mmol) (Example 20) in ethanol (40 mL) was added 0.462 g (3.35 mmol) of cyclopropyl-propynoic acid ethyl ester (Example 99). The reaction mixture was stirred at 82° C. for 30 minutes. The reaction mixture was concentrated and purified by chromatography on silica gel, eluting with MeOH/$CH_2Cl_2$ to afford 0.145 g of the title compound. $[α]_D^{25}$ −10.51 (c 0.5, $CHCl_3$).

$C_{25}H_{30}N_2O_3$ (406.23), LCMS (ESI): 407.25($M^+$+H).

$^1$H NMR ($CDCl_3$, 300 MHz), δ 7.29 (d, 2H), 6.85 (d, 2H) 5.67 (s, 1H), 5.27 (br.s, 1H), 4.53-4.27 (series of m, 4H), 2.74 (s, 1H), 2.38 (br., s, 2H), 1.99-1.34 (m, 13H), 1.07 (d, 2H), 0.85 (d, 2H).

Example 130

(S)-2-(4-Bicyclo[3.3.1]non-9-yl-phenoxymethyl)-5-isobutyl-2,3-dihydro-oxazolo[3,2-a]pyrimidin-7-one

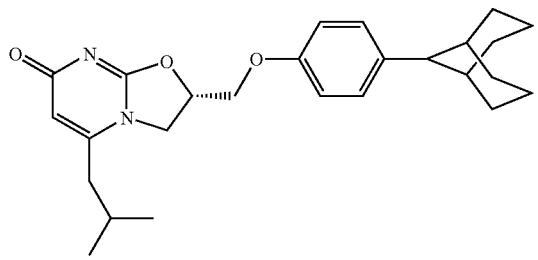 [SMILES: CC(C)Cc1cc(=O)nc2n1C[C@@H](COc1ccc(C3C4CCCC3CCC4)cc1)O2]

Step 1: 5-Methyl-hex-2-ynoic acid ethyl ester

The title compound was prepared from 4-methyl-pent-1-yne and ethyl chloroformate in accordance with the procedures of G. Cai et al., Tetrahedron, 2006, (5697-5708).

$C_9H_{14}O_2$ (154.10), LCMS (CI): 155.11 ($M^+$+H).

$^1$H NMR (300 MHz, $CDCl_3$): δ 4.22 (q, 2H), 2.23 (d, 2H), 1.92 (m, 1H), 1.31 (t, 3H), 1.02 (d, 6H).

Step 2: (S)-2-(4-Bicyclo[3.3.1]non-9-yl-phenoxymethyl)-5-isobutyl-2,3-dihydro-oxazolo-[3,2-a]pyrimidin-7-one To a solution of (S)-5-(4-bicyclo[3.3.1]non-9-yl-phenoxymethyl)-4,5-dihydro-oxazol-2-ylamine (0.600 g, 1.91 mmol) in ethanol (5 mL) was added 0.294 g (2.86 mmol) of 5-methyl-hex-2-ynoic acid ethyl ester. The reaction mixture was heated in a microwave oven at 160° C. for 20 minutes. The reaction mixture was concentrated and purified by chromatography on silica gel eluting with MeOH/$CH_2Cl_2$ to afford 0.283 g of the title compound. $[α]_D^{25}$ −11.17 (c 0.537, $CHCl_3$).

$C_{26}H_{34}N_2O_3$ (422.26), LCMS (ESI): 423.27 ($M^+$+H).

$^1$H NMR ($CDCl_3$, 300 MHz), δ 7.28 (d, 2H), 6.83 (d, 2H), 5.86 (s, 1H), 5.22 (br.s, 1H), 4.29 (m, 4H), 2.74 (s, 1H), 2.39 (br. s, 2H), 2.33 (d, 2H), 2.03-1.32 (m, 13H), 1.03 (d, 6H).

Example 131

(S)-2-(4-Cyclohexyl-phenoxymethyl)-5-ethylsulfanylmethyl-2,3-dihydro-oxazolo[3,2-a]pyrimidin-7-one

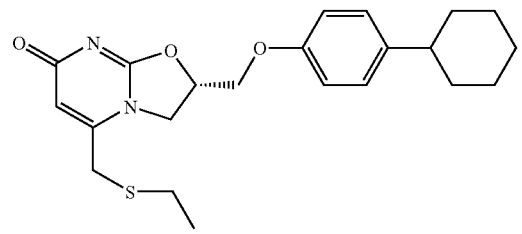 [SMILES: CCSCc1cc(=O)nc2n1C[C@@H](COc1ccc(C3CCCCC3)cc1)O2]

Step 1: 4-Ethylsulfanyl-but-2-ynoic acid ethyl ester

The title compound was prepared from 3-ethylsulfanyl-propyne and ethyl chloroformate in accordance with the procedures of G. Cai et al., Tetrahedron, 2006, (5697-5708).

$C_8H_{12}O_2$ S (172.06), LCMS (ESI): 173.04.($M^+$+H).

$^1$H NMR (300 MHz, $CDCl_3$): δ 4.26 (q, 2H), 3.83 (s, 2H), 2.73 (q, 2H), 1.31 (m, 6H).

Step 2: (S)-2-(4-Cyclohexyl-phenoxymethyl)-5-ethylsulfanylmethyl-2,3-dihydro-oxazolo[3,2-a]pyrimidin-7-one To a solution of (S)-5-(4-cyclohexyl-phenoxymethyl)-4,5-dihydro-oxazol-2-ylamine (0.5 g, 1.82 mmol) in t-butanol (5 mL) was added 4-ethylsulfanyl-but-2-ynoic acid ethyl ester (0.411 g, 2.39 mmol). The reaction mixture was heated in a microwave oven at 170° C. for 20 min. The solvent was removed under vacuum, and the residue purified by flash column chromatography (silica gel, MeOH/$CH_2Cl_2$) to afford 0.416 g of the title compound.

C$_{22}$H$_{28}$N$_2$O$_3$S (400.18), LCMS (ESI): 401.17 (M$^+$+H).
$^1$H NMR (300 MHz, CDCl$_3$): δ 7.14 (d, 2H), 6.78 (d, 2H), 5.84 (s, 1H), 5.25 (br.s, 1H), 4.56-4.40 (m, 2H), 4.33-4.20 (m, 2H), 3.45 (s, 2H), 2.53 (q, 2H), 2.45 (br., s, 1H), 1.89-1.69 (m, 5H), 1.44-1.30 (m, 5H), 1.25 (t, 3H).

Example 132

(S)-6-Benzenesulfonyl-2-(4-cyclohexyl-phenoxymethyl)-2,3-dihydro-oxazolo[3,2-a]pyrimidin-7-one

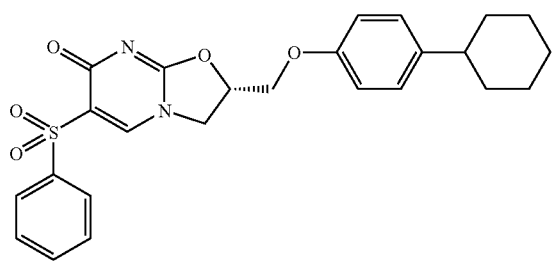 [SMILES: O=c1nc2n(cc1S(=O)(=O)c1ccccc1)C[C@@H](COc1ccc(C3CCCCC3)cc1)O2]

(S)-6-Benzenesulfinyl-2-(4-cyclohexyl-phenoxymethyl)-2,3-dihydro-oxazolo[32-a]pyrimidin-7-one (Diastereomer 1)

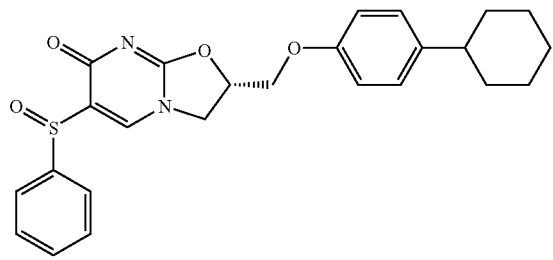 [SMILES: O=c1nc2n(cc1S(=O)c1ccccc1)C[C@@H](COc1ccc(C3CCCCC3)cc1)O2]

(S)-6-Benzenesulfinyl-2-(4-cyclohexyl-phenoxymethyl)-2,3-dihydro-oxazolo[32-a]pyrimidin-7-one (Diastereomer 2)

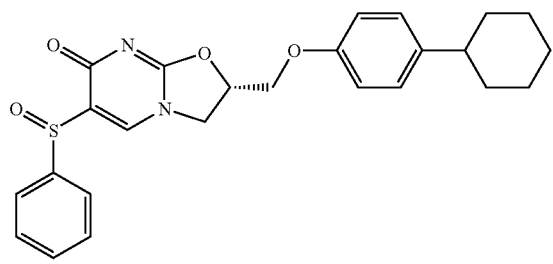 [SMILES: O=c1nc2n(cc1S(=O)c1ccccc1)C[C@@H](COc1ccc(C3CCCCC3)cc1)O2]

To a solution of 2-(4-cyclohexyl-phenoxymethyl)-6-phenylsulfanyl-2,3-dihydro-oxazolo[3,2-a]pyrimidin-7-one (0.313 g, 0.675 mmol) (prepared in accordance with the procedures set forth in Example 93), in HOAc (6 mL) was added sodium perborate tetrahydrate (0.277 g, 1.80 mmol). The reaction mixture was stirred at room temperature overnight. The reaction mixture was then neutralized with NaOH (2N) to PH~9. The mixture was extracted with EtOAc three times. The organic phase was washed with brine and dried (Na$_2$SO$_4$). Silica gel chromatography (0-6% 2-propanol/CH$_2$Cl$_2$) provided 0.026 g of (S)-6-benzenesulfonyl-2-(4-cyclohexyl-phenoxymethyl)-2,3-dihydro-oxazolo[3,2-a]pyrimidin-7-one, 0.022 g of (S)-6-benzenesulfinyl-2-(4-cyclohexyl-phenoxymethyl)-2,3-dihydro-oxazolo[32-a]pyrimidin-7-one (Diastereomer 1) and 0.086 g of (S)-6-benzenesulfinyl-2-(4-cyclohexyl-phenoxymethyl)-2,3-dihydro-oxazolo[32-a]pyrimidin-7-one (diastereomer 2).

(S)-6-Benzenesulfonyl-2-(4-cyclohexyl-phenoxymethyl)-2,3-dihydro-oxazolo[3,2-a]pyrimidin-7-one C$_{25}$H$_{26}$N$_2$O$_5$S (466.15), LCMS (ESI): 467.17(MH$^+$).
$^1$H NMR (CDCl$_3$, 300 MHz), δ 8.36 (s, 1H), 8.13 (d, 2H), 7.46-7.64 (m, 3H), 7.11 (d, 2H), 6.78 (d, 2H), 5.34 (m, 1H), 4.16-4.58 (m, 4H), 2.44 (m, 1H), 1.67-1.90 (m, 5H) 1.16-1.50 (m, 5H).

(S)-6-Benzenesulfinyl-2-(4-cyclohexyl-phenoxymethyl)-2,3-dihydro-oxazolo[32-a]pyrimidin-7-one (Diastereomer 1). [α]$_D^{25}$ +28.80 (c 0.5, CHCl$_3$).
C$_{25}$H$_{26}$N$_2$O$_4$S (450.16), LCMS (ESI): 451.17(MH$^+$).
$^1$H NMR (CDCl$_3$, 300 MHz), $^1$H NMR (CDCl$_3$, 300 MHz), δ 7.90 (m, 3H), 7.47 (m, 3H), 7.14 (d, 2H), 6.80 (d, 2H), 5.26 (m, 1H), 4.42 (d, 2H), .4.29 (AB-m, 2H), 2.45 (m, 1H), 1.67-1.90 (m, 5H) 1.20-1.53 (m, 5H).

(S)-6-Benzenesulfinyl-2-(4-cyclohexyl-phenoxymethyl)-2,3-dihydro-oxazolo[32-a]pyrimidin-7-one (Diastereomer 2). [α]$_D^{25}$ -21.60 (c 0.5, CHCl$_3$).
C$_{25}$H$_{26}$N$_2$O$_4$S (450.16), LCMS (ESI): 451.16(MH$^+$).
$^1$H NMR (CDCl$_3$, 300 MHz), δ 7.90 (m, 3H), 7.48 (m, 3H), 7.08 (d, 2H), 6.71 (d, 2H), 5.31 (m, 1H), 4.34-4.51 (m, 2H), .4.26 (AB-m, 2H), 2.43 (br.s,, 1H), 1.65-1.96 (m, 5H) 1.13-1.54 (m, 5H).

Example 133

(S)-2-(4-Cyclohexyl-phenoxymethyl)-6-methanesulfonyl-2,3-dihydro-oxazolo[3,2a]pyrimidin-7-one

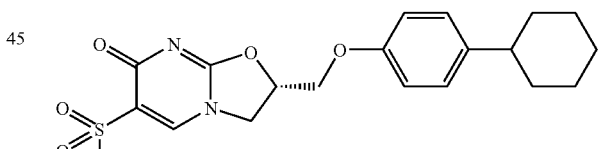

(S)-2-(4-Cyclohexyl-phenoxymethyl)-6-methanesulfinyl-2,3-dihydro-oxazolo[3,2-a]pyrimidin-7-one (Diastereomer 1)

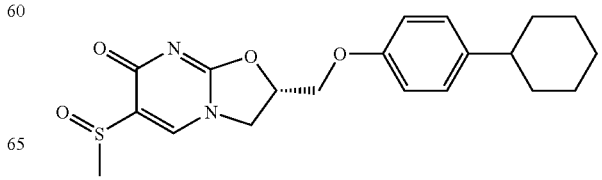

(S)-2-(4-Cyclohexyl-phenoxymethyl)-6-methanesulfinyl-2,3-dihydro-oxazolo[3,2-a]pyrimidin-7-one (Diastereomer 2)

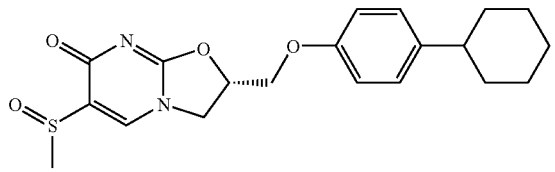 [SMILES: CS(=O)c1cn2c(nc1=O)O[C@H](COc1ccc(C3CCCCC3)cc1)C2]

To a solution of 2-(4-cyclohexyl-phenoxymethyl)-6-methylsulfanyl-2,3-dihydro-oxazolo[3,2-a]pyrimidin-7-one (0.284 g, 0.763 mmol), prepared in accordance with the procedures set forth in Example 98, in HOAc (6 mL) was added sodium perborate tetrahydrate (0.313 g, 2.04 mmol). The reaction mixture was stirred at room temperature overnight. The reaction mixture was then neutralized with NaOH (2N) to PH~9 after which it was extracted with EtOAc three times. The organic phase was washed with brine and dried (Na$_2$SO$_4$). Silica gel chromatography (0-8% EtOH/CH$_2$Cl$_2$) provided 0.03 g of (S)-2-(4-cyclohexyl-phenoxymethyl)-6-methanesulfonyl-2,3-dihydro-oxazolo[3,2a]pyrimidin-7-one, 0.042 g of (S)-2-(4-cyclohexyl-phenoxymethyl)-6-methanesulfinyl-2,3-dihydro-oxazolo[3,2-a]pyrimidin-7-one (Diastereomer 1) and 0.011 g of (S)-2-(4-cyclohexyl-phenoxymethyl)-6-methanesulfinyl-2,3-dihydro-oxazolo[3,2-a]pyrimidin-7-one (Diastereomer 2).

(S)-2-(4-Cyclohexyl-phenoxymethyl)-6-methanesulfonyl-2,3-dihydro-oxazolo[3,2 a]pyrimidin-7-one
C$_{20}$H$_{24}$N$_2$O$_5$S (404.14), LCMS (ESI): 405.14 (MH$^+$).
$^1$H NMR (CDCl$_3$, 300 MHz), δ 8.22 (s, 1H), 7.14 (d, 2H), 6.80 (d, 2H), 5.39 (m, 1H), 4.19-4.57 (m, 4H), 3.30 (s, 3H), 2.46 (m, 1H), 1.17-1.92 (m, 10H).

(S)-2-(4-Cyclohexyl-phenoxymethyl)-6-methanesulfinyl-2,3-dihydro-oxazolo[3,2-a]pyrimidin-7-one (Diastereomer 1). [α]$_D^{25}$ +81.65 (c 0.485, CHCl$_3$)
C$_{20}$H$_{24}$N$_2$O$_4$S (388.14), LCMS (ESI): 389.15 (MH$^+$).
$^1$H NMR (CDCl$_3$, 300 MHz), δ 7.78 (s, 1H), 7.14 (d, 2H), 6.80 (d, 2H), 5.36 (m, 1H), 4.47 (m, 2H), 4.32 (AB-m, 2H), 2.95 (s, 3H), 2.46 (m, 1H) 1.17-1.92 (m, 10H).

(S)-2-(4-Cyclohexyl-phenoxymethyl)-6-methanesulfinyl-2,3-dihydro-oxazolo[3,2-a]pyrimidin-7-one (Diastereomer 2)
C$_{20}$H$_{24}$N$_2$O$_4$S (388.14), LCMS (ESI): 389.15 (MH$^+$).
$^1$H NMR (CDCl$_3$, 300 MHz), δ 7.78 (s, 1H), 7.14 (d, 2H), 6.80 (d, 2H), 5.34 (m, 1H), 4.47 (d, 2H), 4.32 (AB-m, 2H), 2.93 (s, 3H), 2.46 (m, 1H) 1.17-1.92 (m, 10H).

Example 134

(S)-5-Benzenesulfonylmethyl-2-(4-cyclohexyl-phenoxymethyl)-2,3-dihydro-oxazolo[3,2-a]pyrimidin-7-one

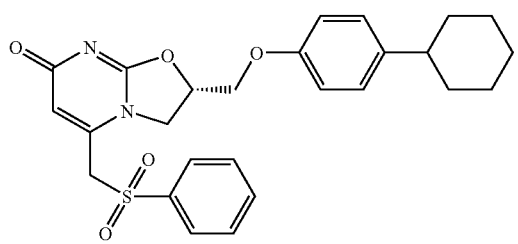 [SMILES: O=c1cc(CS(=O)(=O)c2ccccc2)n2c(n1)O[C@H](COc1ccc(C3CCCCC3)cc1)C2]

Step 1: (S)-2-(4-Cyclohexyl-phenoxymethyl)-5-phenylsulfanylmethyl-2,3-dihydro-oxazolo[3,2-a]pyrimidin-7-one To a solution of (S)-5-benzenesulfonylmethyl-2-(4-cyclohexyl-phenoxymethyl) -2,3-dihydro-oxazolo[3,2-a]pyrimidin-7-one (0.5 g, 1.11 mmol), prepared in accordance with the procedures described in Step 1 and 2 of Example 120, in HOAc (20 mL) was added sodium perborate tetrahydrate (0.446 g, 2.90 mmol). The reaction mixture was stirred at room temperature for 9 hours. The reaction mixture was neutralized with NaOH (2N) to pH~7 and further to pH~10 with Na$_2$CO$_3$. The mixture was extracted with EtOAc three times. The organic phase was washed with brine and dried (Na$_2$SO$_4$). Silica gel chromatography (2-8% methanol/CH$_2$Cl$_2$) provided 0.425 g of (S)-2-(4-cyclohexyl-phenoxymethyl)-5-phenylsulfanylmethyl-2,3-dihydro-oxazolo[3,2-a]pyrimidin-7-one. [α]$_D^{25}$ −3.80 (c 0.5, CHCl$_3$).
C$_{26}$H$_{28}$N$_2$O$_5$S (480.17), LCMS (ESI): 481.12 (M$^+$+H).
$^1$H NMR (300 MHz, CDCl$_3$): δ 7.83 (m, 2H), 7.73 (m, 1H), 7.60 (m, 2H), 7.13 (d, 2H), 6.84 (d, 2H), 5.33 (s, 1H), 5.28 (m, 1H), 4.65 (t, 1H), 4.54 (m, 1H), 4.25 (AB-m, 2H), 4.17 (s, 2H), 2.43 (br., s, 1H), 1.94-1.69 (m, 5H), 1.50-1.14 (m, 5H).

Example 135

(S)-2-(4-Cyclohexyl-phenoxymethyl)-5-ethanesulfonylmethyl-2,3-dihydro-oxazolo[3,2-a]pyrimidin-7-one

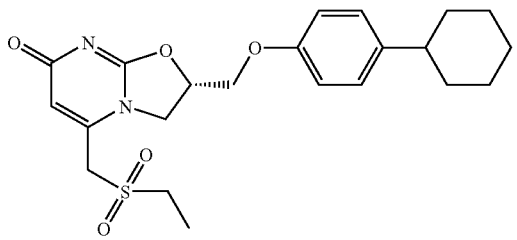 [SMILES: CCS(=O)(=O)Cc1cc(=O)nc2n1C[C@@H](COc1ccc(C3CCCCC3)cc1)O2]

To a solution of 2-(4-cyclohexyl-phenoxymethyl)-5-ethylsulfanylmethyl-2,3-dihydro-oxazolo[3,2-a]pyrimidin-7-one (0.3 g, 0.75 mmol) in HOAc (20 mL) was added sodium perborate tetrahydrate (0.3 g, 1.95 mmol). The reaction mixture was stirred at room temperature overnight. The reaction mixture was neutralized with sodium hydroxide (2N) to pH~7 and further to pH~10 with aqueous sodium carbonate. The mixture was extracted with EtOAc three times. The organic phase was washed with brine and dried (Na$_2$SO$_4$). Silica gel chromatography (MeOH/CH$_2$Cl$_2$) provided 0.254 g of the title compound. [α]$_D^{25}$ +5.45 (c 0.5, CHCl$_3$).
C$_{22}$H$_{28}$N$_2$O$_5$S (432.17), LCMS (ESI): 433.15 (M$^+$+H).
$^1$H NMR (300 MHz, CDCl$_3$): δ 7.13 (d, 2H), 6.83 (d, 2H), 6.01 (s, 1H), 5.27 (br.s, 1H), 4.80-4.20 (m, 4H), 4.09 (s, 2H), 3.17 (q, 2H), 2.47 (br.s, 1H), 2.00-1.67 (m, 5H), 1.65-1.07 (m, 8H).

Example 136

(S)-2-(2-p-Tolyl-benzo[b]thiophen-6-yloxymethyl)-2,3-dihydro-oxazolo[3,2-a]pyrimidin-7-one

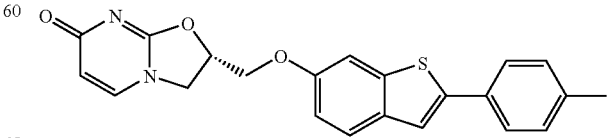

The title compound was prepared from (S)-2-toluene-4-sulfonic acid methyl-2,3-dihydro-oxazolo[3,2-a]pyrimidin- 7-one and 2-p-tolyl-benzo[b]thiophen-6-ol according to the procedure described in Example 128, Step 3.

$C_{22}H_{18}N_2O_3S$ (390.10), LCMS (ESI): 391.13 (M$^+$+H).

$^1$H NMR (DMSO-d$_6$ 300 MHz) δ: 7.79-7.71 (m, 3H), 7.63-7.54 (m, 3H), 7.33-7.26 (m, 2H), 6.96 (dd, 1H), 5.83 (d, 1H), 5.39-5.37 (m, 1H), 4.49-4.32 (m, 3H), 4.15 (dd, 1H), 3.32 (s, 3H).

Example 137

(S)-2-[2-(4-Ethyl-phenyl)-benzo[b]thiophen-6-yloxymethyl]-2,3-dihydro-oxazolo[3,2-a]pyrimidin-7-one

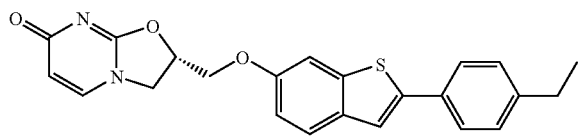 [SMILES: CCc1ccc(-c2cc3ccc(OC[C@@H]4Cn5ccc(=O)nc5O4)cc3s2)cc1]

The title compound was prepared from (S)-2-toluene-4-sulfonic acid methyl-2,3-dihydro-oxazolo[3,2-a]pyrimidin-7-one and 2-(4-ethyl-phenyl)-benzo[b]thiophen-6-ol according to the procedure described in Example 128, Step 3.

$C_{23}H_{20}N_2O_3S$ (404.11), LCMS (ESI): 405.15 (M$^+$+H).

$^1$H NMR (DMSO-d$_6$ 300 MHz) δ: 7.80-7.71 (m, 3H), 7.65-7.54 (m, 3H), 7.31-7.28 (m, 2H), 7.01 (dd, 1H), 5.84 (d, 1H), 5.39-5.38 (m, 1H), 4.49-4.36 (m, 3H), 4.13 (dd, 1H), 2.66 (q, 2H), 1.20 (t, 3H).

Example 138

(S)-2-[2-(4-Isopropyl-phenyl)-benzo[b]thiophen-6-yloxymethyl]-2,3-dihydro-oxazolo[3,2-a]pyrimidin-7-one

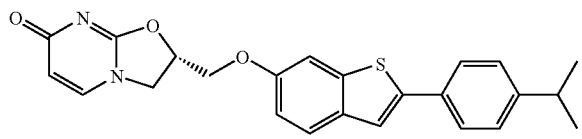 [SMILES: CC(C)c1ccc(-c2cc3ccc(OC[C@@H]4Cn5ccc(=O)nc5O4)cc3s2)cc1]

The title compound was prepared from (S)-2-toluene-4-sulfonic acid methyl-2,3-dihydro-oxazolo[3,2-a]pyrimidin-7-one and 2-(4-isopropyl-phenyl)-benzo[b]thiophen-6-ol according to the procedure described in Example 128, Step 3.

$C_{24}H_{22}N_2O_3S$ (418.13), LCMS (ESI): 419.16 (M$^+$+H).

$^1$H NMR (DMSO-d$_6$, 300 MHz) δ: 7.78-7.58 (m, 6H), 7.32 (d, 2H), 6.97 (dd, 1H), 5.83 (d, 1H), 5.38-5.36 (m, 1H), 4.45-4.38 (m, 2H), 4.16-4.07 (m, 2H), 2.93-2.88 (m, 1H), 1.21 (d, 6H).

Example 139

(S)-2-[2-(4-Propyl-phenyl)-benzo[b]thiophen-6-yloxymethyl]-2,3-dihydro-oxazolo[3,2-a]-pyrimidin-7-one

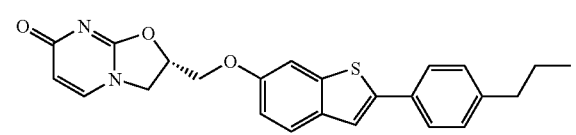 [SMILES: CCCc1ccc(-c2cc3ccc(OC[C@@H]4Cn5ccc(=O)nc5O4)cc3s2)cc1]

The title compound was prepared from (S)-2-toluene-4-sulfonic acid methyl-2,3-dihydro-oxazolo[3,2-a]pyrimidin-7-one and 2-(4-n-propyl-phenyl)-benzo[b]thiophen-6-ol according to the procedure described in Example 128, Step 3.

$C_{24}H_{22}N_2O_3S$ (418.13), LCMS (ESI): 419.16 (M$^+$+H).

$^1$H NMR (DMSO-d$_6$ 300 MHz) δ: 7.79-7.59 (m, 6H), 7.28 (d, 2H), 7.01 (dd, 1H), 5.83 (d, 1H), 5.39-5.38 (m, 1H), 4.48-4.40 (m, 2H), 4.17-4.07 (m, 2H), 2.59 (t, 2H), 1.65-1.58 (m, 2H), 0.91 (t, 3H).

Example 140

(S)-2-[2-(4-tert-Butyl-phenyl)-benzo[b]thiophen-6-yloxymethyl]-2,3-dihydro-oxazolo[3,2-a]pyrimidin-7-one

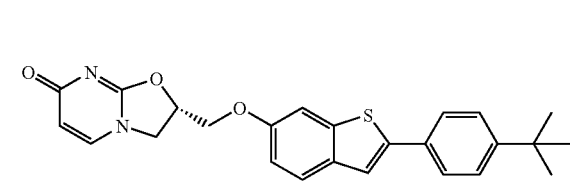 [SMILES: CC(C)(C)c1ccc(-c2cc3ccc(OC[C@@H]4Cn5ccc(=O)nc5O4)cc3s2)cc1]

The title compound was prepared from (S)-2-toluene-4-sulfonic acid methyl-2,3-dihydro-oxazolo[3,2-a]pyrimidin-7-one and 2-(4-t-butyl-phenyl)-benzo[b]thiophen-6-ol according to the procedure described in Example 128, Step 3.

$C_{25}H_{24}N_2O_3S$ (432.15), LCMS (ESI): 433.18 (M$^+$+H).

$^1$H NMR (DMSO-d$_6$ 300 MHz) δ: 7.79-7.52 (m, 6H), 7.48 (d, 2H), 7.01 (dd, 1H), 5.84 (d, 1H), 5.39-5.38 (m, 1H), 4.48-4.33 (m, 3H), 4.14 (dd, 1H), 1.31 (s, 9H).

Example 141

(S)-2-[2-(2-Chloro-pyridin-4-yl)-benzo[b]thiophen-6-yloxymethyl]-2,3-dihydro-oxazolo[3,2-a]pyrimidin-7-one

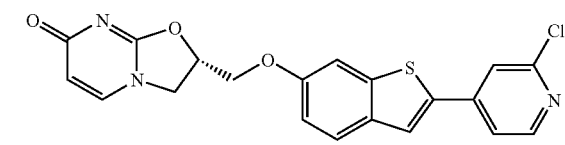 [SMILES: O=c1ccn2c(n1)O[C@H](COc1ccc3cc(-c4ccnc(Cl)c4)sc3c1)C2]

The title compound was prepared from (S)-2-toluene-4-sulfonic acid methyl-2,3-dihydro-oxazolo[3,2-a]pyrimidin-7-one and 2-(2-chloro-pyridin-4-yl)-benzo[b]thiophen-6-ol according to the procedure described in Example 128, Step 3.

$C_{20}H_{14}ClN_3O_3S$ (411.04), LCMS (ESI): 412.07 (M$^-$+H).

$^1$H NMR (DMSO-d$_6$ 300 MHz) δ: 8.44 (d, 1H), 8.22 (s, 1H), 7.85-7.69 (m, 5H), 7.07 (dd, 1H), 5.84 (d, 1H), 5.41-5.39 (m, 1H), 4.51-4.39 (m, 3H), 4.15 (dd, 1H).

Example 142

(S)-2-(tert-Butyl-dimethyl-silanyloxymethyl)-2,3-dihydro-oxazolo[3,2-a]pyrimidin-7-one

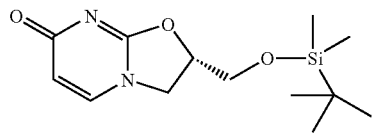 [SMILES: CC(C)(C)[Si](C)(C)OC[C@@H]1Cn2ccc(=O)nc2O1]

Step 1: (S)-5-(tert-Butyl-dimethyl-silanyloxymethyl)-4,5-dihydro-oxazol-2-ylamine To a gently stirred solution of sodium hydrogen cyanamide (3.1 g, 48.4 mmol) in methanol (70 mL) was added dropwise (2S)-tert-butyl-dimethyl-oxiranylmethoxy-silane (8.9 g, 47.3 mmol) in methanol. The reaction mixture was stirred at room temperature overnight after which the reaction mixture was concentrated to remove methanol. Diethyl ether was added (150 mL) along with 50 ml of water. The contents were transferred to a separatory funnel, the organic layer was removed, dried over $Na_2SO_4$ and concentrated under vacuum to give 7.62 g (70%) of (S)-5-(tert-butyl-dimethyl-silanyloxymethyl)-4,5-dihydro-oxazol-2-ylamine.

$C_{10}H_{22}N_2O_2Si$ (230.39), LCMS (ESI): N/A ($M^+$+H). $^1H$ NMR ($CDCl_3$, 300 MHz): δ 4.5 (m, 1H), 3.55-3.71 (m, 3H), 3.34-3.44 (m, 3H), 0.82 (s, 9H), 0.00 (s, 6H).

Step 2: (S)-2-(tert-Butyl-dimethyl-silanyloxymethyl)-2,3-dihydro-oxazolo[3,2-a]pyrimidin-7-one To a solution of (S)-5-(tert-butyl-dimethyl-silanyloxymethyl)-4,5-dihydro-oxazol-2-ylamine (6.65 g, 28.9 mmol) in ethanol (150 mL) was added ethyl propiolate (2.92 mL, 28.9 mmol). The reaction mixture was stirred at reflux for 2 hours. The mixture was cooled to room temperature, concentrated under vacuum and purified by column chromatography on silica gel (0-10% methanol in dichloromethane). This afforded 2.45 g (30%) of the title compound.

$C_{13}H_{22}N_2O_3Si$ (282.42), LCMS (ESI): 283.20 ($M^+$+H).
$^1H$ NMR ($CDCl_3$, 300 MHz): δ 7.10-7.13 (d, 1H), 5.94-5.97 (d, 1H), 4.92-4.93 (m, 1H), 4.09-4.15 (m, 2H), 3.93 (dd, 1H), 3.72 (dd, 1H), 0.74 (s, 9H), 0.00 (s, 3H), −0.03 (s 3H).

Example 143

(S)-2-Benzyloxymethyl-2,3-dihydro-oxazolo[3,2-a]pyrimidin-7-one

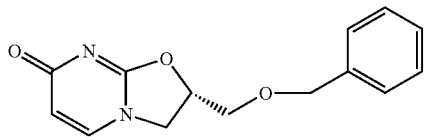 [SMILES: O=c1ccn2c(n1)O[C@H](COCc1ccccc1)C2]

Step 1: (S)-5-(benzyloxymethyl)-(4,5-dihydro-oxazol-2-yl)amine

To a vigorously stirred solution of sodium hydrogen cyanamide (1.95 g, 30.4 mmol) in methanol (30.5 mL) was added dropwise (S)-2-benzyloxymethyl-oxirane (5 g, 30.4 mmol) in methanol. The reaction mixture was stirred at room temperature overnight after which the reaction mixture was concentrated to remove methanol. Ethyl acetate was added (150 mL) along with 50 ml of water. The contents were transferred to a separatory funnel, the organic layer was removed, dried over $Na_2SO_4$ and concentrated under vacuum to give 6.01 g (96%) of the title compound.

$^1H$ NMR ($CDCl_3$, 300 MHz), δ 7.41-7.35 (m, 5H), 4.55 (s, 2H), 4.82-4.72 (m, 1H), 4.17-3.90 (m, 1H), 3.82 (dd, 1H), 3.61-3.40 (m, 2H).

Step 2: (S)-2-Benzyloxymethyl-2,3-dihydro-oxazolo[3,2-a]pyrimidin-7-one

To a solution of (S)-5-(benzyloxymethyl)-(4,5-dihydro-oxazol-2-yl)amine (6.02 g, 29.4 mmol) in ethanol (210 mL) was added ethyl propiolate (2.97 mL, 29.4 mmol). The reaction mixture was stirred at reflux for 2.5 hours. The mixture was cooled to room temperature, concentrated under vacuum and purified by column chromatography on silica gel (4:1 ethyl acetate:heptanes to 10% methanol in dichloromethane) to provide 2.09 g (28%) of the title compound. $[\alpha]_D^{25}$ −30.09 (c 0.545, $CHCl_3$).

$C_{14}H_{14}N_2O_3$ (258.10), LCMS (ESI): 259.10 ($M^+$+H).
$^1H$ NMR (DMSO-$d_6$, 300 MHz) δ 7.73 (d, 1H), 7.38-7.24 (m, 5H), 5.79 (d, 1H), 5.20-5.12 (m, 1H), 4.55 (s, 2H), 4.28 (t, 1H), 4.02 (d, 1H), 3.81-3.68 (m, 2H).

Example 144

(S)-2-(4-Cyclohexyl-phenoxymethyl)-5-ethoxy-2,3-dihydro-oxazolo[3,2-a]pyrimidin-7-one

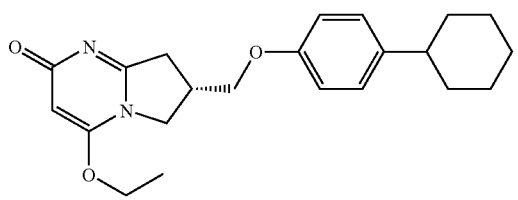 [SMILES: CCOc1cc(=O)nc2n1C[C@@H](COc1ccc(C3CCCCC3)cc1)C2]

To a solution of (S)-5-(4-cyclohexyl-phenoxymethyl)-4,5-dihydro-oxazol-2-yl-amine (0.98 g, 3.58 mmol) (prepared in accordance with the procedures described in Steps 1 and 2 of Example 1 starting from R-epichlorohydrin and 4-cyclohexylphenol) in 50 ml of ethanol was added freshly prepared 3-ethoxy-propynoic acid ethyl ester (0.65 g, 4.58 mmol), prepared from 6 ml of 50% ethoxyacetylene and 3.3 ml of ethyl chloroformate (*Synthesis*, 1989, 123-4). The mixture was stirred for 15 min at room temperature after which it was stirred at 60-65 degrees C. for 6h. The reaction mixture was concentrated to a yellow solid, dissolved in dichloromethane and flash chromatographed on silica gel eluting with dichloromethane/ammonia/methanol to provide 0.544 g of the title compound as a white solid. $[\alpha]_D^{25}$ −1.00 (c 0.5, $CHCl_3$).

$C_{21}H_{26}N_2O_4$ (370.19), LCMS (ESI): 371.19 ($M^+$+H).
$^1H$ NMR ($CDCl_3$, 300 MHz), δ 7.13 (d, 2H), 6.82 (d, 2H), 5.31 (s, 1H), 5.16-5.28 (m, 1H), 4.09-4.34(m, 6H), 2.36-2.55 (br s, 1H), 1.54-1.91 (m, 5H), 1.13-1.51 (m, 8H).

Example 145

2-[2-(4-Cyclohexyl-phenyl)-ethyl]-2,3-dihydro-oxazolo[3,2-a]pyrimidin-7-one

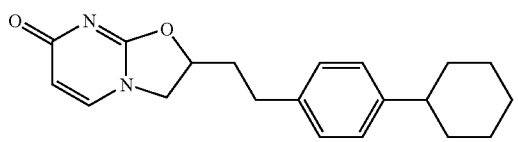 [SMILES: O=c1ccn2c(n1)OC(CCc1ccc(C3CCCCC3)cc1)C2]

Step1: Diphenyl-phosphinic acid 4-cyclohexyl-benzyl ester

To a stirred solution of 4-cyclohexylbenzyl alcohol (1 g, 5.26 mmol) in 45 ml of dry dichloromethane, 5 ml of triethylamine and 41 mg of dimethylaminopyridine was added 1.05 ml (1.25 g) of diphenylphosphinic chloride. The mixture was stirred at room temperature for 3 h after which it was concentrated to approximately 10 ml. The mixture was diluted with dichloromethane, washed with cold 10% sodium bicarbonate, water, dried (sodium sulfate), filtered and concentrated to approximately 10 ml. The resulting solution was chromatographed on silica gel, eluting with ethyl acetate/heptane to provide 1.92 g of the title compound.

$C_{25}H_{27}O_2P$ (390.17), LCMS (ESI): 391.15 (M$^+$+H).

$^1$H NMR (CDCl$_3$, 300 MHz), δ 7.75-7.91 (m, 4H), 7.36-7.57 (m, 6H), 7.29 (d, 2), 7.18 (d, 2), 5.02 (d, 2), 2.49 (br s, 1H), 1.70-1.96 (m, 5H), 1.15-1.50 (m, 5H).

Step2: 1-But-3-enyl-4-cyclohexyl-benzene

To a stirred mixture of diphenyl-phosphinic acid 4-cyclohexyl-benzyl ester (1 g, 2.56 mmol) and 1.22 ml (7.69 mmol) of allyltrimethylsilane in 12 ml of dry dimethoxy-ethane at 0° C. was added 0.46 ml of trimethylsilyltriflate. The mixture was stirred at 0° C. for 1 h, poured into saturated bicarbonate, extracted with ethyl acetate, washed with water, dried (sodium sulfate) filtered and concentrated. The material was purified by chromatography on silica gel, eluting with ethyl acetate/heptane to provide 0.45 g of the title compound.

$^1$H NMR (CDCl$_3$, 300 MHz), δ 7.12 (s, 4H), 5.80-5.96 (m, 1H), 5.02, 5.09 (dd, 1H), 4.93, 4.99 (dd, 1H), 2.64-2.72 (m, 2H), 2.48 (br s, 1H), 2.33-2.42 (q, 2H), 1.70-1.94 (m, 5H), 1.17-1.52 (m, 5H).

Step3 : 2-[2-(4-Cyclohexyl-phenyl)-ethyl]-2,3-dihydro-oxazolo[3,2-a]pyrimidin-7-one To 0.303 g (1.32 mmol) of 2-(4-cyclohexyl-benzyl)-oxirane (prepared from 0.45 g of 1-but-3-enyl-4-cyclohexyl-benzene and 0.97 g of 3-chloroperbenzoic acid) in 1 ml of methanol was added a solution of 85 mg of NaNHCN in 1.5 ml of methanol. The mixture was stirred at room temperature for 20h, after which it was concentrated to a suspension which was triturated with ether, filtered and the filtrate concentrated and purified on silica gel eluting with ethyl acetate/ammonia/methanol to provide 0.134 g (0.423 mmol) of 5-[2-(4-cyclohexyl-phenyl)-ethyl]-4,5-dihydro-oxazol-2-ylamine.

To a stirred solution of 5-[2-(4-cyclohexyl-phenyl)-ethyl]-4,5-dihydro-oxazol-2-ylamine (0.134 g, 0.493 mmol) in 5 ml of ethanol was added 50 μL (0.494 mmol) of ethyl propiolate. The mixture was stirred at 80° C. for 6h and allowed to cool to room temperature. The mixture was concentrated to a solid which was purified by chromatography on silica gel eluting with ethyl acetate followed by methanol/ammonia/dichloromethane to provide 70 mg of the title compound.

$C_{20}H_{24}N_2O_2$ (324.18), LCMS (ESI): 325.19 (M$^+$+H).

$^1$H NMR (CDCl$_3$, 300 MHz), δ 7.14 (m, 5H), 6.06 (d, 1H), 4.91 (m, 1H), 4.18 (t, 1H), 3.74 (t, 1H), 2.73-2.95 (m, 2H), 2.49 (br s, 1H), 2.21-2.34 (m, 1H), 2.01-2.15 (m, 1H), 1.70-1.97 (m, 5H), 1.13-1.52 (m, 5H).

Example 146

2-[(4-Cyclohexyl-phenylamino)-methyl]-2,3-dihydro-oxazolo[3,2-a]pyrimidin-7-one

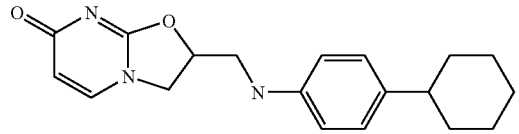 [SMILES: O=c1ccn2c(n1)OC(CNc1ccc(C3CCCCC3)cc1)C2]

Step 1: (4-Cyclohexyl-phenyl)-oxiranylmethyl-amine

To a stirred solution of 4-cyclohexylaniline (5 g, 28.6 mmol) in 75 ml of dry THF at −70 to −75° C. was added slowly by syringe a solution of 17.7 ml of 1.6 M n-butyllithium. When addition was complete, the resulting mixture was stirred at −70 to −75° C. for 0.5 h. To the stirred mixture was then added 3.61 ml (28.5 mmol) of chlorotrimethylsilane at −70 to −75° C. The mixture was then allowed to warm to RT and stirred at RT for 1.75 h. The mixture was then again cooled to −70 to −75° C. after which was slowly added 17.5 ml of 1.6 M n-butyllithium in hexanes. The mixture was allowed to stir at −70 to −75° C. for 0.5 h after which was added 2.45 ml (28.6 mmol) of epibromohydrin. The mixture was allowed to warm to room temperature and stirred for 2 h at room temperature. The mixture was then poured into 250 ml of cold saturated aqueous sodium bicarbonate, extracted with ethyl acetate, washed with brine, dried (sodium sulfate) and concentrated to provide an orange oil which was then purified by chromatography on silica gel, eluting with ethyl acetate/heptane to provide 3.06 g of the title compound.

$^1$H NMR (CDCl$_3$, 300 MHz), δ 7.04 (d, 2H), 6.60 (d, 2H), 3.76 (br s, 1H), 3.44-3.56 (m, 1H), 3.14-3.27 (m, 2H), 2.80 (m, 1H), 2.68s (m, 1H), 2.37 (br s, 1H), 1.66-1.96 (m, 5H), 1.09-1.66 (m, 5H).

Step 2: 2-[(4-Cyclohexyl-phenylamino)-methyl]-2,3-dihydro-oxazolo[3,2-a]pyrimidin-7-one To (4-cyclohexyl-phenyl)-oxiranylmethyl-amine (3.06 g, 13.2 mmol) and 0.881 g (13.7 mmol) of NaNHCN was added 20 ml of methanol. The mixture was stirred under nitrogen for 15 h after which it was concentrated. The material was triturated with ether, filtered and again concentrated. The resulting material was purified by flash chromatography on silica gel eluting with 0-50% ethyl acetate/methanol/ammonia-dichloromethane to provide 1.13 g of 5-[(4-cyclohexyl-phenylamino)-methyl]-4,5-dihydro-oxazol-2-ylamine.

To a solution of 5-[(4-cyclohexyl-phenylamino)-methyl]-4,5-dihydro-oxazol-2-ylamine (1.13 g, 4.14 mmol) in 50 ml of ethanol was added 0.42 ml (0.415 mmol) of ethyl propiolate. The mixture was stirred at reflux for 6 h under nitrogen after which it was allowed to cool to room temperature. The resulting white crystals were isolated by filtration, washed with ethanol, and dried at room temperature under high vacuum to provide 0.294 g of the title compound. The filtrate from the filtration was concentrated to 10 ml and allowed to stand for 6 h. The resulting white crystals were isolated by filtration and dried under high vacuum to provide an additional 0.059 g of the title compound.

$C_{19}H_{23}N_3O_2$ (325.41), LCMS (ESI): 326.22 (M$^+$+H).

¹H NMR (DMSO-d₆, 300 MHz), δ 7.71 (d, 1), 6.94 (d, 2), 6.60 (d, 2H), 5.69-5.86 (m, 2H), 5.04-5.18 (m, 1H), 4.31 (t, 1H), 3.96 (t, 1H), 3.35-3.52 (m, 2H), 2.32 (br s, 1H), 1.60-1.87 (m, 5H), 1.07-1.43 (m, 5H).

Biological Examples

Example 147

A calcium ion ($Ca^{2+}$) mobilization assay was used to identify and determine the activity for allosteric modulators of the rat or human mGluR2 receptor. Two formats were used: (1) examine the ability of glutamate to affect the potency of the modulator, by looking at a concentration-response curve of compound at different submaximal glutamate concentrations, and (2) look at the ability of the modulator to affect the potency of glutamate by looking at a concentration-response curve of glutamate at a maximal modulator concentration.

To monitor functional receptor response using calcium mobilization, a cell line stably expressing the rat or human mGluR2 receptor (normally coupled to its intracellular effector molecules through an inhibitory G-protein, Gαi) and Gα₁₆, in a tetracycline-inducible vector was created. Gα16 can promiscuously couple Gs and Gi-coupled receptors to the inositol phospholipid signaling pathway by activating phospholipase Cβ resulting in a $Ca^{2+}$ signal (normally Gαq-mediated), that can be monitored with fluorescence plate readers such as FLIPR (Molecular Devices, Fluorescence Imaging Plate Reader), FDSS6000 (Hamamatsu, Fluorescence Drug Screening System), or FlexStation (Molecular Devices). The $Ca^{2+}$ mobilization assay was based on the detection of intracellular calcium changes using a selective, calcium-chelating dye: Fluo-3, Fluo-4, or Calcium-3. A large fluorescence intensity increase was observed upon calcium association with the dye. The dye was delivered either with the acetoxymethyl ester, and washed off, or using a no-wash kit (Molecular Devices). Fluorescence signals stimulated by glutamate were recorded and used to generate the following pharmacological parameters: (1) the potency (EC50) of the compound(s) of interest at approx. EC10 for glutamate at the rat and human mGluR2 receptors respectively, and (2) a foldshift of the glutamate EC50 by maximal concentration of compound(s) of interest.

The compounds of formula (I) of this invention tested in accordance with this procedure exhibited the potency (EC50) in the range of from about 3 micromolar (μM) to about 0.5 nanomolar (nM).

The efficacy of the compounds of formula (I) of this invention in treating a variety of diseases as disclosed herein can be confirmed by any of the methods known to one skilled in the art. For instance, the efficacy in treating anxiety can be confirmed by using Vogel conflict test. See, for example, Tatarczynska et al., Psychopharmacology (Berl). 2001 October; 158(1):94-9 incorporated herein by reference in its entirety. Specifically, Tatarczynska et al. discloses the antianxiety-like effects of antagonists of group I and agonists of group II and III metabotropic glutamate receptors.

The preclinical anxiety and psychosis models also include stress induced hyperthermia, fear potentiated startle and PCP-induced hyperlocomotion. See Rorick-Kehn et al., J. Pharmacol. Exp. Ther. 2006 February; 316(2):905-13. Epub 2005 Oct. 13. Also see, Johnson et al., Psychopharmacology (Berl). 2005 April; 179(1):271-83. Epub 2005 Feb. 17. Fear-potentiated startle and elevated plus maze models have been used by Helton et al., J Pharmacol Exp Ther. 1998 February; 284(2):651-660 in order to demonstrate the anxiolytic and side-effect profile of LY354740: a potent, highly selective, orally active agonist for group II metabotropic glutamate receptors.

Various anxiety models to show efficacy in humans are also known in the art. See Kellner et al., Psychopharmacology (Berl). 2005 April; 179(1):310-5. Epub 2004 Sep. 30, where the effects of a metabotropic glutamate(2/3) receptor agonist on panic anxiety induced by cholecystokinin tetrapeptide in healthy humans has been reported.

In addition, the efficacy of the compounds of formula (I) of this invention in treating schizophrenia may also be ascertained by various known models in the art. For instance, PCP-induced hyperlocomotion, PCP-disrupted prepulse inhibition, stress-induced hyperthermia, and elevated plus maze models have been used to demonstrate the efficacy of allosteric modulators of mGluR2. See, Galici et al., J Pharmacol Exp Ther. 2006 July; 318(1):173-85. Epub 2006 Apr. 11, where it is shown that biphenyl-indanone A, a positive allosteric modulator of the mGluR2, has antipsychotic- and anxiolytic-like effects in mice.

The efficacy of the compounds of formula (I) of this invention in improving the working memory in humans can be ascertained by a variety of methods known in the art. For instance, Krystal et al., Psychopharmacology (Berl). 2005 April; 179(1):303-9. Epub 2004 Aug. 10, reported that the attenuation of the disruptive effects of the NMDA glutamate receptor antagonist, ketamine, on working memory by pretreatment with the group II metabotropic glutamate receptor agonist, LY354740, in healthy human subjects. In another example, Patil et al., Nature Medicine. 2007 September; 13(9):1102-7. Epub 2007 Sep. 2. reported that the group II metabotropic glutamate receptor agonist, LY2140023, showed statistically significant improvements in both positive and negative symptoms of schizophrenia compared to placebo.

The compounds of formula (I) of this invention are also useful in treating sleep disorders and depression. Feinberg et al., Pharmacol Biochem Behav. 2002, 73(2) 467-74, have reported that the selective group mGluR2/3 receptor agonist, LY379268, suppresses rapid eye movement (REM) sleep and fast EEG in the rat. Gewirtz et al., Pharmacol Biochem Behav. 2002 September; 73(2):317-26, have examined the effects of mGluR2/3 agonists on BDNF mRNA expression in medial prefrontal cortex induced by the hallucinogen and $5HT_{2A/2B/2C}$ agonist. Also, see Schechter et al., NeuroRx. 2005 October; 2(4):590-611. Review, where innovative approaches for the development of antidepressant drugs are reviewed.

The activity of allosteric modulators of mGluR2 in pain models has also been reported in the literature. See, Jones et al., Neuropharmacology. 2005; 49 Suppl 1:206-18, where analgesic effects of the selective group II (mGlu2/3) metabotropic glutamate receptor agonists are disclosed.

The efficacy of compounds of formula (I) of this invention in treating epilepsy can also be ascertained by various methods used in the art. For example, see, Alexander et al., Epilepsy Res. 2006, 71(1), 1-22, where metabotropic glutamate receptors as a strategic target for the treatment of epilepsy is discussed. Also see, Klodzinska et al., Pol J Pharmacol. 1999, 51(6), 543-5, which discloses selective group II glutamate metabotropic receptor agonist LY354740 attenuates pentylenetetrazole- and picrotoxin-induced seizures. Roles of metabotropic glutamate receptor subtypes in modulation of pentylenetetrazole-induced seizure activity in mice is disclosed by Thomsen et al., Neuropharmacology. 1998, 37(12), 1465-73. Finally, Thomsen et al., J Neurochem. 1994, 62(6), 2492-5, disclose that (S)-4-carboxy-3-hydroxyphenylglycine, an antagonist of metabotropic glutamate receptor Example 148

Stress Induced Hyperthermia (Anxiety Model)

Stress-induced hyperthermia (SIH) reflects the elevation in core body temperature experienced by mammals following a stressful experience. Clinically active anxiolytics prevent SIH, indicating that this model may be useful in identifying novel anxiolytic agents (See, Olivier et al. Eur J Pharmacol. 2003, 463, 117-32). SIH was measured in mice using the rectal test procedure adaptation of the classic SIH paradigm described by Borsini et al, Psychopharmacology (Berl). 1989, 98(2), 207-11. Individually housed mice were subjected to two sequential rectal temperature measurements, separated by a 10-minute interval. The first measurement captured the animal's basal core body temperature (T1), while the second temperature (T2) captured body temperature following the mild stress imposed by the first temperature measurement. The difference between the first and second temperature (T2-T1 or $\Delta$T) is the SIH. Temperature measurements were made to the nearest 0.1° C. with a lubricated thermistor probe inserted 2 cm into the rectum of each subject. Test compounds were administered 60 minutes before the first temperature measurement to allow for any stress effect created by the injection to dissipate completely.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of the formula I:

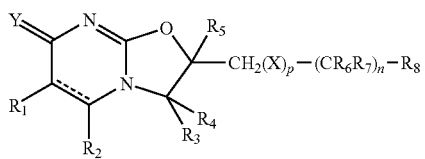

(I)

wherein:
----- is a single or a double bond;
p is 0 or 1;
n is an integer from 0 to 3;
X is oxygen or sulfur;
Y is oxygen or sulfur;
$R_1$ and $R_2$ are the same or different and independently of each other selected from the group consisting of hydrogen, $CF_3$, straight or branched chain $(C_1-C_{10})$alkyl, mono- or di-fluoro$(C_1-C_4)$alkyl, mono- or di-fluoro$(C_1-C_4)$alkoxy$(C_0-C_4)$alkyl, mono- or di-fluoro$(C_1-C_4)$alkylsulfanyl$(C_0-C_4)$alkyl, mono- or di-fluoro$(C_1-C_4)$alkylsulfinyl$(C_0-C_4)$alkyl, mono- or di-fluoro$(C_1-C_4)$alkylsulfonyl$(C_0-C_4)$alkyl, $(C_1-C_{10})$alkoxy$(C_0-C_4)$alkyl, $(C_1-C_{10})$alkylsulfanyl$(C_0-C_4)$alkyl, $(C_1-C_{10})$alkylsulfinyl$(C_0-C_4)$alkyl, $(C_1-C_{10})$alkylsulfonyl$(C_0-C_4)$alkyl, $(C_1-C_{10})$alkoxy mono- or di-fluoro$(C_1-C_4)$alkyl, $(C_1-C_{10})$alkylsulfanyl mono- or di-fluoro$(C_1-C_4)$alkyl, $(C_1-C_{10})$alkylsulfinyl mono- or di-fluoro$(C_1-C_4)$alkyl, $(C_1-C_{10})$alkylsulfonyl mono- or di-fluoro$(C_1-C_4)$alkyl, $(C_6,C_{10})$aryl$(C_0-C_4)$alkyl, $(C_6,C_{10})$aryl mono- or difluoro$(C_2-C_4)$alkyloxy, $(C_6,C_{10})$aryloxy$(C_0-C_4)$alkyl, $(C_6,C_{10})$arylsulfanyl$(C_0-C_4$alkyl), $(C_6,C_{10})$arylsulfinyl$(C_0-C_4)$alkyl, $(C_6,C_{10})$arylsulfonyl$(C_0-C_4)$alkyl), $(C_3-C_8)$cycloalkyl$(C_0-C_4)$alkyl, mono- or difluoro$(C_3-C_8)$cycloalkyl$(C_0-C_4)$alkyl, $C_3-C_8)$cycloalkoxy$(C_0-C_4)$alkyl, mono- or difluoro$(C_3-C_8)$cycloalkyloxy$(C_0-C_4)$alkyl, $(C_3-C_8)$cycloalkyl mono- or difluoro$(C_1-C_4)$alkyl, $(C_3-C_8)$cycloalkyl mono- or difluoro $(C_2-C_4)$alkyloxy, $(C_3-C_8)$cycloalkylsulfanyl$(C_0-C_4)$alkyl, $(C_3-C_8)$cycloalkylsulfinyl$(C_0-C_4)$alkyl, $(C_3-C_8)$cycloalkylsulfonyl$(C_0-C_4)$alkyl, hydroxy$(C_1-C_4)$alkyl, heteroaryl$(C_0-C_4)$alkyl, heteroaryl mono- or difluoro$(C_1-C_4)$alkyl, heteroaryloxy$(C_0-C_4)$alkyl, heteroaryloxy mono- or difluoro$(C_2-C_4)$alkyl, heteroarylsulfanyl$(C_0-C_4)$alkyl, heteroarylsulfinyl$(C_0-C_4)$alkyl, heteroarylsulfonyl$(C_0-C_4)$alkyl, saturated heterocyclic$(C_0-C_4)$alkyl, saturated heterocyclic mono- or di-fluoro$(C_1-C_4)$alkyl, saturated heterocyclyloxy$(C_0-C_4)$alkyl, saturated heterocyclyloxy mono- or di-fluoro$(C_2-C_4)$alkyl, saturated heterocyclylsulfanyl$(C_0-C_4)$alkyl, heterocyclylsulfinyl$(C_0-C_4)$alkyl, heterocyclylsulfonyl$(C_0-C_4)$alkyl, —$CO_2R_{22}$ or —$CONR_{23}R_{24}$ wherein $R_{22}$, $R_{23}$ and $R_{24}$ are the same or different and independently of each other selected from hydrogen or $(C_1-C_4)$alkyl; and wherein $R_1$ and $R_2$ are optionally further substituted;
$R_3$ and $R_4$ are the same or different and independently of each other selected from the group consisting of hydrogen, $(C_1-C_4)$alkyl, $(C_3-C_8)$cycloalkyl and $(C_6,C_{10})$aryl$(C_1-C_4)$alkyl; or
$R_3$ and $R_4$ taken together with the carbon atom to which they are attached form a substituted or unsubstituted $C_5-C_7$ carbocyclic ring;
$R_5$, $R_6$ and $R_7$ are the same or different and independently of each other selected from the group consisting of hydrogen, $(C_1-C_4)$alkyl and $(C_3-C_8)$cycloalkyl;
$R_8$ is selected from the group consisting of substituted phenyl, substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted $(C_3-C_8)$cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, substituted or unsubstituted tetrahydrodibenzofuranyl and substituted or unsubstituted hexahydrodibenzofuranyl;
wherein substituted refers to subsrtituents are selected from the group consisting of $CF_3$, $OCF_3$, halogen, CN, $SF_5$, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6-C_{16})$spirocycloalkyl, substituted or unsubstituted $(C_6,C_{10})$aryl$(CR_9R_{10})_m$, substituted or unsubstituted heteroaryl$(CR_9R_{10})_m$, substituted or unsubstituted $(C_6,C_{10})$aryl $C_3-C_8$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain ($C_1$-$C_{20}$)alkoxy, substituted or unsubstituted ($C_3$-$C_{10}$)cycloalkoxy, substituted or unsubstituted ($C_6$,$C_{10}$)aryloxy, substituted or unsubstituted heteroaryloxy, substituted or unsubstituted piperidinyl$(CR_9R_{10})_m$, substituted or unsubstituted piperazinyl$(CR_9R_{10})_m$, substituted or unsubstituted ($C_4$-$C_7$) lactam, substituted or unsubstituted tetrahydropyranyl$(CR_9R_{10})_m$, substituted or unsubstituted tetrahydrofuranyl$(CR_9R_{10})_m$, substituted or unsubstituted 1,3-dioxanyl, substituted or unsubstituted 1,3-dioxolanyl, ($C_1$-$C_4$)alkoxyethoxy, substituted or unsubstituted ($C_3$-$C_8$)cycloalkyloxyethoxy, substituted or unsubstituted ($C_6$,$C_{10}$)aryloxyethoxy and substituted or unsubstituted heteroaryloxyethoxy; wherein m is an integer from 0 to 10;

$R_9$ and $R_{10}$ are the same or different and independently of each other chosen from hydrogen or ($C_1$-$C_4$)alkyl; or $R_9$ and $R_{10}$ taken together with the carbon atom to which they are attached form a substituted or unsubstituted $C_3$-$C_8$ carbocyclic ring, and wherein the substituted $C_3$-$C_8$ carbocyclic ring is substituted by the aforementioned substituents;

or a salt thereof or an enantiomer, stereoisomer or a tautomer thereof or a racemic mixture thereof; and wherein when $R^8$ is substituted phenyl, $R^2$ is not methyl, ethyl or propyl; and wherein $R^8$ is substituted pheny, the substitution is not 2-methyl on the phenyl ring of $R^8$.

2. The compound as set forth in claim 1, wherein

----- is a double bond;

p is 1;

n is 0;

X and Y are oxygen;

$R_1$ and $R_2$ are the same or different and independently of each other selected from hydrogen, $CF_3$, straight or branched ($C_1$-$C_{10}$)alkyl, mono- or di-fluoro($C_1$-$C_4$)alkyl, mono- or di-fluoro($C_1$-$C_4$)alkoxy($C_0$-$C_4$)alkyl, ($C_1$-$C_{10}$)alkoxy($C_0$-$C_4$)alkyl, ($C_6$,$C_{10}$)aryl, ($C_6$,$C_{10}$)aryl($C_1$-$C_4$)alkyl, ($C_3$-$C_8$)cycloalkyl($C_0$-$C_4$)alkyl, ($C_3$-$C_8$)cycloalkoxy($C_0$-$C_4$)alkyl, hydroxy($C_1$-$C_4$)alkyl or —$CO_2C_2H_5$;

$R_3$, $R_4$ and $R_5$ are hydrogen;

$R_8$ is selected from the group consisting of substituted or unsubstituted indanyl, substituted or unsubstituted tetralinyl, substituted or unsubstituted benzocycloheptanyl, substituted or unsubstituted hexahydrofluorenyl and substituted or unsubstituted cyclohexyl; wherein said substituents are selected from the group consisting of $CF_3$, $OCF_3$, $SF_5$, fluorine, chlorine, bromine, CN, straight or branched chain ($C_1$-$C_{20}$)alkyl, substituted or unsubstituted ($C_3$-$C_{10}$)cycloalkyl$(CR_9R_{10})_m$, substituted or unsubstituted ($C_6$,$C_{10}$)aryl$(CR_9R_{10})_m$, substituted or unsubstituted ($C_6$,$C_{10}$)aryl($C_3$-$C_8$)cycloalkyl, substituted or unsubstituted ($C_8$-$C_{13}$)bicyclic, substituted or unsubstituted adamantyl, substituted or unsubstituted indanyl, substituted or unsubstituted tetralinyl, substituted or unsubstituted benzocycloheptyl, straight or branched chain ($C_1$-$C_{20}$)alkoxy, substituted or unsubstituted ($C_3$-$C_{10}$)cycloalkoxy, substituted or unsubstituted ($C_6$,$C_{10}$)aryloxy, substituted or unsubstituted heteroaryloxy and substituted or unsubstituted tetrahydropyranyl $(CR_9R_{10})_m$; wherein m is an integer from 0 to 2;

$R_9$ and $R_{10}$ are the same or different and independently of each other chosen from hydrogen or ($C_1$-$C_4$)alkyl; or $R_9$ and $R_{10}$ taken together with the carbon atom to which they are attached form a substituted or unsubstituted $C_3$-$C_8$ carbocyclic ring; and wherein the substituted $C_3$-$C_8$ carbocyclic ring is substituted by the aforementioned substituents;

or a salt thereof or an enantiomer, stereoisomer or a tautomer thereof or a racemic mixture thereof.

3. The compound, which is selected from the group consisting of:

2-(4-isopropyl-phenoxymethyl)-2,3-dihydro-oxazolo[3,2-a]pyrimidin-7-one;

2-[4-(1,1,3,3-tetramethyl-butyl)-phenoxymethyl]-2,3-dihydro-oxazolo[3,2-a]-pyrimidin-7-one;

2-(3-tert-butyl-phenoxymethyl)-2,3-dihydro-oxazolo[3,2-a]pyrimidin-7-one;

2-(4-tert-butyl-phenoxymethyl)-2,3-dihydro-oxazolo[3,2-a]pyrimidin-7-one;

2-[4-(1,1-dimethyl-propyl)-phenoxymethyl]-2,3-dihydro-oxazolo[3,2-a]pyrimidin-7-one;

2-(3,4-dimethyl-phenoxymethyl)-2,3-dihydro-oxazolo[3,2-a]pyrimidin-7-one;

2-(4-isopropyl-3-methyl-phenoxymethyl)-2,3-dihydro-oxazolo[3,2-a]pyrimidin-7-one;

2-(4-tert-butyl-2-methyl-phenoxymethyl)-2,3-dihydro-oxazolo[3,2-a]pyrimidin-7-one;

2-(2,4-di-tert-butyl-phenoxymethyl)-2,3-dihydro-oxazolo[3,2-a]pyrimidin-7-one;

2-[4-(1-methyl-1-phenyl-ethyl)-phenoxymethyl]-2,3-dihydro-oxazolo[3,2-a]-pyrimidin-7-one;

2-[4-(1-phenyl-ethyl)-phenoxymethyl]-2,3-dihydro-oxazolo[3,2-a]pyrimidin-7-one;

2-[2-chloro-4-(1,1-dimethyl-propyl)-phenoxymethyl]-2,3-dihydro-oxazolo[3,2-a]pyrimidin-7-one;

2-(4-bromo-phenoxymethyl)-2,3-dihydro-oxazolo[3,2-a]pyrimidin-7-one;

2-(4-chloro-phenoxymethyl)-2,3-dihydro-oxazolo[3,2-a]pyrimidin-7-one;

2-(4-fluoro-phenoxymethyl)-2,3-dihydro-oxazolo[3,2-a]pyrimidin-7-one;

2-(3,4-dichloro-phenoxymethyl)-2,3-dihydro-oxazolo[3,2-a]pyrimidin-7-one;

2-(3,4-difluoro-phenoxymethyl)-2,3-dihydro-oxazolo[3,2-a]pyrimidin-7-one;

2-chloro-4-(7-oxo-2,3-dihydro-7H-oxazolo[3,2-a]pyrimidin-2-ylmethoxy)-benzonitrile;

2-(4-trifluoromethyl-phenoxymethyl)-2,3-dihydro-oxazolo[3,2-a]pyrimidin-7-one;

2-(3-trifluoromethoxy-phenoxymethyl)-2,3-dihydro-oxazolo[3,2-a]pyrimidin-7-one;

2-(4-trifluoromethoxy-phenoxymethyl)-2,3-dihydro-oxazolo[3,2-a]pyrimidin-7-one;

2-(3,4-dimethoxy-phenoxymethyl)-2,3-dihydro-oxazolo[3,2-a]pyrimidin-7-one;

2-(4-cyclopentyl-phenoxymethyl)-2,3-dihydro-oxazolo[3,2-a]pyrimidin-7-one;

2-(4-cyclohexyl-phenoxymethyl)-2,3-dihydro-oxazolo[3,2-a]pyrimidin-7-one;

2-(4-cyclohexyl-phenoxymethyl)-5-methyl-2,3-dihydro-oxazolo[3,2-a]pyrimidin-7-one;

2-(4-cyclohexyl-phenoxymethyl)-5-ethyl-2,3-dihydro-oxazolo[3,2-a]pyrimidin-7-one;

2-(4-cyclohexyl-phenoxymethyl)-5-trifluoromethyl-2,3-dihydro-oxazolo[3,2-a]pyrimidin-7-one;

2-[4-(4,4-dimethyl-cyclohexyl)-phenoxymethyl]-2,3-dihydro-oxazolo[3,2-a]pyrimidin-7-one;
2-[4-(3,3-dimethyl-cyclohexyl)-phenoxymethyl]-2,3-dihydro-oxazolo[3,2-a]pyrimidin-7-one;
2-[4-(4-tert-butyl-cyclohexyl)-phenoxymethyl)-2,3-dihydro-oxazolo[3,2-a]-pyrimidin-7-one;
2-(biphenyl-4-yloxymethyl)-2,3-dihydro-oxazolo[3,2-a] pyrimidin-7-one;
2-[4-(tetrahydro-pyran-4-yl)-phenoxymethyl]-2,3-dihydro-oxazolo[3,2-a]-pyrimidin-7-one;
2-(4-indan-1-yl-phenoxymethyl)-2,3-dihydro-oxazolo[3,2-a]pyrimidin-7-one;
2-(4-tricyclo[3.3.1.13,7]decan-2-yl-phenoxymethyl)-2,3-dihydro-oxazolo[3,2-a]-pyrimidin-7-one;
2-(4-imidazol-1-yl-phenoxymethyl)-2,3-dihydro-oxazolo [3,2-a]pyrimidin-7-one;
2-(4-(1-phenyl)-cyclohexyl)-phenoxymethyl)-2,3-dihydro-oxazolo[3,2-a]pyrimidin-7-one;
2-(4-cyclohexyl-phenoxymethyl)-2,3,5,6-tetrahydro-oxazolo[3,2-a]pyrimidin-7-one;
2-(4-tert-butyl-phenoxymethyl)-2,3,5,6-tetrahydro-oxazolo[3,2-a]pyrimidin-7-one;
(S)-2-(4-cyclohexyl-phenoxymethyl)-6-methylsulfanyl-2,3-dihydro-oxazolo[3,2-a]pyrimidin-7-one;
(S)-6-benzenesulfonyl-2-(4-cyclohexyl-phenoxymethyl)-2,3-dihydro-oxazolo[3,2-a]pyrimidin-7-one;
6-benzenesulfinyl-2-(4-cyclohexyl-phenoxymethyl)-2,3-dihydro-oxazolo[32-a]pyrimidin-7-one;
(S)-2-(4-cyclohexyl-phenoxymethyl)-6-methanesulfonyl-2,3-dihydro-oxazolo[3,2a]pyrimidin-7-one;
(S)-2-(4-cyclohexyl-phenoxymethyl)-6-methanesulfinyl-2,3-dihydro-oxazolo[3,2-a]pyrimidin-7-one;
(S)-2-(4-cyclohexyl-phenoxymethyl)-5-phenylsulfanylmethyl-2,3-dihydro-oxazolo[3,2-a]pyrimidin-7-one;
(S)-5-benzenesulfonylmethyl-2-(4-cyclohexyl-phenoxymethyl)-2,3-dihydro-oxazolo[3,2-a]pyrimidin-7-one;
2-(4-cyclohexyl-phenoxymethyl)-5-ethanesulfonylmethyl-2,3-dihydro-oxazolo[3,2-a]pyrimidin-7-one;
2-[4-(1,1-dimethyl-propyl)-phenoxymethyl]-2,3-dihydro-oxazolo[3,2-a]pyrimidin-7-one;
2-(4-isopropyl-3-methyl-phenoxymethyl)-2,3-dihydro-oxazolo[3,2-a]pyrimidin-7-one;
2-[4-(1-methyl-1-phenyl-ethyl)-phenoxymethyl]-2,3-dihydro-oxazolo[3,2-a]-pyrimidin-7-one;
2-[4-(1-phenyl-ethyl)-phenoxymethyl]-2,3-dihydro-oxazolo[3,2-a]pyrimidin-7-one;
2-(4-cyclopentyl-phenoxymethyl)-2,3-dihydro-oxazolo [3,2-a]pyrimidin-7-one;
2-(4-cyclohexyl-phenoxymethyl)-5-methyl-2,3-dihydro-oxazolo[3,2-a]pyrimidin-7-one;
2-(4-cyclohexyl-phenoxymethyl)-5-ethyl-2,3-dihydro-oxazolo[3,2-a]pyrimidin-7-one;
2-(4-cyclohexyl-phenoxymethyl)-5-trifluoromethyl-2,3-dihydro-oxazolo[3,2-a]pyrimidin-7-one;
2-[4-(4,4-dimethyl-cyclohexyl)-phenoxymethyl]-2,3-dihydro-oxazolo[3,2-a]pyrimidin-7-one;
2-[4-(4-tert-butyl-cyclohexyl)-phenoxymethyl]-2,3-dihydro-oxazolo[3,2-a]-pyrimidin-7-one;
2-(4-indan-1-yl-phenoxymethyl)-2,3-dihydro-oxazolo[3,2-a]pyrimidin-7-one;
(S)-2-(4-cyclohexyl-3,5-dimethyl-phenoxymethyl)-2,3-dihydro-oxazolo[3,2-a]pyrimidin-7-one;
2-[3-methyl-4-(3,3,5,5-tetramethyl-cyclohexyl)-phenoxymethyl]-2,3-dihydro-oxazolo[3,2-a]pyrimidin-7-one;
(S)-2-(4-cyclohexyl-phenoxymethyl)-6-isopropyl-2,3-dihydro-oxazolo[3,2-a]pyrimidin-7-one;
2-(4-cyclohexyl-phenoxymethyl)-6-(2-methoxy-ethyl)-2,3-dihydro-oxazolo[3,2-a]pyrimidin-7-one;
2-(4-cyclohexyl-phenoxymethyl)-5,6-diethyl-2,3-dihydro-oxazolo[3,2-a]pyrimidin-7-one;
2-(4-cyclohexyl-phenoxymethyl)-6-phenylsulfanyl-2,3-dihydro-oxazolo[3,2-a]pyrimidin-7-one;
(S)-2-(4-cyclohexyl-phenoxymethyl)-5-hydroxymethyl-2,3-dihydro-oxazolo[3,2-a]pyrimidin-7-one;
(S)-5-cyclohexyl-2-(4-cyclohexyl-phenoxymethyl)-2,3-dihydro-oxazolo[3,2-a]pyrimidin-7-one;
(S)-2-(4-cyclohexyl-phenoxymethyl)-5-(1-hydroxy-1-methyl-ethyl)-2,3-dihydro-oxazolo[3,2-a]pyrimidin-7-one;
(S)-2-(4-cyclohexyl-phenoxymethyl)-5-(2-hydroxy-ethyl)-2,3-dihydro-oxazolo[3,2-a]pyrimidin-7-one;
(S)-2-(4'-propyl-biphenyl-4-yloxymethyl)-2,3-dihydro-oxazolo[3,2-a]pyrimidin-7-one;
(S)-2-(2',3'-dimethyl-biphenyl-4-yloxymethyl)-2,3-dihydro-oxazolo[3,2-a]pyrimidin-7-one;
(S)-2-(4'-tert-butyl-biphenyl-4-yloxymethyl)-2,3-dihydro-oxazolo[3,2-a]pyrimidin-7-one;
(S)-2-(4'-ethoxy-biphenyl-4-yloxymethyl)-2,3-dihydro-oxazolo[3,2-a]pyrimidin-7-one;
(S)-2-(2'-chloro-biphenyl-4-yloxymethyl)-2,3-dihydro-oxazolo[3,2-a]pyrimidin-7-one;
2-(4-cyclohexyl-phenoxymethyl)-5-ethylsulfanylmethyl-2,3-dihydro-oxazolo[3,2-a]pyrimidin-7-one;
2-(4-tert-butyl-phenoxymethyl)-6-ethyl-2,3-dihydro-oxazolo[3,2-a]pyrimidin-7-one;
2-(4-bicyclo[3.3.1]non-9-yl-phenoxymethyl)-5-fluoromethyl-2,3-dihydro-oxazolo[3,2-a]pyrimidin-7-one;
2-(4-tert-butyl-phenoxymethyl)-5-methoxymethyl-2,3-dihydro-oxazolo[3,2-a]pyrimidin-7-one;
2-(4-tert-butyl-phenoxymethyl)-5-fluoromethyl-2,3-dihydro-oxazolo[3,2-a]pyrimidin-7-one;
(S)-2-(4-tert-butyl-phenoxymethyl)-5-ethyl-2,3-dihydro-oxazolo[3,2-a]pyrimidin-7-one; and
2-(4-cyclohexyl-phenoxymethyl)-2-methyl-2,3-dihydro-oxazolo[3,2-a]pyrimidin-7-one;
or a salt thereof or an enantiomer, stereoisomer or a tautomer thereof or a racemic mixture thereof.
4. The compound, which is selected from the group consisting of:
2(S)-(4-bromo-phenoxymethyl)-2,3(S)-dihydro-oxazolo [3,2-a]pyrimidin-7-one;
2(S)-[4-(1,1,3,3-tetramethyl-butyl)-phenoxymethyl]-2,3-dihydro-oxazolo[3,2-a]-pyrimidin-7-one;
2(S)-(4-tert-butyl-phenoxymethyl)-2,3-dihydro-oxazolo [3,2-a]pyrimidin-7-one;
(S)-2-[4-(4-trifluoromethyl-phenoxy)-benzyloxy]-2,3-dihydro-oxazolo[3,2a]pyrimidin-7-one;
2(S)-(4-cyclohexyl-phenoxymethyl)-2,3-dihydro-oxazolo [3,2-a]pyrimidin-7-one;
(S)-2-(4-cyclohexyl-phenoxymethyl)-5-ethyl-2,3-dihydro-oxazolo[3,2-a]pyrimidin-7-one;
(S)-2-(4-cyclohexyl-3-methyl-phenoxymethyl)-2,3-dihydro-oxazolo[3,2-a]pyrimidin-7-one;
(S)-2-[4-(3,3-dimethyl-cyclohexyl)-phenoxymethyl]-2,3-dihydro-oxazolo[3,2-a]pyrimidin-7-one;
(S)-2-[4-(4,4-difluoro-cyclohexyl)-phenoxymethyl]-2,3-dihydro-oxazolo[3,2-a]pyrimidin-7-one;
(S)-2-(4-cyclohexyloxy-phenoxymethyl)-2,3-dihydro-oxazolo[3,2-a]pyrimidin-7-one;
(S)-2-(4-phenoxy-phenoxymethyl)-2,3-dihydro-oxazolo [3,2-a]pyrimidin-7-one;

(S)-2-(4-bicyclo[3.3.1]non-9-yl-phenoxymethyl)-2,3-di-hydro-oxazolo[3,2-a]pyrimidin-7-one;
(S)-2-(4-tert-butyloxy-phenoxymethyl)-2,3-dihydro-oxazolo[3,2-a]pyrimidin-7-one;
(S)-2-(4-bicyclo[3.3.1]non-9-yl-phenoxymethyl)-5-ethyl-2,3-dihydro-oxazolo[3,2-a]pyrimidin-7-one;
(2S,6R)-2-(4-cyclohexyl-phenoxymethyl)-6-methyl-2,3,5,6-tetrahydro-oxazolo[3,2-a]pyrimidin-7-one;
(2S,6S)-2-(4-cyclohexyl-phenoxymethyl)-6-methyl-2,3,5,6-tetrahydro-oxazolo[3,2-a]pyrimidin-7-one;
(S)-2-(4-cyclohexyl-phenoxymethyl)-6-methyl-2,3-dihydro-oxazolo[3,2-a]pyrimidin-7-one;
(2S,6R)-2-(4-cyclohexyl-phenoxymethyl)-6-ethyl-2,3,5,6-tetrahydro-oxazolo[3,2-a]pyrimidin-7-one;
(2S,6S)-2-(4-cyclohexyl-phenoxymethyl)-6-ethyl-2,3,5,6-tetrahydro-oxazolo[3,2a]-pyrimidin-7-one;
(S)-2-[4-(3,3,5,5-tetramethyl-cyclohexyl)-phenoxymethyl]-2,3-dihydro-oxazolo[3,2a]-pyrimidin-7-one;
(S)-2-(4-cyclohexyl-phenoxymethyl)-5-propyl-2,3-dihydro-oxazolo[3,2-a]pyrimidin-7-one;
(S)-2-(4-cyclohexyl-phenoxymethyl)-5-phenyl-2,3-dihydro-oxazolo[3,2-a]pyrimidin-7-one;
(S)-2-[4-(4-tert-butyl-phenoxy)-phenoxymethyl]-2,3-dihydro-oxazolo[3,2-a]pyrimidin-7-one;
(S)-2-(4-cyclohexyl-phenoxymethyl)-7-oxo-2,3-dihydro-7H-oxazolo[3,2-a]pyrimidine-5-carboxylic acid ethyl ester;
(S)-2-[4-(4-cyclohexyl-phenoxy)-phenoxymethyl]-2,3-dihydro-oxazolo[3,2-a]pyrimidin-7-one;
(S)-2-(4-cyclohexyl-phenoxymethyl)-6-ethyl-2,3-dihydro-oxazolo[3,2-a]pyrimidin-7-one;
(S)-5-ethyl-2-[4-(3,3,5,5-tetramethyl-cyclohexyl)-phenoxymethyl]-2,3-dihydro-oxazolo[3,2-a]pyrimidin-7-one;
(S)-2-(4-pentafluorosulfur-benzyloxymethyl)-2,3-dihydro-oxazolo[3,2a]pyrimidin-7-one;
(S)-5-ethyl-2-[4-(3,3,5,5-tetramethyl-cyclohexyl)-phenoxymethyl]-2,3-dihydro-oxazolo[3,2-a]pyrimidin-7-one;
(S)-2-(4-cyclohexyl-3-isopropyl-phenoxymethyl)-2,3-dihydro-oxazolo[3,2-a]pyrimidin-7-one;
(S)-2-(4-cyclohexyl-3-ethyl-phenoxymethyl)-2,3-dihydro-oxazolo[3,2-a]pyrimidin-7-one;
(S)-2-(4-cyclohexyl-phenoxymethyl)-5-cyclopropyl-2,3-dihydro-oxazolo[3,2-a]pyrimidin-7-one;
(S)-5-n-butyl-2-(4-cyclohexyl-phenoxymethyl)-2,3-dihydro-oxazolo[3,2-a]pyrimidin-7-one;
(S)-2-(4-cyclohexyl-phenoxymethyl)-5-cyclopentyl-2,3-dihydro-oxazolo[3,2-a]pyrimidin-7-one;
(S)-2-(4-cyclohexyl-phenoxymethyl)-5-isobutyl-2,3-dihydro-oxazolo[3,2-a]pyrimidin-7-one;
(S)-2-(4-cyclohexyl-phenoxymethyl)-5-fluoromethyl-2,3-dihydro-oxazolo[3,2-a]pyrimidin-7-one;
(S)-2-(4-cyclohexyl-phenoxymethyl)-5-methoxymethyl-2,3-dihydro-oxazolo[3,2-a]pyrimidin-7-one;
(S)-2-(4-cyclohexyl-phenoxymethyl)-5-(1-fluoro-1-methyl-ethyl)-2,3-dihydro-oxazolo[3,2-a]pyrimidin-7-one;
(S)-5-fluoromethyl-2-[4-(3,3,5,5-tetramethyl-cyclohexyl)-phenoxymethyl]-2,3-dihydro-oxazolo[3,2-a]pyrimidin-7-one;
(S)-2-(4-bicyclo[3.3.1]non-9-yl-phenoxymethyl)-5-methoxymethyl-2,3-dihydro-oxazolo[3,2-a]pyrimidin-7-one;
(S)-2-(4-bicyclo[3.3.1]non-9-yl-phenoxymethyl)-5-methyl-2,3-dihydro-oxazolo[3,2-a]pyrimidin-7-one;
(S)-2-(4-bicyclo[3.3.1]non-9-yl-phenoxymethyl)-5-butyl-2,3-dihydro-oxazolo[3,2-a]pyrimidin-7-one;
(S)-2-(4-bicyclo[3.3.1]non-9-yl-phenoxymethyl)-5-cyclopentyl-2,3-dihydro-oxazolo[3,2-a]pyrimidin-7one;
(S)-5-methyl-2-[4-(1,1,3,3-tetramethyl-butyl)-phenoxymethyl]-2,3-dihydro-oxazolo[3,2-a]pyrimidin-7-one;
(S)-5-ethyl-2-[4-(1,1,3,3-tetramethyl-butyl)-phenoxymethyl]-2,3-dihydro-oxazolo[3,2-a]pyrimidin-7-one;
(S)-5-fluoromethyl-2-[4-(1,1,3,3-tetramethyl-butyl)-phenoxymethyl]-2,3-dihydro-oxazolo[3,2-a]pyrimidin-7-one;
(S)-5-methoxymethyl-2-[4-(1,1,3,3-tetramethyl-butyl)-phenoxymethyl]-2,3-dihydro-oxazolo[3,2-a]pyrimidin-7-one;
(S)-2-(4-cyclohexyl-phenoxymethyl)-5-ethoxymethyl-2,3-dihydro-oxazolo[3,2-a]pyrimidin-7-one;
(S)-2-[4-(4-isopropyl-phenoxy)-phenoxymethyl]-2,3-dihydro-oxazolo[3,2-a]pyrimidin-7-one;
(S)-2-(4-bicyclo[3.3.1]non-9-yl-phenoxymethyl)-5-cyclopropyl-2,3-dihydro-oxazolo[3,2-a]pyrimidin-7-one;
(S)-2-(4-bicyclo[3.3.1]non-9-yl-phenoxymethyl)-5-isobutyl-2,3-dihydro-oxazolo[3,2-a]pyrimidin-7-one; and
(S)-2-(4-cyclohexyl-phenoxymethyl)-5-ethoxy-2,3-dihydro-oxazolo[3,2-a]pyrimidin-7-one;
2[R]-(4-bromo-phenoxymethyl)-2,3[R]-dihydro-oxazolo[3,2-a]pyrimidin-7-one;
2[R]-[4-(1,1,3,3-tetramethyl-butyl)-phenoxymethyl]-2,3-dihydro-oxazolo[3,2-a]-pyrimidin-7-one;
2[R]-(4-tert-butyl-phenoxymethyl)-2,3-dihydro-oxazolo[3,2-a]pyrimidin-7-one; and
2[R]-(4-cyclohexyl-phenoxymethyl)-2,3-dihydro-oxazolo[3,2-a]pyrimidin-7-one; or a salt thereof.

5. A compound having the formula III:

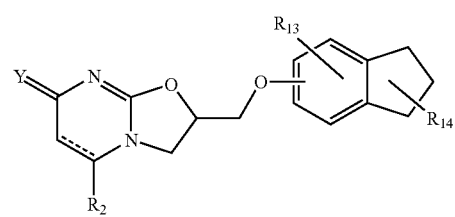

(III)

wherein:
----- is a double bond;
$R_2$ is hydrogen, $CF_3$, straight or branched $(C_1$-$C_{10})$alkyl, $(C_6,C_{10})$aryl or $(C_6,C_{10})$aryl$(C_1$-$C_4)$alkyl;
if $R_{13}$ is attached to the aromatic ring, then
$R_{13}$ is hydrogen, $CF_3$, $OCF_3$, fluorine, chlorine, bromine, $(C_1$-$C_4)$alkyl, $(C_3$-$C_6)$cycloalkyl or $(C_1$-$C_4)$alkoxy;
if $R_{13}$ and $R_{14}$ are both attached to the saturated ring, then
$R_{13}$ and $R_{14}$ are the same or different and independently of each other chosen from hydrogen, $(C_1$-$C_4)$alkyl or phenyl$(CR_9R_{10})_m$; or
$R_{13}$ and $R_{14}$ taken together with the carbon atom or carbon atoms to which they are attached form a substituted or unsubstituted $C_3$-$C_6$ carbocyclic ring; and wherein
m is an integer from 0 to 3;
$R_9$ and $R_{10}$ are the same or different and independently of each other chosen from hydrogen or $(C_1$-$C_4)$alkyl;
and wherein substituted refers to a substituent selected from the group consisting of halogen, straight or branched chain $C_1$-$C_{10}$alkyl and phenyl;

or a salt thereof or an enantiomer, stereoisomer or a tautomer thereof or a racemic mixture thereof.

6. The compound as set forth in claim 5, which is:
2-(indan-5-yloxymethyl)-2,3-dihydro-oxazolo[3,2-a]pyrimidin-7-one; or
a salt thereof or an enantiomer, stereoisomer or a tautomer thereof or a racemic mixture thereof.

7. A compound having the formula IV:

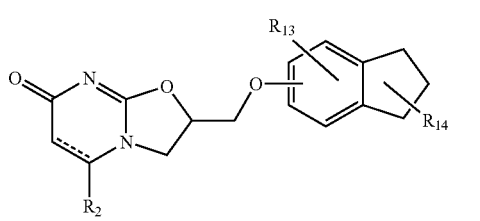
(IV)

wherein:
----- is a double bond;
$R_2$ is hydrogen, $CF_3$, straight or branched $(C_1-C_{10})$alkyl, $(C_6,C_{10})$aryl or $(C_6,C_{10})$aryl$(C_1-C_4)$alkyl;
b if $R_{13}$ is attached to the aromatic ring, then
$R_{13}$ is hydrogen, $CF_3$, $OCF_3$, fluorine, chlorine, bromine, $(C_1-C_4)$alkyl, $(C_3-C_6)$cycloalkyl or $(C_1-C_4)$alkoxy;
if $R_{13}$ and $R_{14}$ are both attached to the saturated ring, then
$R_{13}$ and $R_{14}$ are the same or different and independently of each other chosen from hydrogen, $(C_1-C_4)$alkyl or phenyl$(CR_9R_{10})_m$; or
$R_{13}$ and $R_{14}$ taken together with the carbon atom or carbon atoms to which they are attached form a substituted or unsubstituted $C_3-C_6$ carbocyclic ring; and wherein
m is 0 or 1;
$R_9$ and $R_{10}$ are the same or different and independently of each other chosen from hydrogen or $(C_1-C_4)$alkyl;
and wherein substituted refers to substituent selected from the group consisting of halogen, straight or branched chain $C_1-C_{10}$alkyl and phenyl; or
a salt thereof or an enantiomer, stereoisomer or a tautomer thereof or a racemic mixture thereof.

8. The compound as set forth in claim 7, which is:
2-(5,6,7,8-tetrahydro-naphthalen-2-yloxymethyl)-2,3-dihydro-oxazolo[3,2a]-pyrimidin-7-one; or
a salt thereof or an enantiomer, stereoisomer or a tautomer thereof or a racemic mixture thereof.

9. A compound having the formula V:

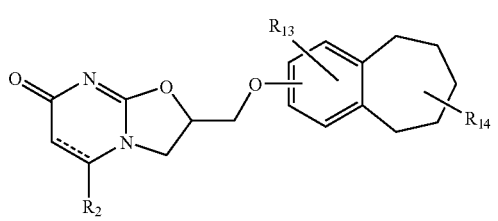
(V)

wherein:
----- is a double bond;
$R_2$ is hydrogen, $CF_3$, straight or branched $(C_1-C_{10})$alkyl, $(C_6,C_{10})$aryl or $(C_6,C_{10})$aryl$(C_1-C_4)$alkyl;
if $R_{13}$ is attached to the aromatic ring, then
$R_{13}$ is hydrogen, $CF_3$, $OCF_3$, fluorine, chlorine, bromine, $(C_1-C_4)$alkyl, $(C_3-C_6)$cycloalkyl or $(C_1-C_4)$alkoxy;
if $R_{13}$ and $R_{14}$ are both attached to the saturated ring, then
$R_{13}$ and $R_{14}$ are the same or different and independently of each other chosen from hydrogen, $(C_1-C_4)$alkyl or phenyl$(CR_9R_{10})_m$; or
$R_{13}$ and $R_{14}$ taken together with the carbon atom or carbon atoms to which they are attached form a substituted or unsubstituted $C_3-C_6$ carbocyclic ring; and wherein m is 0 or 1
$R_9$ and $R_{10}$ are the same or different and independently of each other chosen from hydrogen or $(C_1-C_4)$alkyl;
and wherein substituted refers to substituent selected from the group consisting of halogen, straight or branched chain $C_1-C_{10}$alkyl and phenyl; or
a salt thereof or an enantiomer, stereoisomer or a tautomer thereof or a racemic mixture thereof.

10. The compound as set forth in claim 1, having the formula VI:

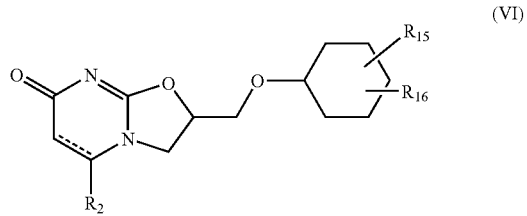
(VI)

wherein:
----- is a double bond;
$R_2$ is hydrogen, $CF_3$, straight or branched $(C_1-C_{10})$alkyl, $(C_6,C_{10})$aryl or $(C_6,C_{10})$aryl$(C_1-C_4)$alkyl;
$R_{15}$ and $R_{16}$ are the same or different and independently of each other selected from the group consisting of hydrogen, fluorine, straight or branched chain $(C_1-C_{20})$alkyl, substituted or unsubstituted $(C_3-C_{10})$cycloalkyl $(CR_9R_{10})_m$, substituted or unsubstituted $(C_6,C_{10})$aryl $(CR_9R_{10})_m$, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted piperidinyl$(CR_9R_{10})_m$, substituted or unsubstituted piperazinyl$(CR_9R_{10})_m$, substituted or unsubstituted $(C_6,C_{10})$aryloxy and substituted or unsubstituted heteroaryloxy; and wherein
m is 0 or 1;
$R_9$ and $R_{10}$ are the same or different and independently of each other chosen from hydrogen or $(C_1-C_4)$alkyl;
and wherein substituted refers to substituent selected from the group consisting of halogen, straight or branched chain $C_1-C_{10}$alkyl and phenyl; or
a salt thereof or an enantiomer, stereoisomer or a tautomer thereof or a racemic mixture thereof.

11. The compound as set forth in claim 10, which is:
2-(4-tert-butyl-cyclohexyloxymethyl)-2,3-dihydro-oxazolo[3,2-a]pyrimidin-7-one; or a salt thereof or an enantiomer, stereoisomer or a tautomer thereof or a racemic mixture thereof.

12. The compound as set forth in claim 1, having the formula VII:

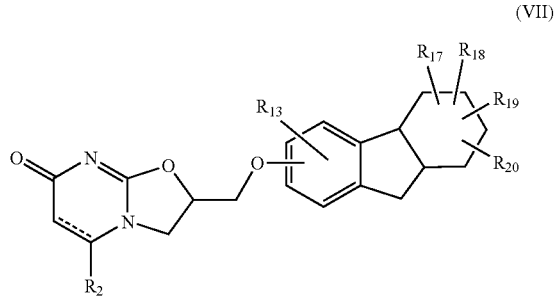
(VII)

wherein:
----- is a double bond;

$R_2$ is hydrogen, $CF_3$, straight or branched $(C_1-C_{10})$alkyl, $(C_6,C_{10})$aryl or $(C_6,C_{10})$aryl$(C_1-C_4)$alkyl;

if $R_{13}$ is attached to the aromatic ring, then $R_{13}$ is hydrogen, $CF_3$, $OCF_3$, fluorine, chlorine, bromine, $(C_1-C_4)$alkyl, $(C_3-C_6)$cycloalkyl or $(C_1-C_4)$alkoxy;

if $R_{13}$ is attached to the saturated ring, then $R_{13}$ is chosen from hydrogen, $(C_1-C_4)$alkyl or phenyl $(CR_9R_{10})_m$; and wherein m is 0 or 1;

$R_9$ and $R_{10}$ are the same or different and independently of each other chosen from hydrogen or $(C_1-C_4)$alkyl; and $R_{17}$, $R_{18}$, $R_{19}$ and $R_{20}$ are the same or different and independently selected from hydrogen or $(C_1-C_4)$alkyl; or a salt thereof or an enantiomer, stereoisomer or a tautomer thereof or a racemic mixture thereof.

13. The compound as set forth in claim 12, which is:
(S)-2-(5,6,7,8,8a,9-hexahydro-4bH-fluoren-2-yloxymethyl)-2,3-dihydro-oxazolo[3,2-a]pyrimidin-7-one; or
(S)-2-(5,6,7,8,8a,9-hexahydro-4bH-fluoren-2-phenoxymethyl)-5-ethyl-2,3-dihydro-oxazolo[3,2-a]pyrimidin-7-one;

or a salt thereof.

14. The compound as set forth in claim 1, wherein
----- is a double bond;
p is 1;
n is 0;
X and Y are oxygen;
$R_1$, $R_3$, $R_4$ and $R_5$ are hydrogen;
$R_2$ is hydrogen, $CF_3$, straight or branched $(C_1-C_{10})$alkyl, $(C_6,C_{10})$aryl or $(C_6,C_{10})$aryl$(C_1-C_4)$alkyl;
$R_8$ is selected from the group consisting of substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, substituted or unsubstituted tetrahydrodibenzofuranyl and substituted or unsubstituted hexahydrodibenzofuranyl; wherein substituted refers to substituent selected from the group consisting of $CF_3$, $OCF_3$, fluorine, chlorine, bromine, CN, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_6,C_{10})$aryloxy, substituted or unsubstituted heteroaryloxy, substituted or unsubstituted piperidinyl$(CR_9R_{10})_m$, substituted or unsubstituted piperazinyl$(CR_9R_{10})_m$ and substituted or unsubstituted tetrahydropyranyl$(CR_9R_{10})_m$; wherein m is 0 or 1;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ ring; and wherein substituted $C_3-C_8$ carbocyclic ring refers to substituent selected from the group consisting of halogen, straight or branched chain $C_1-C_{10}$alkyl and phenyl;

or a salt thereof or an enantiomer, stereoisomer or a tautomer thereof or a racemic mixture thereof.

15. The compound as set forth in claim 14, which is selected from the group consisting of:
2-(1H-indol-5-yloxymethyl)-2,3-dihydro-oxazolo[3,2-a]pyrimidin-7-one;
(S)-2-(6-cyclohexyl-pyridin-3-yloxymethyl)-2,3-dihydro-oxazolo[3,2-a]pyrimidin-7-one;
(S)-2-(benzothiazol-2-yloxymethyl)-2,3-dihydro-oxazolo[3,2a]pyrimidin-7-one; (S)-2-(6-tert-butyl-benzothiazol-2-yloxymethyl)-2,3-dihydro-oxazolo[3,2-a]pyrimidin-7-one;
(S)-2-(2,5-diphenyl-thiazol-4-yloxymethyl)-2,3-dihydro-oxazolo[3,2-a]pyrimidin-7-one;
2-(5a,6,7,8,9,9a-hexahydro-dibenzofuran-3-yl-oxymethyl)-2,3-dihydro-oxazolo[3,2-a]pyrimidin-7-one;
2-(6,7,8,9-tetrahydro-dibenzofuran-3-yl-oxymethyl)-2,3-dihydro-oxazolo[3,2-a]pyrimidin-7-one;
(S)-2-(benzo[b]thiophen-6-yloxymethyl)-2,3-dihydro-oxazolo[3,2-a]pyrimidin-7-one;
2-(2-p-tolyl-benzo[b]thiophen-6-yloxymethyl)-2,3-dihydro-oxazolo[3,2-a]pyrimidin-7-one;
2-[2-(4-ethyl-phenyl)-benzo[b]thiophen-6-yloxymethyl]-2,3-dihydro-oxazolo[3,2-a]pyrimidin-7-one;
2-[2-(4-isopropyl-phenyl)-benzo[b]thiophen-6-yloxymethyl]-2,3-dihydro-oxazolo[3,2-a]pyrimidin-7-one;
2-[2-(4-propyl-phenyl)-benzo[b]thiophen-6-yloxymethyl]-2,3-dihydro-oxazolo[3,2-a]-pyrimidin-7-one;
2-[2-(4-tert-butyl-phenyl)-benzo[b]thiophen-6-yloxymethyl]-2,3-dihydro-oxazolo[3,2-a]pyrimidin-7-one;
2-[2-(2-chloro-pyridin-4-yl)-benzo[b]thiophen-6-yloxymethyl]-2,3-dihydro-oxazolo[3,2-a]pyrimidin-7-one;

or a salt thereof or an enantiomer, stereoisomer or a tautomer thereof or a racemic mixture thereof.

16. A compound of the formula

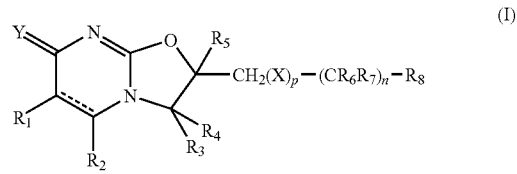

(I)

wherein ----- is a double bond;
p is 0 or 1;
n is 0 or 1;
Y is oxygen or
X is oxygen or $NR_{21}$, wherein $R_{21}$ is hydrogen;
$R_1$, $R_3$, $R_4$, $R_5$, $R_6$ and $R_7$ are hydrogen;
$R_2$ is hydrogen, $CF_3$, straight or branched $(C_1-C_{10})$alkyl, $(C_6,C_{10})$aryl or $(C_6,C_{10})$aryl$(C_1-C_4)$alkyl;
$R_8$ is selected from the group consisting of substituted phenyl, substituted or unsubstituted indanyl, substituted or unsubstituted tetralinyl, substituted or unsubstituted benzocycloheptanyl, substituted or unsubstituted hexahydrofluorenyl and substituted or unsubstituted cyclohexyl; wherein said substituents are selected from the group consisting of $CF_3$, $OCF_3$, fluorine, chlorine, bromine, CN, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$ and substituted or unsubstituted tetrahydropyranyl$(CR_9R_{10})_m$; wherein m is an integer from 0 to 3;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ carbocyclic ring; and wherein substituted $C_3-C_8$ carbocyclic refers to substituent selected from the group consisting of halogen, straight or branched chain $C_1-C_{10}$alkyl and phenyl;

or a salt thereof or an enantiomer, stereoisomer or a tautomer thereof wherein when $R^8$ is substituted phenyl, $R^2$ is not methyl, ethyl, or propyl; and wherein $R^8$ is substituted phenyl, the substitution is not 2-methyl on the phenyl ring of $R^8$.

17. The compound, which is selected from the group consisting of:
2-benzyloxymethyl-2,3-dihydro-oxazolo[3,2-a]pyrimidin-7-one;
3-(4-tert-butyl-benzyloxymethyl)-2,3-dihydro-oxazolo[3,2-a]pyrimidin-7-one;
(S)-2-benzyloxymethyl-2,3-dihydro-oxazolo[3,2-a]pyrimidin-7-one;
2-[2-(4-cyclohexyl-phenyl)-ethyl]-2,3-dihydro-oxazolo[3,2-a]pyrimidin-7-one; and
2-[(4-cyclohexyl-phenylamino)-methyl]-2,3-dihydro-oxazolo[3,2-a]pyrimidin-7-one;
or a salt thereof or an enantiomer, stereoisomer or a tautomer thereof or a racemic mixture thereof.

18. The compound as set forth in claim 1, wherein
----- is a double bond;
p is 1;
n is 0;
X is sulfur;
Y is oxygen;
$R_1$, $R_3$, $R_4$ and $R_5$ are hydrogen;
$R_2$ is hydrogen, $CF_3$, straight or branched $(C_1-C_{10})$alkyl, $(C_6,C_{10})$aryl or $(C_6,C_{10})$aryl$(C_1-C_4)$alkyl;
$R_8$ is selected from the group consisting of substituted phenyl, substituted or unsubstituted indanyl, substituted or unsubstituted tetralinyl, substituted or unsubstituted benzocycloheptanyl, substituted or unsubstituted hexahydrofluorenyl and substituted or unsubstituted cyclohexyl; wherein
said substituents are selected from the group consisting of $CF_3$, $OCF_3$, fluorine, chlorine, bromine, CN, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$ and substituted or unsubstituted tetrahydropyranyl$(CR_9R_{10})_m$; wherein m is an integer from 0 to 3;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ carbocyclic ring;

and wherein substituted $C_3-C_8$ carbocyclic refers to substituent selected from the group consisting of halogen, straight or branched chain $C_1-C_{10}$alkyl and phenyl;

or a salt thereof or an enantiomer, stereoisomer or a tautomer thereof or a racemic mixture thereof.

19. The compound as set forth in claim 18, which is:
2-(4-tert-butyl-phenylsulfanylmethyl)-2,3-dihydro-oxazolo[3,2-a]pyrimidin-7-one;
or a salt thereof or an enantiomer, stereoisomer or a tautomer thereof or a racemic mixture thereof.

20. A pharmaceutical composition comprising one or more compounds of claim 1 or a pharmaceutically acceptable salt, an enantiomer, a stereoisomer or a tautomer thereof or a racemic mixture thereof in combination with one or more pharmaceutically acceptable carriers, diluents or excipients.

21. A pharmaceutical composition comprising one or more compounds of claim 3 or a pharmaceutically acceptable salt, an enantiomer, a stereoisomer or a tautomer thereof or a racemic mixture thereof in combination with one or more pharmaceutically acceptable carriers, diluents or excipients.

22. A pharmaceutical composition comprising one or more compounds of claim 4 or a pharmaceutically acceptable salt, an enantiomer, a stereoisomer or a tautomer thereof or a racemic mixture thereof in combination with one or more pharmaceutically acceptable carriers, diluents or excipients.

23. A pharmaceutical composition comprising one or more compounds of claim 5 or a pharmaceutically acceptable salt, an enantiomer, a stereoisomer or a tautomer thereof or a racemic mixture thereof in combination with one or more pharmaceutically acceptable carriers, diluents or excipients.

24. A pharmaceutical composition comprising one or more compounds of claim 7 or a pharmaceutically acceptable salt, an enantiomer, a stereoisomer or a tautomer thereof or a racemic mixture thereof in combination with one or more pharmaceutically acceptable carriers, diluents or excipients.

25. A pharmaceutical composition comprising one or more compounds of claim 9 or a pharmaceutically acceptable salt, an enantiomer, a stereoisomer or a tautomer thereof or a racemic mixture thereof in combination with one or more pharmaceutically acceptable carriers, diluents or excipients.

26. A pharmaceutical composition comprising one or more compounds of claim 10 or a pharmaceutically acceptable salt, an enantiomer, a stereoisomer or a tautomer thereof or a racemic mixture thereof in combination with one or more pharmaceutically acceptable carriers, diluents or excipients.

27. A pharmaceutical composition comprising one or more compounds of claim 12 or a pharmaceutically acceptable salt, an enantiomer, a stereoisomer or a tautomer thereof or a racemic mixture thereof in combination with one or more pharmaceutically acceptable carriers, diluents or excipients.

28. A compound of the formula I:

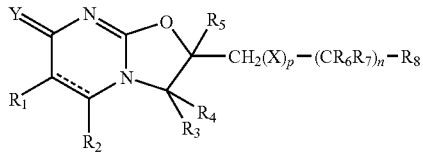

wherein:
----- is a single or a double bond;
p is 0 or 1;
n is an integer from 0 to 3;
X is oxygen or sulfur; or $NR_{21}$, wherein $R_{21}$ is hydrogen or $(C_1-C_4)$alkyl;
Y is oxygen or sulfur;
$R_1$ and $R_2$ are the same or different and independently of each other selected from the group consisting of hydrogen, $CF_3$, straight or branched chain $(C_1-C_{10})$alkyl, mono- or di-fluoro$(C_1-C_4)$alkyl, mono- or di-fluoro$(C_1-C_4)$alkoxy$(C_0-C_4)$alkyl, mono- or di-fluoro$(C_1-C_4)$alkylsulfanyl$(C_0-C_4)$alkyl, mono- or di-fluoro$(C_1-C_4)$alkylsulfinyl$(C_0-C_4)$alkyl, mono- or di-fluoro$(C_1-C_4)$alkylsulfonyl$(C_0-C_4)$alkyl, $(C_1-C_{10})$alkoxy$(C_0-C_4)$alkyl, $(C_1-C_{10})$alkylsulfanyl$(C_0-C_4)$alkyl, $(C_1-C_{10})$alkylsulfinyl$(C_0-C_4)$alkyl, $(C_1-C_{10})$alkylsulfonyl$(C_0-C_4)$alkyl, $(C_1-C_{10})$alkoxy mono- or di-fluoro$(C_1-C_4)$alkyl, $(C_1-C_{10})$alkylsulfanyl mono- or di-fluoro$(C_1-C_4)$alkyl, $(C_1-C_{10})$alkylsulfinyl mono- or di-fluoro$(C_1-C_4)$alkyl, $(C_1-C_{10})$alkylsulfonyl mono- or di-fluoro$(C_1-C_4)$alkyl, $(C_6,C_{10})$aryl$(C_0-C_4)$alkyl, $(C_6,C_{10})$aryl mono- or difluoro$(C_2-C_4)$alkyloxy, $(C_6,C_{10})$aryloxy$(C_0-C_4)$alkyl, $(C_6,C_{10})$arylsulfanyl$(C_0-C_4)$alkyl,$(C_6,C_{10})$arylsulfinyl $(C_0-C_4)$alkyl, $(C_6,C_{10})$aryl sulfonyl$(C_0-C_4$alkyl $(C_3-C_8)$cycloalkyl$(C_0-C_4)$alkyl, mono- or difluoro$(C_3-C_8)$cycloalkyl$(C_0-C_4)$alkyl, $(C_3-C_8)$cycloalkoxy$(C_0-C_4)$alkyl, mono- or difluoro$(C_3-C_8)$cycloalkyloxy$(C_0-C_4)$alkyl, $(C_3-C_8)$cycloalkyl mono- or difluoro $(C_1-C_4)$alkyl, $(C_3-C_8)$cycloalkyl mono- or difluoro $(C_2-C_4)$alkyloxy, $(C_3-C_8)$cycloalkylsulfanyl$(C_0-C_4)$alkyl, $(C_3-C_8)$cycloalkylsulfinyl$(C_0-C_4)$alkyl, $(C_3-C_8)$cycloalkylsulfonyl$(C_0-C_4)$alkyl, hydroxy$(C_1-C_4)$alkyl, heteroaryl$(C_0-C_4)$alkyl, heteroaryl mono- or difluoro $(C_1-C_4)$alkyl, heteroaryloxy$(C_0-C_4)$alkyl, heteroaryloxy mono- or difluoro$(C_2-C_4)$alkyl, heteroarylsulfanyl $(C_0-C_4)$alkyl, heteroarylsulfinyl$(C_0-C_4)$alkyl, heteroarylsulfonyl$(C_0-C_4)$alkyl, saturated heterocyclic $(C_0-C_4)$alkyl, saturated heterocyclic mono- or di-fluoro $(C_1-C_4)$alkyl, saturated heterocyclyloxy$(C_0-C_4)$alkyl, saturated heterocyclyloxy mono- or di-fluoro$(C_2-C_4)$ alkyl, saturated heterocyclylsulfanyl$(C_0-C_4)$alkyl, heterocyclylsulfinyl$(C_0-C_4)$alkyl, heterocyclylsulfonyl $(C_0-C_4)$alkyl, —$CO_2R_{22}$ or —$CONR_{23}R_{24}$ wherein $R_{22}$, $R_{23}$ and $R_{24}$ are the same or different and independently of each other selected from hydrogen or $(C_1-C_4)$alkyl; and wherein $R_1$ and $R_2$ are optionally further substituted;
$R_3$ and $R_4$ are the same or different and independently of each other selected from the group consisting of hydrogen, $(C_1-C_4)$alkyl, $(C_3-C_8)$cycloalkyl and $(C_6,C_{10})$aryl $(C_1-C_4)$alkyl; or
$R_3$ and $R_4$ taken together with the carbon atom to which they are attached form a substituted or unsubstituted $C_5-C_7$ carbocyclic ring;

$R_5$, $R_6$ and $R_7$ are the same or different and independently of each other selected from the group consisting of hydrogen, $(C_1-C_4)$alkyl and $(C_3-C_8)$cycloalkyl;

$R_8$ is selected from the group consisting of substituted phenyl, substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted $(C_3-C_8)$cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, substituted or unsubstituted tetrahydrodibenzofuranyl and substituted or unsubstituted hexahydrodibenzofuranyl;

wherein substituted refers to substituent selected from the group consisting of $CF_3$, $OCF_3$, halogen, CN, $SF_5$, straight or branched chain $(C_1-C_{20})$alkyl, $(C_1-C_4)$ alkylsulfonyl, substituted or unsubstituted $(C_3-C_{10})$ cycloalkyl$(CR_9R_{10})_m$, substituted or unsubstituted $(C_6-C_{16})$spirocycloalkyl, substituted or unsubstituted $(C_6,C_{10})$aryl$(CR_9R_{10})_m$, substituted or unsubstituted heteroaryl$(CR_9R_{10})_m$, substituted or unsubstituted $(C_6,C_{10})$aryl $C_3-C_8$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3-C_{10})$cycloalkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$, substituted or unsubstituted $(C_4-C_7)$ lactam, substituted or unsubstituted tetrahydropyranyl$(CR_9R_{10})_m$, substituted or unsubstituted tetrahydrofuranyl$(CR_9R_{10})_m$, substituted or unsubstituted 1,3-dioxanyl, substituted or unsubstituted 1,3-dioxolanyl, $(C_1-C_4)$alkoxyethoxy, substituted or unsubstituted $(C_3-C_8)$cycloalkyloxyethoxy, substituted or unsubstituted $(C_6,C_{10})$aryloxyethoxy and substituted or unsubstituted heteroaryloxyethoxy; wherein m is an integer from 0 to 10;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ carbocyclic ring;

and wherein said substituted $C_3-C_8$ carbocyclic ring of $R_9$ and $r_{10}$ taken together with the carbon atom to which they are attached are substituted with substituents selected form the aforementioned substituents;

or a salt thereof or an enantiomer, stereoisomer or a tautomer thereof or a racemic mixture thereof.

29. A compound of the formula I:

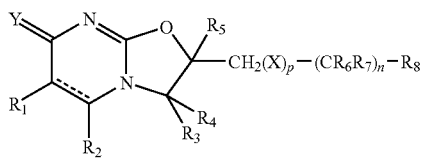

wherein:
----- is a single or a double bond;
p is 0 or 1;
n is an integer from 0 to 3;
X is oxygen or sulfur;
Y is oxygen or sulfur;
$R_1$ and $R_2$ are the same or different and independently of each other selected from the group consisting of hydrogen, $CF_3$, straight or branched chain $(C_1-C_{10})$alkyl, mono- or di-fluoro$(C_1-C_4)$alkyl, $(C_6,C_{10})$aryl$(C_0-C_4)$alkyl, $(C_3-C_8)$cycloalkyl$(C_0-C_4)$alkyl, hydroxy$(C_1-C_4)$alkyl, heteroaryl, saturated heterocyclic, —$CO_2R_{22}$ or —$CONR_{23}R_{24}$ wherein $R_{22}$, $R_{23}$ and $R_{24}$ are the same or different and independently of each other selected from hydrogen or $(C_1-C_4)$alkyl;
$R_3$ and $R_4$ are the same or different and independently of each other selected from the group consisting of hydrogen, $(C_1-C_4)$alkyl, and $(C_6,C_{10})$aryl $(C_1-C_4)$alkyl; or
$R_3$ and $R_4$ taken together with the carbon atom to which they are attached form a substituted or unsubstituted $C_5-C_7$ carbocyclic ring;
$R_5$, $R_6$ and $R_7$ are the same or different and independently of each other selected from the group consisting of hydrogen, $(C_1-C_4)$alkyl;
$R_8$ is selected from the group consisting of, substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted $(C_3-C_8)$cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, and substituted or unsubstituted hexahydrodibenzofuranyl;
wherein substituted refers to subsrtituents selected from the group consisting of $CF_3$, $OCF_3$, halogen, CN, $SF_5$, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6-C_{16})$spirocycloalkyl, substituted or unsubstituted $(C_6,C_{10})$aryl$(CR_9R_{10})_m$, substituted or unsubstituted heteroaryl$(CR_9R_{10})_m$, substituted or unsubstituted $(C_6,C_{10})$aryl$(C_3-C_8$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3-C_{10})$cycloalkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$, substituted or unsubstituted $(C_4-C_7)$ lactam, substituted or unsubstituted tetrahydropyranyl$(CR_9R_{10})_m$, substituted or unsubstituted tetrahydrofuranyl$(CR_9R_{10})_m$, substituted or unsubstituted 1,3-dioxanyl, substituted or unsubstituted 1,3-dioxolanyl, $(C_1-C_4)$alkoxyethoxy, substituted or unsubstituted $(C_3-C_8)$cycloalkyloxyethoxy, substituted or unsubstituted $(C_6,C_{10})$aryloxyethoxy and substituted or unsubstituted heteroaryloxyethoxy; wherein
m is an integer from 0 to 10;
$R_9$ and $R_{10}$ are the same or different and independently of each other chosen from hydrogen or $(C_1-C_4)$alkyl; or
$R_9$ and $R_{10}$ taken together with the carbon atom to which they are attached form a substituted or unsubstituted $C_3-C_8$ carbocyclic ring,
and wherein said substituted $C_3-C_8$ carbocyclic ring of $R_9$ and $R_{10}$ taken together with the carbon atom to which they are attached are substituted with sustitutents selected from the aforementioned sustituents;
or a salt thereof or an enantiomer, stereoisomer or a tautomer thereof or a racemic mixture thereof; and
wherein when $R^8$ is substituted phenyl, $R^2$ is not methyl, ethyl or propyl; and wherein $R^8$ is substituted phenyl, the substitution is not 2-methyl on the phenyl ring of $R^8$.

30. A compound of the formula I:

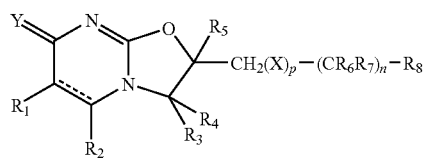

wherein:
----- is a double bond;
p is 0 or 1;
n is an integer from 0 to 3;
X is oxygen or sulfur; or $NR_{21}$, wherein $R_{21}$ is hydrogen or $(C_1-C_4)$alkyl;
Y is oxygen or sulfur;
$R_1$ and $R_2$ are the same or different and independently of each other selected from the group consisting of hydrogen, $CF_3$, straight or branched chain $(C_1-C_{10})$alkyl, mono- or di-fluoro$(C_1-C_4)$alkyl, $(C_6,C_{10})$aryl$(C_0-C_4)$alkyl$(C_3-C_8)$cycloalkyl$(C_0-C_4)$alkyl, hydroxy$(C_1-C_4)$alkyl, heteroaryl, saturated heterocyclic, —$CO_2R_{22}$ or —$CONR_{23}R_{24}$ wherein $R_{22}$, $R_{23}$ and $R_{24}$ are the same or different and independently of each other selected from hydrogen or $(C_1-C_4)$alkyl;
$R_3$ and $R_4$ are the same or different and independently of each other selected from the group consisting of hydrogen, $(C_1-C_4)$alkyl, and $(C_6,C_{10})$aryl$(C_1-C_4)$alkyl; or
$R_3$ and $R_4$ taken together with the carbon atom to which they are attached form a substituted or unsubstituted $C_5-C_7$ carbocyclic ring;
$R_5$, $R_6$ and $R_7$ are the same or different and independently of each other selected from the group consisting of hydrogen $(C_1-C_4)$alkyl;
$R_8$ is selected from the group consisting of, substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted $(C_3-C_8)$cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, and substituted or unsubstituted hexahydrodibenzofuranyl;

wherein substituted refers to subsrtituent selected from the group consisting of $CF_3$, $OCF_3$, halogen, CN, $SF_5$, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6-C_{16})$spirocycloalkyl, substituted or unsubstituted $(C_6,C_{10})$aryl$(CR_9R_{10})_m$, substituted or unsubstituted heteroaryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3-C_{10})$cycloalkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$, substituted or unsubstituted $(C_4-C_7)$lactam, substituted or unsubstituted tetrahydropyranyl$(CR_9R_{10})_m$, substituted or unsubstituted tetrahydrofuranyl$(CR_9R_{10})_m$, substituted or unsubstituted 1,3-dioxanyl, substituted or unsubstituted 1,3-dioxolanyl, $(C_1-C_4)$alkoxyethoxy, substituted or unsubstituted $(C_3-C_8)$cycloalkyloxyethoxy, substituted or unsubstituted $(C_6,C_{10})$aryloxyethoxy and substituted or unsubstituted heteroaryloxyethoxy; wherein m is an integer from 0 to 10;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ carbocyclic ring;

and wherein said substituted $C_3-C_8$ carbocyclic ring of $R_9$ and $R_{10}$ taken together with the carbon atom to which they are attached are substituted with substituents are selected form the aforementioned substituents;

or a salt thereof or an enantiomer, stereoisomer or a tautomer thereof or a racemic mixture thereof.

31. A compound of the formula I:

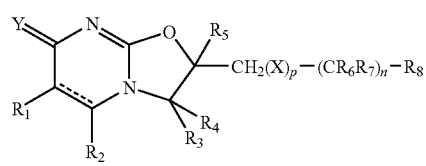

(I)

wherein:
----- is single or a double bond;
p is 0 or 1;
n is an integer from 0 to 3;
X is oxygen, sulfur, or $NR_{21}$, wherein $R_{21}$ is hydrogen or $(C_1-C_4)$alkyl;
Y is oxygen or sulfur;
$R_1$ and $R_2$ are the same or different and independently of each other selected from the group consisting of hydrogen, $CF_3$, straight or branched chain $(C_1-C_{10})$alkyl, mono- or di-fluoro$(C_1-C_4)$alkyl, $(C_6,C_{10})$aryl$(C_0-C_4)$alkyl$(C_3-C_8)$cycloalkyl$(C_0-C_4)$alkyl, hydroxy$(C_1-C_4)$alkyl, heteroaryl, saturated heterocyclic, $-CO_2R_{22}$ or $-CONR_{23}R_{24}$ wherein $R_{22}$, $R_{23}$ and $R_{24}$ are the same or different and independently of each other selected from hydrogen or $(C_1-C_4)$alkyl;

$R_3$ and $R_4$ are the same or different and independently of each other selected from the group consisting of hydrogen, $(C_1-C_4)$alkyl, and $(C_6,C_{10})$aryl$(C_1-C_4)$alkyl; or $R_3$ and $R_4$ taken together with the carbon atom to which they are attached form a substituted or unsubstituted $C_5-C_7$ carbocyclic ring;

$R_5$, $R_6$ and $R_7$ are the same or different and independently of each other selected from the group consisting of hydrogen $(C_1-C_4)$alkyl;

$R_8$ is selected from the group consisting of substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted $(C_3-C_8)$cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, and substituted or unsubstituted hexahydrodibenzofuranyl;

wherein substituted refers to substituent selected from the group consisting of $CF_3$, $OCF_3$, halogen, CN, $SF_5$, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6-C_{16})$spirocycloalkyl, substituted or unsubstituted $(C_6,C_{10})$aryl$(CR_9R_{10})_m$, substituted or unsubstituted heteroaryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3-C_{10})$cycloalkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$, substituted or unsubstituted $(C_4-C_7)$lactam, substituted or unsubstituted tetrahydropyranyl$(CR_9R_{10})_m$, substituted or unsubstituted tetrahydrofuranyl$(CR_9R_{10})_m$, substituted or unsubstituted 1,3-dioxanyl, substituted or unsubstituted 1,3-dioxolanyl, $(C_1-C_4)$alkoxyethoxy, substituted or unsubstituted $(C_3-C_8)$cycloalkyloxyethoxy, substituted or unsubstituted $(C_6,C_{10})$aryloxyethoxy and substituted or unsubstituted heteroaryloxyethoxy; wherein m is an integer from 0 to 10;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ carbocyclic ring;

and wherein said substituents on the substituted $C_3-C_8$ carbocyclic ring, formed when $R_9$ and $R_{10}$ taken together with the carbon atom to which they are attached, are selected from the aforementioned substituents;

or a salt thereof or an enantiomer, stereoisomer or a tautomer thereof or a racemic mixture thereof.

32. The compound as set forth in claim 29, wherein

----- is a double bond;

p is 1;

n is 0;

X and Y are oxygen;

$R_2$ is hydrogen, $CF_3$, straight or branched $(C_1-C_{10})$alkyl, $(C_6,C_{10})$aryl, $(C_6,C_{10})$aryl$(C_1-C_4)$alkyl; or —$CO_2C_2H_5$;

$R_1$, $R_3$, $R_4$ and $R_5$ are hydrogen;

$R_8$ is selected from the group consisting of, substituted or unsubstituted indanyl, substituted or unsubstituted tetralinyl, substituted or unsubstituted benzoclycloheptanyl, substituted or unsubstituted hexahydrofluorenyl and substituted or unsubstituted cyclohexyl; wherein said substituents are selected from the group consisting of $CF_3$, $OCF_3$, $SF_3$ fluorine, chlorine, bromine, CN, straight or branched chain $(C_1-C_{20})$alkyl, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3,C_{10})$cycloalkoxy, substituted or unsubstituted $(C_6,C_{10})$aryloxy, substituted or unsubstituted heteroaryloxy, substituted or unsubstituted tetrahydropyranyl $(CR_9R_{10})_m$; wherein m is 0 or 2;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ ring; wherein the substituents on the unsubstituted $C_3-C_8$ carbocyclic ring formed when $R_9$ and $R_{10}$ are taken with the carbon atom to which they are attached are selected from the aforementioned substituents;

or a salt thereof or an enantiomer, stereoisomer or a tautomer thereof or a racemic mixture thereof.

33. The compound as set forth in claim 29, wherein

----- is a double bond;

p is 1;

n is 0;

X and Y are oxygen;

$R_1$, $R_3$, $R_4$ and $R_5$ are hydrogen;

$R_2$ is hydrogen, $CF_3$, straight or branched $(C_1-C_{10})$alkyl, $(C_6,C_{10})$aryl, $(C_6,C_{10})$aryl$(C_0-C_4)$alkyl $R_8$ is selected from the group consisting of, substituted or unsubstituted furanyl, substituted or unsubstituted benzofuranyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, and substituted or unsubstituted quinolinyl: wherein said substituents are selected from the group consisting of $CF_3$, $OCF_3$, fluorine, chlorine, bromine, CN, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6,C_{10})$aryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$ and substituted or unsubstituted tetrahydropyranyl$(CR_9R_{10})_m$; wherein m is 0 or 2;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ ring;

and wherein said substituents are selected from the group consisting of halogen, straight or brtanched chain $C_1-C_{10}$alkyl and phenyl;

or a salt thereof or an enantiomer, stereoisomer or a tautomer thereof or a racemic mixture thereof.

34. The compound as set forth in claim 33, which is selected from the group consisting of:

2-(1H-indol-5-yloxymethyl)-2,3-dihydro-oxazolo[3,2-a]pyrimidin-7-one;

(S)-2-(6-cyclohexyl-pyridin-3-yloxymethyl)-2,3-dihydro-oxazolo[3,2-a]pyrimidin-7-one;

(S)-2-(benzothiazol-2-yloxymethyl)-2,3-dihydro-oxazolo[3,2a]pyrimidin-7-one;

(S)-2-(6-tert-butyl-benzothiazol-2-yloxymethyl)-2,3-dihydro-oxazolo[3,2-a]pyrimidin-7-one;

(S)-2-(2,5-diphenyl-thiazol-4-yloxymethyl)-2,3-dihydro-oxazolo[3,2-a]pyrimidin-7-one;

or a salt thereof or an enantiomer, stereoisomer or a tautomer thereof or a racemic mixture thereof.

35. A compound as set forth in claim 29, wherein

----- is a double bond;

p is 1;

n is 1;

X and Y are oxygen;

$R_2$ is hydrogen, $CF_3$, straight or branched $(C_1-C_{10})$alkyl, $(C_6,C_{10})$aryl, $(C_6,C_{10})$aryl$(C_1-C_4)$alkyl, $R_1$, $R_3$, $R_4$ and $R_5$ are hydrogen;

$R_8$ is selected from the group consisting of, substituted or unsubstituted indanyl, substituted or unsubstituted tetralinyl, substituted or unsubstituted benzocycloheptanyl, substituted or unsubstituted hexahydrofluorenyl and substituted or unsubstituted cyclohexyl; wherein said substituents are selected from the group consisting of $CF_3$, $OCF_3$, fluorine, chlorine, bromine, CN, straight or branched chain $(C_1-C_{20})$alkyl, $(C_1-C_4)$alkylsulfonyl, substituted or unsubstituted cycloalkyl $(CR_9R_{10})_m$, substituted or unsubstituted $(C_6,C_{10})$aryl $(CR_9R_{10})_m$, substituted or unsubstituted $(C_6,C_{10})$aryl $(C_3-C_0)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_6,C_{10})$aryl-oxy, substituted or unsubstituted heteroaryloxy, substituted or unsubstituted piperazinyl$(CR_9R_{10})_m$ and substituted or unsubstituted tetrahydropyranyl $(CR_9R_{10})_m$; wherein m is an integer from 0 to 3;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ carbocyclic ring; wherein the subtituents on the substituted $C_3-C_8$ carbocyclic ring formed when $R_9$ and $R_{10}$ are taken together with the carbon atom to which they are attached are selected from the group consisting of halogen, straight or branched chain $C_1-C_{10}$alkyl and phenyl;

or a salt thereof or an enantiomer, stereoisomer or a tautomer thereof.

36. . A compound of the formula:

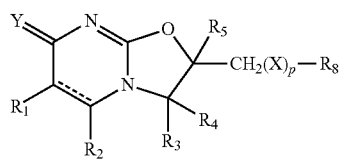

(I)

wherein:

----- is a single or a double bond;

p is 0 or 1;

X is oxygen, sulfur, or $NR_{21}$, wherein $R_{21}$ is hydrogen or $(C_1-C_4)$alkyl;

Y is oxygen or sulfur;

$R_1$ and $R_2$ are the same or different and independently of each other selected from the group consisting of hydrogen, $CF_3$, straight or branched chain $(C_1-C_{10})$alkyl, mono- or di-fluoro$(C_1-C_4)$alkyl, $(C_6,C_{10})$aryl$(C_0-C_4)$alkyl, $(C_3-C_8)$cycloalkyl$(C_0-C_4)$alkyl, hydroxy$(C_1-C_4)$alkyl, heteroaryl, saturated heterocyclic, —$CO_2R_{22}$ or —$CONR_{23}R_{24}$ wherein $R_{22}$, $R_{23}$ and $R_{24}$ are the same or different and independently of each other selected from hydrogen or $(C_1-C_4)$alkyl;

$R_3$ and $R_4$ are the same or different and independently of each other selected from the group consisting of hydrogen, $(C_1-C_4)$alkyl, and $(C_6,C_{10})$aryl$(C_1-C_4)$alkyl; or $R_3$ and $R_4$ taken together with the carbon atom to which they are attached form a substituted or unsubstituted $C_5-C_7$ carbocyclic ring;

$R_5$ is hydrogen or $(C_1-C_4)$alkyl;

$R_8$ is selected from the group consisting of, substituted or unsubstituted naphthyl, substituted or unsubstituted indanyl, substituted or unsubstituted tetralinyl, substituted or unsubstituted benzocycloheptanyl, substituted or unsubstituted hexahydrofluorenyl, substituted or unsubstituted $(C_3-C_8)$cycloalkyl, substituted or unsubstituted furanyl, substituted or unsubstituted benzofuranyl, substituted or unsubstituted thiophenyl, substituted or unsubstituted benzothiophenyl, substituted or unsubstituted indolyl, substituted or unsubstituted benzothiazolyl, substituted or unsubstituted thiazolyl, substituted or unsubstituted pyrrolyl, substituted or unsubstituted pyridyl, substituted or unsubstituted tetrahydroisoquinolinyl, substituted or unsubstituted tetrahydroquinolinyl, substituted or unsubstituted isoquinolinyl, substituted or unsubstituted quinolinyl, and substituted or unsubstituted hexahydrodibenzofuranyl;

wherein substituted refers to subsrtituent selected from the group consisting of $CF_3$, $OCF_3$, halogen, CN, $SF_5$, straight or branched chain $(C_1-C_{20})$alkyl, $(C_1-C_4)$alkylsulfonyl, substituted or unsubstituted $(C_3-C_{10})$cycloalkyl$(CR_9R_{10})_m$, substituted or unsubstituted $(C_6-C_{16})$spirocycloalkyl, substituted or unsubstituted $(C_6,C_{10})$aryl$(CR_9R_{10})_m$, substituted or unsubstituted heteroaryl$(CR_9R_{10})_m$, substituted or unsubstituted $(C_6,C_{10})$aryl$(C_3-C_8)$cycloalkyl, substituted or unsubstituted $(C_8-C_{13})$bicyclic, substituted or unsubstituted adamantyl, substituted or unsubstituted indanyl, substituted or unsubstituted tetralinyl, substituted or unsubstituted benzocycloheptyl, straight or branched chain $(C_1-C_{20})$alkoxy, substituted or unsubstituted $(C_3-C_{10})$cycloalkoxy, substituted or unsubstituted $(C_6,C_{10})$aryloxy, substituted or unsubstituted heteroaryloxy, substituted or unsubstituted piperidinyl $(CR_9R_{10})_m$, substituted or unsubstituted piperazinyl $(CR_9R_{10})_m$, substituted or unsubstituted $(C_4-C_7)$ lactam, substituted or unsubstituted tetrahydropyranyl$(CR_9R_{10})_m$, substituted or unsubstituted tetrahydrofuranyl$(CR_9R_{10})_m$, substituted or unsubstituted 1,3-dioxanyl, substituted or unsubstituted 1,3-dioxolanyl, $(C_1-C_4)$alkoxyethoxy, substituted or unsubstituted $(C_3-C_8)$cycloalkyloxyethoxy, substituted or unsubstituted $(C_6,C_{10})$aryloxyethoxy and substituted or unsubstituted heteroaryloxyethoxy; wherein m is an integer from 0 to 10;

$R_9$ and $R_{10}$ are the same or different and independently of each other chosen from hydrogen or $(C_1-C_4)$alkyl; or $R_9$ and $R_{10}$ taken together with the carbon atom to which they are attached form a substituted or unsubstituted $C_3-C_8$ carbocyclic ring;

and wherein said substituents on $R_9$ and $R_{10}$ are selected from the aforementioned substituents;

or a salt thereof or an enantiomer, stereoisomer or a tautomer thereof or a racemic mixture thereof.

37. A pharmaceutical composition comprising one or more compounds of claim 28 or a pharmaceutically acceptable salt, an enantiomer, a stereoisomer or a tautomer thereof or a racemic mixture thereof in combination with one or more pharmaceutically acceptable carriers, diluents or excipients.

38. A pharmaceutical composition comprising one or more compounds of claim 29 or a pharmaceutically acceptable salt, an enantiomer, a stereoisomer or a tautomer thereof or a racemic mixture thereof in combination with one or more pharmaceutically acceptable carriers, diluents or excipients.

39. A pharmaceutical composition comprising one or more compounds of claim 30 or a pharmaceutically acceptable salt, an enantiomer, a stereoisomer or a tautomer thereof or a racemic mixture thereof in combination with one or more pharmaceutically acceptable carriers, diluents or excipients.

40. A pharmaceutical composition comprising one or more compounds of claim 31 or a pharmaceutically acceptable salt, an enantiomer, a stereoisomer or a tautomer thereof or a racemic mixture thereof in combination with one or more pharmaceutically acceptable carriers, diluents or excipients.

41. A pharmaceutical composition comprising one or more compounds of claim 36 or a pharmaceutically acceptable salt, an enantiomer, a stereoisomer or a tautomer thereof or a racemic mixture thereof in combination with one or more pharmaceutically acceptable carriers, diluents or excipients.

42. The compound according to claim 1 which is selected from the group consisting of:
- 2-(4-tert-Butyl-cyclohexyloxymethyl)-2,3-dihydro-oxazolo[3,2-a]pyrimidin-7-one,
- (S)-2-(5,6,7,8,8a,9-Hexahydro-4bH-fluoren-2-yloxymethyl)-2,3-dihydro-oxazolo[3,2-a]pyrimidin-7-one,
- (S)-2-(6-Cyclohexyl-pyridin-3-yloxymethyl)-2,3-dihydro-oxazolo[3,2-a]pyrimidin-7-one,
- (S)-2-(Benzothiazol-2-yloxymethyl)-2,3-dihydro-oxazolo[3,2a]pyrimidin-7-one,
- (S)-2-(2,5-Diphenyl-thiazol-4-yloxymethyl)-2,3-dihydro-oxazolo[3,2-a]pyrimidin-7-one,
- 2-(5,6,7,8-Tetrahydro-naphthalen-2-yloxymethyl)-2,3-dihydro-oxazolo[3,2a]-pyrimidin-7-one,
- 2-(1H-Indol-5-yloxymethyl)-2,3-dihydro-oxazolo[3,2-a]pyrimidin-7-one,
- (S)-2-(4-Cyclohexyl-phenoxymethyl)-6methyl-2,3-dihydro-oxazolo[3,2-a]pyrimidin-7-one,
- (S)-2-(6-tert-Butyl-benzothiazol-2-yloxymethyl)-2,3-dihydro-oxazolo[3,2-a]pyrimidin-7-one,
- 2-(5a,6,7,8,9,9a-Hexahydro-dibenzofuran-3-yl-oxymethyl)-2,3-dihydro-oxazolo[3,2-a]pyrimidin-7-one,
- 2-(6,7,8,9-Tetrahydro-dibenzofuran-3-yl-oxymethyl)-2,3-dihydro-oxazolo[3,2-a]pyrimidin-7-one,
- (S)-2-(Benzo[b]thiophen-6-yloxymethyl)-2,3-dihydro-oxazolo[3,2-a]pyrimidin-7-one,
- (S)-2-(2-p-Tolyl-benzo[b]thiophen-6-yloxymethyl)-2,3-dihydro-oxazolo[3,2-a]pyrimidin-7-one,
- (S)-2-[2-(4-Ethyl-phenyl)-benzo[b]thiophen-6-yloxymethyl]-2,3-dihydro-oxazolo[3,2-a]pyrimidin-7-one,
- (S)-2-[2-(4-Isopropyl-phenyl)-benzo[b]thiophen-6-yloxymethyl]-2,3-dihydro-oxazolo[3,2-a]pyrimidin-7-one,
- (S)-2-[2-(4-Propyl-phenyl)-benzo[b]thiophen-6-yloxymethyl]-2,3-dihydro-oxazolo[3,2-a]-pyrimidin-7-one,
- (S)-2-[2-(4-tert-Butyl-phenyl)-benzo[b]thiophen-6-yloxymethyl]-2,3-dihydro-oxazolo[3,2-a]pyrimidin-7-one,
- (S)-2-[2-(2-Chloro-pyridin-4-yl)-benzo[b]thiophen-6-yloxymethyl]-2,3-dihydro-oxazolo[3,2-a]pyrimidin-7-one, or a salt thereof or an enantiomer, stereoisomer or a tautomer thereof or a racemic mixture thereof.

\* \* \* \* \*

UNITED STATES PATENT AND TRADEMARK OFFICE
CERTIFICATE OF CORRECTION

PATENT NO. : 8,642,603 B2
APPLICATION NO. : 12/554129
DATED : February 4, 2014
INVENTOR(S) : Bin Cao et al.

Page 1 of 9

It is certified that error appears in the above-identified patent and that said Letters Patent is hereby corrected as shown below:

In the Title Page of the Patent:

Page 1, left-hand column, section "OTHER PUBLICATIONS", line 2 of this section: please replace "Cycloalkyl[1,2-e]Oxazolo[3,2-a]Pyrlmidin-8/9-Ones:" with --Cycloalkyl[1,2-e]Oxazolo[3,2-a]Pyrimidin-8/9-Ones:--;

Page 1, right-hand column, section "OTHER PUBLICATIONS", line 6 of this column: please replace "(1995)" with --(1955)--;

Page 1, right-hand column, section "ABSTRACT", line 6 of this section: please replace "

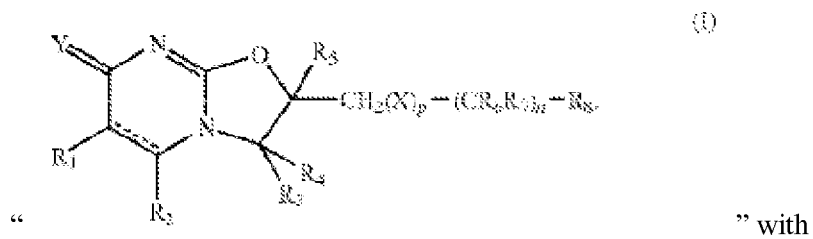

" with

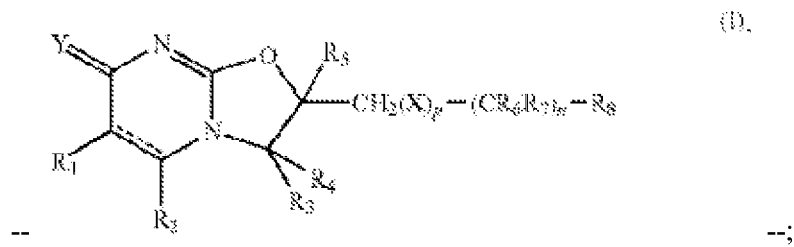

--;

Signed and Sealed this
Fifth Day of July, 2016

Michelle K. Lee
*Director of the United States Patent and Trademark Office*

CERTIFICATE OF CORRECTION (continued)
U.S. Pat. No. 8,642,603 B2

Page 2, left-hand column, section "OTHER PUBLICATIONS", line 46 of this section: please replace "Randonmized" with --Randomized--;

Page 2, right-hand column, section "OTHER PUBLICATIONS", line 10 of this section: please replace "Amine" with --Amino--;

Page 2, right-hand column, section "OTHER PUBLICATIONS", line 37 of this section: please replace "treatmetn" with --treatment--;

Page 2, right-hand column, section "OTHER PUBLICATIONS", line 42 of this section: please replace "Pshchopharmacology" with --Psychopharmacology--;

In the Specification:

Column 15, line 57: please replace "form" with --formula (II) may be enumerated:--;

Column 17, lines 31-33: please replace "(S)-2-(4-cyclohexyl-phenoxymethyl)-5-ethoxy-2,3-dihydro-oxazolo[3,2-a]pyrimidin-7-one; ula (II) may be enumerated:" with --(S)-2-(4-cyclohexyl-phenoxymethyl)-5-ethoxy-2,3-dihydro-oxazolo[3,2-a]pyrimidin-7-one.--;

Column 18, line 35: please replace

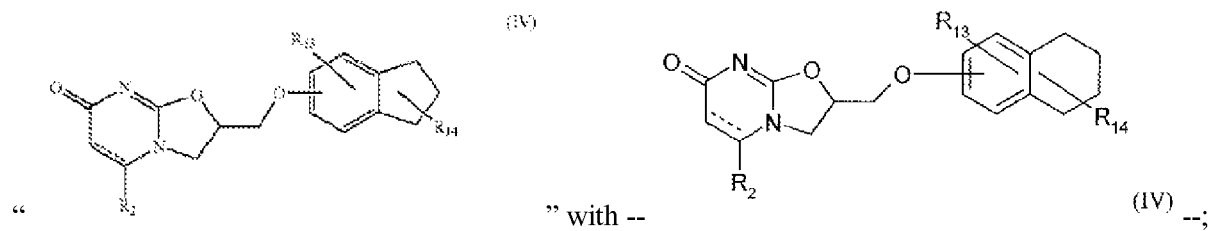

" with -- --;

Column 55, line 55: please replace

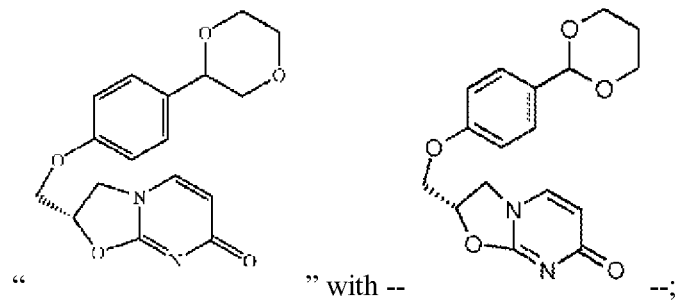

" with -- --;

CERTIFICATE OF CORRECTION (continued)
U.S. Pat. No. 8,642,603 B2

In the Claims:

Column 134, claim number 1, lines 7-8: please replace "$C_3$-$C_8$)cycloalkoxy($C_0$-$C_4$)alkyl" with --($C_3$-$C_8$)cycloalkoxy($C_0$-$C_4$)alkyl--;

Column 134, claim number 1, line 57: please replace "subsrtituents" with --substituents--;

Column 134, claim number 1, line 65: please replace "($C_6$,$C_{10}$)aryl $C_3$-$C_8$cycloalkyl" with --($C_6$,$C_{10}$)aryl($C_3$-$C_8$)cycloalkyl--;

Column 135, claim number 1, line 30: please replace "pheny," with --phenyl,--;

Column 137, claim number 3, lines 13-14: please replace "2-(4-tricyclo[3.3.1.13,7]decan-2-yl-phenoxymethyl)-2,3-dihydro-oxazolo[3,2-a]-pyrimidin-7-one;" with --2-(4-tricyclo[3.3.1.1$^{3,7}$]decan-2-yl-phenoxymethyl)-2,3-dihydro-oxazolo[3,2-a]-pyrimidin-7-one;--;

Column 137, claim number 3, lines 28-29: please replace "6-benzenesulfinyl-2-(4-cyclohexyl-phenoxymethyl)-2,3-dihydro-oxazolo[32-a]pyrimidin-7-one;" with --6-benzenesulfinyl-2-(4-cyclohexyl-phenoxymethyl)-2,3-dihydro-oxazolo[3,2-a]pyrimidin-7-one;--;

Column 137, claim number 3, lines 30-31: please replace "(S)-2-(4-cyclohexyl-phenoxymethyl)-6-methanesulfonyl-2,3-dihydro-oxazolo[3,2a]pyrimidin-7-one;" with --(S)-2-(4-cyclohexyl-phenoxymethyl)-6-methanesulfonyl-2,3-dihydro-oxazolo[3,2-a]pyrimidin-7-one;--;

Column 138, claim number 4, lines 52-53: please replace "(S)-2-[4-(4-trifluoromethyl-phenoxy)-benzyloxy]-2,3-dihydro-oxazolo[3,2a]pyrimidin-7-one;" with --(S)-2-[4-(4-trifluoromethyl-phenoxy)-benzyloxy]-2,3-dihydro-oxazolo[3,2-a]pyrimidin-7-one;--;

Column 140, claim number 4, line 24: please delete "and";

Column 140, claim number 4, lines 27-34: please replace
"2[R]-(4-bromo-phenoxymethyl)-2,3[R]-dihydro-oxazolo[3,2-a]pyrimidin-7-one;
2[R]-[4-(1,1,3,3-tetramethyl-butyl)-phenoxymethyl]-2,3-dihydro-oxazolo[3,2-a]-pyrimidin- 2[R]-(4-tert-butyl-phenoxymethyl)-2,3-dihydro-oxazolo[3,2-a]pyrimidin-7-one; and 2[R]-(4-cyclohexyl-phenoxymethyl)-2,3-dihydro-oxazolo[3,2-a]pyrimidin-7-one; or a salt thereof." with --2(R)-(4-bromo-phenoxymethyl)-2,3(R)-dihydro-oxazolo[3,2-a]pyrimidin-7-one;

2(R)-[4-(1,1,3,3-tetramethyl-butyl)-phenoxymethyl]-2,3-dihydro-oxazolo[3,2-a]-pyrimidin-7-one;

2(R)-(4-tert-butyl-phenoxymethyl)-2,3-dihydro-oxazolo[3,2-a]pyrimidin-7-one; and 2(R)-(4-cyclohexyl-phenoxymethyl)-2,3-dihydro-oxazolo[3,2-a]pyrimidin-7-one; or a salt thereof.--;

Column 140, claim number 5, line 36: please replace

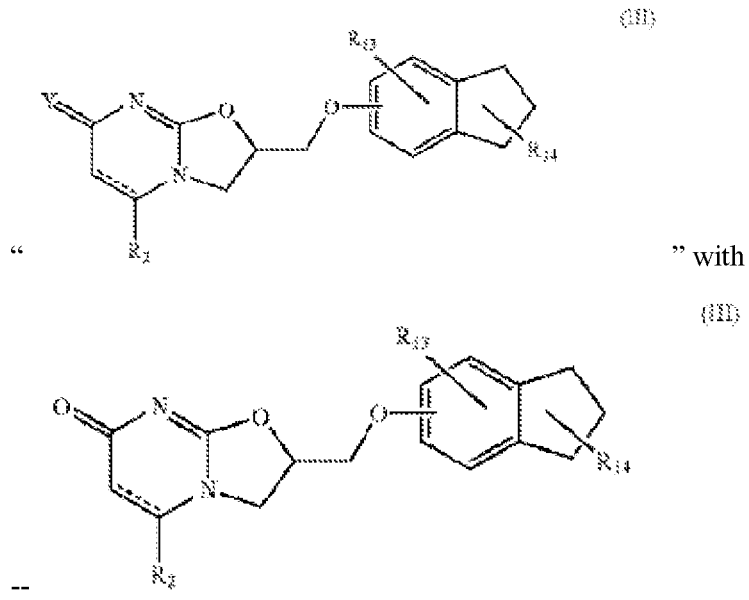

" with " "--;

Column 141, claim number 7, line 9: please replace

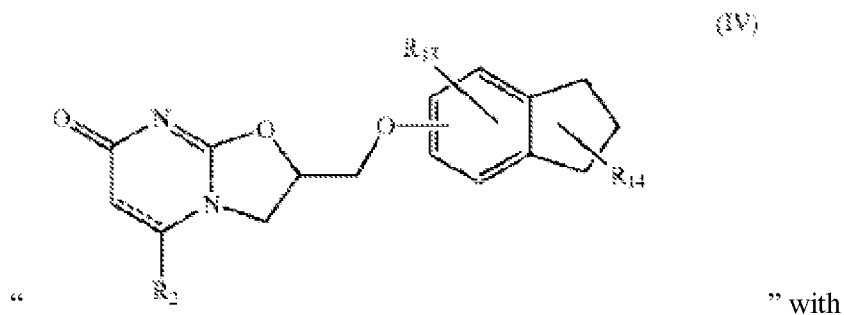

" with

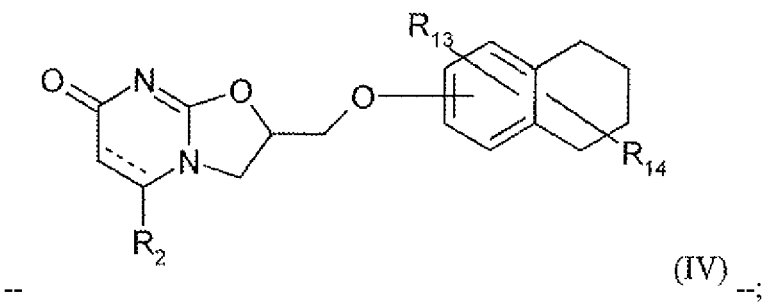

(IV)

Column 141, claim number 7, line 22: please delete "b";

Column 141, claim number 8, line 40-41: please replace "2-(5,6,7,8-tetrahydro-naphthalen-2-yloxymethyl)-2,3-dihydro-oxazolo[3,2a]-pyrimidin-7-one;" with --2-(5,6,7,8-tetrahydro-naphthalen-2-yloxymethyl)-2,3-dihydro-oxazolo[3,2-a]-pyrimidin-7-one;--;

Column 142, claim number 10, lines 28-29: please replace "$(C_3-C_{10})$cycloalkyl$(CR_9R_{10})_m$,substituted" with --$(C_3-C_{10})$cycloalkyl$(CR_9R_{10})_m$, substituted--;

Column 142, claim number 11, line 50: please replace "enantomer" with --enantiomer--;

Column 144, claim number 14, line 3: please replace "$C_3-C_8$ ring" with --$C_3-C_8$ carbocyclic ring--;

Column 144, claim number 15, lines 16-19: please replace
"(S)-2-(benzothiazol-2-yloxymethyl)-2,3-dihydro-oxazolo[3,2a]pyrimidin-7-one; (S)-2-(6-tert-butyl-benzothiazol-2-yloxymethyl)-2,3-dihydro-oxazolo[3,2-a]pyrimidin-7-one;" with
--(S)-2-(benzothiazol-2-yloxymethyl)-2,3-dihydro-oxazolo[3,2-a]pyrimidin-7-one;
(S)-2-(6-tert-butyl-benzothiazol-2-yloxymethyl)-2,3-dihydro-oxazolo[3,2-a]pyrimidin-7-one;--;

Column 144, claim number 16, line 43: please replace "formula" with --formula (I)--;

Column 144, claim number 16, line 57: please replace "or" with --;--;

Column 147, claim number 28, line 18: please replace "oxygen or sulfur; or $NR_{21}$," with --oxygen, sulfur, or $NR_{21}$,--;

Column 147, claim number 28, lines 37-38: please replace "$(C_6,C_{10})$arylsulfanyl$(C_0$-$C_4)$alkyl,$(C_6,C_{10})$arylsulfinyl$(C_0$-$C_4)$alkyl, $(C_6,C_{10})$aryl sulfonyl$(C_0$-$C_4$alkyl" with --$(C_6,C_{10})$arylsulfanyl$(C_0$-$C_4)$alkyl, $(C_6,C_{10})$arylsulfinyl$(C_0$-$C_4)$alkyl, $(C_6,C_{10})$arylsulfonyl$(C_0$-$C_4)$alkyl,--;

Column 148, claim number 28, line 4-5: please delete "substituted phenyl,";

Column 148, claim number 28, line 33: please replace "$(C_6,C_{10})$aryl $C_3$-$C_8$ cycloalkyl" with --$(C_6,C_{10})$aryl$(C_3$-$C_8)$cycloalkyl--;

Column 148, claim number 28, line 62: please replace "$r_{10}$" with --$R_{10}$--;

Column 148, claim number 28, line 65: please replace "form" with --from--;

Column 149, claim number 29, line 36: please replace "of," with --of--;

Column 149, claim number 29, line 61: please replace "$(C_6,C_{10})$aryl$(C_3$-$C_8$cycloalkyl," with --$(C_6,C_{10})$aryl$(C_3$-$C_8)$cycloalkyl,--;

Column 150, claim number 29, lines 26-29: please delete "; and wherein when $R_8$ is substituted phenyl, $R_2$ is not methyl, ethyl or propyl; and wherein $R_8$ is substituted phenyl, the substitution is not 2-methyl on the phenyl ring of $R_8$";

Column 150, claim number 30, line 45: please replace "oxygen or sulfur; or $NR_{21}$," with --oxygen, sulfur, or $NR_{21}$,--;

Column 150, claim number 30, lines 51-52: please replace "$(C_6,C_{10})$aryl$(C_0$-$C_4)$alkyl$(C_3$-$C_8)$cycloalkyl$(C_0$-$C_4)$alkyl," with --$(C_6,C_{10})$aryl$(C_0$-$C_4)$alkyl, $(C_3$-$C_8)$cycloalkyl$(C_0$-$C_4)$alkyl,--;

Column 150, claim number 30, line 65: please replace "hydrogen" with --hydrogen and--;

Column 151, claim number 30, line 10: please replace "pyrrolyl,substituted" with --pyrrolyl, substituted--;

Column 151, claim number 30, line 16: please replace "subsrtituent" with --substituents--;

Column 151, claim number 30, line 37: please replace "1,3-dioxanyl,substituted" with --1,3-dioxanyl, substituted--;

Column 151, claim number 30, lines 49-53: please replace "and wherein said substituted $C_3$-$C_8$ carbocyclic ring of $R_9$ and $R_{10}$ taken together with the carbon atom to which they are attached are substituted with substituents are selected form the aforementioned substituents;" with --and wherein said substituted $C_3$-$C_8$ carbocyclic ring of $R_9$ and $R_{10}$ taken together with the carbon atom to which they are attached are substituted with substituents that are selected from the aforementioned substituents;--;

Column 152, claim number 31, lines 8-9: please replace "$(C_6,C_{10})aryl(C_0$-$C_4)alkyl(C_3$-$C_8)cycloalkyl(C_0$-$C_4)alkyl,$" with --$(C_6,C_{10})aryl(C_0$-$C_4)alkyl, (C_3$-$C_8)cycloalkyl(C_0$-$C_4)alkyl,$--;

Column 152, claim number 31, line 22: please replace "hydrogen" with --hydrogen and--;

Column 152, claim number 31, line 61: please replace "1,3-dioxanyl,substituted" with --1,3-dioxanyl, substituted--;

Column 153, claim number 32, line 20: please replace "$(C_6,C_{10})aryl(C_1$-$C_4)alkyl;$" with --$(C_6,C_{10})aryl(C_1$-$C_4)alkyl,$--;

Column 153, claim number 32, line 23: please replace "of," with --of--;

Column 153, claim number 32, line 29: please replace "$SF_3$" with --$SF_5$,--;

Column 153, claim number 32, line 42: please replace "substituted" with --and substituted--;

Column 153, claim number 32, line 44: please replace "m is 0 or 2;" with --m is an integer from 0 to 2;--;

Column 153, claim number 32, line 50: please replace "$C_3$-$C_8$ ring" with --$C_3$-$C_8$ carbocyclic ring--;

Column 153, claim number 32, lines 50-51: please replace "unsubstituted" with --substituted--;

Column 153, claim number 33, line 64: please replace "$(C_6,C_{10})$aryl$(C_0-C_4)$alkyl" with --$(C_6,C_{10})$aryl$(C_0-C_4)$alkyl;--;

Column 153, claim number 33, line 65: please replace "of," with --of--;

Column 154, claim number 33, line 7: please replace ":" with --;--;

Column 154, claim number 33, line 25: please replace "2" with --1--;

Column 154, claim number 33, line 33: please replace "brtanched" with --branched--;

Column 154, claim number 35, line 57: please replace "$(C_6,C_{10})$aryl$(C_1-C_4)$alkyl," with --$(C_6,C_{10})$aryl$(C_1-C_4)$alkyl;--;

Column 154, claim number 35, line 58: please replace "$R_1$, $R_3$, $R_4$ and $R_5$ are hydrogen;" with --$R_1$, $R_3$, $R_4$, $R_5$, $R_6$ and $R_7$ are hydrogen;--;

Column 154, claim number 35, line 59: please replace "of," with --of--;

Column 155, claim number 35, lines 2-3: please replace "$(C_6,C_{10})$aryl$(C_3-C_0)$cycloalkyl," with --$(C_6,C_{10})$aryl$(C_3-C_8)$cycloalkyl,--;

Column 155, claim number 35, lines 8-9: please replace "$(C_6,C_{10})$aryl-oxy," with --$(C_6,C_{10})$aryloxy,--;

Column 155, claim number 35, line 19: please replace "subtituents" with --substituents--;

Column 155, claim number 36, line 27: please replace "formula" with --formula (I)--;

Column 155, claim number 36, line 60: please replace "of," with --of--;

CERTIFICATE OF CORRECTION (continued)
U.S. Pat. No. 8,642,603 B2

Column 156, claim number 36, line 4: please replace "pyrrolyl,substituted" with --pyrrolyl, substituted--;

Column 156, claim number 36, line 11: please replace "subsrtituent" with --substituents--;

Column 156, claim number 36, line 33: please replace "1,3-dioxanyl,substituted" with --1,3-dioxanyl, substituted--; and Column 157, claim number 42, line 25-26: please replace "(S )-2-( 4-Cyclohexyl-phenoxymethyl)-6methyl-2,3-dihydro-oxazolo[3,2-a]pyrimidin-7-one," with --(S )-2-( 4-Cyclohexyl-phenoxymethyl)-6-methyl-2,3-dihydro-oxazolo[3,2-a]pyrimidin-7-one,--.